US011898177B2

(12) United States Patent
Cascao-Pereira et al.

(10) Patent No.: US 11,898,177 B2
(45) Date of Patent: Feb. 13, 2024

(54) VARIANT MALTOHEXAOSE-FORMING ALPHA-AMYLASE VARIANTS

(71) Applicant: DANISCO US INC., Palo Alto, CA (US)

(72) Inventors: Luis G Cascao-Pereira, Redwood City, CA (US); David A Estell, San Mateo, CA (US); Marc Anton Bernhard Kolkman, Oegstgeest (NL); Harm Mulder, Voorhout (NL)

(73) Assignee: DANISCO US INC., Palo Alto, CA (US)

( * ) Notice: Subject to any disclaimer, the term of this patent is extended or adjusted under 35 U.S.C. 154(b) by 117 days.

(21) Appl. No.: 17/373,307

(22) Filed: Jul. 12, 2021

(65) Prior Publication Data
US 2022/0002696 A1   Jan. 6, 2022

Related U.S. Application Data

(63) Continuation of application No. 16/572,804, filed on Sep. 17, 2019, now abandoned, which is a continuation of application No. 15/160,624, filed on May 20, 2016, now Pat. No. 10,457,924, which is a continuation of application No. 14/354,425, filed as application No. PCT/US2012/062209 on Oct. 26, 2012, now abandoned.

(60) Provisional application No. 61/668,359, filed on Jul. 5, 2012, provisional application No. 61/552,910, filed on Oct. 28, 2011.

(51) Int. Cl.
C12N 9/28     (2006.01)
A21D 8/04     (2006.01)
C11D 3/386    (2006.01)
D06L 1/14     (2006.01)
D06L 4/40     (2017.01)

(52) U.S. Cl.
CPC ........... *C12N 9/2417* (2013.01); *A21D 8/042* (2013.01); *C11D 3/386* (2013.01); *C12Y 302/01001* (2013.01); *D06L 1/14* (2013.01); *D06L 4/40* (2017.01)

(58) Field of Classification Search
None
See application file for complete search history.

(56) References Cited

U.S. PATENT DOCUMENTS 9,284,544 B2 * 3/2016 Jackson ............. C11D 3/38681
2008/0293607 A1 11/2008 Jones et al.

FOREIGN PATENT DOCUMENTS

| DE | 102005062984 A1 | 7/2007 |
| WO | 1999/019467 A1 | 4/1999 |
| WO | 1999/023211 A1 | 5/1999 |
| WO | 2000/029560 A1 | 5/2000 |
| WO | 2000/060059 A2 | 10/2000 |
| WO | 2000/060060 A2 | 10/2000 |
| WO | 2001/066712 A2 | 9/2001 |
| WO | 2002/010355 A2 | 2/2002 |
| WO | 2002/092797 A2 | 11/2002 |
| WO | 2006/002643 A2 | 1/2006 |
| WO | 2008/153805 A2 | 12/2008 |
| WO | 2009/061381 A2 | 5/2009 |
| WO | 2010/115021 A2 | 10/2010 |

OTHER PUBLICATIONS

Tsukamoto, A., et al. "Nucleotide Sequence of the Maltohexaose-Producing Amylase Gene from an Alkalophilic *Bacillus* sp. #707 and Structural Similarity to Liquiefying Type a-Amylases." Biochem. Biophys. Res. Commun. 151 (1): 25-31, 1988.
Suzuki, Y., et al. "Amino Acid Residues Stabilizing a Bacillus a-Amylase against Irreversible Thermoinactivation." J. Biol. Chem. 264(32): 18933-18938, 1989.
Sumitani, J., et al. "New type of starch-binding domain: the direct repeat motif in the C-terminal region of *Bacillus* sp. 195 a-amylase contributes to starch binding and raw starch degrading." J. Biochem. 350: 477-484, 2000.
Nielsen, J.E., et al., "Protein engineering of bacterial a-amylases." Biochimica et Biophysica Acta. 1543(2): 253-274, 2000.
Kimura et al. Cloning of gene for maltohexaose producing amylae of alkalophilic Bacillus and hyper-production of the enzyme in Bacillus subtilis cells, Applied Microbiology Biotechnology (1988), vol. 27, pp. 372-377.
International Search Report and the Written Opinion of the International Searching Authority for International Application No. PCT/US12/062209 dated Apr. 24, 2013.
International Preliminary Report on Patentability for International Application No. PCT/US12/062209 dated Apr. 29, 2014.
Igarashi et al., Enzymatic properties of a novel liquefying alpha-amylase from an alkaliphilic Bacillus isolate and entire nucleotide and amino acid sequences., Appl Environ Microbiol. (1998), vol. 64(9), pp. 3282-3289.
Igarashi et al., "Enzymatic properties of a novel liquefying alpha-amylase from an alkaliphilic Bacillus isolate nd entire nucleotide and amino acid sequences," Appl. Environ. Microbiol., 1988, vol. 64, No. 9, pp. 3282-3289.
Geneseq Database Accession No. ANK67158, Alpha Amylase, Bessler, C., et al., Dec. 13, 2017.
Geneseq Database Accession No. ANK67157, Alpha Amylase, Bessler, C., et al., Dec. 13, 2017.
European Extended Search Report for European Patent Application No. 16201637.2; dated Sep. 22, 2017.
Database, "Giucan 1 ,4-alpha-maltohexaosidase", 2009, accession No. UNIPROTC3C5B3.

(Continued)

*Primary Examiner* — Suzanne M Noakes
*Assistant Examiner* — Jae W Lee

(57) ABSTRACT

Disclosed are compositions and methods relating to variant maltohexaose-forming alpha-amylases. The variant alpha-amylases are useful, for example, for starch liquefaction and saccharification, for cleaning starchy stains in laundry, dishwashing, and other applications, for textile processing (e.g., desizing), in animal feed for improving digestibility, and for baking and brewing.

8 Claims, 2 Drawing Sheets

Specification includes a Sequence Listing.

(56) References Cited

OTHER PUBLICATIONS

Database, "Fuii=Aipha-amylase", 2005, accession No. UNIPROT:Q4MY42.
Database Geneseq [Online] May 27, 2010 (May 27, 2010), "*Bacillus* sp. 707 alpha-amylase mutein RI72Q." XP002690603, Database Accession No. AXX25955.
Database Geneseq [Online] Dec. 13, 2007 (Dec. 13, 2007), "Bacillus alpha-amylase AA560 variant #45." XP002690605, Database Accession No. ANK67158.
Database Geneseq [Online] Dec. 13, 2007 (Dec. 13, 2007), "Bacillus alpha-amylase AA560 variant #44." XP002690604, Database Accession No. ANK67157.
Database Genebank [Online] Jun. 2, 1988 (Jun. 2, 1988), "*Bacillus* sp. (alkalophilic) G6-amylase gene, complete eds.", Tsukamoto, A., et al., Database Accession No. M18862.1.
Christophersen, C., et al., "Enzymatic Characterisation of Novamyl®, a Thermostable a-Amylase." Starch 50: 39-45, 1998.
Alpha-amylase [*Bacillus flexus*], last viewed on Aug. 5, 2015.
List of references dated Mar. 6, 2015 for U.S. Appl. No. 14/354,425.
List of references dated Mar. 4, 2016 for U.S. Appl. No. 14/354,425.
List of references dated Aug. 10, 2015 for U.S. Appl. No. 14/354,425.
Information Disclosure Statement (IDS) Form (SB08) Mailed on Jul. 18, 2014 for U.S. Appl. No. 14/354,425.
Branden et al., Introduction to Protein Structure, Garland Publishing Inc., New York, 1991, p. 247.
Witkowski et al., Conversion of a β-Ketoacyl Synthase to a Malonyl Decarboxylase by Replacement of the Active-Site Cysteine with Glutamine, Biochemistry, 1999, pp. 11643-11650, vol. 38.
Seffernick et al., Melamine Deaminase and Atrazine Chlorohydrolase: 98 Percent Identical but Functionally Different, J. Bacteriol, 2001, pp. 2405-2410, vol. 183(8).

\* cited by examiner

```
CLUSTAL W (1.83) multiple sequence alignment

Amy707          HHNGTNGTMMQYFEWYLPNDGNHWNRLNSDASNLKSKGITAVWIPPAWKGASQNDVGYGA
AA560           HHNGTNGTMMQYFEWYLPNDGNHWNRLRSDASNLKDKGISAVWIPPAWKGASQNDVGYGA
                ***************************.******.***:********************

Amy707          YDLYDLGEFNQKGTVRTKYGTRSQLQAAVTSLKNNGIQVYGDVVMNHKGGADATEMVRAV
AA560           YDLYDLGEFNQKGTIRTKYGTRNQLQAAVNALKSNGIQVYGDVVMNHKGGADATEMVRAV
                **************:*******.******..**.***.**********************

Amy707          EVNPNNRNQEVTGEYTIEAWTRFDFPGRGNTHSSFKWRWYHFDGVDWDQSRRLNNRIYKF
AA560           EVNPNNRNQEVSGEYTIEAWTKFDFPGRGNTHSNFKWRWYHFDGVDWDQSRKLNNRIYKF
                ***********:*********:***********.*****************:********

Amy707          RGHGKAWDWEVDTENGNYDYLMYADIDMDHPEVVNELRNWGVWYTNTLGLDGFRIDAVKH
AA560           RGDGKGWDWEVDTENGNYDYLMYADIDMDHPEVVNELRNWGVWYTNTLGLDGFRIDAVKH
                **.**.******************************************************

Amy707          IKYSFTRDWINHVRSATGKNMFAVAEFWKNDLGAIENYLQKTNWNHSVFDVPLHYNLYNA
AA560           IKYSFTRDWINHVRSATGKNMFAVAEFWKNDLGAIENYLNKTNWNHSVFDVPLHYNLYNA
                ***************************************:*******************

Amy707          SKSGGNYDMRNIFNGTVVQRHPSHAVTFVDNHDSQPEEALESFVEEWFKPLAYALTLTRE
AA560           SKSGGNYDMRQIFNGTVVQRHPMHAVTFVDNHDSQPEEALESFVEEWFKPLAYALTLTRE
                **********:********** **************************************

Amy707          QGYPSVFYGDYYGIPTHGVPAMRSKIDPILEARQKYAYGKQNDYLDHHNIIGWTREGNTA
AA560           QGYPSVFYGDYYGIPTHGVPAMKSKIDPILEARQKYAYGRQNDYLDHHNIIGWTREGNTA
                **********************:****************:********************

Amy707          HPNSGLATIMSDGAGGSKWMFVGRNKAGQVWSDITGNRTGTVTINADGWGNFSVNGGSVS
AA560           HPNSGLATIMSDGAGGNKWMFVGRNKAGQVWTDITGNRAGTVTINADGWGNFSVNGGSVS
                ****************.**************:*****:**********************

Amy707          IWVNK      (SEQ ID NO: 3)
AA560           IWVNK      (SEQ ID NO: 4)
                *****
```

Fig 1

SEQUENCE LISTING

<160> NUMBER OF SEQ ID NOS: 5

<210> SEQ ID NO 1
<211> LENGTH: 1542
<212> TYPE: DNA
<213> ORGANISM: Artificial Sequence
<220> FEATURE:
<223> OTHER INFORMATION: Synthetic construct: codon-modified nucleotide
      sequence in the plasmid pHPLT-Amy707 that encodes the mature form
      of Bacillus sp. 707 al -continued

```
<400> SEQUENCE: 1
atgaaacaac aaaaacggct ttacgcccga ttgctgacgc tgttatttgc gctcatcttc      60
ttgctgcctc attctgcagc ttcagcacat cataatggca caaacggcac gatgatgcag     120
tattttgaat ggtatctgcc gaacgatgga accattggaa ccgcctgaa tagcgatgcg     180 agcaacctga aaagcaaagg catcacagca gtttggattc cgccggcatg gaaaggagca     240
agccaaaacg acgtcggcta tggagcgtat gatctgtatg acctgggcga atttaaccaa     300
aaaggcacgg tccgcacgaa atatggcacg cgcagccaac ttcaagcagc agtcacgagc     360
cttaaaaaca acggcatcca ggtctatgga gatgtcgtca tgaaccataa aggcggagca     420
gatgcgacag aaatggtcag agcggtcgaa gtcaacccga acaaccgcaa tcaagaagtc     480
acgggcgaat atacaatcga agcgtggacg cgctttgatt ttccgggcag aggcaataca     540
catagcagct ttaaatggcg ctggtatcat tttgatggcg tcgattggga tcaaagccgc     600
agactgaaca accgcatcta taaatttcgc ggccatggca agcatggga ttgggaagtc     660 gatacggaaa acggcaacta tgactatctg atgtatgcgg acatcgatat ggatcatccg     720
gaagtcgtca cgaactgag aaattggggc gtctggtata caaatacgct gggcctggat     780
ggctttagaa tcgacgcggt caaacatatc aaatatagct ttacgcgcga ctggatcaat     840
catgtcagaa gcgcgacggg caaaaatatg tttgcggtcg cggaattttg gaaaaatgat     900
ctgggcgcga tcgaaaacta tctgcaaaaa acgaactgga accatagcgt ctttgatgtc     960
ccgctgcatt ataacctgta acgcgagc aaaagcggcg gcaattatga tatgcgcaac    1020
atctttaacg gcacggtcgt tcaaagacat ccgagccatg cggtcacgtt tgtcgataac    1080
catgatagcc aaccggaaga agcgctggaa agctttgtcg aagaatggtt taaaccgctg    1140
gcgtatgcac tgacactgac gagagaacaa ggatatccga gcgtctttta tggcgactat    1200
tatggcatcc gacacatgg agttccggcg atgagaagca aaatcgaccc gatcctggaa    1260
gcgagacaga aatatgcgta tggcaaacag aacgactatc tggaccatca taacatcatc    1320
ggctggacga gaaggaaa tacgcgcat ccgaattcag gactggcgac gattatgtca    1380
gatggagcgg gcggaagcaa atggatgttt gtcggcagaa acaaagcagg acaagtctgg    1440
agcgatatca cggcaatag aacgggaacg gtcacgatca atgcagatgg ctggggcaac    1500
tttagcgtta atggcggaag cgtcagcatc tgggtcaaca aa                      1542
```

<210> SEQ ID NO 2
<211> LENGTH: 514
<212> TYPE: PRT
<213> ORGANISM: Artificial Sequence
<220> FEATURE:
<223> OTHER INFORMATION: Synthetic construct: amino acid sequence of the
      precursor form of Bacillus sp. 707 alpha-amylase produced from the
      plasmid pHPLT-Amy707

<400> SEQUENCE: 2

```
Met Lys Gln Gln Lys Arg Leu Tyr Ala Arg Leu Leu Thr Leu Leu Phe
1               5                   10                  15

Ala Leu Ile Phe Leu Leu Pro His Ser Ala Ala Ser Ala His His Asn
            20                  25                  30

Gly Thr Asn Gly Thr Met Met Gln Tyr Phe Glu Trp Tyr Leu Pro Asn
        35                  40                  45

Asp Gly Asn His Trp Asn Arg Leu Asn Ser Asp Ala Ser Asn Leu Lys
    50                  55                  60
```

```
Ser Lys Gly Ile Thr Ala Val Trp Ile Pro Pro Ala Trp Lys Gly Ala
 65                  70                  75                  80

Ser Gln Asn Asp Val Gly Tyr Gly Ala Tyr Asp Leu Tyr Asp Leu Gly
                 85                  90                  95

Glu Phe Asn Gln Lys Gly Thr Val Arg Thr Lys Tyr Gly Thr Arg Ser
            100                 105                 110

Gln Leu Gln Ala Ala Val Thr Ser Leu Lys Asn Asn Gly Ile Gln Val
        115                 120                 125

Tyr Gly Asp Val Val Met Asn His Lys Gly Gly Ala Asp Ala Thr Glu
    130                 135                 140

Met Val Arg Ala Val Glu Val Asn Pro Asn Asn Arg Asn Gln Glu Val
145                 150                 155                 160

Thr Gly Glu Tyr Thr Ile Glu Ala Trp Thr Arg Phe Asp Phe Pro Gly
                165                 170                 175

Arg Gly Asn Thr His Ser Ser Phe Lys Trp Arg Trp Tyr His Phe Asp
            180                 185                 190

Gly Val Asp Trp Asp Gln Ser Arg Arg Leu Asn Asn Arg Ile Tyr Lys
        195                 200                 205

Phe Arg Gly His Gly Lys Ala Trp Asp Trp Glu Val Asp Thr Glu Asn
    210                 215                 220

Gly Asn Tyr Asp Tyr Leu Met Tyr Ala Asp Ile Asp Met Asp His Pro
225                 230                 235                 240

Glu Val Val Asn Glu Leu Arg Asn Trp Gly Val Trp Tyr Thr Asn Thr
                245                 250                 255

Leu Gly Leu Asp Gly Phe Arg Ile Asp Ala Val Lys His Ile Lys Tyr
            260                 265                 270

Ser Phe Thr Arg Asp Trp Ile Asn His Val Arg Ser Ala Thr Gly Lys
        275                 280                 285

Asn Met Phe Ala Val Ala Glu Phe Trp Lys Asn Asp Leu Gly Ala Ile
    290                 295                 300

Glu Asn Tyr Leu Gln Lys Thr Asn Trp Asn His Ser Val Phe Asp Val
305                 310                 315                 320

Pro Leu His Tyr Asn Leu Tyr Asn Ala Ser Lys Ser Gly Gly Asn Tyr
                325                 330                 335

Asp Met Arg Asn Ile Phe Asn Gly Thr Val Val Gln Arg His Pro Ser
            340                 345                 350

His Ala Val Thr Phe Val Asp Asn His Asp Ser Gln Pro Glu Glu Ala
        355                 360                 365

Leu Glu Ser Phe Val Glu Glu Trp Phe Lys Pro Leu Ala Tyr Ala Leu
    370                 375                 380

Thr Leu Thr Arg Glu Gln Gly Tyr Pro Ser Val Phe Tyr Gly Asp Tyr
385                 390                 395                 400

Tyr Gly Ile Pro Thr His Gly Val Pro Ala Met Arg Ser Lys Ile Asp
                405                 410                 415

Pro Ile Leu Glu Ala Arg Gln Lys Tyr Ala Tyr Gly Lys Gln Asn Asp
            420                 425                 430

Tyr Leu Asp His His Asn Ile Ile Gly Trp Thr Arg Glu Gly Asn Thr
        435                 440                 445

Ala His Pro Asn Ser Gly Leu Ala Thr Ile Met Ser Asp Gly Ala Gly
    450                 455                 460

Gly Ser Lys Trp Met Phe Val Gly Arg Asn Lys Ala Gly Gln Val Trp
465                 470                 475                 480
```

```
Ser Asp Ile Thr Gly Asn Arg Thr Gly Thr Val Thr Ile Asn Ala Asp
            485                 490                 495

Gly Trp Gly Asn Phe Ser Val Asn Gly Ser Val Ser Ile Trp Val
        500                 505                 510

Asn Lys

<210> SEQ ID NO 3
<211> LENGTH: 485
<212> TYPE: PRT
<213> ORGANISM: Artificial Sequence
<220> FEATURE:
<223> OTHER INFORMATION: Synthetic construct: mature form of Bacillus
      sp. 707 alpha-amylase produced from the plasmid pHPLT-Amy707

<400> SEQUENCE: 3

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
            20                  25                  30

Asn Leu Lys Ser Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Thr Gly Glu Tyr Thr Ile Glu Ala Trp Thr Arg Phe Asp
    130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
                165                 170                 175

Ile Tyr Lys Phe Arg Gly His Gly Lys Ala Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Gln Lys Thr Asn Trp Asn His Ser Val
        275                 280                 285

Phe Asp Val Pro Leu His Tyr Asn Leu Tyr Asn Ala Ser Lys Ser Gly
    290                 295                 300

Gly Asn Tyr Asp Met Arg Asn Ile Phe Asn Gly Thr Val Val Gln Arg
305                 310                 315                 320
```

```
His Pro Ser His Ala Val Thr Phe Val Asp Asn His Asp Ser Gln Pro
                325                 330                 335

Glu Glu Ala Leu Glu Ser Phe Val Glu Trp Phe Lys Pro Leu Ala
            340                 345                 350

Tyr Ala Leu Thr Leu Thr Arg Glu Gln Gly Tyr Pro Ser Val Phe Tyr
            355                 360                 365

Gly Asp Tyr Tyr Gly Ile Pro Thr His Gly Val Pro Ala Met Arg Ser
370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
            420                 425                 430

Gly Ala Gly Gly Ser Lys Trp Met Phe Val Gly Arg Asn Lys Ala Gly
            435                 440                 445

Gln Val Trp Ser Asp Ile Thr Gly Asn Arg Thr Gly Thr Val Thr Ile
            450                 455                 460

Asn Ala Asp Gly Trp Gly Asn Phe Ser Val Asn Gly Gly Ser Val Ser
465                 470                 475                 480

Ile Trp Val Asn Lys
                485

<210> SEQ ID NO 4
<211> LENGTH: 485
<212> TYPE: PRT
<213> ORGANISM: Bacillus sp.
<220> FEATURE:
<221> NAME/KEY: misc_feature
<223> OTHER INFORMATION: AA560 alpha-amylase derived from Bacillus sp.
      DSM 12649

<400> SEQUENCE: 4

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Ser Ala Val Trp Ile Pro Pro Ala Trp
        35                  40                  45

Lys Gly Ala Ser Gln Asn Asp Val Gly Tyr Gly Ala Tyr Asp Leu Tyr
50                  55                  60

Asp Leu Gly Glu Phe Asn Gln Lys Gly Thr Ile Arg Thr Lys Tyr Gly
65                  70                  75                  80

Thr Arg Asn Gln Leu Gln Ala Ala Val Asn Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Ser Gly Glu Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Lys Leu Asn Asn Arg
                165                 170                 175
```

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
            195                 200                 205

Asp His Pro Glu Val Val Asn Glu Leu Arg Asn Trp Gly Val Trp Tyr
        210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
            245                 250                 255

Thr Gly Lys Asn Met Phe Ala Val Ala Glu Phe Trp Lys Asn Asp Leu
            260                 265                 270

Gly Ala Ile Glu Asn Tyr Leu Asn Lys Thr Asn Trp Asn His Ser Val
            275                 280                 285

Phe Asp Val Pro Leu His Tyr Asn Leu Tyr Asn Ala Ser Lys Ser Gly
            290                 295                 300

Gly Asn Tyr Asp Met Arg Gln Ile Phe Asn Gly Thr Val Val Gln Arg
305                 310                 315                 320

His Pro Met His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

Tyr Ala Leu Thr Leu Thr Arg Glu Gln Gly Tyr Pro Ser Val Phe Tyr
            355                 360                 365

Gly Asp Tyr Tyr Gly Ile Pro Thr His Gly Val Pro Ala Met Lys Ser
370                 375                 380

Lys Ile Asp Pro Ile Leu Glu Ala Arg Gln Lys Tyr Ala Tyr Gly Arg
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
            420                 425                 430

Gly Ala Gly Gly Asn Lys Trp Met Phe Val Gly Arg Asn Lys Ala Gly
            435                 440                 445

Gln Val Trp Thr Asp Ile Thr Gly Asn Arg Ala Gly Thr Val Thr Ile
            450                 455                 460

Asn Ala Asp Gly Trp Gly Asn Phe Ser Val Asn Gly Gly Ser Val Ser
465                 470                 475                 480

Ile Trp Val Asn Lys
            485

<210> SEQ ID NO 5
<211> LENGTH: 2397
<212> TYPE: DNA
<213> ORGANISM: Bacillus sp.
<220> FEATURE:
<221> NAME/KEY: misc_feature
<223> OTHER INFORMATION: Genebank Accession No. M18862, which encodes
      Bacillus sp. 707 alpha-amylase

<400> SEQUENCE: 5
ggatcccgtc tacggagaag cgagtattga attttttgct gtaacagaaa gcgagcgtgg    60
gaaaggattt ggctttcaat tactaacggt tgctttaaat tggctattta cgattgatac   120
gattcattca attacactct gtgtcgattc tagtaatgaa catgcgattc atttatataa   180
aaaagttgga ttcaggcatg ttcatgattt gagttatttt actaaagaag tatctcatta   240

```
aaaacatgat tgaggaaaga cggttttcga ctaattgtgg tcaaagtaga aaattgaatg      300
aatattacga agcatgaggc taagacataa ctaaagtgtc taaatgaaaa accgaacgaa      360
aaatgaacga agcgaagtgt atttcaagaa aggttaccgt tcgctattta tcaccgttcg      420
gttatttttt agataagcca cttttgtcgc ggcctctttt tggtgccgat aaatgagaat      480
aaagaataaa aagtcaatat tgcttagcta aatgaatgtc aaggtggtta tattatccta      540
tttattttca gaaaataaaa aaacgtttgc gcaattgttt tatagcataa taatataacc      600
ttgccaattg atatttaagt cgagtgaaat caattgcgca aattaatgag tgtgttcaag      660
gagagtgatg aatgtagcag tttagtcatg tacttgtttt tggaaagcgc ttacaattag      720
gagggtggat gaaaatgaga acaggaaaaa agggtttttt aagtatttta ttagcgttct      780
tattggtgat tacttcaata ccgtttactt tagtagatgt agaagcacat cataacggta      840
cgaacgggac aatgatgcaa tactttgaat ggtatctacc taatgacgga atcattgga      900 atcgattaaa ctctgatgcg agtaacctta aaagcaaagg gattacagcg gtgtggattc      960
ctccagcatg gaagggcgct tctcaaaatg acgtaggata cggagcctat gacctgtatg     1020
atctgggaga atttaatcaa aaaggtaccg tccgtacaaa atatggaaca cgtagtcagt     1080
tacaagctgc ggtaacctcc ttaaaaaata atggaattca agtatatggt gacgttgtta     1140
tgaatcacaa aggtggcgca gacgctactg aaatggtaag ggccgttgaa gtgaatccca     1200
ataaccgtaa ccaagaagtg actggtgaat ataccattga agcttggact agatttgatt     1260
ttccagggcg aggaaatact cattctagct ttaaatggag atggtatcat tttgatggtg     1320
tggattggga tcagtcacgt agactgaaca atcgcatcta taaatttaga ggtcatggca     1380
aagcttggga ttgggaagtt gatacggaaa atggtaatta tgattattta atgtacgctg     1440
atattgatat ggatcaccca gaagtagtaa atgaattaag aaattggggt gtttggtaca     1500
caaacacatt aggactcgat ggatttagaa tagatgcggt taaacatata aagtatagct     1560
ttacgcgcga ttggattaat cacgttagaa gtgcaacagg taaaaatatg tttgcggttg     1620
ctgagttttg gaagaatgat ttaggtgcaa ttgaaaacta tctgcagaaa acaaactgga     1680
accattcagt ctttgatgtg ccgttacatt ataatcttta taatgcatca aaaagcggag     1740
ggaactatga tatgcgaaac atatttaatg gaacggttgt tcaacgacat ccaagtcatg     1800
ctgtaacatt tgttgataat catgattcgc agcctgaaga agcattagaa tcttttgttg     1860
aagaatggtt taaccatta gcgtatgcgc ttacattaac gcgtgaacaa ggataccctt     1920
ctgtatttta cggagattat tatgggattc caacacatgg agtgccagca atgagatcaa     1980
aaatcgatcc gatttagaa gcacgtcaaa agtatgcata cggaaaacaa aatgattact     2040
tagaccatca taatatcatt ggttggacgc gtgaagggaa tacagcacac cccaattcag     2100
gtctagctac catcatgtct gatggagcgg gtggaagtaa gtggatgttt gttgggcgta     2160
ataaggctgg tcaagtatgg agtgatatta caggaaaccg tacaggtacg gttacaatca     2220
atgcagacgg ttgggcaat ttctctgtga atggagggtc agtttctatt tgggtcaaca     2280
aataaaagtg gaaagaaga ggccgtaggt taatatggtc ttttcttttc ttttaaggag     2340
gttcaatgaa tttgtcggtt atccaattat tacatgctga gctgttagat tattcgt     2397
```

VARIANT MALTOHEXAOSE-FORMING ALPHA-AMYLASE VARIANTS

PRIORITY

The present application is a continuation of U.S. patent application Ser. No. 16/572,804 filed Sep. 17, 2019, which is a continuation of U.S. patent application Ser. No. 15/160,624, filed May 20, 206, which is a continuation of U.S. patent application Ser. No. 14/354,425, filed Apr. 25, 2014, which is a U.S. National Phase Application of International Application No. PCT/US2012/062209, filed Oct. 26, 2012, which claims priority to U.S. Provisional Application Ser. No. 61/552,910, filed on Oct. 28, 2011, and U.S. Provisional Application Ser. No. 61/668,359, filed on Jul. 5, 2012, which are hereby incorporated by reference in their entirety.

SEQUENCE LISTING

The sequence listing submitted via EFS, in compliance with 37 C.F.R. § 1.52(e), is incorporated herein by reference. The sequence listing text file submitted via EFS contains the file "20190912_NB40279USCNT2_SeqLst.txt" created on Sep. 12, 2019, which is 19 KB in size.

FIELD OF THE INVENTION

Disclosed are compositions and methods relating to variant maltohexaose-forming α-amylases. The variant α-amylases are useful, for example, for starch liquefaction and saccharification, cleaning starchy stains, textile desizing, baking, and brewing.

BACKGROUND

Starch consists of a mixture of amylose (15-30% w/w) and amylopectin (70-85% w/w). Amylose consists of linear chains of α-1,4-linked glucose units having a molecular weight (MW) from about 60,000 to about 800,000. Amylopectin is a branched polymer containing α-1,6 branch points every 24-30 glucose units; its MW may be as high as 100 million.

Sugars from starch, in the form of concentrated dextrose syrups, are currently produced by an enzyme catalyzed process involving: (1) liquefaction (or viscosity reduction) of solid starch with an α-amylase into dextrins having an average degree of polymerization of about 7-10, and (2) saccharification of the resulting liquefied starch (i.e. starch hydrolysate) with amyloglucosidase (also called glucoamylase or GA). The resulting syrup has a high glucose content. Much of the glucose syrup that is commercially produced is subsequently enzymatically isomerized to a dextrose/fructose mixture known as isosyrup. The resulting syrup also may be fermented with microorganisms, such as yeast, to produce commercial products including ethanol, citric acid, lactic acid, succinic acid, itaconic acid, monosodium glutamate, gluconates, lysine, other organic acids, other amino acids, and other biochemicals, for example. Fermentation and saccharification can be conducted simultaneously (i.e., an SSF process) to achieve greater economy and efficiency.

α-amylases hydrolyze starch, glycogen, and related polysaccharides by cleaving internal α-1,4-glucosidic bonds at random. α-amylases, particularly from Bacilli, have been used for a variety of different purposes, including starch liquefaction and saccharification, textile desizing, starch modification in the paper and pulp industry, brewing, baking, production of syrups for the food industry, production of feedstocks for fermentation processes, and in animal feed to increase digestibility. These enzymes can also be used to remove starchy soils and stains during dishwashing and laundry washing.

SUMMARY

The present compositions and methods relate to variant maltohexaose-forming amylase polypeptides, and methods of use, thereof. Aspects and embodiments of the present compositions and methods are summarized in the following separately-numbered paragraphs:

1. In one aspect, a variant α-amylase polypeptide derived from a parental α-amylase polypeptide is provided, comprising at least one combinable mutation at a productive amino acid position; wherein: (i) the combinable mutation is the substitution of an amino acid residue present in the parental α-amylase with a different amino acid residue, which improves at least one desirable property of the variant α-amylase compared to the parental α-amylase, while not significantly decreasing either expression, activity, or stability of the variant α-amylase, compared to the parental α-amylase, (ii) the productive position is an amino acid position that can be substituted with a plurality of different amino acid residues, each of which substitutions result in a variant α-amylase that meets the requirements of (i), and (iii) the combinable mutation corresponds to a mutation listed in Lists A, B, C, or D, or in Table C or D, which use SEQ ID NO: 3 for numbering.

2. In some embodiments of the variant amylase of paragraph 1, each of the at least one combinable mutations produces a variant amylase wherein the minimum performance indices (PI) relative to the parental amylase for (i) protein expression, (ii) activity, and (iii) detergent stability or thermostability are greater than or equal to 0.9, and the PI for any one of (i), (ii), or (iii) that is greater than or equal to 1.0.

3. In some embodiments of the variant amylase of paragraph 1, each of the at least one combinable mutations produces a variant amylase wherein the minimum performance indices (PI) relative to the parental amylase for (i) protein expression, (ii) activity, and (iii) detergent stability or thermostability are greater than or equal to 0.8, and the PI for any one of (i), (ii), or (iii) that is greater than or equal to 1.2.

4. In some embodiments of the variant amylase of paragraph 1, each of the at least one combinable mutations produces a variant amylase wherein the minimum performance indices (PI) relative to the parental amylase for (i) protein expression, (ii) activity, and (iii) detergent stability or thermostability are greater than or equal to 0.5, and the PI for any one of (i), (ii), or (iii) that is greater than or equal to 1.5.

5. In some embodiments of the variant amylase of any of the preceding paragraphs, each of the at least one combinable mutations have a suitability score of +++, ++++, or +++++, referring to Table B.

6. In some embodiments of the variant amylase of any of the preceding paragraphs, each of the at least one combinable mutation have a suitability score of ++++, or +++++, referring to Table B.

7. In some embodiments of the variant amylase of any of the preceding paragraphs, each of the at least one combinable mutation has a suitability score of +++++, referring to Table B.

8. In some embodiments of the variant amylase of any of the preceding paragraphs, each of the at least one combinable mutation has a productivity score of 1 or 2.

9. In some embodiments, the variant amylase of any of the preceding paragraphs includes a plurality of combinable mutations.

10. In some embodiments, the variant amylase of any of the preceding paragraphs further comprises a deletion corresponding to a residue selected from the group consisting of Arg-181, Gly-182, His-183, and Gly-184, using SEQ ID NO: 3 for numbering.

11. In some embodiments, the variant amylase of any of the preceding paragraphs further comprises deletions corresponding to residues Arg-181 and Gly-182, using SEQ ID NO: 3 for numbering.

12. In some embodiments of the variant amylase of any of the preceding paragraphs, the parental α-amylase or the variant α-amylase has at least 60% amino acid sequence identity to the amino acid sequence of SEQ ID NO: 3 or SEQ ID NO: 4, or wherein the parental α-amylase or the variant α-amylase is encoded by a nucleic acid that hybridizes under stringent conditions to the nucleic acid of SEQ ID NO: 1 or SEQ ID NO: 5.

13. In some embodiments of the variant amylase of any of the preceding paragraphs, the parental α-amylase or the variant α-amylase has at least 70% amino acid sequence identity to the amino acid sequence of SEQ ID NO: 3 or SEQ ID NO: 4, or wherein the parental α-amylase or the variant α-amylase is encoded by a nucleic acid that hybridizes under stringent conditions to the nucleic acid of SEQ ID NO: 1 or SEQ ID NO: 5.

14. In some embodiments of the variant amylase of any of the preceding paragraphs, the parental α-amylase or the variant α-amylase has at least 80% amino acid sequence identity to the amino acid sequence of SEQ ID NO: 3 or SEQ ID NO: 4, or wherein the parental α-amylase or the variant α-amylase is encoded by a nucleic acid that hybridizes under stringent conditions to the nucleic acid of SEQ ID NO: 1 or SEQ ID NO: 5.

15. In some embodiments of the variant amylase of any of the preceding paragraphs, the parental α-amylase or the variant α-amylase has at least 90% amino acid sequence identity to the amino acid sequence of SEQ ID NO: 3 or SEQ ID NO: 4, or wherein the parental α-amylase or the variant α-amylase is encoded by a nucleic acid that hybridizes under stringent conditions to the nucleic acid of SEQ ID NO: 1 or SEQ ID NO: 5.

16. In another aspect, a composition comprising the variant amylase of any of paragraphs 1-15 is provided.

17. In some embodiments of the composition of paragraph 16, the composition is effective for removing starchy stains from laundry, dishes, or textiles.

18. In some embodiments, the composition of paragraphs 16 or 17 further comprises a surfactant.

19. In some embodiments of the composition of paragraphs 16-18, the composition is a detergent composition.

20. In some embodiments of the composition of paragraphs 16-19, the composition is a laundry detergent or a laundry detergent additive.

21. In some embodiments of the composition of paragraphs 16-20, the composition is a manual or automatic dishwashing detergent.

22. In some embodiments, the composition of paragraphs 16-21 further comprises one or more additional enzymes selected from the group consisting of protease, hemicellulase, cellulase, peroxidase, lipolytic enzyme, metallolipolytic enzyme, xylanase, lipase, phospholipase, esterase, perhydrolase, cutinase, pectinase, pectate lyase, mannanase, keratinase, reductase, oxidase, phenoloxidase, lipoxygenase, ligninase, pullulanase, tannase, pentosanase, malanase, ß-glucanase, arabinosidase, hyaluronidase, chondroitinase, laccase, and an amylase other than the amylase of any one of paragraphs 1-15.

23. In some embodiments, the composition of paragraph 16 is for liquifying starch.

24. In some embodiments, the composition of paragraph 16 is for saccharifying a composition comprising starch, for SSF post liquefaction, or for direct SSF without prior liquefaction.

25. In some embodiments, the composition of paragraph 16 is for producing a fermented beverage.

26. In some embodiments, the composition of paragraph 16 is for producing a baked food product.

27. In some embodiments, the composition of paragraph 16 is for textile desizing.

28. In another aspect, a method for removing a starchy stain or soil from a surface is provided, comprising: contacting the surface in the presence of a aqueous composition comprising an effective amount of the variant amylase of any of the paragraphs 1-15 and, allowing the polypeptide to hydrolyze starch components present in the starchy stain to produce smaller starch-derived molecules that dissolve in the aqueous composition, and rinsing the surface, thereby removing the starchy stain from the surface.

29. In some embodiments of the method of paragraph 28, the aqueous composition further comprises a surfactant.

30. In some embodiments of the method of paragraphs 28-29, the surface is a textile surface.

31. In some embodiments of the method of paragraphs 28-29, the surface is on dishes.

32. In some embodiments of the method of paragraphs 28-29, the surface is a soiled hard surface.

33. In some embodiments of the method of paragraphs 28-32, the composition further comprises at least one additional enzymes selected from the group consisting of protease, hemicellulase, cellulase, peroxidase, lipolytic enzyme, metallolipolytic enzyme, xylanase, lipase, phospholipase, esterase, perhydrolase, cutinase, pectinase, pectate lyase, mannanase, keratinase, reductase, oxidase, phenoloxidase, lipoxygenase, ligninase, pullulanase, tannase, pentosanase, malanase, ß-glucanase, arabinosidase, hyaluronidase, chondroitinase, laccase, and an amylase other than the amylase of any one of paragraphs 1-15.

34. In another aspect, a method of saccharifying a composition comprising starch to produce a composition comprising glucose is provided, wherein the method comprises: (i) contacting the solution comprising starch with effective amount of the variant amylase of any of the paragraphs 1-15; and (ii) saccharifying the solution comprising starch to produce the composition comprising glucose; wherein the variant amylase catalyzes the saccharification of the starch solution to glucose.

35. In some embodiments of the method of paragraph 34, the composition comprising starch comprises liquefied starch, gelatinized starch, or granular starch.

36. In some embodiments of the method of paragraphs 34 or 35, saccharification is conducted at a temperature range of about 30° C. to about 75° C.

37. In some embodiments of the method of paragraph 36, the temperature range is 47° C.-74° C.

38. In some embodiments of the method of any of paragraphs 34-37, saccharification is conducted over a pH range of pH 2.0-7.5.

39. In some embodiments of the method of paragraph 38, the pH range is pH 3.5-5.5.

40. In some embodiments of the method of paragraph 39, the pH range is pH 3.5-4.5.

41. In some embodiments, the method of any of paragraphs 34-40, further comprises fermenting the glucose composition to produce an end of fermentation (EOF) product.

42. In some embodiments of the method of paragraph 41, the fermentation is a simultaneous saccharification and fermentation (SSF) reaction.

43. In some embodiments of the method of paragraphs 41 or 42, the fermentation is conducted for 48-70 hours at pH 2-8 and in a temperature range of 25° C.-70° C.

44. In some embodiments of the method of any of paragraphs 41-43, the EOF product comprises ethanol.

45. In some embodiments of the method of any of paragraphs 41-44, the EOF product comprises 8-18% (v/v) ethanol.

46. In some embodiments of the method of paragraphs 41-45, the method further comprises contacting a mash and/or a wort with an amylase.

47. In some embodiments of the method of paragraph 46, the method further comprises: (a) preparing a mash; (b) filtering the mash to obtain a wort; and (c) fermenting the wort to obtain a fermented beverage, wherein the variant amylase of any one of paragraphs 1-16 and 74-80 is added to: (i) the mash of step (a) and/or (ii) the wort of step (b) and/or (iii) the wort of step (c).

48. In some embodiments of the method of any of paragraphs 41-47, the EOF product comprises a metabolite.

49. In some embodiments of the method of paragraph 48, the metabolite is citric acid, lactic acid, succinic acid, monosodium glutamate, gluconic acid, sodium gluconate, calcium gluconate, potassium gluconate, glucono delta-lactone, sodium erythorbate, omega 3 fatty acid, butanol, an amino acid, lysine, itaconic acid, 1,3-propanediol, or isoprene.

50. In some embodiments, the method of any of paragraphs 34-49 further comprises adding glucoamylase, hexokinase, xylanase, glucose isomerase, xylose isomerase, phosphatase, phytase, pullulanase, β-amylase, α-amylase that is not the variant α-amylase, protease, cellulase, hemicellulase, lipase, cutinase, isoamylase, redox enzyme, esterase, transferase, pectinase, alpha-glucosidase, beta-glucosidase, or a combination thereof, to the starch solution.

51. In some embodiments of the method of paragraph 50, the glucoamylase is added to 0.1-2 glucoamylase units (GAU)/g ds.

52. In some embodiments of the method of any of paragraphs 34-51, the amylase is expressed and secreted by a host cell.

53. In some embodiments of the method of paragraph 52, the composition comprising starch is contacted with the host cell.

54. In some embodiments of the method of paragraphs 52 or 53, the host cell further expresses and secretes a glucoamylase or other enzyme.

55. In some embodiments of the method of any of paragraphs 52-54, the host cell is capable of fermenting the composition.

56. In another aspect, a composition comprising glucose produced by the method of any one of paragraphs 34-55 is provided.

57. In another aspect, a liquefied starch produced by the method of any one of paragraphs 34-55 is provided.

58. In another aspect, a fermented beverage produced by the method of any one of paragraphs 34-55 is provided.

59. In another aspect, the use of an amylase of any of paragraphs 1-15 in the production of a composition comprising glucose is provided.

60. In another aspect, the use of an amylase of any of paragraphs 1-15 in the production of a liquefied starch is provided.

61. In another aspect, the use of an amylase of any of paragraphs 1-15 in the production of a fermented beverage is provided.

62. In another aspect, the use of an amylase of any of paragraphs 1-15 in cleaning starchy stains is provided.

63. In another aspect, the use of an amylase of any of paragraphs 1-15 in textile desizing is provided.

64. In some embodiments of the method according to any one of paragraphs 34-55, the fermented beverage of paragraph 58, or the use of paragraph 61, the fermented beverage or end of fermentation product is selected from the group consisting of (i) a beer selected from the group consisting of full malted beer, beer brewed under the "Reinheitsgebot", ale, IPA, lager, bitter, Happoshu (second beer), third beer, dry beer, near beer, light beer, low alcohol beer, low calorie beer, porter, bock beer, stout, malt liquor, non-alcoholic beer, and non-alcoholic malt liquor; and (ii) cereal or malt beverages selected from the group consisting of fruit flavoured malt beverages, liquor flavoured malt beverages, and coffee flavoured malt beverages.

65. In another aspect, a method of producing a food composition is provided, comprising combining: (i) one or more food ingredients, and (ii) a variant α-amylase of any of paragraphs 1-15, wherein the variant α-amylase thereof catalyzes the hydrolysis of starch components present in the food ingredients to produce glucose.

66. In some embodiments of the method of paragraph 65, the food composition is selected from the group consisting of a food product, a baking composition, a food additive, an animal food product, a feed product, a feed additive, an oil, a meat, and a lard.

67. In some embodiments of the method of any one of paragraphs 65-66, the one or more food ingredients comprise a baking ingredient or an additive.

68. In some embodiments of the method of any one of paragraphs 65-67, the one or more food ingredients is/are selected from the group consisting of flour; an anti-staling amylase; a phospholipase; a phospholipid; a maltogenic alpha-amylase or a variant, homologue, or mutants thereof which has maltogenic alpha-amylase activity; a bakery xylanase; and a lipase.

69. In some embodiments of the method of paragraph 65, the one or more food ingredients is/are selected from the group consisting of: (i) a maltogenic alpha-amylase from *Bacillus stearothermophilus*, (ii) a bakery xylanase is from *Bacillus, Aspergillus, Thermomyces* or *Trichoderma*, (iii) a glycolipase from *Fusarium heterosporum*.

70. In some embodiments of the method of any one of paragraphs 65-69, the food composition comprises a dough or a dough product, preferably a processed dough product.

71. In some embodiments, the method of any one of paragraphs 65-70 further comprises baking the food composition to produce a baked good.

72. In some embodiments, the method of any one of paragraphs 65-70, further comprises: (i) providing a starch medium; (ii) adding to the starch medium an amylase; and (iii) applying heat to the starch medium during or after step (b) to produce a bakery product.

73. In another aspect, a method of desizing a textile is provided, comprising contacting a desizing composition with a sized textile for a time sufficient to desize the textile, wherein the desizing composition comprises a variant α-amylase of any one of paragraphs 1-15.

74. In another aspect, an isolated polynucleotide encoding a polypeptide of any of paragraphs 1-15 is provided.

75. In another aspect, an expression vector comprising the polynucleotide of paragraph 74 is provided.

76. In another aspect, a host cell comprising the expression vector of paragraph 75 is provided.

These and other aspects and embodiments of the compositions and methods will be apparent from the present description and drawings.

BRIEF DESCRIPTION OF THE DRAWINGS

FIG. 1 is a Clustal alignment, using default parameters, of Amy707 amylase and AA560 amylase.

BRIEF DESCRIPTION OF THE SEQUENCES

Figure 2:
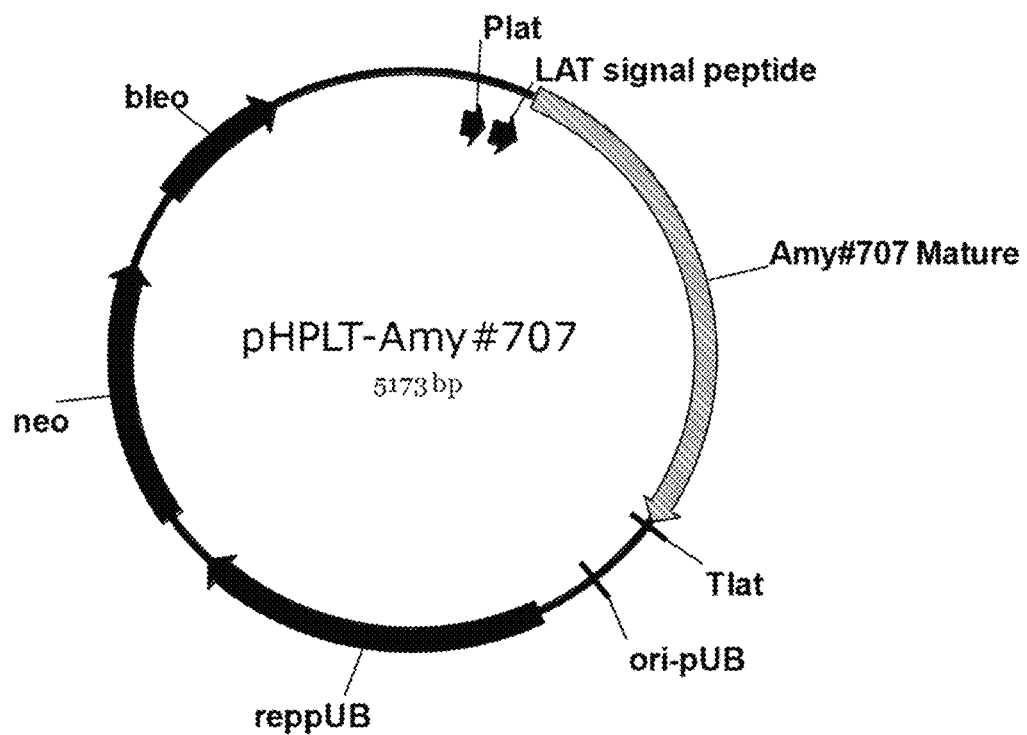
FIG. 2 is a map of the pHPLT vector comprising the Amy707 gene (pHPLT-Amy707).

SEQ ID NO: 1 sets forth a codon-modified nucleotide sequence in the plasmid pHPLT-Amy707 that encodes the mature form of *Bacillus* sp. 707 α-amylase. The sequence encoding the LAT signal peptide is underlined.

SEQ ID NO: 2 sets forth the amino acid sequence of the precursor form of *Bacillus* sp. 707 α-amylase produced from the plasmid pHPLT-Amy707. The LAT signal peptide is underlined.

SEQ ID NO: 3 sets forth the amino acid sequence of the mature form of *Bacillus* sp. 707 α-amylase produced from the plasmid pHPLT-Amy707.

SEQ ID NO: 4 sets forth the amino acid sequence of the mature form of AA560 α-amylase derived from *Bacillus* sp. DSM 12649 (i.e., the parent of STAINZYME™).

SEQ ID NO: 5 sets forth Genebank Accession No. M18862, which encodes *Bacillus* sp. 707 α-amylase.

DETAILED DESCRIPTION

Described are compositions and methods relating to variant maltohexaose-forming amylase enzymes. The variants were discovered by a combination of experimental approaches, as detailed in the appended Examples. The approaches include the use of site evaluation libraries (SELs) and structure-based analysis. Exemplary applications for the variant amylase enzymes are for starch liquefaction and saccharification, for cleaning starchy stains in laundry, dishwashing, and other applications, for textile processing (e.g., desizing), in animal feed for improving digestibility, and for baking and brewing. These and other aspects of the compositions and methods are described in detail, below.

Prior to describing the various aspects and embodiments of the present compositions and methods, the following definitions and abbreviations are described.

1. Definitions and Abbreviations

In accordance with this detailed description, the following abbreviations and definitions apply. Note that the singular forms "a," "an," and "the" include plural referents unless the context clearly dictates otherwise. Thus, for example, reference to "an enzyme" includes a plurality of such enzymes, and reference to "the dosage" includes reference to one or more dosages and equivalents thereof known to those skilled in the art, and so forth.

The present document is organized into a number of sections for ease of reading; however, the reader will appreciate that statements made in one section may apply to other sections. In this manner, the headings used for different sections of the disclosure should not be construed as limiting.

Unless defined otherwise, all technical and scientific terms used herein have the same meaning as commonly understood by one of ordinary skill in the art. The following terms are provided below.

1.1. Abbreviations and Acronyms

The following abbreviations/acronyms have the following meanings unless otherwise specified:

| | |
|---|---|
| ABTS | 2,2-azino-bis-3-ethylbenzothiazoline-6-sulfonic acid |
| AE or AEO | alcohol ethoxylate |
| AES or AEOS | alcohol ethoxysulfate |
| AkAA | *Aspergillus kawachii* α-amylase |
| AnGA | *Aspergillus niger* glucoamylase |
| AOS | α-olefinsulfonate |
| AS | alkyl sulfate |
| cDNA | complementary DNA |
| CMC | carboxymethylcellulose |
| DE | dextrose equivalent |
| DNA | deoxyribonucleic acid |
| DPn | degree of saccharide polymerization having n subunits |
| ds or DS | dry solids |
| DT1VIPA | diethylenetriaminepentaacetic acid |
| EC | Enzyme Commission |
| EDTA | ethylenediaminetetraacetic acid |
| EO | ethylene oxide (polymer fragment) |
| EOF | End of Fermentation |
| GA | glucoamylase |
| GAU/g ds | glucoamylase activity unit/gram dry solids |
| HFCS | high fructose corn syrup |
| HgGA | *Humicola grisea* glucoamylase |
| IPTG | isopropyl β-D-thiogalactoside |
| IRS | insoluble residual starch |
| kDa | kiloDalton |
| LAS | linear alkylbenzenesulfonate |
| LAT, BLA | *B. licheniformis* amylase |

| | |
|---|---|
| MW | molecular weight |
| MWU | modified Wohlgemuth unit; $1.6 \times 10^{-5}$ mg/MWU = unit of activity |
| NCBI | National Center for Biotechnology Information |
| NOBS | nonanoyloxybenzenesulfonate |
| NTA | nitriloacetic acid |
| OxAm | Purastar HPAM 5000 L (Danisco US Inc.) |
| PAHBAH | p-hydroxybenzoic acid hydrazide |
| PEG | polyethyleneglycol |
| pI | isoelectric point |
| PI | performance index |
| ppm | parts per million, e. g., μg protein per gram dry solid |
| PVA | poly(vinyl alcohol) |
| PVP | poly(vinylpyrrolidone) |
| RCF | relative centrifugal/centripetal force (i. e., x gravity) |
| RNA | ribonucleic acid |
| SAS | alkanesulfonate |
| SDS-PAGE | sodium dodecyl sulfate polyacrylamide gel electrophoresis |
| SSF | simultaneous saccharification and fermentation |
| SSU/g solid | soluble starch unit/gram dry solids |
| sp. | species |
| TAED | tetraacetylethylenedi amine |
| Tm | melting temperature |
| TrGA | *Trichoderma reesei* glucoamylase |
| w/v | weight/volume |
| w/w | weight/weight |
| v/v | volume/volume |
| wt % | weight percent |
| ° C. | degrees Centigrade |
| $H_2O$ | water |
| $dH_2O$ or DI | deionized water |
| $dIH_2O$ | deionized water, Milli-Q filtration |
| g or gm | grams |
| μg | micrograms |
| mg | milligrams |
| kg | kilograms |
| μL and μl | microliters |
| mL and ml | milliliters |
| mm | millimeters |
| μm | micrometer |
| M | molar |
| mM | millimolar |
| μM | micromolar |
| U | units |
| sec | seconds |
| min(s) | minute/minutes |
| hr(s) | hour/hours |
| DO | dissolved oxygen |
| Ncm | Newton centimeter |
| ETOH | ethanol |
| eq. | equivalents |
| N | normal |
| uPWA | variant α-amylase derived from *Pyrococcus woesei* |
| PWA | α-amylase from *Pyrococcus woesei* |
| MWCO | molecular weight cut-off |
| SSRL | Stanford Synchrotron Radiation Lightsource |
| PDB | Protein Database |
| CAZy | Carbohydrate-Active Enzymes database |
| Tris-HCl | tris(hydroxymethyl)aminomethane hydrochloride |
| HEPES | 4-(2-hydroxyethyl)-1-piperazineethanesulfonic acid |

1.2. Definitions

The terms "amylase" or "amylolytic enzyme" refer to an enzyme that is, among other things, capable of catalyzing the degradation of starch. α-Amylases are hydrolases that cleave the α-D-(1→4) 0-glycosidic linkages in starch. Generally, α-amylases (EC 3.2.1.1; α-D-(1→4)-glucan glucanohydrolase) are defined as endo-acting enzymes cleaving α-D-(1→4) 0-glycosidic linkages within the starch molecule in a random fashion yielding polysaccharides containing three or more (1-4)-α-linked D-glucose units. In contrast, the exo-acting amylolytic enzymes, such as β-amylases (EC 3.2.1.2; α-D-(1→4)-glucan maltohydrolase) and some product-specific amylases like maltogenic α-amylase (EC 3.2.1.133) cleave the polysaccharide molecule from the non-reducing end of the substrate. β-amylases, α-glucosidases (EC 3.2.1.20; α-D-glucoside glucohydrolase), glucoamylase (EC 3.2.1.3; α-D-(1→4)-glucan glucohydrolase), and product-specific amylases like the maltotetraosidases (EC 3.2.1.60) and the maltohexaosidases (EC 3.2.1.98) can produce malto-oligosaccharides of a specific length or enriched syrups of specific maltooligosaccharides. Some bacterial α-amylases predominantly produce maltotetraose (G4), maltopentaose (G5) or maltohexaose (G6) from starch and related α-1,4-glucans, while most α-amylases further convert them to glucose and or maltose as final products. G6 amylases such as AA560 amylase derived from *Bacillus* sp. DSM 12649 (i.e., the parent of STAINZYME™) and *Bacillus* sp. 707 amylase, which are also called maltohexaose-forming α-amylases (EC 3.2.1.98), are technically exo acting, but have similar structures compared to α-amylases, and in some cases appear to respond to the some of the same beneficial mutations.

"Enzyme units" herein refer to the amount of product formed per time under the specified conditions of the assay. For example, a "glucoamylase activity unit" (GAU) is defined as the amount of enzyme that produces 1 g of glucose per hour from soluble starch substrate (4% DS) at 60° C., pH 4.2. A "soluble starch unit" (SSU) is the amount of enzyme that produces 1 mg of glucose per minute from soluble starch substrate (4% DS) at pH 4.5, 50° C. DS refers to "dry solids."

The term "starch" refers to any material comprised of the complex polysaccharide carbohydrates of plants, comprised of amylose and amylopectin with the formula $(C_6H_{10}O_5)_x$, wherein X can be any number. The term includes plant-based materials such as grains, cereal, grasses, tubers and roots, and more specifically materials obtained from wheat, barley, corn, rye, rice, sorghum, brans, cassava, millet, milo, potato, sweet potato, and tapioca. The term "starch" includes granular starch. The term "granular starch" refers to raw, i.e., uncooked starch, e.g., starch that has not been subject to gelatinization.

The terms, "wild-type," "parental," or "reference," with respect to a polypeptide, refer to a naturally-occurring polypeptide that does not include a man-made substitution, insertion, or deletion at one or more amino acid positions. Similarly, the terms "wild-type," "parental," or "reference," with respect to a polynucleotide, refer to a naturally-occurring polynucleotide that does not include a man-made nucleoside change. However, note that a polynucleotide encoding a wild-type, parental, or reference polypeptide is not limited to a naturally-occurring polynucleotide, and encompasses any polynucleotide encoding the wild-type, parental, or reference polypeptide.

Reference to the wild-type polypeptide is understood to include the mature form of the polypeptide. A "mature" polypeptide or variant, thereof, is one in which a signal sequence is absent, for example, cleaved from an immature form of the polypeptide during or following expression of the polypeptide.

The term "variant," with respect to a polypeptide, refers to a polypeptide that differs from a specified wild-type, parental, or reference polypeptide in that it includes one or more naturally-occurring or man-made substitutions, insertions, or deletions of an amino acid. Similarly, the term "variant," with respect to a polynucleotide, refers to a polynucleotide that differs in nucleotide sequence from a specified wild-type, parental, or reference polynucleotide. The identity of the wild-type, parental, or reference polypeptide or polynucleotide will be apparent from context.

In the case of the present α-amylases, "activity" refers to α-amylase activity, which can be measured as described, herein.

The term "recombinant," when used in reference to a subject cell, nucleic acid, protein or vector, indicates that the subject has been modified from its native state. Thus, for example, recombinant cells express genes that are not found within the native (non-recombinant) form of the cell, or express native genes at different levels or under different conditions than found in nature. Recombinant nucleic acids differ from a native sequence by one or more nucleotides and/or are operably linked to heterologous sequences, e.g., a heterologous promoter in an expression vector. Recombinant proteins may differ from a native sequence by one or more amino acids and/or are fused with heterologous sequences. A vector comprising a nucleic acid encoding an amylase is a recombinant vector.

"Combinatorial variants" are variants comprising two or more mutations, e.g., 2, 3, 4, 5, 6, 7, 8, 9, 10, etc., substitutions, deletions, and/or insertions.

As used herein, "combinable mutations" are mutations at any amino acid position that can be used to make combinatorial variants. Combinable mutations improve at least one desired property of the molecule (in this case, an α-amylase), while not significantly decreasing either expression, activity, or stability. Combinable mutations can be grouped as follows:

Group A: A mutation that produces a variant wherein the minimum performance indices (PI) relative to a defined parental protein for: (i) protein expression, (ii) activity, (iii) CS-28 microswatch activity at pH 8 (16° C., 32° C., or 50° C.) or pH10 (16° C. or 50° C.), and (iv) detergent stability or thermostability are greater than or equal to 0.9, and in addition have a PI for any one of these tests that is greater than or equal to 1.0.

Group B: A mutation that produces a variant wherein the minimum performance indices (PI) relative to a defined parental protein for: (i) protein expression, (ii) activity, (iii) CS-28 microswatch activity at pH 8 (16° C., 32° C., or 50° C.) or pH10 (16° C. or 50° C.), and (iv) detergent stability or thermostability are greater than or equal to 0.8, and in addition have a PI for any one of these tests that is greater than or equal to 1.2.

Group C: A mutation that produces a variant wherein the minimum performance indices (PI) relative to a defined parental protein for: (i) protein expression, (ii) activity, (iii) CS-28 microswatch activity at pH 8 (16° C., 32° C., or 50° C.) or pH10 (16° C. or 50° C.), and (iv) detergent stability or thermostability are greater than or equal to 0.5, and in addition have a PI for any one of these tests that is greater than or equal to 1.5.

The properties of combinable mutations are summarized in the following Table.

TABLE A

Performance properties for each group of combinable mutations

| Group | Expression | Cleaning (pH 6 or 8) | Synthetic substrate activity | Stability (detergent or thermal*) | Minimum PI in one or more tests |
|---|---|---|---|---|---|
| A | ≥0.9 | ≥0.9 | ≥0.9 | ≥0.9 | X ≥ 1.0 |
| B | ≥0.8 | ≥0.8 | ≥0.8 | ≥0.8 | X ≥ 1.2 |
| C | ≥0.5 | ≥0.5 | ≥0.5 | ≥0.5 | X ≥ 1.5 |

*Thermal stability not measured for the full SEL libraries

Preferred combinable mutations are at "productive positions," as described, below. In the case of the present α-amylases, "activity" refers to α-amylase activity, which can be measured as described, herein.

As used herein, "productive positions" are amino acid positions that are tolerant to substitution with different amino acid residues, wherein the resulting variants meet a set of performance criteria for combinability, as set forth above. Productive positions can be assigned a Productivity Score as follows:

A. For the 24-site SEL libraries: Positions where less than 15% of the substitutions at a given position fall within groups A, B, or C are given a Productivity Score of "1". Positions where less than 40%, but greater than, or equal to 15% of the substitutions at a given position fall within groups A, B, or C are given a Productivity Score of "2". Positions where less than 75%, but greater than, or equal to 40% of the substitutions at a given position fall within groups A, B, or C are given a Productivity Score of "3". Positions where 75% or more of the substitutions at a given position fall within groups A, B, or C are given a Productivity Score of "4".

B. For the full SEL libraries: Positions where less than 15% of the substitutions at a given position fall within groups A, B, or C are given a Productivity Score of "1". Positions where less than 30%, but greater than, or equal to 15% of the substitutions at a given position fall within groups A, B, or C are given a Productivity Score of "2". Positions where less than 50%, but greater than, or equal to 30% of the substitutions at a given position fall within groups A, B, or C are given a Productivity Score of "3". Positions where 50% or more of the substitutions at a given position fall within groups A, B, or C are given a Productivity Score of "4".

Preferred productive positions are combinable mutations.

As used herein, "suitability score" refers to the ability of one or more combinable mutations to be used to make combinatorial variants, based on the performance criteria for combinability, (i.e., A, B, and C, as set forth, above) in which each of the mutations fall. A higher suitability score indicates a mutation or mutations that are more suitable for use in making combinatorial variants.

Suitability scores are described in the following Table.

TABLE B

Definitions of suitability scores

| Substitutions Occur in Group(s) | Suitability Score |
| --- | --- |
| A, B and C | +++++ |
| A and B | ++++ |
| A or (B and C) | +++ |
| B | ++ |
| C | + |

The terms "recovered," "isolated," and "separated," refer to a compound, protein (polypeptides), cell, nucleic acid, amino acid, or other specified material or component that is removed from at least one other material or component with which it is naturally associated as found in nature. An "isolated" polypeptides, thereof, includes, but is not limited to, a culture broth containing secreted polypeptide expressed in a heterologous host cell.

The term "purified" refers to material (e.g., an isolated polypeptide or polynucleotide) that is in a relatively pure state, e.g., at least about 90% pure, at least about 95% pure, at least about 98% pure, or even at least about 99% pure.

The term "enriched" refers to material (e.g., an isolated polypeptide or polynucleotide) that is in about 50% pure, at least about 60% pure, at least about 70% pure, or even at least about 70% pure.

The terms "thermostable" and "thermostability," with reference to an enzyme, refer to the ability of the enzyme to retain activity after exposure to an elevated temperature. The thermostability of an enzyme, such as an amylase enzyme, is measured by its half-life ($t_{1/2}$) given in minutes, hours, or days, during which half the enzyme activity is lost under defined conditions. The half-life may be calculated by measuring residual α-amylase activity following exposure to (i.e., challenge by) an elevated temperature.

A "pH range," with reference to an enzyme, refers to the range of pH values under which the enzyme exhibits catalytic activity.

The terms "pH stable" and "pH stability," with reference to an enzyme, relate to the ability of the enzyme to retain activity over a wide range of pH values for a predetermined period of time (e.g., 15 min., 30 min., 1 hour).

The term "amino acid sequence" is synonymous with the terms "polypeptide," "protein," and "peptide," and are used interchangeably. Where such amino acid sequences exhibit activity, they may be referred to as an "enzyme." The conventional one-letter or three-letter codes for amino acid residues are used, with amino acid sequences being presented in the standard amino-to-carboxy terminal orientation (i.e., N→C).

The term "nucleic acid" encompasses DNA, RNA, heteroduplexes, and synthetic molecules capable of encoding a polypeptide. Nucleic acids may be single stranded or double stranded, and may be chemical modifications. The terms "nucleic acid" and "polynucleotide" are used interchangeably. Because the genetic code is degenerate, more than one codon may be used to encode a particular amino acid, and the present compositions and methods encompass nucleotide sequences that encode a particular amino acid sequence. Unless otherwise indicated, nucleic acid sequences are presented in 5'-to-3' orientation.

"Hybridization" refers to the process by which one strand of nucleic acid forms a duplex with, i.e., base pairs with, a complementary strand, as occurs during blot hybridization techniques and PCR techniques. Stringent hybridization conditions are exemplified by hybridization under the following conditions: 65° C. and 0.1×SSC (where 1×SSC=0.15 M NaCl, 0.015 M $Na_3$ citrate, pH 7.0). Hybridized, duplex nucleic acids are characterized by a melting temperature ($T_m$), where one-half of the hybridized nucleic acids are unpaired with the complementary strand. Mismatched nucleotides within the duplex lower the $T_m$. A nucleic acid encoding a variant α-amylase may have a $T_m$ reduced by 1° C.-3° C. or more compared to a duplex formed between the nucleotide of SEQ ID NO: 2 and its identical complement.

A "synthetic" molecule is produced by in vitro chemical or enzymatic synthesis rather than by an organism.

The terms "transformed," "stably transformed," and "transgenic," used with reference to a cell means that the cell contains a non-native (e.g., heterologous) nucleic acid sequence integrated into its genome or carried as an episome that is maintained through multiple generations.

The term "introduced" in the context of inserting a nucleic acid sequence into a cell, means "transfection", "transformation" or "transduction," as known in the art.

A "host strain" or "host cell" is an organism into which an expression vector, phage, virus, or other DNA construct, including a polynucleotide encoding a polypeptide of interest (e.g., an amylase) has been introduced. Exemplary host strains are microorganism cells (e.g., bacteria, filamentous fungi, and yeast) capable of expressing the polypeptide of interest and/or fermenting saccharides. The term "host cell" includes protoplasts created from cells.

The term "heterologous" with reference to a polynucleotide or protein refers to a polynucleotide or protein that does not naturally occur in a host cell.

The term "endogenous" with reference to a polynucleotide or protein refers to a polynucleotide or protein that occurs naturally in the host cell.

The term "expression" refers to the process by which a polypeptide is produced based on a nucleic acid sequence. The process includes both transcription and translation.

A "selective marker" or "selectable marker" refers to a gene capable of being expressed in a host to facilitate selection of host cells carrying the gene. Examples of selectable markers include but are not limited to antimicrobials (e.g., hygromycin, bleomycin, or chloramphenicol) and/or genes that confer a metabolic advantage, such as a nutritional advantage on the host cell.

A "vector" refers to a polynucleotide sequence designed to introduce nucleic acids into one or more cell types. Vectors include cloning vectors, expression vectors, shuttle vectors, plasmids, phage particles, cassettes and the like.

An "expression vector" refers to a DNA construct comprising a DNA sequence encoding a polypeptide of interest, which coding sequence is operably linked to a suitable control sequence capable of effecting expression of the DNA in a suitable host. Such control sequences may include a promoter to effect transcription, an optional operator sequence to control transcription, a sequence encoding suitable ribosome binding sites on the mRNA, enhancers and sequences which control termination of transcription and translation.

The term "operably linked" means that specified components are in a relationship (including but not limited to juxtaposition) permitting them to function in an intended manner. For example, a regulatory sequence is operably linked to a coding sequence such that expression of the coding sequence is under control of the regulatory sequences.

A "signal sequence" is a sequence of amino acids attached to the N-terminal portion of a protein, which facilitates the secretion of the protein outside the cell. The mature form of an extracellular protein lacks the signal sequence, which is cleaved off during the secretion process.

"Biologically active" refer to a sequence having a specified biological activity, such an enzymatic activity.

The term "specific activity" refers to the number of moles of substrate that can be converted to product by an enzyme or enzyme preparation per unit time under specific conditions. Specific activity is generally expressed as units (U)/mg of protein.

As used herein, "water hardness" is a measure of the minerals (e.g., calcium and magnesium) present in water.

A "swatch" is a piece of material such as a fabric that has a stain applied thereto. The material can be, for example, fabrics made of cotton, polyester or mixtures of natural and synthetic fibers. The swatch can further be paper, such as filter paper or nitrocellulose, or a piece of a hard material such as ceramic, metal, or glass. For amylases, the stain is starch based, but can include blood, milk, ink, grass, tea, wine, spinach, gravy, chocolate, egg, cheese, clay, pigment, oil, or mixtures of these compounds.

A "smaller swatch" is a section of the swatch that has been cut with a single hole punch device, or has been cut with a custom manufactured 96-hole punch device, where the pattern of the multi-hole punch is matched to standard 96-well microtiter plates, or the section has been otherwise removed from the swatch. The swatch can be of textile, paper, metal, or other suitable material. The smaller swatch can have the stain affixed either before or after it is placed into the well of a 24-, 48- or 96-well microtiter plate. The smaller swatch can also be made by applying a stain to a small piece of material. For example, the smaller swatch can be a stained piece of fabric ⅝" or 0.25" in diameter. The custom manufactured punch is designed in such a manner that it delivers 96 swatches simultaneously to all wells of a 96-well plate. The device allows delivery of more than one swatch per well by simply loading the same 96-well plate multiple times. Multi-hole punch devices can be conceived of to deliver simultaneously swatches to any format plate, including but not limited to 24-well, 48-well, and 96-well plates. In another conceivable method, the soiled test platform can be a bead made of metal, plastic, glass, ceramic, or another suitable material that is coated with the soil substrate. The one or more coated beads are then placed into wells of 96-, 48-, or 24-well plates or larger formats, containing suitable buffer and enzyme.

"A cultured cell material comprising an amylase" or similar language, refers to a cell lysate or supernatant (including media) that includes an amylase as a component. The cell material may be from a heterologous host that is grown in culture for the purpose of producing the amylase.

"Percent sequence identity" means that a particular sequence has at least a certain percentage of amino acid residues identical to those in a specified reference sequence, when aligned using the CLUSTAL W algorithm with default parameters. See Thompson et al. (1994) *Nucleic Acids Res.* 22:4673-4680. Default parameters for the CLUSTAL W algorithm are:

Gap opening penalty: 10.0
Gap extension penalty: 0.05
Protein weight matrix: BLOSUM series
DNA weight matrix: IUB
Delay divergent sequences %: 40
Gap separation distance: 8
DNA transitions weight: 0.50
List hydrophilic residues: GPSNDQEKR
Use negative matrix: OFF
Toggle Residue specific penalties: ON
Toggle hydrophilic penalties: ON
Toggle end gap separation penalty OFF.

Deletions are counted as non-identical residues, compared to a reference sequence. Deletions occurring at either termini are included. For example, a variant with five amino acid deletions of the C-terminus of the mature CspAmy2 polypeptide of SEQ ID NO: 1 would have a percent sequence identity of 99% (612/617 identical residues×100, rounded to the nearest whole number) relative to the mature polypeptide. Such a variant would be encompassed by a variant having "at least 99% sequence identity" to a mature amylase polypeptide.

"Fused" polypeptide sequences are connected, i.e., operably linked, via a peptide bond between two subject polypeptide sequences.

The term "filamentous fungi" refers to all filamentous forms of the subdivision Eumycotina, particularly Pezizomycotina species.

The term "degree of polymerization" (DP) refers to the number (n) of anhydro-glucopyranose units in a given saccharide. Examples of DP1 are the monosaccharides glucose and fructose. Examples of DP2 are the disaccharides maltose and sucrose. The term "DE," or "dextrose equivalent," is defined as the percentage of reducing sugar, i.e., D-glucose, as a fraction of total carbohydrate in a syrup.

The term "dry solids content" (ds) refers to the total solids of a slurry in a dry weight percent basis. The term "slurry" refers to an aqueous mixture containing insoluble solids.

The phrase "simultaneous saccharification and fermentation (SSF)" refers to a process in the production of biochemicals in which a microbial organism, such as an ethanologenic microorganism, and at least one enzyme, such as an amylase, are present during the same process step. SSF includes the contemporaneous hydrolysis of starch substrates (granular, liquefied, or solubilized) to saccharides, including glucose, and the fermentation of the saccharides into alcohol or other biochemical or biomaterial in the same reactor vessel.

An "ethanologenic microorganism" refers to a microorganism with the ability to convert a sugar or oligosaccharide to ethanol.

The term "fermented beverage" refers to any beverage produced by a method comprising a fermentation process, such as a microbial fermentation, e.g., a bacterial and/or fungal fermentation. "Beer" is an example of such a fermented beverage, and the term "beer" is meant to comprise any fermented wort produced by fermentation/brewing of a starch-containing plant material. Often, beer is produced exclusively from malt or adjunct, or any combination of malt and adjunct. Examples of beers include: full malted beer, beer brewed under the "Reinheitsgebot," ale, India pale ale, lager, pilsner, bitter, Happoshu (second beer), third beer, dry beer, near beer, light beer, low alcohol beer, low calorie beer, porter, bock, dopplebock, stout, porter, malt liquor, non-alcoholic beer, non-alcoholic malt liquor and the like, but also alternative cereal and malt beverages such as fruit flavored malt beverages, e.g., citrus flavored, such as lemon-, orange-, lime-, or berry-flavored malt beverages, liquor flavored malt beverages, e.g., vodka-, rum-, or tequila-flavored malt liquor, or coffee flavored malt beverages, such as caffeine-flavored malt liquor, and the like.

The term "malt" refers to any malted cereal grain, such as malted barley or wheat.

The term "adjunct" refers to any starch and/or sugar containing plant material that is not malt, such as barley or wheat malt. Examples of adjuncts include common corn grits, refined corn grits, brewer's milled yeast, rice, sorghum, refined corn starch, barley, barley starch, dehusked barley, wheat, wheat starch, torrified cereal, cereal flakes, rye, oats, potato, tapioca, cassava and syrups, such as corn syrup, sugar cane syrup, inverted sugar syrup, barley and/or wheat syrups, and the like.

The term "mash" refers to an aqueous slurry of any starch and/or sugar containing plant material, such as grist, e.g., comprising crushed barley malt, crushed barley, and/or other adjunct or a combination thereof, mixed with water later to be separated into wort and spent grains.

The term "wort" refers to the unfermented liquor run-off following extracting the grist during mashing.

"Iodine-positive starch" or "IPS" refers to (1) amylose that is not hydrolyzed after liquefaction and saccharification, or (2) a retrograded starch polymer. When saccharified starch or saccharide liquor is tested with iodine, the high DPn amylose or the retrograded starch polymer binds iodine and produces a characteristic blue color. The saccharide liquor is thus termed "iodine-positive saccharide," "blue saccharide," or "blue sac."

The terms "retrograded starch" or "starch retrogradation" refer to changes that occur spontaneously in a starch paste or gel on ageing.

The term "about" refers to ±15% to the referenced value.

2. α-Amylase Variants

An aspect of the present compositions and methods is variant amylase enzymes discovered using a combination of experimental approaches, including the use of site evaluation libraries (SELs) and structure-based analysis.

2.1 α-Amylase Variants Based on SEL Libraries of Amy707 α-Amylase

In one aspect, variant α-amylase polypeptides are provided. The variant amylases have one or more mutations, as set forth, herein, with respect to a parental α-amylase having a similar fold and/or 60% or greater amino acid sequence identity to Bacillus sp. 707 amylase (SEQ ID NO: 3) or AA560 amylase (SEQ ID NO: 4).

In some embodiments, the parent enzyme is Amy707 α-amylase derived from Bacillus sp. 707 (#707) having the amino acid sequence of SEQ ID NO: 3:

```
HHNGTNGTMM QYFEWYLPND GNHWNRLNSD

ASNLKSKGIT AVWIPPAWKG

ASQNDVGYGA YDLYDLGEFN QKGTVRTKYG

TRSQLQAAVT SLKNNGIQVY

GDVVMNHKGG ADATEMVRAV EVNPNNRNQE

VTGEYTIEAW TRFDFPGRGN

THSSFKWRWY HFDGVDWDQS RRLNNRIYKF

RGHGKAWDWE VDTENGNYDY

LMYADIDMDH PEVVNELRNW GVWYTNTLGL

DGFRIDAVKH IKYSFTRDWI

NHVRSATGKN MFAVAEFWKN DLGAIENYLQ

KTNWNHSVFD VPLHYNLYNA

SKSGGNYDMR NIFNGTVVQR HPSHAVTFVD

NHDSQPEEAL ESFVEEWFKP

LAYALTLTRE QGYPSVFYGD YYGIPTHGVP

AMRSKIDPIL EARQKYAYGK

QNDYLDHHNI IGWTREGNTA HPNSGLATIM

SDGAGGSKWM FVGRNKAGQV

WSDITGNRTG TVTINADGWG NFSVNGGSVS

IWVNK
```

In some embodiments, the parent enzyme is AA560 α-amylase derived from Bacillus sp. DSM 12649 having the amino acid sequence of SEQ ID NO: 4:

```
HHNGTNGTMM QYFEWYLPND GNHWNRLRSD

ASNLKDKGIS AVWIPPAWKG

ASQNDVGYGA YDLYDLGEFN QKGTIRTKYG

TRNQLQAAVN ALKSNGIQVY
```

```
-continued
GDVVMNHKGG ADATEMVRAV EVNPNNRNQE

VSGEYTIEAW TKFDFPGRGN

THSNFKWRWY HFDGVDWDQS RKLNNRIYKF

RGDGKGWDWE VDTENGNYDY

LMYADIDMDH PEVVNELRNW GVWYTNTLGL

DGFRIDAVKH IKYSFTRDWI

NHVRSATGKN MFAVAEFWKN DLGAIENYLN

KTNWNHSVFD VPLHYNLYNA

SKSGGNYDMR QIFNGTVVQR HPMHAVTFVD

NHDSQPEEAL ESFVEEWFKP

LAYALTLTRE QGYPSVFYGD YYGIPTHGVP

AMKSKIDPIL EARQKYAYGR

QNDYLDHHNI IGWTREGNTA HPNSGLATIM

SDGAGGNKWM FVGRNKAGQV

WTDITGNRAG TVTINADGWG NFSVNGGSVS

IWVNK
```

α-amylase variants that include combinable mutations were identified by making a site evaluation library (SEL) based on Amy707 (SEQ ID NO: 3) and testing the resulting variants for various performance criteria, such as detergent stability, thermostability, cleaning performance, and expression levels, the detailed procedures for which are described in the Examples or otherwise known. Each variant was assayed for the different enzymatic and biochemical properties, and characterized by a performance index (PI) value, which compared the relative performance of the variant to Amy707 amylase for each performance criteria. A PI that is greater than 1 (i.e., PI>1) indicated improved performance by a variant as compared to Amy707, while a PI of 1 (i.e., PI=1) indicated a variant that performed the same as the Amy707, and a PI that is less than 1 (i.e., PI<1) indicated a variant that performed worse than the Amy707. PI values were then used to identify combinable mutations and productive positions.

Combinable mutations are mutations at any amino acid position that improve at least one desired property of the molecule, while not significantly decreasing expression, activity, or stability. Combinable mutations are assigned to one of three Groups (i.e., A, B, or C), as set forth, herein. Preferred combinable mutations are at productive positions. Productive positions are amino acid positions that are tolerant to substitution with different amino acid residues, wherein the resulting variants meet a set of performance criteria for combinability, as set forth herein.

Combinable mutations and productive positions are not to be confused with previously-identified, single-site mutations, some of which have subsequently been found by trial and error to work in combination with other mutations. Previously-identified, single-site mutations are invariably "winners" with respect to improving any one performance or stability feature. While this makes them attractive mutations to include in variant amylases, these "winners" tend to adversely affect other performance or stability features of the variants, which often requires making additional mutations to correct the defects.

In contrast, combinable mutations may be only incrementally beneficial in improving any one performance or stability feature of an variant amylase. However, they are carefully selected to be minimally detrimental to other desired performance or stability features, making them well suited for use in combination with other combinable mutations to construct variant amylases having desired improved enzymatic and biochemical properties without being crippled in others, resulting in robust variants having a good balance of performance, stability, and expression potential.

Further based on measured enzymatic and biochemical properties of the variant amylases, the suitability scores of the different mutations for making combinatorial variants were determined. The suitability score refers to the ability of one or more combinable mutations to be used to make combinatorial variants, based on the performance criteria for combinability (i.e., A, B, and C, as set forth, above), in which each of the mutations fall.

The suitability scores of individual substitutions in Amy707 are shown in Table C. The position numbering is based on the amino acid sequence of the mature Amy707 polypeptide (SEQ ID NO: 3). Wild-type residues at the indicated positions are given a suitability score of +++. Substitutions more likely to be combinable with other mutations are given a suitability score of ++++, or even +++++. In general, preferred suitability scores are +++, ++++, or +++++, ++++ or +++++, or even +++++.

TABLE C

Suitability scores of individual substitutions in Amy707

| POS | Prod. Score | (+) | (++) | (+++)* | (++++) | (+++++) |
|---|---|---|---|---|---|---|
| 1 | 4 | E | C | HFKNQRT | AILMW | |
| 2 | 4 | | A | HCDEFGIKNPQSW | LM | |
| 3 | 4 | | | NCDFKLQSTV | AEM | |
| 4 | 4 | | DKM | GFHPSTW | EIL | |
| 5 | 4 | | CN | THIQSVW | DGM | A |
| 6 | 3 | EGQT | | NS | | A |
| 7 | 4 | A | DILTY | GMS | HPQRV | |

TABLE C-continued

Suitability scores of individual substitutions in Amy707

| | | VARIANTS SUITABILITY SCORE | | | | |
|---|---|---|---|---|---|---|
| POS | Prod. Score | (+) | (++) | (+++)* | (++++) | (+++++) |
| 10 | 1 | IL | | M | | |
| 12 | 1 | | | Y | A | |
| 16 | 3 | HT | | YAENW | D | |
| 17 | 3 | D | V | LS | AGT | |
| 18 | 1 | AE | | P | | |
| 19 | 1 | L | | N | | D |
| 20 | 3 | | EHI | DS | GNY | AC |
| 22 | 4 | GMV | I | NELQSTW | | R |
| 23 | 2 | | | HQ | FMT | |
| 25 | 4 | | M | NSTV | ACGKY | |
| 26 | 2 | | | RKQT | | |
| 27 | 2 | | A | LIV | | |
| 28 | 4 | | | NADQWY | CEGHKR | |
| 29 | 4 | | | SCDEFHKMRTVWY | AN | |
| 30 | 2 | | | DEMNQR | | |
| 31 | 1 | | | AS | | |
| 32 | 4 | | CDEG | SN | MWY | ILQR |
| 33 | 4 | | | NHIKQTVWY | CDMR | |
| 34 | 1 | | | LFM | | |
| 35 | 4 | | CEFIL | KMNQ | AGH | |
| 36 | 2 | | | SDGKQT | | |
| 40 | 1 | K | | T | N | |
| 41 | 3 | IKM | DQ | A | S | C |
| 47 | 2 | | GMP | AS | | |
| 50 | 2 | | | GC | | S |
| 52 | 2 | | L | ST | KM | R |
| 53 | 1 | | | Q | A | |
| 54 | 4 | | M | NADEFGQSVW | C | |
| 56 | 2 | | NS | V | E | |
| 61 | 1 | | | Y | F | |
| 63 | 2 | | NQ | LM | | |
| 64 | 1 | | | YH | | |
| 66 | 1 | | V | L | M | |
| 68 | 2 | | D | EA | Q | |
| 70 | 4 | | R | NEGHKV | CDFIMS | L |
| 72 | 1 | | | K | | R |

TABLE C-continued

Suitability scores of individual substitutions in Amy707

| POS | Prod. Score | (+) | (++) | (+++)* | (++++) | (+++++) |
|---|---|---|---|---|---|---|
| 73 | 4 | D | EW | GQRT | KMSY | |
| 74 | 2 | | G | T | | S |
| 75 | 1 | | M | VI | | |
| 77 | 2 | A | S | TI | NV | |
| 81 | 3 | | | TACDFIKNPS | | |
| 82 | 3 | | Q | RACFSVY | IKM | |
| 83 | 2 | | M | SKNQRT | | |
| 84 | 3 | | CFL | QEN | DK | M |
| 86 | 4 | | H | QEIRTVWY | K | |
| 87 | 3 | | | ADKT | M | |
| 88 | 1 | | | A | M | |
| 89 | 2 | | | VAC | I | |
| 90 | 2 | | | TGMQRS | | |
| 91 | 3 | | M | SHKQRTV | AEN | |
| 93 | 1 | | H | KR | | |
| 94 | 4 | | | NFH | ACDGKLM | QR |
| 95 | 4 | G | D | NCFHIQRSTY | A | |
| 96 | 2 | DEN | | G | | |
| 97 | 1 | V | | I | | |
| 98 | 3 | | | QCDEGHKR | A | |
| 99 | 2 | | A | VC | I | |
| 100 | 2 | | | Y | CFI | |
| 101 | 1 | A | | G | | |
| 103 | 2 | F | I | VL | CT | A |
| 110 | 2 | | PS | GA | | |
| 111 | 1 | S | | A | | |
| 112 | 1 | C | | D | E | |
| 113 | 4 | | IVY | A | CEFGHKMR | |
| 115 | 1 | | | E | Q | |
| 116 | 4 | | PV | MDIQ | ACEFGLNRW | T |
| 117 | 3 | L | | VEPS | R | T |
| 118 | 3 | | DLV | RW | EQT | G |
| 119 | 1 | | | AC | S | |
| 122 | 1 | | | VC | | |
| 123 | 2 | ACL | | N | | |
| 124 | 1 | NT | | P | | |

TABLE C-continued

Suitability scores of individual substitutions in Amy707

| POS | Prod. Score | (+) | (++) | (+++)* | (++++) | (+++++) |
|---|---|---|---|---|---|---|
| 125 | 4 | | Y | NGHISTW | CFLMR | |
| 126 | 1 | | | N | D | |
| 128 | 2 | | E | N | LY | C |
| 129 | 1 | | V | Q | | |
| 132 | 1 | | | TS | | |
| 133 | 3 | | | GAHQST | DP | |
| 134 | 2 | | V | ES | DT | P |
| 135 | 2 | | Q | YFL | CM | |
| 136 | 4 | | FY | TCKLQR | DGMNP | |
| 138 | 2 | DLMN | | E | | |
| 139 | 2 | | CG | A | | |
| 140 | 1 | | | WF | Y | |
| 142 | 3 | | T | RS | CEFGHKY | |
| 144 | 3 | | | DEISY | KM | |
| 145 | 1 | | | FMY | | |
| 146 | 4 | ACDEFGHMRSWY | | P | | |
| 147 | 2 | | | GDIL | A | |
| 149 | 4 | | PW | GCDEFHKRV | AL | |
| 150 | 2 | L | HM | NPS | R | |
| 151 | 4 | | D | TEGHILMQV | | |
| 153 | 1 | | N | S | | |
| 154 | 2 | | LRY | S | | |
| 155 | 1 | | W | F | | |
| 156 | 2 | | AD | KS | | |
| 158 | 2 | | AL | RKQ | CN | |
| 160 | 4 | GILMP | F | YAC | HQS | DEKNR |
| 162 | 1 | M | | F | | |
| 165 | 1 | | | V | CT | |
| 167 | 1 | M | F | W | | |
| 168 | 1 | C | | D | | |
| 169 | 4 | FGIKWY | S | QCMN | | ADEHV |
| 170 | 2 | | | SC | AEK | |
| 171 | 2 | | | RT | MS | |
| 172 | 4 | | Y | RCEGHQ | AMS | |
| 173 | 4 | | DKN | L | ACFHWY | |
| 174 | 4 | | | NDGHILPSTV | | |

TABLE C-continued

| Suitability scores of individual substitutions in Amy707 | | | | | | |
|---|---|---|---|---|---|---|
| | | VARIANTS SUITABILITY SCORE | | | | |
| POS | Prod. Score | (+) | (++) | (+++)* | (++++) | (+++++) |
| 175 | 3 | | M | NRS | ADEL | |
| 176 | 1 | | KT | R | | |
| 178 | 1 | W | | Y | | |
| 179 | 2 | CL | | KM | Q | |
| 181 | 4 | ALNT | | REF | CIMQV | SY |
| 182 | 1 | C | | GD | | |
| 183 | 4 | | N | HCQVWY | DEFLMP | A |
| 184 | 2 | AEL | D | G | N | C |
| 186 | 2 | | | AG | EN | D |
| 195 | 2 | FY | | NW | L | |
| 196 | 1 | | | G | C | |
| 203 | 1 | | | Y | | N |
| 206 | 2 | NS | H | IM | C | T |
| 210 | 3 | ACEMNQR S | | H | | D |
| 211 | 4 | | L | P | CDMNQS | AFKV |
| 215 | 3 | FL | | NKM | DQ | |
| 216 | 3 | GLN | | EY | ACST | HQ |
| 217 | 1 | | M | L | | |
| 218 | 3 | ACEFHM | K | R | | |
| 219 | 3 | ACM | | NRT | D | |
| 221 | 1 | IV | | G | | |
| 222 | 4 | | EM | VDFGNY | AHILRST | |
| 225 | 2 | A | | TR | K | |
| 226 | 2 | Y | | NDE | AK | |
| 227 | 2 | | | TE | AK | |
| 228 | 1 | | | L | IM | |
| 229 | 2 | FV | C | G | | |
| 230 | 1 | | M | L | | |
| 231 | 2 | | | DE | GT | |
| 233 | 3 | L | CHMY | FAW | | |
| 235 | 2 | | | ILMV | | |
| 238 | 1 | I | | V | | |
| 243 | 1 | | | YF | | |
| 244 | 2 | | | S | N | DEHQ |
| 245 | 1 | E | M | F | | |
| 247 | 2 | | L | RT | AE | |

TABLE C-continued

Suitability scores of individual substitutions in Amy707

| POS | Prod. Score | (+) | (++) | (+++)* | (++++) | (+++++) |
|-----|---|---|---|---|---|---|
| 249 | 2 | M | FL | W | | |
| 250 | 2 | | | ILMV | | |
| 251 | 4 | | AH | NPTVY | CGW | KLQRS |
| 252 | 2 | | | HDEKN | | |
| 253 | 1 | | M | V | | |
| 257 | 2 | | | TMS | A | |
| 258 | 3 | IMV | PS | GDN | K | R |
| 259 | 3 | | DERT | KCP | AGHQ | |
| 260 | 2 | | | N | DP | KR |
| 261 | 3 | | G | MCI | AEQT | |
| 262 | 4 | ACDEGLQS | HKRY | FM | | |
| 263 | 1 | | | AS | | |
| 265 | 1 | | | AS | G | |
| 273 | 4 | | CK | GV | DEHLMPQSTY | |
| 276 | 1 | C | | ET | | |
| 280 | 2 | | MV | QDHK | N | |
| 283 | 1 | | | NG | D | |
| 285 | 2 | | | NEKST | M | |
| 286 | 3 | F | N | HLV | ACEM | T |
| 287 | 2 | ADNY | | S | | |
| 288 | 2 | L | C | V | IT | |
| 292 | 1 | LM | | P | | |
| 296 | 1 | | | NQ | | |
| 297 | 1 | | | L | | M |
| 298 | 2 | | | YFRW | | |
| 299 | 3 | | MY | NGHRST | | |
| 301 | 1 | | | SAG | | |
| 302 | 2 | | T | KCM | EQS | R |
| 303 | 4 | | | SEQR | ACDGLM | |
| 304 | 2 | | C | GKRSV | | |
| 306 | 2 | | | NG | AD | |
| 307 | 1 | | | YAF | | |
| 310 | 1 | | | RQS | | |
| 311 | 4 | | | NFT | DEGHKLMQRY | |
| 312 | 2 | | L | IV | M | |
| 313 | 1 | | MY | F | | |

TABLE C-continued

Suitability scores of individual substitutions in Amy707

| | | VARIANTS SUITABILITY SCORE | | | | |
|---|---|---|---|---|---|---|
| POS | Prod. Score | (+) | (++) | (+++)* | (++++) | (+++++) |
| 314 | 4 | | M | NADEGHIKLSTVY | Q | |
| 317 | 1 | | L | V | | |
| 318 | 2 | | MS | VCI | LT | |
| 319 | 3 | Y | | QADEGHNR | | |
| 320 | 4 | | DY | RHNST | AEKMQ | |
| 321 | 1 | | | HWY | | |
| 322 | 1 | D | | P | | |
| 323 | 4 | A | P | SFHIL | CGRVY | DEMT |
| 324 | 2 | ACM | K | H | Y | |
| 326 | 3 | H | C | VNT | AM | |
| 327 | 1 | | | T | L | |
| 328 | 1 | | | FV | | |
| 329 | 1 | | | V | I | |
| 334 | 1 | T | | S | | |
| 337 | 3 | Y | A | ECDST | NQ | |
| 339 | 2 | GT | | A | S | |
| 341 | 2 | FGK | | EH | ADY | |
| 343 | 1 | | | FTY | | |
| 344 | 1 | | | VI | C | |
| 345 | 4 | | | EAGHKLMNQSTY | | |
| 346 | 4 | | | E | ACHKRTVY | DGMNQS |
| 347 | 1 | A | D | W | | |
| 350 | 1 | | | PE | | |
| 351 | 2 | | AC | LM | Q | |
| 352 | 1 | | | AS | | |
| 354 | 1 | | | AS | | |
| 355 | 2 | | | LIKMV | | |
| 356 | 2 | Q | CV | T | IL | |
| 357 | 2 | H | A | L | M | |
| 358 | 2 | AI | G | T | C | |
| 359 | 2 | I | W | RV | | |
| 360 | 4 | | | EACFHLNPQRTVY | K | |
| 361 | 4 | V | HT | QDSW | C | AEG |
| 363 | 3 | IW | V | YE | ADKNQ | M |
| 364 | 2 | CG | | P | | A |

TABLE C-continued

Suitability scores of individual substitutions in Amy707

| POS | Prod. Score | (+) | (++) | (+++)* | (++++) | (+++++) |
|---|---|---|---|---|---|---|
| 365 | 2 | GV | | S | AN | |
| 366 | 2 | C | | V | IL | |
| 367 | 1 | | | FY | | |
| 368 | 2 | | GL | Y | MQ | |
| 369 | 1 | S | A | G | | |
| 372 | 3 | | R | YHIKM | QTV | |
| 374 | 2 | C | | IQ | NS | |
| 375 | 4 | | Q | PDGHIRTVY | AEKM | |
| 377 | 2 | | A | HKM | GT | |
| 378 | 2 | | L | GEHMN | | |
| 379 | 3 | | AL | VIQS | MNRY | |
| 380 | 2 | | | PDEGHKQS | | |
| 381 | 2 | | | AGNQRST | | |
| 382 | 1 | | K | M | | |
| 386 | 1 | | LV | I | | |
| 387 | 2 | EN | | DG | | |
| 388 | 4 | | FINS | PACFGKLQRTVY | D | |
| 389 | 3 | | F | IV | EGLMQS | |
| 390 | 1 | M | | LV | | |
| 391 | 4 | | S | ECHIW | AGKLNR | |
| 392 | 2 | | | ACG | | S |
| 394 | 3 | | EH | QCDGLRV | Y | |
| 395 | 4 | | V | KDEMST | AGQR | |
| 396 | 2 | | | YN | K | M |
| 397 | 1 | | | AG | | |
| 400 | 4 | | AI | KF | GHLMQTVW | |
| 401 | 1 | | | QH | M | |
| 402 | 3 | | V | NCIKLSY | | |
| 403 | 1 | | ET | D | | |
| 405 | 2 | A | | LCMNTV | | |
| 406 | 2 | ACL | Q | D | N | |
| 408 | 4 | | | HEGNQRST | KMP | |
| 410 | 1 | | N | I | | |
| 411 | 1 | | | I | V | |
| 412 | 1 | | | GAS | | |
| 413 | 2 | | | WFHIY | L | |

TABLE C-continued

Suitability scores of individual substitutions in Amy707

| POS | Prod. Score | (+) | (++) | (+++)* | (++++) | (+++++) |
|---|---|---|---|---|---|---|
| 414 | 2 | | | TACV | S | |
| 415 | 2 | W | CY | R | | |
| 416 | 4 | | | EFHQ TABLE C-continued Suitability scores of individual substitutions in Amy707

| POS | Prod. Score | (+) | (++) | (+++)* | (++++) | (+++++) |
|---|---|---|---|---|---|---|
| 457 | 2 | T | | NGHQR | | |
| 458 | 4 | L | D | RHSTVY | CEKMN | |
| 459 | 4 | ADEGH | CP | TL | NS | |
| 460 | 3 | KN | | GQ | EHS | |
| 461 | 4 | | F | TDV | ACEGKLNPQRY | |
| 463 | 2 | | L | TEKPQR | | |
| 465 | 2 | | Q | N | DG | |
| 466 | 4 | | | ADEGKNPQRS | | |
| 467 | 1 | | | D | E | |
| 469 | 1 | | Y | W | | |
| 471 | 3 | | | NHQRY | CDE | |
| 473 | 1 | | | SP | | |
| 474 | 1 | | | V | S | |
| 475 | 1 | | | NDE | | |
| 476 | 2 | | FIN | GDR | E | |
| 477 | 3 | PT | DK | GAR | NQ | |
| 478 | 1 | | A | SG | | |
| 479 | 1 | | | VT | | |
| 481 | 2 | | | I | LTV | |
| 482 | 1 | | | WY | | |
| 483 | 3 | | | VHMR | CGST | |
| 484 | 3 | | | NAEGHQRS | | |
| 485 | 3 | | MP | KHQST | | |

*The first listed amino acid residue is the wild-type residue.

The suitability scores of a subset of substitutions in Amy707, which were identified in limited, 24-site SEL libraries, are shown in Table D. As before, position numbering is based on the amino acid sequence of the mature Amy707 polypeptide (SEQ ID NO: 3), wild-type residues at the indicated positions are given a suitability score of +++, substitutions more likely to be combinable with other mutations are given a suitability score of ++++, or even +++++, and, in general, preferred suitability scores are +++, ++++, or +++++, ++++ or +++++, or even +++++.

TABLE D

Suitability scores of a subset of individual substitutions in Amy707

| POS | Productivity score | (+) | (++) | (+++)* | (++++) | (+++++) |
|---|---|---|---|---|---|---|
| 1 | 3 | | | HILTFWQ | ACK | RM |
| 83 | 3 | | A | SCTNG | IRK | |
| 125 | 4 | | RTY | NLMVGH | ISFW | C |
| 128 | 2 | EY | D | NL | | C |

TABLE D-continued

Suitability scores of a subset of individual substitutions in Amy707

| POS | Productivity score | VARIANTS SUITABILITY SCORE | | | | |
|---|---|---|---|---|---|---|
| | | (+) | (++) | (+++)* | (++++) | (+++++) |
| 131 | 2 | RKS | | VCT | | |
| 160 | 4 | L | | YIG | ARKSHQ | CDEN |
| 179 | 3 | LEVNW | | KICM | Q | G |
| 183 | 4 | | T | HGLF | RCSDEMVNWYQ | AP |
| 184 | 3 | I | ALQ | G | CN | DE |
| 186 | 2 | | R | ADSG | EMN | |
| 244 | 2 | | | STN | KDEHQ | |
| 280 | 2 | | CT | QDE | IKN | |
| 306 | 3 | | | NIKDTEVG | AR | |
| 320 | 3 | | HQ | RDEN | AST | K |
| 321 | 2 | MV | | HFY | | |
| 380 | 3 | | | PDTEGHQ | C | KS |
| 408 | 3 | | | HIMNPQ | RSTEG | K |
| 434 | 4 | L | | AIRDEMGPHQ | CKSTVN | |
| 454 | 2 | | M | ICSV | | |
| 475 | 2 | | | NRCSD | | |
| 476 | 2 | | | GRNHQ | CDE | |
| 477 | 2 | T | A | GKDNQ | | R |
| 484 | 3 | W | DG | NTQ | ARS | |

*The first listed amino acid residue is the wild-type residue.

While evaluating mutations based on suitability score represents one refined aspect of the present compositions and methods, the identification of productive positions, which are tolerant to substitution with different amino acid residues, represents a number of significant embodiments.

Each productive position identified in the following lists with specified criteria, and each substitution identified in parenthesis following the numerical position identifier in each of these lists, represents a mutation, identified by experimental data, that either directly contributes to the performance of an amylase variant, or is determined to be combinable with other mutations to produce a amylase variant with improved performance.

The productive positions in Amy 707 that fall within the previously described Productivity Scores of "4" (for the full SEL libraries) and the substitutions within those positions that are combinable are listed, below, in LIST A. Position numbering is based on the mature Amy707 protein listed in SEQ ID NO: 3.

List A

1(H,A,C,E,F,I,K,L,M,N,Q,R,T,W); 2(H,A,C,D,E,F,G,I,K,L,M,N,P,Q,S,W); 3(N,A,C,D,E,F,K,L,M,Q,S,T,V); 4(G,D,E,F,H,I,K,L,M,P,S,T,W); 5(T,A,C,D,G,H,I,M,N,Q,S,V,W); 7(G,A,D,H,I,L,M,P,Q,R,S,T,V,Y); 22(N,E,G,I,L,M,Q,R,S,T,V,W); 25(N,A,C,G,K,M,S,T,V,Y); 28(N,A,C,D,E,G,H,K,Q,R,W,Y); 29(S,A,C,D,E,F,H,K,M,N,R,T,V,W,Y); 32(S,C,D,E,G,I,L,M,N,Q,R,W,Y); 33(N,C,D,H,I,K,M,Q,R,T,V,W,Y); 35(K,A,C,E,F,G,H,I,L,M,N,Q); 54(N,A,C,D,E,F,G,M,Q,S,V,W); 70(N,C,D,E,F,G,H,I,K,L,M,R,S,V); 73(G,D,E,K,M,Q,R,S,T,W,Y); 86(Q,E,H,I,K,R,T,V,W,Y); 94(N,A,C,D,F,G,H,K,L,M,Q,R); 95(N,A,C,D,F,G,H,I,Q,R,S,T,Y); 113(A,C,E,F,G,H,I,K,M,R,V,Y); 116(M,A,C,D,E,F,G,I,L,N,P,Q,R,T,V,W); 125(N,C,F,G,H,I,L,M,R,S,T,W,Y); 136(T,C,D,F,G,K,L,M,N,P,Q,R,Y); 146(P,A,C,D,E,F,G,H,M,R,S,W,Y); 149(G,A,C,D,E,F,H,K,L,P,R,V,W); 151(T,D,E,G,H,I,L,M,Q,V); 160(Y,A,C,D,E,F,G,H,I,K,L,M,N,P,Q,R,S); 169(Q,A,C,D,E,F,G,H,I,K,M,N,S,V,W,Y); 172(R,A,C,E,G,H,M,Q,S,Y); 173(L,A,C,D,F,H,K,N,W,Y); 174(N,D,G,H,I,L,P,S,T,V); 181(R,A,C,E,F,I,L,M,N,Q,S,T,V,Y); 183(H,A,C,D,E,F,L,M,N,P,Q,V,W,Y); 211(P,A,C,D,F,K,L,M,N,Q,S,V); 222(V,A,D,E,F,G,H,I,L,M,N,R,S,T,Y); 251(N,A,C,G,H,K,L,P,Q,R,S,T,V,W,Y); 262(F,A,C,D,E,G,H,K,L,M,Q,R,S,Y); 273(G,C,D,E,H,K,L,M,P,Q,S,T,V,Y); 303(S,A,C,D,E,G,L,M,Q,R); 311(N,D,E,F,G,H,K,L,M,Q,R,T,Y); 314(N,A,D,E,G,H,I,K,L,M,Q,S,T,V,Y); 320(R,A,D,E,H,K,M,N,Q,S,T,Y); 323(S,A,C,D,E,F,G,H,I,L,M,P,R,T,V,Y); 345(E,A,G,H,K,L,M,N,Q,S,T,Y); 346(E,A,C,D,G,H,K,M,N,Q,R,S,T,V,Y); 360(E,A,C,F,H,K,L,N,P,Q,R,T,V,Y); 361(Q,A,C,D,E,G,H,S,T,V,W); 375(P,A,D,E,G,H,I,K,M,Q,R,T,V,Y); 388(P,A,C,D,F,G,H,K,L,N,Q,R,S,T,V,Y); 391(E,A,C,G,H,I,K,L,N,R,S,W); 395(K,A,D,E,G,M,Q,R,S,T,V); 400(K,A,F,G,H,I,L,M,Q,T,V,W); 408(H,E,G,K,M,N,P,Q,R,S,T); 416(E,A,D,F,G,H,K,

L,N,Q,R,T,V,W,Y); 418(N,A,D,I,K,L,M,Q,S,T,V); 419(T,D,E,H,K,L,M,N,P,Q,R,S,W,Y); 420(A,D,F,G,H,I,L,M,Q,R,S,T,V,W); 421(H,A,C,D,E,I,K,L,M,N,R,V,W,Y); 422(P,A,C,E,F,G,L,M,T,V,Y); 423(N,C,D,E,F,H,I,L,R,S,T); 424(S,A,C,D,E,G,I,N,Q,T,V,W); 434(A,C,D,E,F,H,I,K,M,N,P,Q,R,S,T,V); 435(G,A,C,E,K,M,N,P,Q,R,T); 452(S,A,C,E,F,H,K,N,Q,T,W,Y); 458(R,C,D,E,H,K,L,M,N,S,T,V,Y); 459(T,A,C,D,E,G,H,L,N,P,S); 461(T,A,C,D,E,F,G,K,L,N,P,Q,R,V,Y); and 466(A,D,E,G,K,N,P,Q,R,S).

The productive positions in Amy 707 that fall within the previously described Productivity Scores of "3 and 4" (for the full SEL libraries) and the substitutions within those positions that are combinable are listed, below, in LIST B. Position numbering is based on the mature Amy707 protein listed in SEQ ID NO: 3.

List B

1(H,A,C,E,F,I,K,L,M,N,Q,R,T,W); 2(H,A,C,D,E,F,G,I,K,L,M,N,P,Q,S,W); 3(N,A,C,D,E,F,K,L,M,Q,S,T,V); 4(G,D,E,F,H,I,K,L,M,P,S,T,W); 5(T,A,C,D,G,H,I,M,N,Q,S,V,W); 6(N,A,E,G,Q,S,T); 7(G,A,D,H,I,L,M,P,Q,R,S,T,V,Y); 16(Y,A,D,E,H,N,T,W); 17(L,A,D,G,S,T,V); 20(D,A,C,E,G,H,I,N,S,Y); 22(N,E,G,I,L,M,Q,R,S,T,V,W); 25(N,A,C,G,K,M,S,T,V,Y); 28(N,A,C,D,E,G,H,K,Q,R,W,Y); 29(S,A,C,D,E,F,H,K,M,N,R,T,V,W,Y); 32(S,C,D,E,G,I,L,M,N,Q,R,W,Y); 33(N,C,D,H,I,K,M,Q,R,T,V,W,Y); 35(K,A,C,E,F,G,H,I,L,M,N,Q); 41(A,C,D,I,K,M,Q,S); 54(N,A,C,D,E,F,G,M,Q,S,V,W); 70(N,C,D,E,F,G,H,I,K,L,M,R,S,V); 73(G,D,E,K,M,Q,R,S,T,W,Y); 81(T,A,C,D,F,I,K,N,P,S); 82(R,A,C,F,I,K,M,Q,S,V,Y); 84(Q,C,D,E,F,K,L,M,N); 86(Q,E,H,I,K,R,T,V,W,Y); 87(A,D,K,M,T); 91(S,A,E,H,K,M,N,Q,R,T,V); 94(N,A,C,D,F,G,H,K,L,M,Q,R); 95(N,A,C,D,F,G,H,I,Q,R,S,T,Y); 98(Q,A,C,D,E,G,H,K,R); 113(A,C,E,F,G,H,I,K,M,R,V,Y); 116(M,A,C,D,E,F,G,I,L,N,P,Q,R,T,V,W); 117(V,E,L,P,R,S,T); 118(R,D,E,G,L,Q,T,V,W); 125(N,C,F,G,H,I,L,M,R,S,T,W,Y); 133(G,A,D,H,P,Q,S,T); 136(T,C,D,F,G,K,L,M,N,P,Q,R,Y); 142(R,C,E,F,G,H,K,S,T,Y); 144(D,E,I,K,M,S,Y); 146(P,A,C,D,E,F,G,H,M,R,S,W,Y); 149(G,A,C,D,E,F,H,K,L,P,R,V,W); 151(T,D,E,G,H,I,L,M,Q,V); 160(Y,A,C,D,E,F,G,H,I,K,L,M,N,P,Q,R,S); 169(Q,A,C,D,E,F,G,H,I,K,M,N,S,V,W,Y); 172(R,A,C,E,G,H,M,Q,S,Y); 173(L,A,C,D,F,H,K,N,W,Y); 174(N,D,G,H,I,L,P,S,T,V); 175(N,A,D,E,L,M,R,S); 181(R,A,C,E,F,I,L,M,N,Q,S,T,V,Y); 183(H,A,C,D,E,F,L,M,N,P,Q,V,W,Y); 210(H,A,C,D,E,M,N,Q,R,S); 211(P,A,C,D,F,K,L,M,N,Q,S,V); 215(N,D,F,K,L,M,Q); 216(E,A,C,G,H,L,N,Q,S,T,Y); 218(R,A,C,E,F,H,K,M); 219(N,A,C,D,M,R,T); 222(V,A,D,E,F,G,H,I,L,M,N,R,S,T,Y); 233(F,A,C,H,L,M,W,Y); 251(N,A,C,G,H,K,L,P,Q,R,S,T,V,W,Y); 258(G,D,I,K,M,N,P,R,S,V); 259(K,A,C,D,E,G,H,P,Q,R,T); 261(M,A,C,E,G,I,Q,T); 262(F,A,C,D,E,G,H,K,L,M,Q,R,S,Y); 273(G,C,D,E,H,K,L,M,P,Q,S,T,V,Y); 286(H,A,C,E,F,L,M,N,T,V); 299(N,G,H,M,R,S,T,Y); 303(S,A,C,D,E,G,L,M,Q,R); 311(N,D,E,F,G,H,K,L,M,Q,R,T,Y); 314(N,A,D,E,G,H,I,K,L,M,Q,S,T,V,Y); 319(Q,A,D,E,G,H,N,R,Y); 320(R,A,D,E,H,K,M,N,Q,S,T,Y); 323(S,A,C,D,E,F,G,H,I,L,M,P,R,T,V,Y); 326(V,A,C,H,M,N,T); 337(E,A,C,D,N,Q,S,T,Y); 345(E,A,G,H,K,L,M,N,Q,S,T,Y); 346(E,A,C,D,G,H,K,M,N,Q,R,S,T,V,Y); 360(E,A,C,F,H,K,L,N,P,Q,R,T,V,Y); 361(Q,A,C,D,E,G,H,S,T,V,W); 363(Y,A,D,E,I,K,M,N,Q,V,W); 372(Y,H,I,K,M,Q,R,T,V); 375(P,A,D,E,G,H,I,K,M,Q,R,T,V,Y); 379(V,A,I,L,M,N,Q,R,S,Y); 388(P,A,C,D,F,G,H,K,L,N,Q,R,S,T,V,Y); 389(I,E,F,G,L,M,Q,S,V); 391(E,A,C,G,H,I,K,L,N,R,S,W); 394(Q,C,D,E,G,H,L,R,V,Y); 395(K,A,D,E,G,M,Q,R,S,T,V); 400(K,A,F,G,H,I,L,M,Q,T,V,W); 402(N,C,I,K,L,S,V,Y); 408(H,E,G,K,M,N,P,Q,R,S,T); 416(E,A,D,F,G,H,K,L,N,Q,R,T,V,W,Y); 418(N,A,D,I,K,L,M,Q,S,T,V); 419(T,D,E,H,K,L,M,N,P,Q,R,S,W,Y); 420(A,D,F,G,H,I,L,M,Q,R,S,T,V,W); 421(H,A,C,D,E,I,K,L,M,N,R,V,W,Y); 422(P,A,C,E,F,G,L,M,T,V,Y); 423(N,C,D,E,F,H,I,L,R,S,T); 424(S,A,C,D,E,G,I,N,Q,T,V,W); 433(G,A,C,D,E,K,M,N,R); 434(A,C,D,E,F,H,I,K,M,N,P,Q,R,S,T,V); 435(G,A,C,E,K,M,N,P,Q,R,T); 437(S,A,C,D,K,N,T); 445(N,A,C,E,G,K,Q,R,T); 446(K,A,C,F,H,M,Q,S,T,Y); 450(V,A,E,I,L,Q,R,S,T); 452(S,A,C,E,F,H,K,N,Q,T,W,Y); 454(I,A,C,F,L,M,R,S,T); 458(R,C,D,E,H,K,L,M,N,S,T,V,Y); 459(T,A,C,D,E,G,H,L,N,P,S); 460(G,E,H,K,N,Q,S); 461(T,A,C,D,E,F,G,K,L,N,P,Q,R,V,Y); 466(A,D,E,G,K,N,P,Q,R,S); 471(N,C,D,E,H,Q,R,Y); 477(G,A,D,K,N,P,Q,R,T); 483(V,C,G,H,M,R,S,T); 484(N,A,E,G,H,Q,R,S); and 485(K,H,M,P,Q,S,T).

The productive positions in Amy 707 that fall within the previously described Productivity Scores of "2, 3 and 4" (for the full SEL libraries) and the substitutions within those positions that are combinable are listed, below, in LIST C. Position numbering is based on the mature Amy707 protein listed in SEQ ID NO: 3.

List C

1(H,A,C,E,F,I,K,L,M,N,Q,R,T,W); 2(H,A,C,D,E,F,G,I,K,L,M,N,P,Q,S,W); 3(N,A,C,D,E,F,K,L,M,Q,S,T,V); 4(G,D,E,F,H,I,K,L,M,P,S,T,W); 5(T,A,C,D,G,H,I,M,N,Q,S,V,W); 6(N,A,E,G,Q,S,T); 7(G,A,D,H,I,L,M,P,Q,R,S,T,V,Y); 16(Y,A,D,E,H,N,T,W); 17(L,A,D,G,S,T,V); 20(D,A,C,E,G,H,I,N,S,Y); 22(N,E,G,I,L,M,Q,R,S,T,V,W); 23(H,F,M,Q,T); 25(N,A,C,G,K,M,S,T,V,Y); 26(R,K,Q,T); 27(L,A,I,V); 28(N,A,C,D,E,G,H,K,Q,R,W,Y); 29(S,A,C,D,E,F,H,K,M,N,R,T,V,W,Y); 30(D,E,M,N,Q,R); 32(S,C,D,E,G,I,L,M,N,Q,R,W,Y); 33(N,C,D,H,I,K,M,Q,R,T,V,W,Y); 35(K,A,C,E,F,G,H,I,L,M,N,Q); 36(S,D,G,K,Q,T); 41(A,C,D,I,K,M,Q,S); 47(A,G,M,P,S); 50(G,C,S); 52(S,K,L,M,R,T); 54(N,A,C,D,E,F,G,M,Q,S,V,W); 56(V,E,N,S); 63(L,M,N,Q); 68(E,A,D,Q); 70(N,C,D,E,F,G,H,I,K,L,M,R,S,V); 73(G,D,E,K,M,Q,R,S,T,W,Y); 74(T,G,S); 77(T,A,I,N,S,V); 81(T,A,C,D,F,I,K,N,P,S); 82(R,A,C,F,I,K,M,Q,S,V,Y); 83(S,K,M,N,Q,R,T); 84(Q,C,D,E,F,K,L,M,N); 86(Q,E,H,I,K,R,T,V,W,Y); 87(A,D,K,M,T); 89(V,A,C,I); 90(T,G,M,Q,R,S); 91(S,A,E,H,K,M,N,Q,R,T,V); 94(N,A,C,D,F,G,H,K,L,M,Q,R); 95(N,A,C,D,F,G,H,I,Q,R,S,T,Y); 96(G,D,E,N); 98(Q,A,C,D,E,G,H,K,R); 99(V,A,C,I); 100(Y,C,F,I); 103(V,A,C,F,I,L,T); 110(G,A,P,S); 113(A,C,E,F,G,H,I,K,M,R,V,Y); 116(M,A,C,D,E,F,G,I,L,N,P,Q,R,T,V,W); 117(V,E,L,P,R,S,T); 118(R,D,E,G,L,Q,T,V,W); 123(N,A,C,L); 125(N,C,F,G,H,I,L,M,R,S,T,W,Y); 128(N,C,E,L,Y); 133(G,A,D,H,P,Q,S,T); 134(E,D,P,S,T,V); 135(Y,C,F,L,M,Q); 136(T,C,D,F,G,K,L,M,N,P,Q,R,Y); 138(E,D,L,M,N); 139(A,C,G); 142(R,C,E,F,G,H,K,S,T,Y); 144(D,E,I,K,M,S,Y); 146(P,A,C,D,E,F,G,H,M,R,S,W,Y); 147(G,A,D,I,L); 149(G,A,C,D,E,F,H,K,L,P,R,V,W); 150(N,H,L,M,P,R,S); 151(T,D,E,G,H,I,L,M,Q,V); 154(S,L,R,Y); 156(K,A,D,S); 158(R,A,C,K,L,N,Q); 160(Y,A,C,D,E,F,G,H,I,K,L,M,N,P,Q,R,S); 169(Q,A,C,D,E,F,G,H,I,K,M,N,S,V,W,Y); 170(S,A,C,E,K); 171(R,M,S,T); 172(R,A,C,E,G,H,M,Q,S,Y); 173(L,A,C,D,F,H,K,N,W,Y); 174(N,D,G,H,I,L,P,S,T,V); 175(N,A,D,E,L,M,R,S); 179(K,C,L,M,Q); 181(R,A,C,E,F,I,L,M,N,Q,S,T,V,Y); 183(H,A,C,D,E,F,L,M,N,P,Q,V,W,Y); 184(G,A,C,D,E,L,N); 186(A,D,E,G,N); 195(N,F,L,W,Y); 206(I,C,H,M,N,S,T); 210(H,A,C,D,E,M,N,Q,R,S); 211(P,A,C,D,F,K,L,M,N,Q,S,V); 215(N,D,F,K,L,M,Q); 216(E,A,C,G,H,L,N,Q,S,T,Y); 218(R,A,C,E,F,H,K,M); 219(N,A,C,D,M,R,T); 222(V,A,D,E,F,G,H,I,L,M,N,R,S,T,Y); 225(T,A,K,R); 226(N,A,D,E,K,Y); 227(T,A,E,K); 229(G,C,F,V); 231(D,E,G,T); 233(F,A,C,H,L,M,W,Y); 235(I,L,M,V); 244(S,D,E,H,N,Q); 247(R,A,E,L,T); 249(W,F,L,M); 250(I,L,M,V); 251(N,A,C,G,H,K,L,P,Q,R,S,T,V,W,Y); 252(H,D,E,K,N); 257(T,A,M,S); 258(G,D,I,K,M,N,P,R,S,V); 259(K,A,C,D,E,G,H,P,Q,R,T); 260(N,D,K,P,R); 261(M,A,C,E,G,I,Q,T); 262(F,A,C,D,E,G,H,K,L,M,Q,R,S,Y); 273(G,C,D,E,H,K,L,M,P,Q,S,T,V,Y); 280(Q,D,H,K,M,N,V); 285

(N,E,K,M,S,T); 286(H,A,C,E,F,L,M,N,T,V); 287(S,A,D,N,Y); 288(V,C,I,L,T); 298(Y,F,R,W); 299(N,G,H,M,R,S,T,Y); 302(K,C,E,M,Q,R,S,T); 303(S,A,C,D,E,G,L,M,Q,R); 304(G,C,K,R,S,V); 306(N,A,D,G); 311(N,D,E,F,G,H,K,L,M,Q,R,T,Y); 312(I,L,M,V); 314(N,A,D,E,G,H,I,K,L,M,Q,S,T,V,Y); 318(V,C,I,L,M,S,T); 319(Q,A,D,E,G,H,N,R,Y); 320(R,A,D,E,H,K,M,N,Q,S,T,Y); 323(S,A,C,D,E,F,G,H,I,L,M,P,R,T,V,Y); 324(H,A,C,K,M,Y); 326(V,A,C,H,M,N,T); 337(E,A,C,D,N,Q,S,T,Y); 339(A,G,S,T); 341(E,A,D,F,G,H,K,Y); 345(E,A,G,H,K,L,M,N,Q,S,T,Y); 346(E,A,C,D,G,H,K,M,N,Q,R,S,T,V,Y); 351(L,A,C,M,Q); 355(L,I,K,M,V); 356(T,C,I,L,Q,V); 357(L,A,H,M); 358(T,A,C,G,I, 359(R,I,V,W); 360(E,A,C,F,H,K,L,N,P,Q,R,T,V,Y); 361(Q,A,C,D,E,G,H,S,T,V,W); 363(Y,A,D,E,I,K,M,N,Q,V,W); 364(P,A,C,G); 365(S,A,G,N,V); 366(V,C,I,L); 368(Y,G,L,M,Q); 372(Y,H,I,K,M,Q,R,T,V); 374(I,C,N,Q,S); 375(P,A,D,E,G,H,I,K,M,Q,R,T,V,Y); 377(H,A,G,K,M,T); 378(G,E,H,L,M,N); 379(V,A,I,L,M,N,Q,R,S,Y); 380(P,D,E,G,H,K,Q,S); 381(A,G,N,Q,R,S,T); 387(D,E,G,N); 388(P,A,C,D,F,G,H,K,L,N,Q,R,S,T,V,Y); 389(I,E,F,G,L,M,Q,S,V); 391(E,A,C,G,H,I,K,L,N,R,S,W); 392(A,C,G,S); 394(Q,C,D,E,G,H,L,R,V,Y); 395(K,A,D,E,G,M,Q,R,S,T,V); 396(Y,K,M,N); 400(K,A,F,G,H,I,L,M,Q,T,V,W); 402(N,C,I,K,L,S,V,Y); 405(L,A,C,M,N,T,V); 406(D,A,C,L,N,Q); 408(H,E,G,K,M,N,P,Q,R,S,T); 413(W,F,H,I,L,Y); 414(T,A,C,S,V); 415(R,C,W,Y); 416(E,A,D,F,G,H,K,L,N,Q,R,T,V,W,Y); 418(N,A,D,I,K,L,M,Q,S,T,V); 419(T,D,E,H,K,L,M,N,P,Q,R,S,W,Y); 420(A,D,F,G,H,I,L,M,Q,R,S,T,V,W); 421(H,A,C,D,E,I,K,L,M,N,R,V,W,Y); 422(P,A,C,E,F,G,L,M,T,V,Y); 423(N,C,D,E,F,H,I,L,R,S,T); 424(S,A,C,D,E,G,I,N,Q,T,V,W); 426(L,A,N,S); 430(M,G,I,L,V); 433(G,A,C,D,E,K,M,N,R); 434(A,C,D,E,F,H,I,K,M,N,P,Q,R,S,T,V); 435(G,A,C,E,K,M,N,P,Q,R,T); 436(G,A,C,D,Q,S); 437(S,A,C,D,K,N,T); 438(K,C,E,H,S); 439(W,H,L,M,Q); 441(F,H,N,Y); 444(R,A,K,Q); 445(N,A,C,E,G,K,Q,R,T); 446(K,A,C,F,H,M,Q,S,T,Y); 450(V,A,E,I,L,Q,R,S,T); 452(S,A,C,E,F,H,K,N,Q,T,W,Y); 454(I,A,C,F,L,M,S,V); 457(N,G,H,Q,R,T); 458(R,C,D,E,H,K,L,M,N,S,T,V,Y); 459(T,A,C,D,E,G,H,L,N,P,S); 460(G,E,H,K,N,Q,S); 461(T,A,C,D,E,F,G,K,L,N,P,Q,R,V,Y); 463(T,E,K,L,P,Q,R); 465(N,D,G,Q); 466(A,D,E,G,K,N,P,Q,R,S); 471(N,C,D,E,H,Q,R,Y); 476(G,D,E,H,N,R); 477(G,A,D,K,N,P,Q,R,T); 481(I,L,T,V); 483(V,C,G,H,M,R,S,T); 484(N,A,E,G,H,Q,R,S); and 485(K,H,M,P,Q,S,T).

The productive positions in Amy 707 that fall within the previously described Productivity Scores of "1, 2, 3 and 4" (for the full SEL libraries) and the substitutions within those positions that are combinable are listed, below, in LIST D. Position numbering is based on the mature Amy707 protein listed in SEQ ID NO: 3.

List D
1(H,A,C,E,F,I,K,L,M,N,Q,R,T,W); 2(H,A,C,D,E,F,G,I,K,L,M,N,P,Q,S,W); 3(N,A,C,D,E,F,K,L,M,Q,S,T,V); 4(G,D,E,F,H,I,K,L,M,P,S,T,W); 5(T,A,C,D,G,H,I,M,N,Q,S,V,W); 6(N,A,E,G,Q,S,T); 7(G,A,D,H,I,L,M,P,Q,R,S,T,V,Y); 10(M,I,L); 12(Y,A); 16(Y,A,D,E,H,N,T,W); 17(L,A,D,G,S,T,V); 18(P,A,E); 19(N,D,L); 20(D,A,C,E,G,H,I,N,S,Y); 22(N,E,G,I,L,M,Q,R,S,T,V,W); 23(H,F,M,Q,T); 25(N,A,C,G,K,M,S,T,V,Y); 26(R,K,Q,T); 27(L,A,I,V); 28(N,A,C,D,E,G,H,K,Q,R,W,Y); 29(S,A,C,D,E,F,H,K,M,N,R,T,V,W,Y); 30(D,E,M,N,Q,R); 31(A,S); 32(S,C,D,E,G,I,L,M,N,Q,R,W,Y); 33(N,C,D,H,I,K,M,Q,R,T,V,W,Y); 34(L,F,M); 35(K,A,C,E,F,G,H,I,L,M,N,Q); 36(S,D,G,K,Q,T); 40(T,K,N); 41(A,C,D,I,K,M,Q,S); 47(A,G,M,P,S); 50(G,C,S); 52(S,K,L,M,R,T); 53(Q,A); 54(N,A,C,D,E,F,G,M,Q,S,V,W); 56(V,E,N,S); 61(Y,F); 63(L,M,N,Q); 64(Y,H); 66(L,M,V); 68(E,A,D,Q); 70(N,C,D,E,F,G,H,I,K,L,M,R,S,V); 72(K,R); 73(G,D,E,K,M,Q,R,S,T,W,Y); 74(T,G,S); 75(V,I,M); 77(T,A,I,N,S,V);

81(T,A,C,D,F,I,K,N,P,S); 82(R,A,C,F,I,K,M,Q,S,V,Y); 83(S,K,M,N,Q,R,T); 84(Q,C,D,E,F,K,L,M,N); 86(Q,E,H,I,K,R,T,V,W,Y); 87(A,D,K,M,T); 88(A,M); 89(V,A,C,I); 90(T,G,M,Q,R,S); 91(S,A,E,H,K,M,N,Q,R,T,V); 93(K,H,R); 94(N,A,C,D,F,G,H,K,L,M,Q,R); 95(N,A,C,D,F,G,H,I,Q,R,S,T,Y); 96(G,D,E,N); 97(I,V); 98(Q,A,C,D,E,G,H,K,R); 99(V,A,C,I); 100(Y,C,F,I); 101(G,A); 103(V,A,C,F,I,L,T); 110(G,A,P,S); 111(A,S); 112(D,C,E); 113(A,C,E,F,G,H,I,K,M,R,V,Y); 115(E,Q); 116(M,A,C,D,E,F,G,I,L,N,P,Q,R,T,V,W); 117(V,E,L,P,R,S,T); 118(R,D,E,G,L,Q,T,V,W); 119(A,C,S); 122(V,C); 123(N,A,C,L); 124(P,N,T); 125(N,C,F,G,H,I,L,M,R,S,T,W,Y); 126(N,D); 128(N,C,E,L,Y); 129(Q,V); 132(T,S); 133(G,A,D,H,P,Q,S,T); 134(E,D,P,S,T,V); 135(Y,C,F,L,M,Q); 136(T,C,D,F,G,K,L,M,N,P,Q,R,Y); 138(E,D,L,M,N); 139(A,C,G); 140(W,F,Y); 142(R,C,E,F,G,H,K,S,T,Y); 144(D,E,I,K,M,S,Y); 145(F,M,Y); 146(P,A,C,D,E,F,G,H,M,R,S,W,Y); 147(G,A,D,I,L); 149(G,A,C,D,E,F,H,K,L,P,R,V,W); 150(N,H,L,M,P,R,S); 151(T,D,E,G,H,I,L,M,Q,V); 153(S,N); 154(S,L,R,Y); 155(F,W); 156(K,A,D,S); 158(R,A,C,K,L,N,Q); 160(Y,A,C,D,E,F,G,H,I,K,L,M,N,P,Q,R,S); 162(F,M); 165(V,C,T); 167(W,F,M); 168(D,C); 169(Q,A,C,D,E,F,G,H,I,K,M,N,S,V,W,Y); 170(S,A,C,E,K); 171(R,M,S,T); 172(R,A,C,E,G,H,M,Q,S,Y); 173(L,A,C,D,F,H,K,N,W,Y); 174(N,D,G,H,I,L,P,S,T,V); 175(N,A,D,E,L,M,R,S); 176(R,K,T); 178(Y,W); 179(K,C,L,M,Q); 181(R,A,C,E,F,I,L,M,N,Q,S,T,V,Y); 182(G,C,D); 183(H,A,C,D,E,F,L,M,N,P,Q,V,W,Y); 184(G,A,C,D,E,L,N); 186(A,D,E,G,N); 195(N,F,L,W,Y); 196(G,C); 203(Y,N); 206(I,C,H,M,N,S,T); 210(H,A,C,D,E,M,N,Q,R,S); 211(P,A,C,D,F,K,L,M,N,Q,S,V); 215(N,D,F,K,L,M,Q); 216(E,A,C,G,H,L,N,Q,S,T,Y); 217(L,M); 218(R,A,C,E,F,H,K,M); 219(N,A,C,D,M,R,T); 221(G,I,V); 222(V,A,D,E,F,G,H,I,L,M,N,R,S,T,Y); 225(T,A,K,R); 226(N,A,D,E,K,Y); 227(T,A,E,K); 228(L,I,M); 229(G,C,F,V); 230(L,M); 231(D,E,G,T); 233(F,A,C,H,L,M,W,Y); 235(I,L,M,V); 238(V,I); 243(Y,F); 244(S,D,E,H,N,Q); 245(F,E,M); 247(R,A,E,L,T); 249(W,F,L,M); 250(I,L,M,V); 251(N,A,C,G,H,K,L,P,Q,R,S,T,V,W,Y); 252(H,D,E,K,N); 253(V,M); 257(T,A,M,S); 258(G,D,I,K,M,N,P,R,S,V); 259(K,A,C,D,E,G,H,P,Q,R,T); 260(N,D,K,P,R); 261(M,A,C,E,G,I,Q,T); 262(F,A,C,D,E,G,H,K,L,M,Q,R,S,Y); 263(A,S); 265(A,G,S); 273(G,C,D,E,H,K,L,M,P,Q,S,T,V,Y); 276(E,C,T); 280(Q,D,H,K,M,N,V); 283(N,D,G); 285(N,E,K,M,S,T); 286(H,A,C,E,F,L,M,N,T,V); 287(S,A,D,N,Y); 288(V,C,I,L,T); 292(P,L,M); 296(N,Q); 297(L,M); 298(Y,F,R,W); 299(N,G,H,M,R,S,T,Y); 301(S,A,G); 302(K,C,E,M,Q,R,S,T); 303(S,A,C,D,E,G,L,M,Q,R); 304(G,C,K,R,S,V); 306(N,A,D,G); 307(Y,A,F); 310(R,Q,S); 311(N,D,E,F,G,H,K,L,M,Q,R,T,Y); 312(I,L,M,V); 313(F,M,Y); 314(N,A,D,E,G,H,I,K,L,M,Q,S,T,V,Y); 317(V,L); 318(V,C,I,L,M,S,T); 319(Q,A,D,E,G,H,N,R,Y); 320(R,A,D,E,H,K,M,N,Q,S,T,Y); 321(H,W,Y); 322(P,D); 323(S,A,C,D,E,F,G,H,I,L,M,P,R,T,V,Y); 324(H,A,C,K,M,Y); 326(V,A,C,H,M,N,T); 327(T,L); 328(F,V); 329(V,I); 334(S,T); 337(E,A,C,D,N,Q,S,T,Y); 339(A,G,S,T); 341(E,A,D,F,G,H,K,Y); 343(F,T,Y); 344(V,C,I); 345(E,A,G,H,K,L,M,N,Q,S,T,Y); 346(E,A,C,D,G,H,K,M,N,Q,R,S,T,V,Y); 347(W,A,D); 350(P,E); 351(L,A,C,M,Q); 352(A,S); 354(A,S); 355(L,I,K,M,V); 356(T,C,I,L,Q,V); 357(L,A,H,M); 358(T,A,C,G,I; 359(R,I,V,W); 360(E,A,C,F,H,K,L,N,P,Q,R,T,V,Y); 361(Q,A,C,D,E,G,H,S,T,V,W); 363(Y,A,D,E,I,K,M,N,Q,V,W); 364(P,A,C,G); 365(S,A,G,N,V); 366(V,C,I,L); 367(F,Y); 368(Y,G,L,M,Q); 369(G,A,S); 372(Y,H,I,K,M,Q,R,T,V); 374(I,C,N,Q,S); 375(P,A,D,E,G,H,I,K,M,Q,R,T,V,Y); 377(H,A,G,K,M,T); 378(G,E,H,L,M,N); 379(V,A,I,L,M,N,Q,R,S,Y); 380(P,D,E,G,H,K,Q,S); 381(A,G,N,Q,R,S,T); 382(M,K); 386(I,L,V); 387(D,E,G,N); 388(P,A,C,D,F,G,H,K,L,N,Q,R,S,T,V,Y); 389(I,E,F,G,L,M,Q,S,V); 390(L,M,V); 391(E,A,C,G,H,I,K,L,N,R,S,W);

392(A,C,G,S); 394(Q,C,D,E,G,H,L,R,V,Y); 395(K,A,D,E,G,M,Q,R,S,T,V); 396(Y,K,M,N); 397(A,G); 400(K,A,F,G,H,I,L,M,Q,T,V,W); 401(Q,H,M); 402(N,C,I,K,L,S,V,Y); 403(D,E,T); 405(L,A,C,M,N,T,V); 406(D,A,C,L,N,Q); 408(H,E,G,K,M,N,P,Q,R,S,T); 410(I,N); 411(I,V); 412(G,A,S); 413(W,F,H,I,L,Y); 414(T,A,C,S,V); 415(R,C,W,Y); 416(E,A,D,F,G,H,K,L,N,Q,R,T,V,W,Y); 417(G,A); 418(N,A,D,I,K,L,M,Q,S,T,V); 419(T,D,E,H,K,L,M,N,P,Q,R,S,W,Y); 420(A,D,F,G,H,I,L,M,Q,R,S,T,V,W); 421(H,A,C,D,E,I,K,L,M,N,R,V,W,Y); 422(P,A,C,E,F,G,L,M,T,V,Y); 423(N,C,D,E,F,H,I,L,R,S,T); 424(S,A,C,D,E,G,I,N,Q,T,V,W); 425(G,A); 426(L,A,N,S); 427(A,C,T); 428(T,N,S); 429(I,M); 430(M,G,I,L,V); 431(S,A,C); 433(G,A,C,D,E,K,M,N,R); 434(A,C,D,E,F,H,I,K,M,N,P,Q,R,S,T,V); 435(G,A,C,E,K,M,N,P,Q,R,T); 436(G,A,C,D,Q,S); 437(S,A,C,D,K,N,T); 438(K,C,E,H,S); 439(W,H,L,M,Q); 441(F,H,N,Y); 442(V,A,C); 444(R,A,K,Q); 445(N,A,C,E,G,K,Q,R,T); 446(K,A,C,F,H,M,Q,S,T,Y); 448(G,F,N); 450(V,A,E,I,L,Q,R,S,T); 451(W,F); 452(S,A,C,E,F,H,K,N,Q,T,W,Y); 454(I,A,C,F,L,M,S,V); 457(N,G,H,Q,R,T); 458(R,C,D,E,H,K,L,M,N,S,T,V,Y); 459(T,A,C,D,E,G,H,L,N,P,S); 460(G,E,H,K,N,Q,S); 461(T,A,C,D,E,F,G,K,L,N,P,Q,R,V,Y); 463(T,E,K,L,P,Q,R); 465(N,D,G,Q); 466(A,D,E,G,K,N,P,Q,R,S); 467(D,E); 469(W,Y); 471(N,C,D,E,H,Q,R,Y); 473(S,P); 474(V,S); 475(N,D,E); 476(G,D,E,H,N,R); 477(G,A,D,K,N,P,Q,R,T); 478(S,A,G); 479(V,T); 481(I,L,T,V); 482(W,Y); 483(V,C,G,H,M,R,S,T); 484(N,A,E,G,H,Q,R,S); and 485(K,H,M,P,Q,S,T).

Although the foregoing mutations were identified using SEL libraries based on Amy707 (SEQ ID NO: 3), it is known that many bacterial (and other) α-amylases share the same fold, and often share significant amino acid sequence identity, and often benefit from the same mutations. In the present case, corresponding amino acid positions in other α-amylases can readily be identified by amino acid sequence alignment with Amy707 (SEQ ID NO: 7) using Clustal W with default parameters. α-amylases in which the foregoing mutations are likely to produce a performance benefit include those having a similar fold and/or having 60% or greater amino acid sequence identity to any of the well-known Bacillus amylases (e.g., from B. lichenifomis, B. stearothermophilus, and B. amyloliquefaciens), Carbohydrate-Active Enzymes database (CAZy) Family 13 amylases, or any amylase that has heretofore been referred to by the descriptive term, "Termamyl-like." The reader will appreciate that where an α-amylase naturally has a mutation listed above (i.e., where the wild-type α-amylase already comprised a residue identified as a mutation), then that particular mutation does not apply to that α-amylase. However, other described mutations may work in combination with the naturally occurring residue at that position. Because of their close sequence identity (over 95%; FIG. 1), and the fact that both are G6 amylases, mutations (including substitutions, insertions, and deletions, that produce a beneficial effect in Amy707 are likely to produce a similar effect in AA560 amylase, and vice versa.

In some embodiments, the present α-amylase variants have at least one combinable mutation at a productive position corresponding to the combinable mutations at productive positions described, above, in Lists A, B, C, and/or D, and/or a combinable mutation as described in Table C or D (which use SEQ ID NO: 3 for numbering) and a defined degree of amino acid sequence homology/identity to SEQ ID NO: 3 or SEQ ID NO: 4, for example, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or even at least 99% amino acid sequence homology/identity. In some embodiments, the suitability score of the at least one mutation is +++, ++++, or +++++. In some embodiments, the suitability score of the at least one mutation is ++++, or +++++. In some embodiments, the suitability score of the at least one mutation is +++++. In some embodiments, the variants have a plurality (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or more) combinable mutations.

In some embodiments, the present α-amylase variants have at least one combinable mutation at a productive position corresponding to the combinable mutations at productive positions described, above, in Lists A, B, C, and/or D, and/or a combinable mutation as described in Table C or D (which use SEQ ID NO: 3 for numbering) and are derived from a parental amylase having a defined degree of amino acid sequence homology/identity to SEQ ID NO: 3 or SEQ ID NO: 4, for example, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or even at least 99% amino acid sequence homology/identity. In some embodiments, the suitability score of the at least one mutation is +++, ++++, or +++++. In some embodiments, the suitability score of the at least one mutation is ++++, or +++++. In some embodiments, the suitability score of the at least one mutation is +++++. In some embodiments, the variants have, 2, 3, 4, 5, 6, 7, 8, 9, 10, 11, 12, 13, 14, 15, 16, 17, 18, 19, 20, or more combinable mutations.

2.2 Additional Mutations

In some embodiments, in addition to one or more of the mutations described above (e.g., in Section 2.1), the present amylases further include one or more mutations that provide a further performance or stability benefit. Exemplary performance benefits include but are not limited to increased hydrolysis of a starch substrate, increased grain, cereal or other starch substrate liquefaction performance, increased cleaning performance, increased thermal stability, increased storage stability, increased solubility, an altered pH profile, decreased calcium dependence, increased specific activity, modified substrate specificity, modified substrate binding, modified pH-dependent activity, modified pH-dependent stability, increased oxidative stability, and increased expression. In some cases, the performance benefit is realized at a relatively low temperature. In some cases, the performance benefit is realized at relatively high temperature.

In some embodiments, the present α-amylase variants additionally have at least one mutation in the calcium binding loop based on the work of Suzuki et al. (1989) *J. Biol. Chem.* 264:18933-938. Exemplary mutations include a deletion or substitution at one or more residues corresponding to Arg-181, Gly-182, His-183, or Gly-184 in SEQ ID NO: 3. In particular embodiments, the mutation corresponds to the deletion of Arg-181 and Gly-182 or His-183 and Gly-184 (using SEQ ID NO: 3 numbering). Homologous residues in other amylases can be determined by structural alignment, or by primary structure alignment.

In some embodiments, the present α-amylase variants additionally have at least one mutation known to produce a performance, stability, or solubility benefit in other microbial α-amylases, including but not limited to those having a similar fold and/or having 60% or greater amino acid sequence identity to Amy707 (SEQ ID NO: 3) or AA560 (SEQ ID NO: 4), any of the well-known Bacillus amylases (e.g., from B. lichenifomis, B. stearothermophilus, and B. amyloliquefaciens), Carbohydrate-Active Enzymes database (CAZy) Family 13 amylases, or any amylase that has heretofore been referred to by the descriptive term, "Termamyl-like." Amino acid sequence identity can be determined using Clustal W with default parameters.

Furthermore, the present amylases may include any number of conservative amino acid substitutions. Exemplary conservative amino acid substitutions are listed in the Table E.

Exemplary heterologous signal sequences are from B. licheniformis amylase (LAT), B. subtilis (AmyE or AprE), and Streptomyces CelA.

2.3. Nucleotides Encoding Variant Amylase Polypeptides

In another aspect, nucleic acids encoding a variant amylase polypeptide are provided. The nucleic acid may encode a particular amylase polypeptide, or an amylase having a specified degree of amino acid sequence identity to the particular amylase.

In one example, the nucleic acid encodes an amylase having at least 60%, at least 65%, at least 70%, at least 75%, at least 76%, at least 77%, at least 78%, at least 79%, at least

TABLE E

Conservative amino acid substitutions

| For Amino Acid | Code | Replace with any of |
| --- | --- | --- |
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, b-Ala, Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4- carboxylic acid, D-or L-1-oxazolidine-4-carboxylic acid |
| Serine | S | D-Ser, Thr, D-Thr, allo-Thr, Met, D-Met, Met(0), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

The reader will appreciate that some of the above mentioned conservative mutations can be produced by genetic manipulation, while others are produced by introducing synthetic amino acids into a polypeptide by genetic or other means.

The present amylase may be "precursor," "immature," or "full-length," in which case they include a signal sequence, or "mature," in which case they lack a signal sequence. Mature forms of the polypeptides are generally the most useful. Unless otherwise noted, the amino acid residue numbering used herein refers to the mature forms of the respective amylase polypeptides. The present amylase polypeptides may also be truncated to remove the N or C-termini, so long as the resulting polypeptides retain amylase activity.

The present amylase may be a "chimeric" or "hybrid" polypeptide, in that it includes at least a portion of a first amylase polypeptide, and at least a portion of a second amylase polypeptide (such chimeric amylases have recently been "rediscovered" as domain-swap amylases). The present amylases may further include heterologous signal sequence, an epitope to allow tracking or purification, or the like.

80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or even at least 99% homology/identity to SEQ ID NO: 3 or SEQ ID NO: 4 (excluding the portion of the nucleic acid that encodes the signal sequence). It will be appreciated that due to the degeneracy of the genetic code, a plurality of nucleic acids may encode the same polypeptide.

In another example, the nucleic acid hybridizes under stringent or very stringent conditions to a nucleic acid encoding (or complementary to a nucleic acid encoding) an amylase having at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or even at least 99% homology/identity to SEQ ID NO: 3 or SEQ ID NO: 4 (excluding the portion of the nucleic acid that encodes the signal sequence). Such hybridization conditions are described herein but are also well known in the art.

In a particular example, the nucleic acid hybridizes under stringent or very stringent conditions to the nucleic acid of SEQ ID NO: 1 or SEQ ID NO: 5, which are shown, below.

SEQ ID NO: 1: Codon optimized nucleic acid encoding SEQ ID NO: 3.
ATGAAACAACAAAAACGGCTTTACGCCCGATTGCTGACGCTGTTATTTG
CGCTCATCTTCTTGCTGCCTCATTCTGCAGCTTCAGCACATCATAATGG
CACAAACGGCACGATGATGCAGTATTTTGAATGGTATCTGCCGAACGAT
GGAAACCATTGGAACCGCCTGAATAGCGATGCGAGCAACCTGAAAAGCA
AAGGCATCACAGCAGTTTGGATTCCGCCGGCATGGAAAGGAGCAAGCCA
AAACGACGTCGGCTATGGAGCGTATGATCTGTATGACCTGGGCGAATTT
AACCAAAAAGGCACGGTCCGCACGAAATATGGCACGCGCAGCCAACTTC
AAGCAGCAGTCACGAGCCTTAAAAACAACGGCATCCAGGTCTATGGAGA
TGTCGTCATGAACCATAAAGGCGGAGCAGATGCGACAGAAATGGTCAGA
GCGGTCGAAGTCAACCCGAACAACCGCAATCAAGAAGTCACGGGCGAAT
ATACAATCGAAGCGTGGACGCGCTTTGATTTTCCGGGCAGAGGCAATAC
ACATAGCAGCTTTAAATGGCGCTGGTATCATTTTGATGGCGTCGATTGG
GATCAAAGCCGCAGACTGAACAACCGCATCTATAAATTTCGCGGCCATG
GCAAAGCATGGGATTGGAAGTCGATACGGAAAACGGCAACTATGACTA
TCTGATGTATGCGGACATCGATATGGATCATCCGGAAGTCGTCAACGAA
CTGAGAAATTGGGGCGTCTGGTATACAAATACGCTGGGCCTGGATGGCT
TTAGAATCGACGCGGTCAAACATATCAAATATAGCTTTACGCGCGACTG
GATCAATCATGTCAGAAGCGCGACGGGCAAAAATATGTTTGCGGTCGCG
GAATTTTGGAAAAATGATCTGGGCGCGATCGAAAACTATCTGCAAAAAA
CGAACTGGAACCATAGCGTCTTTGATGTCCCGCTGCATTATAACCTGTA
TAACGCGAGCAAAAGCGGCGGCAATTATGATATGCGCAACATCTTTAAC
GGCACGGTCGTTCAAAGACATCCGAGCCATGCGGTCACGTTTGTCGATA
ACCATGATAGCCAACCGGAAGAAGCGCTGGAAAGCTTTGTCGAAGAATG
GTTTAAACCGCTGGCGTATGCACTGACACTGACGAGAGAACAAGGATAT
CCGAGCGTCTTTTATGGCGACTATTATGGCATCCCGACACATGGAGTTC
CGGCGATGAGAAGCAAAATCGACCCGATCCTGGAAGCGAGACAGAAATA
TGCGTATGGCAAACAGAACGACTATCTGGACCATCATAACATCATCGGC
TGGACGAGAGAAGGAAATACGGCGCATCCGAATTCAGGACTGGCGACGA
TTATGTCAGATGGAGCGGGCGGAAGCAAATGGATGTTTGTCGGCAGAAA
CAAAGCAGGACAAGTCTGGAGCGATATCACGGGCAATAGAACGGGAACG
GTCACGATCAATGCAGATGGCTGGGGCAACTTTAGCGTTAATGGCGGAA
GCGTCAGCATCTGGGTCAACAAA SEQ ID NO: 5: Genebank Accession No. M18862
GGATCCCGTCTACGGAGAAGCGAGTATTGAATTTTTGCTGTAACAGAA
AGCGAGCGTGGGAAAGGATTTGGCTTTCAATTACTAACGGTTGCTTTAA
ATTGGCTATTTACGATTGATACGATTCATTCAATTACACTCTGTGTCGA
TTCTAGTAATGAACATGCGATTCATTTATATAAAAAAGTTGGATTCAGG
CATGTTCATGATTTGAGTTATTTTACTAAAGAAGTATCTCATTAAAAAC
ATGATTGAGGAAAGACGGTTTTCGACTAATTGTGGTCAAAGTAGAAAAT
TGAATGAATATTACGAAGCATGAGGCTAAGACATAACTAAAGTGTCTAA
ATGAAAAACCGAACGAAAAATGAACGAAGCGAAGTGTATTTCAAGAAAG
GTTACCGTTCGCTATTTATCACCGTTCGGTTATTTTTAGATAAGCCAC
TTTTGTCGCGGCCTCTTTTTGGTGCCGATAAATGAGAATAAAGAATAAA
AAGTCAATATTGCTTAGCTAAATGAATGTCAAGGTGGTTATATTATCCT
ATTTATTTTCAGAAAATAAAAAAACGTTTGCGCAATTGTTTTATAGCAT
AATAATATAACCTTGCCAATTGATATTTAAGTCGAGTGAAATCAATTGC
GCAAATTAATGAGTGTGTTCAAGGAGAGTGATGAATGTAGCAGTTTAGT
CATGTACTTGTTTTTGGAAAGCGCTTACAATTAGGAGGGTGGATGAAAA
TGAGAACAGGAAAAAAGGGTTTTTAAGTATTTTATTAGCGTTCTTATT
GGTGATTACTTCAATACCGTTTACTTTAGTAGATGTAGAAGCACATCAT
AACGGTACGAACGGGACAATGATGCAATACTTTGAATGGTATCTACCTA
ATGACGAAATCATTGGAATCGATTAAACTCTGATGCGAGTAACCTTAA
AAGCAAAGGGATTACAGCGGTGTGGATTCCTCCAGCATGGAAGGGCGCT
TCTCAAAATGACGTAGGATACGGAGCCTATGACCTGTATGATCTGGGAG
AATTTAATCAAAAAGGTACCGTCCGTACAAAATATGGAACACGTAGTCA
GTTACAAGCTGCGGTAACCTCCTTAAAAAATAATGGAATTCAAGTATAT
GGTGACGTTGTTATGAATCACAAAGGTGGCGCAGACGCTACTGAAATGG
TAAGGGCCGTTGAAGTGAATCCCAATAACCGTAACCAAGAAGTGACTGG
TGAATATACCATTGAAGCTTGGACTAGATTTGATTTTCCAGGGCGAGGA
AATACTCATTCTAGCTTTAAATGGAGATGGTATCATTTTGATGGTGTGG
ATTGGGATCAGTCACGTAGACTGAACAATCGCATCTATAAATTTAGAGG
TCATGCAAAGCTTGGGATTGGGAAGTTGATACGGAAAATGGTAATTAT
GATTATTTAATGTACGCTGATATTGATATGGATCACCCAGAAGTAGTAA
ATGAATTAAGAAATTGGGGTGTTTGGTACACAAACACATTAGGACTCGA
TGGATTTAGAATAGATGCGGTTAAACATATAAAGTATAGCTTTACGCGC
GATTGGATTAATCACGTTAGAAGTGCAACAGGTAAAAATATGTTTGCGG
TTGCTGAGTTTTGGAAGAATGATTTAGGTGCAATTGAAAACTATCTGCA
GAAAACAAACTGGAACCATTCAGTCTTTGATGTGCCGTTACATTATAAT
CTTTATAATGCATCAAAAAGCGGAGGGAACTATGATATGCGAAACATAT
TTAATGGAACGGTTGTTCAACGACATCCAAGTCATGCTGTAACATTTGT
TGATAATCATGATTCGCAGCCTGAAGAAGCATTAGAATCTTTTGTTGAA
GAATGGTTTAAACCATTAGCGTATGCGCTTACATTAACGCGTGAACAAG
GATACCCTTCTGTATTTTACGGAGATTATTATGGGATTCCAACACATGG
AGTGCCAGCAATGAGATCAAAAATCGATCCGATTTTAGAAGCACGTCAA
AAGTATGCATACGGAAAACAAAATGATTACTTAGACCATCATAATATCA
TTGGTTGGACGCGTGAAGGGAATACAGCACACCCCAATTCAGGTCTAGC
TACCATCATGTCTGATGGAGCGGGTGGAAGTAAGTGGATGTTTGTTGGG
CGTAATAAGGCTGGTCAAGTATGGAGTGATATTACAGGAAACCGTACAG

```
-continued
GTACGGTTACAATCAATGCAGACGGTTGGGGCAATTTCTCTGTGAATGG

AGGGTCAGTTTCTATTTGGGTCAACAAATAAAAGTGGAAAAGAAGAGGC

CGTAGGTTAATATGGTCTTTTCTTTTCTTTTAAGGAGGTTCAATGAATT

TGTCGGTTATCCAATTATTACATGCTGAGCTGTTAGATTATTCGT
```

Nucleic acids may encode a "full-length" ("fl" or "FL") amylase, which includes a signal sequence, only the mature form of an amylase, which lacks the signal sequence, or a truncated form of an amylase, which lacks the N or C-terminus of the mature form.

A nucleic acid that encodes a α-amylase can be operably linked to various promoters and regulators in a vector suitable for expressing the α-amylase in host cells. Exemplary promoters are from *B. licheniformis* amylase (LAT), *B. subtilis* (AmyE or AprE), and *Streptomyces* CelA. Such a nucleic acid can also be linked to other coding sequences, e.g., to encode a chimeric polypeptide.

3. Production of Variant Amylases

The present variant amylases can be produced in host cells, for example, by secretion or intracellular expression. A cultured cell material (e.g., a whole-cell broth) comprising a variant amylase can be obtained following secretion of the variant amylase into the cell medium. Optionally, the variant amylase can be isolated from the host cells, or even isolated from the cell broth, depending on the desired purity of the final variant amylase. A gene encoding a variant amylase can be cloned and expressed according to methods well known in the art. Suitable host cells include bacterial, fungal (including yeast and filamentous fungi), and plant cells (including algae). Particularly useful host cells include *Aspergillus niger, Aspergillus oryzae* or *Trichoderma reesei*. Other host cells include bacterial cells, e.g., *Bacillus subtilis* or *B. licheniformis*, as well as *Streptomyces*.

The host cell further may express a nucleic acid encoding a homologous or heterologous glucoamylase, i.e., a glucoamylase that is not the same species as the host cell, or one or more other enzymes. The glucoamylase may be a variant glucoamylase, such as one of the glucoamylase variants disclosed in U.S. Pat. No. 8,058,033 (Danisco US Inc.), for example. Additionally, the host may express one or more accessory enzymes, proteins, peptides. These may benefit liquefaction, saccharification, fermentation, SSF, etc processes. Furthermore, the host cell may produce biochemicals in addition to enzymes used to digest the various feedstock(s). Such host cells may be useful for fermentation or simultaneous saccharification and fermentation processes to reduce or eliminate the need to add enzymes.

3.1. Vectors

A DNA construct comprising a nucleic acid encoding variant amylases can be constructed to be expressed in a host cell. Representative nucleic acids that encode variant amylases include SEQ ID NO: 4. Because of the well-known degeneracy in the genetic code, variant polynucleotides that encode an identical amino acid sequence can be designed and made with routine skill. It is also well-known in the art to optimize codon use for a particular host cell. Nucleic acids encoding variant amylases can be incorporated into a vector. Vectors can be transferred to a host cell using well-known transformation techniques, such as those disclosed below.

The vector may be any vector that can be transformed into and replicated within a host cell. For example, a vector comprising a nucleic acid encoding a variant amylase can be transformed and replicated in a bacterial host cell as a means of propagating and amplifying the vector. The vector also may be transformed into an expression host, so that the encoding nucleic acids can be expressed as a functional amylase. Host cells that serve as expression hosts can include filamentous fungi, for example. The Fungal Genetics Stock Center (FGSC) Catalogue of Strains lists suitable vectors for expression in fungal host cells. See FGSC, Catalogue of Strains, University of Missouri, at www.fgsc.net (last modified Jan. 17, 2007). A representative vector is pJG153, a promoterless Cre expression vector that can be replicated in a bacterial host. See Harrison et al. (June 2011) *Applied Environ. Microbiol.* 77: 3916-22. pJG153 can be modified with routine skill to comprise and express a nucleic acid encoding an amylase variant.

A nucleic acid encoding a variant amylase can be operably linked to a suitable promoter, which allows transcription in the host cell. The promoter may be any DNA sequence that shows transcriptional activity in the host cell of choice and may be derived from genes encoding proteins either homologous or heterologous to the host cell. Exemplary promoters for directing the transcription of the DNA sequence encoding a variant amylase, especially in a bacterial host, are the promoter of the lac operon of *E. coli*, the *Streptomyces coelicolor* agarase gene dagA or celA promoters, the promoters of the *Bacillus licheniformis* α-amylase gene (amyL), the promoters of the *Bacillus stearothermophilus* maltogenic amylase gene (amyM), the promoters of the *Bacillus amyloliquefaciens* α-amylase (amyQ), the promoters of the *Bacillus subtilis* xylA and xylB genes etc. For transcription in a fungal host, examples of useful promoters are those derived from the gene encoding *Aspergillus oryzae* TAKA amylase, *Rhizomucor miehei* aspartic proteinase, *Aspergillus niger* neutral α-amylase, *A. niger* acid stable α-amylase, *A. niger* glucoamylase, *Rhizomucor miehei* lipase, *A. oryzae* alkaline protease, *A. oryzae* triose phosphate isomerase, or *A. nidulans* acetamidase. When a gene encoding an amylase is expressed in a bacterial species such as *E. coli*, a suitable promoter can be selected, for example, from a bacteriophage promoter including a T7 promoter and a phage lambda promoter. Examples of suitable promoters for the expression in a yeast species include but are not limited to the Gal 1 and Gal 10 promoters of *Saccharomyces cerevisiae* and the *Pichia pastoris* AOX1 or AOX2 promoters. cbh1 is an endogenous, inducible promoter from *T. reesei*. See Liu et al. (2008) "Improved heterologous gene expression in *Trichoderma reesei* by cellobiohydrolase I gene (cbh1) promoter optimization," *Acta Biochim. Biophys. Sin (Shanghai)* 40(2): 158-65.

The coding sequence can be operably linked to a signal sequence. The DNA encoding the signal sequence may be the DNA sequence naturally associated with the amylase gene to be expressed or from a different Genus or species. A signal sequence and a promoter sequence comprising a DNA construct or vector can be introduced into a fungal host cell and can be derived from the same source. For example, the signal sequence is the cbh1 signal sequence that is operably linked to a cbh1 promoter.

An expression vector may also comprise a suitable transcription terminator and, in eukaryotes, polyadenylation sequences operably linked to the DNA sequence encoding a variant amylase. Termination and polyadenylation sequences may suitably be derived from the same sources as the promoter.

The vector may further comprise a DNA sequence enabling the vector to replicate in the host cell. Examples of such sequences are the origins of replication of plasmids pUC19, pACYC177, pUB110, pE194, pAMB1, and pIJ702.

The vector may also comprise a selectable marker, e.g., a gene the product of which complements a defect in the isolated host cell, such as the dal genes from *B. subtilis* or *B. licheniformis*, or a gene that confers antibiotic resistance such as, e.g., ampicillin, kanamycin, chloramphenicol or tetracycline resistance. Furthermore, the vector may comprise *Aspergillus* selection markers such as amdS, argB, niaD and xxsC, a marker giving rise to hygromycin resistance, or the selection may be accomplished by co-transformation, such as known in the art. See e.g., International PCT Application WO 91/17243.

Intracellular expression may be advantageous in some respects, e.g., when using certain bacteria or fungi as host cells to produce large amounts of amylase for subsequent enrichment or purification. Extracellular secretion of amylase into the culture medium can also be used to make a cultured cell material comprising the isolated amylase.

The expression vector typically includes the components of a cloning vector, such as, for example, an element that permits autonomous replication of the vector in the selected host organism and one or more phenotypically detectable markers for selection purposes. The expression vector normally comprises control nucleotide sequences such as a promoter, operator, ribosome binding site, translation initiation signal and optionally, a repressor gene or one or more activator genes. Additionally, the expression vector may comprise a sequence coding for an amino acid sequence capable of targeting the amylase to a host cell organelle such as a peroxisome, or to a particular host cell compartment. Such a targeting sequence includes but is not limited to the sequence, SKL. For expression under the direction of control sequences, the nucleic acid sequence of the amylase is operably linked to the control sequences in proper manner with respect to expression.

The procedures used to ligate the DNA construct encoding an amylase, the promoter, terminator and other elements, respectively, and to insert them into suitable vectors containing the information necessary for replication, are well known to persons skilled in the art (see, e.g., Sambrook et al., MOLECULAR CLONING: A LABORATORY MANUAL, $2^{nd}$ ed., Cold Spring Harbor, 1989, and $3^{rd}$ ed., 2001).

3.2. Transformation and Culture of Host Cells

An isolated cell, either comprising a DNA construct or an expression vector, is advantageously used as a host cell in the recombinant production of an amylase. The cell may be transformed with the DNA construct encoding the enzyme, conveniently by integrating the DNA construct (in one or more copies) in the host chromosome. This integration is generally considered to be an advantage, as the DNA sequence is more likely to be stably maintained in the cell. Integration of the DNA constructs into the host chromosome may be performed according to conventional methods, e.g., by homologous or heterologous recombination. Alternatively, the cell may be transformed with an expression vector as described above in connection with the different types of host cells.

Examples of suitable bacterial host organisms are Gram positive bacterial species such as Bacillaceae including *Bacillus subtilis, Bacillus licheniformis, Bacillus lentus, Bacillus brevis, Geobacillus* (formerly *Bacillus*) *stearothermophilus, Bacillus alkalophilus, Bacillus amyloliquefaciens, Bacillus coagulans, Bacillus lautus, Bacillus megaterium,* and *Bacillus thuringiensis; Streptomyces* species such as *Streptomyces murinus*; lactic acid bacterial species including *Lactococcus* sp. such as *Lactococcus lactis; Lactobacillus* sp. including *Lactobacillus reuteri; Leuconostoc* sp.; *Pediococcus* sp.; and *Streptococcus* sp. Alternatively, strains of a Gram negative bacterial species belonging to Enterobacteriaceae including *E. coli*, or to Pseudomonadaceae can be selected as the host organism.

A suitable yeast host organism can be selected from the biotechnologically relevant yeasts species such as but not limited to yeast species such as *Pichia* sp., *Hansenula* sp., or *Kluyveromyces, Yarrowinia, Schizosaccharomyces* species or a species of *Saccharomyces*, including *Saccharomyces cerevisiae* or a species belonging to *Schizosaccharomyces* such as, for example, *S. pombe* species. A strain of the methylotrophic yeast species, *Pichia pastoris*, can be used as the host organism. Alternatively, the host organism can be a *Hansenula* species. Suitable host organisms among filamentous fungi include species of *Aspergillus*, e.g., *Aspergillus niger, Aspergillus oryzae, Aspergillus tubigensis, Aspergillus awamori*, or *Aspergillus nidulans*. Alternatively, strains of a *Fusarium* species, e.g., *Fusarium oxysporum* or of a *Rhizomucor* species such as *Rhizomucor miehei* can be used as the host organism. Other suitable strains include *Thermomyces* and *Mucor* species. In addition, *Trichoderma* sp. can be used as a host. A suitable procedure for transformation of *Aspergillus* host cells includes, for example, that described in EP 238023. An amylase expressed by a fungal host cell can be glycosylated, i.e., will comprise a glycosyl moiety. The glycosylation pattern can be the same or different as present in the wild-type amylase. The type and/or degree of glycosylation may impart changes in enzymatic and/or biochemical properties.

It is advantageous to delete genes from expression hosts, where the gene deficiency can be cured by the transformed expression vector. Known methods may be used to obtain a fungal host cell having one or more inactivated genes. Gene inactivation may be accomplished by complete or partial deletion, by insertional inactivation or by any other means that renders a gene nonfunctional for its intended purpose, such that the gene is prevented from expression of a functional protein. Any gene from a *Trichoderma* sp. or other filamentous fungal host that has been cloned can be deleted, for example, cbh1, cbh2, egl1, and egl2 genes. Gene deletion may be accomplished by inserting a form of the desired gene to be inactivated into a plasmid by methods known in the art.

Introduction of a DNA construct or vector into a host cell includes techniques such as transformation; electroporation; nuclear microinjection; transduction; transfection, e.g., lipofection mediated and DEAE-Dextrin mediated transfection; incubation with calcium phosphate DNA precipitate; high velocity bombardment with DNA-coated microprojectiles; and protoplast fusion. General transformation techniques are known in the art. See, e.g., Sambrook et al. (2001), supra. The expression of heterologous protein in *Trichoderma* is described, for example, in U.S. Pat. No. 6,022,725. Reference is also made to Cao et al. (2000) Science 9:991-1001 for transformation of *Aspergillus* strains. Genetically stable transformants can be constructed with vector systems whereby the nucleic acid encoding an amylase is stably integrated into a host cell chromosome. Transformants are then selected and purified by known techniques.

The preparation of *Trichoderma* sp. for transformation, for example, may involve the preparation of protoplasts from fungal mycelia. See Campbell et al. (1989) *Curr. Genet.* 16: 53-56. The mycelia can be obtained from germinated vegetative spores. The mycelia are treated with an enzyme that digests the cell wall, resulting in protoplasts. The protoplasts are protected by the presence of an osmotic stabilizer in the suspending medium. These stabilizers include sorbitol, mannitol, potassium chloride, magnesium sulfate, and the like. Usually the concentration of these stabilizers varies between 0.8 M and 1.2 M, e.g., a 1.2 M solution of sorbitol can be used in the suspension medium.

Uptake of DNA into the host *Trichoderma* sp. strain depends upon the calcium ion concentration. Generally, between about 10-50 mM $CaCl_2$ is used in an uptake solution. Additional suitable compounds include a buffering system, such as TE buffer (10 mM Tris, pH 7.4; 1 mM EDTA) or 10 mM MOPS, pH 6.0 and polyethylene glycol. The polyethylene glycol is believed to fuse the cell membranes, thus permitting the contents of the medium to be delivered into the cytoplasm of the *Trichoderma* sp. strain. This fusion frequently leaves multiple copies of the plasmid DNA integrated into the host chromosome.

Usually transformation of *Trichoderma* sp. uses protoplasts or cells that have been subjected to a permeability treatment, typically at a density of $10^5$ to $10^7$/mL, particularly $2 \times 10^6$/mL. A volume of 100 µL of these protoplasts or cells in an appropriate solution (e.g., 1.2 M sorbitol and 50 mM $CaCl_2$) may be mixed with the desired DNA. Generally, a high concentration of PEG is added to the uptake solution. From 0.1 to 1 volume of 25% PEG 4000 can be added to the protoplast suspension; however, it is useful to add about 0.25 volumes to the protoplast suspension. Additives, such as dimethyl sulfoxide, heparin, spermidine, potassium chloride and the like, may also be added to the uptake solution to facilitate transformation. Similar procedures are available for other fungal host cells. See, e.g., U.S. Pat. No. 6,022,725.

3.3. Expression

A method of producing an amylase may comprise cultivating a host cell as described above under conditions conducive to the production of the enzyme and recovering the enzyme from the cells and/or culture medium.

The medium used to cultivate the cells may be any conventional medium suitable for growing the host cell in question and obtaining expression of an amylase. Suitable media and media components are available from commercial suppliers or may be prepared according to published recipes (e.g., as described in catalogues of the American Type Culture Collection).

An enzyme secreted from the host cells can be used in a whole broth preparation. In the present methods, the preparation of a spent whole fermentation broth of a recombinant microorganism can be achieved using any cultivation method known in the art resulting in the expression of an α-amylase. Fermentation may, therefore, be understood as comprising shake flask cultivation, small- or large-scale fermentation (including continuous, batch, fed-batch, or solid state fermentations) in laboratory or industrial fermenters performed in a suitable medium and under conditions allowing the amylase to be expressed or isolated. The term "spent whole fermentation broth" is defined herein as unfractionated contents of fermentation material that includes culture medium, extracellular proteins (e.g., enzymes), and cellular biomass. It is understood that the term "spent whole fermentation broth" also encompasses cellular biomass that has been lysed or permeabilized using methods well known in the art.

An enzyme secreted from the host cells may conveniently be recovered from the culture medium by well-known procedures, including separating the cells from the medium by centrifugation or filtration, and precipitating proteinaceous components of the medium by means of a salt such as ammonium sulfate, followed by the use of chromatographic procedures such as ion exchange chromatography, affinity chromatography, or the like.

The polynucleotide encoding an amylase in a vector can be operably linked to a control sequence that is capable of providing for the expression of the coding sequence by the host cell, i.e. the vector is an expression vector. The control sequences may be modified, for example by the addition of further transcriptional regulatory elements to make the level of transcription directed by the control sequences more responsive to transcriptional modulators. The control sequences may in particular comprise promoters.

Host cells may be cultured under suitable conditions that allow expression of an amylase. Expression of the enzymes may be constitutive such that they are continually produced, or inducible, requiring a stimulus to initiate expression. In the case of inducible expression, protein production can be initiated when required by, for example, addition of an inducer substance to the culture medium, for example dexamethasone or IPTG or Sophorose. Polypeptides can also be produced recombinantly in an in vitro cell-free system, such as the TNT™ (Promega) rabbit reticulocyte system.

An expression host also can be cultured in the appropriate medium for the host, under aerobic conditions. Shaking or a combination of agitation and aeration can be provided, with production occurring at the appropriate temperature for that host, e.g., from about 25° C. to about 75° C. (e.g., 30° C. to 45° C.), depending on the needs of the host and production of the desired variant amylase. Culturing can occur from about 12 to about 100 hours or greater (and any hour value there between, e.g., from 24 to 72 hours). Typically, the culture broth is at a pH of about 4.0 to about 8.0, again depending on the culture conditions needed for the host relative to production of an amylase.

3.4. Identification of Amylase Activity

To evaluate the expression of an amylase in a host cell, assays can measure the expressed protein, corresponding mRNA, or α-amylase activity. For example, suitable assays include Northern blotting, reverse transcriptase polymerase chain reaction, and in situ hybridization, using an appropriately labeled hybridizing probe. Suitable assays also include measuring amylase activity in a sample, for example, by assays directly measuring reducing sugars such as glucose in the culture media. For example, glucose concentration may be determined using glucose reagent kit No. 15-UV (Sigma Chemical Co.) or an instrument, such as Technicon Autoanalyzer. α-Amylase activity also may be measured by any known method, such as the PAHBAH or ABTS assays, described below.

3.5. Methods for Enriching and Purifying Variants Amylases

Fermentation, separation, and concentration techniques are well known in the art and conventional methods can be used in order to prepare a concentrated a variant α-amylase polypeptide-containing solution.

After fermentation, a fermentation broth is obtained, the microbial cells and various suspended solids, including residual raw fermentation materials, are removed by conventional separation techniques in order to obtain an amylase solution. Filtration, centrifugation, microfiltration, rotary vacuum drum filtration, ultrafiltration, centrifugation followed by ultrafiltration, extraction, or chromatography, or the like, are generally used.

It is desirable to concentrate a variant α-amylase polypeptide-containing solution in order to optimize recovery. Use of unconcentrated solutions requires increased incubation time in order to collect the enriched or purified enzyme precipitate.

The enzyme containing solution is concentrated using conventional concentration techniques until the desired enzyme level is obtained. Concentration of the enzyme containing solution may be achieved by any of the techniques discussed herein. Exemplary methods of enrichment and purification include but are not limited to rotary vacuum filtration and/or ultrafiltration.

The enzyme solution is concentrated into a concentrated enzyme solution until the enzyme activity of the concentrated variant α-amylase polypeptide-containing solution is at a desired level.

Concentration may be performed using, e.g., a precipitation agent, such as a metal halide precipitation agent. Metal halide precipitation agents include but are not limited to alkali metal chlorides, alkali metal bromides and blends of two or more of these metal halides. Exemplary metal halides include sodium chloride, potassium chloride, sodium bromide, potassium bromide and blends of two or more of these metal halides. The metal halide precipitation agent, sodium chloride, can also be used as a preservative.

The metal halide precipitation agent is used in an amount effective to precipitate an amylase. The selection of at least an effective amount and an optimum amount of metal halide effective to cause precipitation of the enzyme, as well as the conditions of the precipitation for maximum recovery including incubation time, pH, temperature and concentration of enzyme, will be readily apparent to one of ordinary skill in the art, after routine testing.

Generally, at least about 5% w/v (weight/volume) to about 25% w/v of metal halide is added to the concentrated enzyme solution, and usually at least 8% w/v. Generally, no more than about 25% w/v of metal halide is added to the concentrated enzyme solution and usually no more than about 20% w/v. The optimal concentration of the metal halide precipitation agent will depend, among others, on the nature of the specific variant α-amylase polypeptide and on its concentration in the concentrated enzyme solution.

Another alternative way to precipitate the enzyme is to use organic compounds. Exemplary organic compound precipitating agents include: 4-hydroxybenzoic acid, alkali metal salts of 4-hydroxybenzoic acid, alkyl esters of 4-hydroxybenzoic acid, and blends of two or more of these organic compounds. The addition of the organic compound precipitation agents can take place prior to, simultaneously with or subsequent to the addition of the metal halide precipitation agent, and the addition of both precipitation agents, organic compound and metal halide, may be carried out sequentially or simultaneously.

Generally, the organic precipitation agents are selected from the group consisting of alkali metal salts of 4-hydroxybenzoic acid, such as sodium or potassium salts, and linear or branched alkyl esters of 4-hydroxybenzoic acid, wherein the alkyl group contains from 1 to 12 carbon atoms, and blends of two or more of these organic compounds. The organic compound precipitation agents can be, for example, linear or branched alkyl esters of 4-hydroxybenzoic acid, wherein the alkyl group contains from 1 to 10 carbon atoms, and blends of two or more of these organic compounds. Exemplary organic compounds are linear alkyl esters of 4-hydroxybenzoic acid, wherein the alkyl group contains from 1 to 6 carbon atoms, and blends of two or more of these organic compounds. Methyl esters of 4-hydroxybenzoic acid, propyl esters of 4-hydroxybenzoic acid, butyl ester of 4-hydroxybenzoic acid, ethyl ester of 4-hydroxybenzoic acid and blends of two or more of these organic compounds can also be used. Additional organic compounds also include but are not limited to 4-hydroxybenzoic acid methyl ester (named methyl PARABEN), 4-hydroxybenzoic acid propyl ester (named propyl PARABEN), which also are both amylase preservative agents. For further descriptions, see, e.g., U.S. Pat. No. 5,281,526.

Addition of the organic compound precipitation agent provides the advantage of high flexibility of the precipitation conditions with respect to pH, temperature, variant amylase concentration, precipitation agent concentration, and time of incubation.

The organic compound precipitation agent is used in an amount effective to improve precipitation of the enzyme by means of the metal halide precipitation agent. The selection of at least an effective amount and an optimum amount of organic compound precipitation agent, as well as the conditions of the precipitation for maximum recovery including incubation time, pH, temperature and concentration of enzyme, will be readily apparent to one of ordinary skill in the art, in light of the present disclosure, after routine testing.

Generally, at least about 0.01% w/v of organic compound precipitation agent is added to the concentrated enzyme solution and usually at least about 0.02% w/v. Generally, no more than about 0.3% w/v of organic compound precipitation agent is added to the concentrated enzyme solution and usually no more than about 0.2% w/v.

The concentrated polypeptide solution, containing the metal halide precipitation agent, and the organic compound precipitation agent, can be adjusted to a pH, which will, of necessity, depend on the enzyme to be enriched or purified. Generally, the pH is adjusted at a level near the isoelectric point of the amylase. The pH can be adjusted at a pH in a range from about 2.5 pH units below the isoelectric point (pI) up to about 2.5 pH units above the isoelectric point.

The incubation time necessary to obtain an enriched or purified enzyme precipitate depends on the nature of the specific enzyme, the concentration of enzyme, and the specific precipitation agent(s) and its (their) concentration. Generally, the time effective to precipitate the enzyme is between about 1 to about 30 hours; usually it does not exceed about 25 hours. In the presence of the organic compound precipitation agent, the time of incubation can still be reduced to less about 10 hours and in most cases even about 6 hours.

Generally, the temperature during incubation is between about 4° C. and about 50° C. Usually, the method is carried out at a temperature between about 10° C. and about 45° C. (e.g., between about 20° C. and about 40° C.). The optimal temperature for inducing precipitation varies according to the solution conditions and the enzyme or precipitation agent(s) used.

The overall recovery of enriched or purified enzyme precipitate, and the efficiency with which the process is conducted, is improved by agitating the solution comprising the enzyme, the added metal halide and the added organic compound. The agitation step is done both during addition of the metal halide and the organic compound, and during the subsequent incubation period. Suitable agitation methods include mechanical stirring or shaking, vigorous aeration, or any similar technique.

After the incubation period, the enriched or purified enzyme is then separated from the dissociated pigment and other impurities and collected by conventional separation techniques, such as filtration, centrifugation, microfiltration, rotary vacuum filtration, ultrafiltration, press filtration, cross membrane microfiltration, cross flow membrane microfiltration, or the like. Further enrichment or purification of the enzyme precipitate can be obtained by washing the precipitate with water. For example, the enriched or purified enzyme precipitate is washed with water containing the metal halide precipitation agent, or with water containing the metal halide and the organic compound precipitation agents.

During fermentation, a variant α-amylase polypeptide accumulates in the culture broth. For the isolation, enrichment, or purification of the desired variant α-amylase, the culture broth is centrifuged or filtered to eliminate cells, and the resulting cell-free liquid is used for enzyme enrichment or purification. In one embodiment, the cell-free broth is subjected to salting out using ammonium sulfate at about 70% saturation; the 70% saturation-precipitation fraction is then dissolved in a buffer and applied to a column such as a Sephadex G-100 column, and eluted to recover the enzyme-active fraction. For further enrichment or purification, a conventional procedure such as ion exchange chromatography may be used.

Enriched or purified enzymes are useful for laundry and cleaning applications. For example, they can be used in laundry detergents and spot removers. They can be made into a final product that is either liquid (solution, slurry) or solid (granular, powder).

A more specific example of enrichment or purification, is described in Sumitani et al. (2000) "New type of starch-binding domain: the direct repeat motif in the C-terminal region of *Bacillus* sp. 195 α-amylase contributes to starch binding and raw starch degrading," Biochem. J. 350: 477-484, and is briefly summarized here. The enzyme obtained from 4 liters of a *Streptomyces lividans* TK24 culture supernatant was treated with $(NH_4)_2SO_4$ at 80% saturation. The precipitate was recovered by centrifugation at 10,000×g (20 min. and 4° C.) and re-dissolved in 20 mM Tris/HCl buffer (pH 7.0) containing 5 mM $CaCl_2$. The solubilized precipitate was then dialyzed against the same buffer. The dialyzed sample was then applied to a Sephacryl S-200 column, which had previously been equilibrated with 20 mM Tris/HCl buffer, (pH 7.0), 5 mM $CaCl_2$, and eluted at a linear flow rate of 7 mL/hr with the same buffer. Fractions from the column were collected and assessed for activity as judged by enzyme assay and SDS-PAGE. The protein was further purified as follows. A Toyopearl HW55 column (Tosoh Bioscience, Montgomeryville, PA; Cat. No. 19812) was equilibrated with 20 mM Tris/HCl buffer (pH 7.0) containing 5 mM $CaCl_2$ and 1.5 M $(NH_4)_2SO_4$. The enzyme was eluted with a linear gradient of 1.5 to 0 M $(NH_4)_2SO_4$ in 20 mM Tris/HCL buffer, pH 7.0 containing 5 mM $CaCl_2$. The active fractions were collected, and the enzyme precipitated with $(NH_4)_2SO_4$ at 80% saturation. The precipitate was recovered, re-dissolved, and dialyzed as described above. The dialyzed sample was then applied to a Mono Q HR5/5 column (Amersham Pharmacia; Cat. No. 17-5167-01) previously equilibrated with 20 mM Tris/HCl buffer (pH 7.0) containing 5 mM $CaCl_2$, at a flow rate of 60 mL/hour. The active fractions are collected and added to a 1.5 M $(NH_4)_2SO_4$ solution. The active enzyme fractions were re-chromatographed on a Toyopearl HW55 column, as before, to yield a homogeneous enzyme as determined by SDS-PAGE. See Sumitani et al. (2000) *Biochem. J.* 350: 477-484, for general discussion of the method and variations thereon.

For production scale recovery, variant α-amylase polypeptides can be enriched or partially purified as generally described above by removing cells via flocculation with polymers. Alternatively, the enzyme can be enriched or purified by microfiltration followed by concentration by ultrafiltration using available membranes and equipment. However, for some applications, the enzyme does not need to be enriched or purified, and whole broth culture can be lysed and used without further treatment. The enzyme can then be processed, for example, into granules.

4. Compositions and Uses of Variant Amylases

Variants amylases are useful for a variety of industrial applications. For example, variant amylases are useful in a starch conversion process, particularly in a saccharification process of a starch that has undergone liquefaction. The desired end-product may be any product that may be produced by the enzymatic conversion of the starch substrate. For example, the desired product may be a syrup rich in glucose and maltose, which can be used in other processes, such as the preparation of HFCS, or which can be converted into a number of other useful products, such as ascorbic acid intermediates (e.g., gluconate; 2-keto-L-gluconic acid; 5-keto-gluconate; and 2,5-diketogluconate); 1,3-propanediol; aromatic amino acids (e.g., tyrosine, phenylalanine and tryptophan); organic acids (e.g., lactate, pyruvate, succinate, isocitrate, and oxaloacetate); amino acids (e.g., serine and glycine); antibiotics; antimicrobials; enzymes; vitamins; and hormones.

The starch conversion process may be a precursor to, or simultaneous with, a fermentation process designed to produce alcohol for fuel or drinking (i.e., potable alcohol). One skilled in the art is aware of various fermentation conditions that may be used in the production of these end-products. Variant amylases are also useful in compositions and methods of food preparation. These various uses of variant amylases are described in more detail below.

4.1. Preparation of Starch Substrates

Those of general skill in the art are well aware of available methods that may be used to prepare starch substrates for use in the processes disclosed herein. For example, a useful starch substrate may be obtained from tubers, roots, stems, legumes, cereals or whole grain. More specifically, the granular starch may be obtained from corn, cobs, wheat, barley, rye, triticale, milo, sago, millet, cassava, tapioca, sorghum, rice, peas, bean, banana, or potatoes. Corn contains about 60-68% starch; barley contains about 55-65% starch; millet contains about 75-80% starch; wheat contains about 60-65% starch; and polished rice contains 70-72% starch. Specifically contemplated starch substrates are corn starch and wheat starch. The starch from a grain may be ground or whole and includes corn solids, such as kernels, bran and/or cobs. The starch may also be highly refined raw starch or feedstock from starch refinery processes. Various starches also are commercially available. For example, corn starch is available from Cerestar, Sigma, and Katayama Chemical Industry Co. (Japan); wheat starch is available from Sigma; sweet potato starch is available from Wako Pure Chemical Industry Co. (Japan); and potato starch is available from Nakaari Chemical Pharmaceutical Co. (Japan).

The starch substrate can be a crude starch from milled whole grain, which contains non-starch fractions, e.g., germ residues and fibers. Milling may comprise either wet milling or dry milling or grinding. In wet milling, whole grain is soaked in water or dilute acid to separate the grain into its component parts, e.g., starch, protein, germ, oil, kernel fibers. Wet milling efficiently separates the germ and meal (i.e., starch granules and protein) and is especially suitable for production of syrups. In dry milling or grinding, whole kernels are ground into a fine powder and often processed without fractionating the grain into its component parts. In some cases, oils from the kernels are recovered. Dry ground grain thus will comprise significant amounts of non-starch carbohydrate compounds, in addition to starch. Dry grinding of the starch substrate can be used for production of ethanol and other biochemicals. The starch to be processed may be a highly refined starch quality, for example, at least 90%, at least 95%, at least 97%, or at least 99.5% pure.

4.2. Gelatinization and Liquefaction of Starch

As used herein, the term "liquefaction" or "liquefy" means a process by which starch is converted to less viscous and shorter chain dextrins. Generally, this process involves gelatinization of starch simultaneously with or followed by the addition of an α-amylase, although additional liquefaction-inducing enzymes optionally may be added. In some embodiments, the starch substrate prepared as described above is slurried with water. The starch slurry may contain starch as a weight percent of dry solids of about 10-55%, about 20-45%, about 30-45%, about 30-40%, or about 30-35%. α-Amylase (EC 3.2.1.1) may be added to the slurry, with a metering pump, for example. The α-amylase typically used for this application is a thermally stable, bacterial α-amylase, such as a *Geobacillus stearothermophilus* α-amylase. The α-amylase is usually supplied, for example, at about 1500 units per kg dry matter of starch. To optimize α-amylase stability and activity, the pH of the slurry typically is adjusted to about pH 5.5-6.5 and about 1 mM of calcium (about 40 ppm free calcium ions) can also be added. *Geobacillus stearothermophilus* variants or other α-amylases may require different conditions. Bacterial α-amylase remaining in the slurry following liquefaction may be deactivated via a number of methods, including lowering the pH in a subsequent reaction step or by removing calcium from the slurry in cases where the enzyme is dependent upon calcium.

The slurry of starch plus the α-amylase may be pumped continuously through a jet cooker, which is steam heated to 105° C. Gelatinization occurs rapidly under these conditions, and the enzymatic activity, combined with the significant shear forces, begins the hydrolysis of the starch substrate. The residence time in the jet cooker is brief. The partly gelatinized starch may be passed into a series of holding tubes maintained at 105-110° C. and held for 5-8 min. to complete the gelatinization process ("primary liquefaction"). Hydrolysis to the required DE is completed in holding tanks at 85-95° C. or higher temperatures for about 1 to 2 hours ("secondary liquefaction"). These tanks may contain baffles to discourage back mixing. As used herein, the term "minutes of secondary liquefaction" refers to the time that has elapsed from the start of secondary liquefaction to the time that the Dextrose Equivalent (DE) is measured. The slurry is then allowed to cool to room temperature. This cooling step can be 30 minutes to 180 minutes, e.g. 90 minutes to 120 minutes. The liquefied starch typically is in the form of a slurry having a dry solids content (w/w) of about 10-50%; about 10-45%; about 15-40%; about 20-40%; about 25-40%; or about 25-35%.

Liquefaction with variant amylases advantageously can be conducted at low pH, eliminating the requirement to adjust the pH to about pH 5.5-6.5. Variants amylases can be used for liquefaction at a pH range of 2 to 7, e.g., pH 3.0-7.5, pH 4.0-6.0, or pH 4.5-5.8. Variant amylases can maintain liquefying activity at a temperature range of about 85° C.-95° C., e.g., 85° C., 90° C., or 95° C. For example, liquefaction can be conducted with 800 μg an amylase in a solution of 25% DS corn starch for 10 min at pH 5.8 and 85° C., or pH 4.5 and 95° C., for example. Liquefying activity can be assayed using any of a number of known viscosity assays in the art.

4.3. Saccharification

The liquefied starch can be saccharified into a syrup rich in lower DP (e.g., DP1+DP2) saccharides, using variant amylases, optionally in the presence of another enzyme(s). The exact composition of the products of saccharification depends on the combination of enzymes used, as well as the type of granular starch processed. Advantageously, the syrup obtainable using the provided variant amylases may contain a weight percent of DP2 of the total oligosaccharides in the saccharified starch exceeding 30%, e.g., 45%-65% or 55%-65%. The weight percent of (DP1+DP2) in the saccharified starch may exceed about 70%, e.g., 75%-85% or 80%-85%. The present amylases also produce a relatively high yield of glucose, e.g., DP1>20%, in the syrup product.

Whereas liquefaction is generally run as a continuous process, saccharification is often conducted as a batch process. Saccharification typically is most effective at temperatures of about 60-65° C. and a pH of about 4.0-4.5, e.g., pH 4.3, necessitating cooling and adjusting the pH of the liquefied starch. Saccharification may be performed, for example, at a temperature between about 40° C., about 50° C., or about 55° C. to about 60° C. or about 65° C. Saccharification is normally conducted in stirred tanks, which may take several hours to fill or empty. Enzymes typically are added either at a fixed ratio to dried solids as the tanks are filled or added as a single dose at the commencement of the filling stage. A saccharification reaction to make a syrup typically is run over about 24-72 hours, for example, 24-48 hours. When a maximum or desired DE has been attained, the reaction is stopped by heating to 85° C. for 5 min., for example. Further incubation will result in a lower DE, eventually to about 90 DE, as accumulated glucose re-polymerizes to isomaltose and/or other reversion products via an enzymatic reversion reaction and/or with the approach of thermodynamic equilibrium. When using an amylase, saccharification optimally is conducted at a temperature range of about 30° C. to about 75° C., e.g., 45° C.-75° C. or 47° C.-74° C. The saccharifying may be conducted over a pH range of about pH 3 to about pH 7, e.g., pH 3.0-pH 7.5, pH 3.5-pH 5.5, pH 3.5, pH 3.8, or pH 4.5.

An amylase may be added to the slurry in the form of a composition. Amylase can be added to a slurry of a granular starch substrate in an amount of about 0.6-10 ppm ds, e.g., 2 ppm ds. An amylase can be added as a whole broth, clarified, enriched, partially purified, or purified enzyme. The specific activity of the amylase may be about 300 U/mg of enzyme, for example, measured with the PAHBAH assay. The amylase also can be added as a whole broth product.

An amylase may be added to the slurry as an isolated enzyme solution. For example, an amylase can be added in the form of a cultured cell material produced by host cells expressing an amylase. An amylase may also be secreted by a host cell into the reaction medium during the fermentation or SSF process, such that the enzyme is provided continuously into the reaction. The host cell producing and secreting amylase may also express an additional enzyme, such as a glucoamylase. For example, U.S. Pat. No. 5,422,267 discloses the use of a glucoamylase in yeast for production of alcoholic beverages. For example, a host cell, e.g., *Trichoderma reesei* or *Aspergillus niger*, may be engineered to co-express an amylase and a glucoamylase, e.g., HgGA, TrGA, or a TrGA variant, during saccharification. The host cell can be genetically modified so as not to express its endogenous glucoamylase and/or other enzymes, proteins or other materials. The host cell can be engineered to express a broad spectrum of various saccharolytic enzymes. For example, the recombinant yeast host cell can comprise nucleic acids encoding a glucoamylase, an alpha-glucosidase, an enzyme that utilizes pentose sugar, an α-amylase, a pullulanse, an isoamylase, and/or an isopullulanase. See, e.g., WO 2011/153516 A2.

4.4. Isomerization

The soluble starch hydrolysate produced by treatment with amylase can be converted into high fructose starch-based syrup (HFSS), such as high fructose corn syrup (HFCS). This conversion can be achieved using a glucose isomerase, particularly a glucose isomerase immobilized on a solid support. The pH is increased to about 6.0 to about 8.0, e.g., pH 7.5 (depending on the isomerase), and Ca' is removed by ion exchange. Suitable isomerases include Sweetzyme®, IT (Novozymes A/S); G-zyme® IMGI, and G-zyme® G993, Ketomax®, G-zyme® G993, G-zyme® G993 liquid, and GenSweet® IGI. Following isomerization, the mixture typically contains about 40-45% fructose, e.g., 42% fructose.

4.5. Fermentation

The soluble starch hydrolysate, particularly a glucose rich syrup, can be fermented by contacting the starch hydrolysate with a fermenting organism typically at a temperature around 32° C., such as from 30° C. to 35° C. for alcohol-producing yeast. The temperature and pH of the fermentation will depend upon the fermenting organism. EOF products include metabolites, such as citric acid, lactic acid, succinic acid, monosodium glutamate, gluconic acid, sodium gluconate, calcium gluconate, potassium gluconate, itaconic acid and other carboxylic acids, glucono delta-lactone, sodium erythorbate, lysine and other amino acids, omega 3 fatty acid, butanol, isoprene, 1,3-propanediol and other biomaterials.

Ethanologenic microorganisms include yeast, such as *Saccharomyces cerevisiae* and bacteria, e.g., *Zymomonas moblis*, expressing alcohol dehydrogenase and pyruvate decarboxylase. The ethanologenic microorganism can express xylose reductase and xylitol dehydrogenase, which convert xylose to xylulose. Improved strains of ethanologenic microorganisms, which can withstand higher temperatures, for example, are known in the art and can be used. See Liu et al. (2011) *Sheng Wu Gong Cheng Xue Bao* 27(7): 1049-56. Commercial sources of yeast include ETHANOL RED® (LeSaffre); Thermosacc® (Lallemand); RED STAR® (Red Star); FERMIOL® (DSM Specialties); and SUPERSTART® (Alltech). Microorganisms that produce other metabolites, such as citric acid and lactic acid, by fermentation are also known in the art. See, e.g., Papagianni (2007) "Advances in citric acid fermentation by *Aspergillus niger*: biochemical aspects, membrane transport and modeling," *Biotechnol. Adv.* 25(3): 244-63; John et al. (2009) "Direct lactic acid fermentation: focus on simultaneous saccharification and lactic acid production," *Biotechnol. Adv.* 27(2): 145-52.

The saccharification and fermentation processes may be carried out as an SSF process. Fermentation may comprise subsequent enrichment, purification, and recovery of ethanol, for example. During the fermentation, the ethanol content of the broth or "beer" may reach about 8-18% v/v, e.g., 14-15% v/v. The broth may be distilled to produce enriched, e.g., 96% pure, solutions of ethanol. Further, $CO_2$ generated by fermentation may be collected with a $CO_2$ scrubber, compressed, and marketed for other uses, e.g., carbonating beverage or dry ice production. Solid waste from the fermentation process may be used as protein-rich products, e.g., livestock feed.

As mentioned above, an SSF process can be conducted with fungal cells that express and secrete amylase continuously throughout SSF. The fungal cells expressing amylase also can be the fermenting microorganism, e.g., an ethanologenic microorganism. Ethanol production thus can be carried out using a fungal cell that expresses sufficient amylase so that less or no enzyme has to be added exogenously. The fungal host cell can be from an appropriately engineered fungal strain. Fungal host cells that express and secrete other enzymes, in addition to amylase, also can be used. Such cells may express glucoamylase and/or a pullulanase, phytase, alpha-glucosidase, isoamylase, beta-amylase cellulase, xylanase, other hemicellulases, protease, beta-glucosidase, pectinase, esterase, redox enzymes, transferase, or other enzyme.

A variation on this process is a "fed-batch fermentation" system, where the substrate is added in increments as the fermentation progresses. Fed-batch systems are useful when catabolite repression may inhibit the metabolism of the cells and where it is desirable to have limited amounts of substrate in the medium. The actual substrate concentration in fed-batch systems is estimated by the changes of measurable factors such as pH, dissolved oxygen and the partial pressure of waste gases, such as $CO_2$. Batch and fed-batch fermentations are common and well known in the art.

Continuous fermentation is an open system where a defined fermentation medium is added continuously to a bioreactor, and an equal amount of conditioned medium is removed simultaneously for processing. Continuous fermentation generally maintains the cultures at a constant high density where cells are primarily in log phase growth. Continuous fermentation permits modulation of cell growth and/or product concentration. For example, a limiting nutrient such as the carbon source or nitrogen source is maintained at a fixed rate and all other parameters are allowed to moderate. Because growth is maintained at a steady state, cell loss due to medium being drawn off should be balanced against the cell growth rate in the fermentation. Methods of optimizing continuous fermentation processes and maximizing the rate of product formation are well known in the art of industrial microbiology.

4.6. Compositions Comprising Variants Amylases

Variant amylases may be combined with a glucoamylase (EC 3.2.1.3), e.g., a *Trichoderma* glucoamylase or variant thereof. An exemplary glucoamylase is *Trichoderma reesei* glucoamylase (TrGA) and variants thereof that possess superior specific activity and thermal stability. See U.S.

Published Applications Nos. 2006/0094080, 2007/0004018, and 2007/0015266 (Danisco US Inc.). Suitable variants of TrGA include those with glucoamylase activity and at least 80%, at least 90%, or at least 95% sequence identity to wild-type TrGA. Variant amylases advantageously increase the yield of glucose produced in a saccharification process catalyzed by TrGA.

Alternatively, the glucoamylase may be another glucoamylase derived from plants (including algae), fungi, or bacteria. For example, the glucoamylases may be *Aspergillus niger* G1 or G2 glucoamylase or its variants (e.g., Boel et al. (1984) *EMBO J.* 3: 1097-1102; WO 92/00381; WO 00/04136 (Novo Nordisk A/S)); and *A. awamori* glucoamylase (e.g., WO 84/02921 (Cetus Corp.)). Other contemplated *Aspergillus* glucoamylase include variants with enhanced thermal stability, e.g., G137A and G139A (Chen et al. (1996) *Prot. Eng.* 9: 499-505); D257E and D293E/Q (Chen et al. (1995) *Prot. Eng.* 8: 575-582); N182 (Chen et al. (1994) *Biochem. J.* 301: 275-281); A246C (Fierobe et al. (1996) *Biochemistry*, 35: 8698-8704); and variants with Pro residues in positions A435 and S436 (Li et al. (1997) *Protein Eng.* 10: 1199-1204). Other contemplated glucoamylases include *Talaromyces* glucoamylases, in particular derived from *T. emersonii* (e.g., WO 99/28448 (Novo Nordisk A/S), *T. leycettanus* (e.g., U.S. Pat. No. RE 32,153 (CPC International, Inc.)), *T. duponti*, or *T. thermophilus* (e.g., U.S. Pat. No. 4,587,215). Contemplated bacterial glucoamylases include glucoamylases from the genus *Clostridium*, in particular *C. thermoamylolyticum* (e.g., EP 135,138 (CPC International, Inc.) and *C. thermohydrosulfuricum* (e.g., WO 86/01831 (Michigan Biotechnology Institute)). Suitable glucoamylases include the glucoamylases derived from *Aspergillus oryzae*, such as a glucoamylase shown in SEQ ID NO:2 in WO 00/04136 (Novo Nordisk A/S). Also suitable are commercial glucoamylases, such as AMG 200L; AMG 300 L; SAN™ SUPER and AMG™ E (Novozymes); OPTIDEX® 300 and OPTIDEX L-400 (Danisco US Inc.); AMIGASE™ and AMIGASE™ PLUS (DSM); G-ZYME® G900 (Enzyme Bio-Systems); and G-ZYME® G990 ZR (*A. niger* glucoamylase with a low protease content). Still other suitable glucoamylases include *Aspergillus fumigatus* glucoamylase, *Talaromyces* glucoamylase, *Thielavia* glucoamylase, *Trametes* glucoamylase, *Thermomyces* glucoamylase, *Athelia* glucoamylase, or *Humicola* glucoamylase (e.g., HgGA). Glucoamylases typically are added in an amount of about 0.1-2 glucoamylase units (GAU)/g ds, e.g., about 0.16 GAU/g ds, 0.23 GAU/g ds, or 0.33 GAU/g ds.

Other suitable enzymes that can be used with amylase include a phytase, protease, pullulanase, β-amylase, isoamylase, a different α-amylase, alpha-glucosidase, cellulase, xylanase, other hemicellulases, beta-glucosidase, transferase, pectinase, lipase, cutinase, esterase, redox enzymes, or a combination thereof. For example, a debranching enzyme, such as an isoamylase (EC 3.2.1.68), may be added in effective amounts well known to the person skilled in the art. A pullulanase (EC 3.2.1.41), e.g., Promozyme®, is also suitable. Pullulanase typically is added at 100 U/kg ds. Further suitable enzymes include proteases, such as fungal and bacterial proteases. Fungal proteases include those obtained from *Aspergillus*, such as *A. niger*, *A. awamori*, *A. oryzae*; *Mucor* (e.g., *M. miehei*); *Rhizopus*; and *Trichoderma*.

β-Amylases (EC 3.2.1.2) are exo-acting maltogenic amylases, which catalyze the hydrolysis of 1,4-α-glucosidic linkages into amylopectin and related glucose polymers, thereby releasing maltose. β-Amylases have been isolated from various plants and microorganisms. See Fogarty et al. (1979) in PROGRESS IN INDUSTRIAL MICROBIOLOGY, Vol. 15, pp. 112-115. These β-Amylases have optimum temperatures in the range from 40° C. to 65° C. and optimum pH in the range from about 4.5 to about 7.0. Contemplated β-amylases include, but are not limited to, β-amylases from barley Spezyme® BBA 1500, Spezyme® DBA, Optimalt™ ME, Optimalt™ BBA (Danisco US Inc.); and Novozym™ WBA (Novozymes A/S).

Compositions comprising the present amylases may be aqueous or non-aqueous formulations, granules, powders, gels, slurries, pastes, etc., which may further comprise any one or more of the additional enzymes listed, herein, along with buffers, salts, preservatives, water, co-solvents, surfactants, and the like. Such compositions may work in combination with endogenous enzymes or other ingredients already present in a slurry, water bath, washing machine, food or drink product, etc, for example, endogenous plant (including algal) enzymes, residual enzymes from a prior processing step, and the like.

5. Compositions and Methods for Baking and Food Preparation

The present invention also relates to a "food composition," including but not limited to a food product, animal feed and/or food/feed additives, comprising an amylase, and methods for preparing such a food composition comprising mixing variant amylase with one or more food ingredients, or uses thereof.

Furthermore, the present invention relates to the use of an amylase in the preparation of a food composition, wherein the food composition is baked subsequent to the addition of the polypeptide of the invention. As used herein the term "baking composition" means any composition and/or additive prepared in the process of providing a baked food product, including but not limited to bakers flour, a dough, a baking additive and/or a baked product. The food composition or additive may be liquid or solid.

As used herein, the term "flour" means milled or ground cereal grain. The term "flour" also may mean Sago or tuber products that have been ground or mashed. In some embodiments, flour may also contain components in addition to the milled or mashed cereal or plant matter. An example of an additional component, although not intended to be limiting, is a leavening agent. Cereal grains include wheat, oat, rye, and barley. Tuber products include tapioca flour, cassava flour, and custard powder. The term "flour" also includes ground corn flour, maize-meal, rice flour, whole-meal flour, self-rising flour, tapioca flour, cassava flour, ground rice, enriched flower, and custard powder.

For the commercial and home use of flour for baking and food production, it is important to maintain an appropriate level of α-amylase activity in the flour. A level of activity that is too high may result in a product that is sticky and/or doughy and therefore unmarketable. Flour with insufficient α-amylase activity may not contain enough sugar for proper yeast function, resulting in dry, crumbly bread, or baked products. Accordingly, an amylase, by itself or in combination with another α-amylase(s), may be added to the flour to augment the level of endogenous α-amylase activity in flour.

An amylase can further be added alone or in a combination with other amylases to prevent or retard staling, i.e., crumb firming of baked products. The amount of anti-staling amylase will typically be in the range of 0.01-10 mg of enzyme protein per kg of flour, e.g., 0.5 mg/kg ds. Additional anti-staling amylases that can be used in combination with an amylase include an endo-amylase, e.g., a bacterial endo-amylase from *Bacillus*. The additional amylase can be another maltogenic α-amylase (EC 3.2.1.133), e.g., from *Bacillus*. Novamyl® is an exemplary maltogenic α-amylase from *B. stearothermophilus* strain NCIB 11837 and is described in Christophersen et al. (1997) Starch 50: 39-45. Other examples of anti-staling endo-amylases include bacterial α-amylases derived from *Bacillus*, such as *B. licheniformis* or *B. amyloliquefaciens*. The anti-staling amylase may be an exo-amylase, such as β-amylase, e.g., from plant sources, such as soy bean, or from microbial sources, such as *Bacillus*.

The baking composition comprising an amylase further can comprise a phospholipase or enzyme with phospholipase activity. An enzyme with phospholipase activity has an activity that can be measured in Lipase Units (LU). The phospholipase may have $A_1$ or $A_2$ activity to remove fatty acid from the phospholipids, forming a lysophospholipid. It may or may not have lipase activity, i.e., activity on triglyceride substrates. The phospholipase typically has a temperature optimum in the range of 30-90° C., e.g., 30-70° C. The added phospholipases can be of animal origin, for example, from pancreas, e.g., bovine or porcine pancreas, snake venom or bee venom. Alternatively, the phospholipase may be of microbial origin, e.g., from filamentous fungi, yeast or bacteria, for example.

The phospholipase is added in an amount that improves the softness of the bread during the initial period after baking, particularly the first 24 hours. The amount of phospholipase will typically be in the range of 0.01-10 mg of enzyme protein per kg of flour, e.g., 0.1-5 mg/kg. That is, phospholipase activity generally will be in the range of 20-1000 LU/kg of flour, where a Lipase Unit is defined as the amount of enzyme required to release 1 µmol butyric acid per minute at 30° C., pH 7.0, with gum arabic as emulsifier and tributyrin as substrate.

Compositions of dough generally comprise wheat meal or wheat flour and/or other types of meal, flour or starch such as corn flour, cornstarch, rye meal, rye flour, oat flour, oatmeal, soy flour, sorghum meal, sorghum flour, potato meal, potato flour or potato starch. The dough may be fresh, frozen or par-baked. The dough can be a leavened dough or a dough to be subjected to leavening. The dough may be leavened in various ways, such as by adding chemical leavening agents, e.g., sodium bicarbonate or by adding a leaven, i.e., fermenting dough. Dough also may be leavened by adding a suitable yeast culture, such as a culture of *Saccharomyces cerevisiae* (baker's yeast), e.g., a commercially available strain of *S. cerevisiae*.

The dough may also comprise other conventional dough ingredients, e.g., proteins, such as milk powder, gluten, and soy; eggs (e.g., whole eggs, egg yolks or egg whites); an oxidant, such as ascorbic acid, potassium bromate, potassium iodate, azodicarbonamide (ADA) or ammonium persulfate; an amino acid such as L-cysteine; a sugar; or a salt, such as sodium chloride, calcium acetate, sodium sulfate or calcium sulfate. The dough further may comprise fat, e.g., triglyceride, such as granulated fat or shortening. The dough further may comprise an emulsifier such as mono- or diglycerides, diacetyl tartaric acid esters of mono- or diglycerides, sugar esters of fatty acids, polyglycerol esters of fatty acids, lactic acid esters of monoglycerides, acetic acid esters of monoglycerides, polyoxyethylene stearates, or lysolecithin. In particular, the dough can be made without addition of emulsifiers.

The dough product may be any processed dough product, including fried, deep fried, roasted, baked, steamed and boiled doughs, such as steamed bread and rice cakes. In one embodiment, the food product is a bakery product. Typical bakery (baked) products include bread—such as loaves, rolls, buns, bagels, pizza bases etc. pastry, pretzels, tortillas, cakes, cookies, biscuits, crackers etc.

Optionally, an additional enzyme may be used together with the anti-staling amylase and the phospholipase. The additional enzyme may be a second amylase, such as an amyloglucosidase, a β-amylase, a cyclodextrin glucanotransferase, or the additional enzyme may be a peptidase, in particular an exopeptidase, a transglutaminase, a lipase, a cellulase, a xylanase, a protease, a protein disulfide isomerase, e.g., a protein disulfide isomerase as disclosed in WO 95/00636, for example, a glycosyltransferase, a branching enzyme (1,4-α-glucan branching enzyme), a 4-α-glucanotransferase (dextrin glycosyltransferase) or an oxidoreductase, e.g., a peroxidase, a laccase, a glucose oxidase, a pyranose oxidase, a lipooxygenase, an L-amino acid oxidase or a carbohydrate oxidase. The additional enzyme(s) may be of any origin, including mammalian and plant, and particularly of microbial (bacterial, yeast or fungal) origin and may be obtained by techniques conventionally used in the art.

The xylanase is typically of microbial origin, e.g., derived from a bacterium or fungus, such as a strain of *Aspergillus*. Xylanases include Pentopan® and Novozym 384®, for example, which are commercially available xylanase preparations produced from *Trichoderma reesei*. The amyloglucosidase may be an *A. niger* amyloglucosidase (such as AMG®). Other useful amylase products include Grindamyl® A 1000 or A 5000 (Grindsted Products, Denmark) and Amylase® H or Amylase® P (DSM). The glucose oxidase may be a fungal glucose oxidase, in particular an *Aspergillus niger* glucose oxidase (such as Gluzyme®). An exemplary protease is Neutrase®.

The process may be used for any kind of baked product prepared from dough, either of a soft or a crisp character, either of a white, light or dark type. Examples are bread, particularly white, whole-meal or rye bread, typically in the form of loaves or rolls, such as, but not limited to, French baguette-type bread, pita bread, tortillas, cakes, pancakes, biscuits, cookies, pie crusts, crisp bread, steamed bread, pizza and the like.

An amylase may be used in a pre-mix, comprising flour together with an anti-staling amylase, a phospholipase, and/or a phospholipid. The pre-mix may contain other dough-improving and/or bread-improving additives, e.g., any of the additives, including enzymes, mentioned above. An amylase can be a component of an enzyme preparation comprising an anti-staling amylase and a phospholipase, for use as a baking additive.

The enzyme preparation is optionally in the form of a granulate or agglomerated powder. The preparation can have a narrow particle size distribution with more than 95% (by weight) of the particles in the range from 25 to 500 µm. Granulates and agglomerated powders may be prepared by conventional methods, e.g., by spraying an amylase onto a carrier in a fluid-bed granulator. The carrier may consist of particulate cores having a suitable particle size. The carrier may be soluble or insoluble, e.g., a salt (such as NaCl or sodium sulfate), a sugar (such as sucrose or lactose), a sugar alcohol (such as sorbitol), starch, rice, corn grits, or soy.

Enveloped particles, i.e., α-amylase particles, can comprise an amylase. To prepare enveloped α-amylase particles, the enzyme is contacted with a food grade lipid in sufficient quantity to suspend all of the α-amylase particles. Food grade lipids, as used herein, may be any naturally organic compound that is insoluble in water but is soluble in non-polar organic solvents such as hydrocarbon or diethyl ether. Suitable food grade lipids include, but are not limited to, triglycerides either in the form of fats or oils that are either saturated or unsaturated. Examples of fatty acids and combinations thereof which make up the saturated triglycerides include, but are not limited to, butyric (derived from milk fat), palmitic (derived from animal and plant fat), and/or stearic (derived from animal and plant fat). Examples of fatty acids and combinations thereof which make up the unsaturated triglycerides include, but are not limited to, palmitoleic (derived from animal and plant fat), oleic (derived from animal and plant fat), linoleic (derived from plant oils), and/or linolenic (derived from linseed oil). Other suitable food grade lipids include, but are not limited to, monoglycerides and diglycerides derived from the triglycerides discussed above, phospholipids and glycolipids.

The food grade lipid, particularly in the liquid form, is contacted with a powdered form of the α-amylase particles in such a fashion that the lipid material covers at least a portion of the surface of at least a majority, e.g., 100% of the α-amylase particles. Thus, each α-amylase particle is individually enveloped in a lipid. For example, all or substantially all of the α-amylase particles are provided with a thin, continuous, enveloping film of lipid. This can be accomplished by first pouring a quantity of lipid into a container, and then slurrying the α-amylase particles so that the lipid thoroughly wets the surface of each α-amylase particle. After a short period of stirring, the enveloped α-amylase particles, carrying a substantial amount of the lipids on their surfaces, are recovered. The thickness of the coating so applied to the particles of α-amylase can be controlled by selection of the type of lipid used and by repeating the operation in order to build up a thicker film, when desired.

The storing, handling and incorporation of the loaded delivery vehicle can be accomplished by means of a packaged mix. The packaged mix can comprise the enveloped α-amylase. However, the packaged mix may further contain additional ingredients as required by the manufacturer or baker. After the enveloped α-amylase has been incorporated into the dough, the baker continues through the normal production process for that product.

The advantages of enveloping the α-amylase particles are two-fold. First, the food grade lipid protects the enzyme from thermal denaturation during the baking process for those enzymes that are heat labile. Consequently, while the α-amylase is stabilized and protected during the proving and baking stages, it is released from the protective coating in the final baked good product, where it hydrolyzes the glucosidic linkages in polyglucans. The loaded delivery vehicle also provides a sustained release of the active enzyme into the baked good. That is, following the baking process, active α-amylase is continually released from the protective coating at a rate that counteracts, and therefore reduces the rate of, staling mechanisms.

In general, the amount of lipid applied to the α-amylase particles can vary from a few percent of the total weight of the α-amylase to many times that weight, depending upon the nature of the lipid, the manner in which it is applied to the α-amylase particles, the composition of the dough mixture to be treated, and the severity of the dough-mixing operation involved.

The loaded delivery vehicle, i.e., the lipid-enveloped enzyme, is added to the ingredients used to prepare a baked good in an effective amount to extend the shelf-life of the baked good. The baker computes the amount of enveloped α-amylase, prepared as discussed above, that will be required to achieve the desired anti-staling effect. The amount of the enveloped α-amylase required is calculated based on the concentration of enzyme enveloped and on the proportion of α-amylase to flour specified. A wide range of concentrations has been found to be effective, although, as has been discussed, observable improvements in anti-staling do not correspond linearly with the α-amylase concentration, but above certain minimal levels, large increases in α-amylase concentration produce little additional improvement. The α-amylase concentration actually used in a particular bakery production could be much higher than the minimum necessary to provide the baker with some insurance against inadvertent under-measurement errors by the baker. The lower limit of enzyme concentration is determined by the minimum anti-staling effect the baker wishes to achieve.

A method of preparing a baked good may comprise: a) preparing lipid-coated α-amylase particles, where substantially all of the α-amylase particles are coated; b) mixing a dough containing flour; c) adding the lipid-coated α-amylase to the dough before the mixing is complete and terminating the mixing before the lipid coating is removed from the α-amylase; d) proofing the dough; and e) baking the dough to provide the baked good, where the α-amylase is inactive during the mixing, proofing and baking stages and is active in the baked good.

The enveloped α-amylase can be added to the dough during the mix cycle, e.g., near the end of the mix cycle. The enveloped α-amylase is added at a point in the mixing stage that allows sufficient distribution of the enveloped α-amylase throughout the dough; however, the mixing stage is terminated before the protective coating becomes stripped from the α-amylase particle(s). Depending on the type and volume of dough, and mixer action and speed, anywhere from one to six minutes or more might be required to mix the enveloped α-amylase into the dough, but two to four minutes is average. Thus, several variables may determine the precise procedure. First, the quantity of enveloped α-amylase should have a total volume sufficient to allow the enveloped α-amylase to be spread throughout the dough mix. If the preparation of enveloped α-amylase is highly concentrated, additional oil may need to be added to the pre-mix before the enveloped α-amylase is added to the dough. Recipes and production processes may require specific modifications; however, good results generally can be achieved when 25% of the oil specified in a bread dough formula is held out of the dough and is used as a carrier for a concentrated enveloped α-amylase when added near the end of the mix cycle. In bread or other baked goods, particularly those having a low fat content, e.g., French-style breads, an enveloped α-amylase mixture of approximately 1% of the dry flour weight is sufficient to admix the enveloped α-amylase properly with the dough. The range of suitable percentages is wide and depends on the formula, finished product, and production methodology requirements of the individual baker. Second, the enveloped α-amylase suspension should be added to the mix with sufficient time for complete mixture into the dough, but not for such a time that excessive mechanical action strips the protective lipid coating from the enveloped α-amylase particles.

In a further aspect of the invention, the food composition is an oil, meat, lard, composition comprising an amylase. In this context the term "oil/meat/lard" composition" means any composition, based on, made from and/or containing oil, meat or lard, respectively. Another aspect the invention relates to a method of preparing an oil or meat or lard composition and/or additive comprising an amylase, comprising mixing the polypeptide of the invention with a oil/meat/lard composition and/or additive ingredients.

In a further aspect of the invention, the food composition is an animal feed composition, animal feed additive and/or pet food comprising an amylase and variants thereof. The present invention further relates to a method for preparing such an animal feed composition, animal feed additive composition and/or pet food comprising mixing an amylase and variants thereof with one or more animal feed ingredients and/or animal feed additive ingredients and/or pet food ingredients. Furthermore, the present invention relates to the use of an amylase in the preparation of an animal feed composition and/or animal feed additive composition and/or pet food.

The term "animal" includes all non-ruminant and ruminant animals. In a particular embodiment, the animal is a non-ruminant animal, such as a horse and a mono-gastric animal. Examples of mono-gastric animals include, but are not limited to, pigs and swine, such as piglets, growing pigs, sows; poultry such as turkeys, ducks, chicken, broiler chicks, layers; fish such as salmon, trout, tilapia, catfish and carps; and crustaceans such as shrimps and prawns. In a further embodiment the animal is a ruminant animal including, but not limited to, cattle, young calves, goats, sheep, giraffes, bison, moose, elk, yaks, water buffalo, deer, camels, alpacas, llamas, antelope, pronghorn and nilgai.

In the present context, it is intended that the term "pet food" is understood to mean a food for a household animal such as, but not limited to dogs, cats, gerbils, hamsters, chinchillas, fancy rats, guinea pigs; avian pets, such as *canaries*, parakeets, and parrots; reptile pets, such as turtles, lizards and snakes; and aquatic pets, such as tropical fish and frogs.

The terms "animal feed composition," "feedstuff" and "fodder" are used interchangeably and may comprise one or more feed materials selected from the group comprising a) cereals, such as small grains (e.g., wheat, barley, rye, oats and combinations thereof) and/or large grains such as maize or sorghum; b) by products from cereals, such as corn gluten meal, Distillers Dried Grain Solubles (DDGS) (particularly corn based Distillers Dried Grain Solubles (cDDGS), wheat bran, wheat middlings, wheat shorts, rice bran, rice hulls, oat hulls, palm kernel, and citrus pulp; c) protein obtained from sources such as soya, sunflower, peanut, lupin, peas, fava beans, cotton, canola, fish meal, dried plasma protein, meat and bone meal, potato protein, whey, copra, sesame; d) oils and fats obtained from vegetable and animal sources; e) minerals and vitamins.

6. Textile Desizing Compositions and Use

Also contemplated are compositions and methods of treating fabrics (e.g., to desize a textile) using an amylase. Fabric-treating methods are well known in the art (see, e.g., U.S. Pat. No. 6,077,316). For example, the feel and appearance of a fabric can be improved by a method comprising contacting the fabric with an amylase in a solution. The fabric can be treated with the solution under pressure.

An amylase can be applied during or after the weaving of a textile, or during the desizing stage, or one or more additional fabric processing steps. During the weaving of textiles, the threads are exposed to considerable mechanical strain. Prior to weaving on mechanical looms, warp yarns are often coated with sizing starch or starch derivatives to increase their tensile strength and to prevent breaking. An amylase can be applied during or after the weaving to remove these sizing starch or starch derivatives. After weaving, an amylase can be used to remove the size coating before further processing the fabric to ensure a homogeneous and wash-proof result.

An amylase can be used alone or with other desizing chemical reagents and/or desizing enzymes to desize fabrics, including cotton-containing fabrics, as detergent additives, e.g., in aqueous compositions. An amylase also can be used in compositions and methods for producing a stonewashed look on indigo-dyed denim fabric and garments. For the manufacture of clothes, the fabric can be cut and sewn into clothes or garments, which are afterwards finished. In particular, for the manufacture of denim jeans, different enzymatic finishing methods have been developed. The finishing of denim garment normally is initiated with an enzymatic desizing step, during which garments are subjected to the action of amylolytic enzymes to provide softness to the fabric and make the cotton more accessible to the subsequent enzymatic finishing steps. An amylase can be used in methods of finishing denim garments (e.g., a "bio-stoning process"), enzymatic desizing and providing softness to fabrics, and/or finishing process.

7. Cleaning Compositions

An aspect of the present compositions and methods is a cleaning composition that includes an amylase as a component. An amylase polypeptide can be used as a component in detergent compositions for hand washing, laundry washing, dishwashing, and other hard-surface cleaning.

7.1. Overview

Preferably, an amylase is incorporated into detergents at or near a concentration conventionally used for amylase in detergents. For example, an amylase polypeptide may be added in amount corresponding to 0.00001-1 mg (calculated as pure enzyme protein) of amylase per liter of wash/dishwash liquor. Exemplary formulations are provided herein, as exemplified by the following:

An amylase polypeptide may be a component of a detergent composition, as the only enzyme or with other enzymes including other amylolytic enzymes. As such, it may be included in the detergent composition in the form of a non-dusting granulate, a stabilized liquid, or a protected enzyme. Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1,000 to 20,000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in, for example, GB 1483591. Liquid enzyme preparations may, for instance, be stabilized by adding a polyol such as propylene glycol, a sugar or sugar alcohol, lactic acid or boric acid according to established methods. Other enzyme stabilizers are known in the art. Protected enzymes may be prepared according to the method disclosed in for example EP 238 216. Polyols have long been recognized as stabilizers of proteins, as well as improving protein solubility.

The detergent composition may be in any useful form, e.g., as powders, granules, pastes, or liquid. A liquid detergent may be aqueous, typically containing up to about 70% of water and 0% to about 30% of organic solvent. It may also be in the form of a compact gel type containing only about 30% water.

The detergent composition comprises one or more surfactants, each of which may be anionic, nonionic, cationic, or zwitterionic. The detergent will usually contain 0% to about 50% of anionic surfactant, such as linear alkylbenzenesulfonate (LAS); α-olefinsulfonate (AOS); alkyl sulfate (fatty alcohol sulfate) (AS); alcohol ethoxysulfate (AEOS or AES); secondary alkanesulfonates (SAS); α-sulfo fatty acid methyl esters; alkyl- or alkenylsuccinic acid; or soap. The composition may also contain 0% to about 40% of nonionic surfactant such as alcohol ethoxylate (AEO or AE), carboxylated alcohol ethoxylates, nonylphenol ethoxylate, alkylpolyglycoside, alkyldimethylamineoxide, ethoxylated fatty acid monoethanolamide, fatty acid monoethanolamide, or polyhydroxy alkyl fatty acid amide (as described for example in WO 92/06154).

The detergent composition may additionally comprise one or more other enzymes, such as proteases, another amylolytic enzyme, cutinase, lipase, cellulase, pectate lyase, perhydrolase, xylanase, peroxidase, and/or laccase in any combination.

The detergent may contain about 1% to about 65% of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g., SKS-6 from Hoechst). The detergent may also be unbuilt, i.e. essentially free of detergent builder. The enzymes can be used in any composition compatible with the stability of the enzyme. Enzymes generally can be protected against deleterious components by known forms of encapsulation, for example, by granulation or sequestration in hydro gels. Enzymes, and specifically amylases, either with or without starch binding domains, can be used in a variety of compositions including laundry and dishwashing applications, surface cleaners, as well as in compositions for ethanol production from starch or biomass.

The detergent may comprise one or more polymers. Examples include carboxymethylcellulose (CMC), poly(vinylpyrrolidone) (PVP), polyethyleneglycol (PEG), poly(vinyl alcohol) (PVA), polycarboxylates such as polyacrylates, maleic/acrylic acid copolymers and lauryl methacrylate/acrylic acid copolymers.

The detergent may contain a bleaching system, which may comprise a $H_2O_2$ source such as perborate or percarbonate, which may be combined with a peracid-forming bleach activator such as tetraacetylethylenediamine (TAED) or nonanoyloxybenzenesulfonate (NOBS). Alternatively, the bleaching system may comprise peroxyacids (e.g., the amide, imide, or sulfone type peroxyacids). The bleaching system can also be an enzymatic bleaching system, for example, perhydrolase, such as that described in International PCT Application WO 2005/056783.

The enzymes of the detergent composition may be stabilized using conventional stabilizing agents, e.g., a polyol such as propylene glycol or glycerol; a sugar or sugar alcohol; lactic acid; boric acid or a boric acid derivative such as, e.g., an aromatic borate ester; and the composition may be formulated as described in, e.g., WO 92/19709 and WO 92/19708.

The detergent may also contain other conventional detergent ingredients such as e.g., fabric conditioners including clays, foam boosters, suds suppressors, anti-corrosion agents, soil-suspending agents, anti-soil redeposition agents, dyes, bactericides, tarnish inhibiters, optical brighteners, or perfumes.

The pH (measured in aqueous solution at use concentration) is usually neutral or alkaline, e.g., pH about 7.0 to about 11.0.

Particular forms of detergent compositions for inclusion of the present α-amylase are described, below.

7.2. Heavy Duty Liquid (HDL) Laundry Detergent Composition

Exemplary HDL laundry detergent compositions includes a detersive surfactant (10%-40% wt/wt), including an anionic detersive surfactant (selected from a group of linear or branched or random chain, substituted or unsubstituted alkyl sulphates, alkyl sulphonates, alkyl alkoxylated sulphate, alkyl phosphates, alkyl phosphonates, alkyl carboxylates, and/or mixtures thereof), and optionally non-ionic surfactant (selected from a group of linear or branched or random chain, substituted or unsubstituted alkyl alkoxylated alcohol, for example a $C_8$-$C_{18}$ alkyl ethoxylated alcohol and/or $C_6$-$C_{12}$ alkyl phenol alkoxylates), wherein the weight ratio of anionic detersive surfactant (with a hydrophilic index (HIc) of from 6.0 to 9) to non-ionic detersive surfactant is greater than 1:1. Suitable detersive surfactants also include cationic detersive surfactants (selected from a group of alkyl pyridinium compounds, alkyl quarternary ammonium compounds, alkyl quarternary phosphonium compounds, alkyl ternary sulphonium compounds, and/or mixtures thereof); zwitterionic and/or amphoteric detersive surfactants (selected from a group of alkanolamine sulphobetaines); ampholytic surfactants; semi-polar non-ionic surfactants and mixtures thereof.

The composition may optionally include, a surfactancy boosting polymer consisting of amphiphilic alkoxylated grease cleaning polymers (selected from a group of alkoxylated polymers having branched hydrophilic and hydrophobic properties, such as alkoxylated polyalkyleneimines in the range of 0.05 wt %-10 wt %) and/or random graft polymers (typically comprising of hydrophilic backbone comprising monomers selected from the group consisting of: unsaturated $C_1$-$C_6$ carboxylic acids, ethers, alcohols, aldehydes, ketones, esters, sugar units, alkoxy units, maleic anhydride, saturated polyalcohols such as glycerol, and mixtures thereof; and hydrophobic side chain(s) selected from the group consisting of: $C_4$-$C_{25}$ alkyl group, polypropylene, polybutylene, vinyl ester of a saturated $C_1$-$C_6$ monocarboxylic acid, $C_1$-$C_6$ alkyl ester of acrylic or methacrylic acid, and mixtures thereof.

The composition may include additional polymers such as soil release polymers (include anionically end-capped polyesters, for example SRP1, polymers comprising at least one monomer unit selected from saccharide, dicarboxylic acid, polyol and combinations thereof, in random or block configuration, ethylene terephthalate-based polymers and co-polymers thereof in random or block configuration, for example Repel-o-tex SF, SF-2 and SRP6, Texcare SRA100, SRA300, SRN100, SRN170, SRN240, SRN300 and SRN325, Marloquest SL), anti-redeposition polymers (0.1 wt % to 10 wt %, include carboxylate polymers, such as polymers comprising at least one monomer selected from acrylic acid, maleic acid (or maleic anhydride), fumaric acid, itaconic acid, aconitic acid, mesaconic acid, citraconic acid, methylenemalonic acid, and any mixture thereof, vinylpyrrolidone homopolymer, and/or polyethylene glycol, molecular weight in the range of from 500 to 100,000 Da);

cellulosic polymer (including those selected from alkyl cellulose, alkyl alkoxyalkyl cellulose, carboxyalkyl cellulose, alkyl carboxyalkyl cellulose examples of which include carboxymethyl cellulose, methyl cellulose, methyl hydroxyethyl cellulose, methyl carboxymethyl cellulose, and mixtures thereof) and polymeric carboxylate (such as maleate/acrylate random copolymer or polyacrylate homopolymer).

The composition may further include saturated or unsaturated fatty acid, preferably saturated or unsaturated $C_{12}$-$C_{24}$ fatty acid (0 wt % to 10 wt %); deposition aids (examples for which include polysaccharides, preferably cellulosic polymers, poly diallyl dimethyl ammonium halides (DADMAC), and co-polymers of DAD MAC with vinyl pyrrolidone, acrylamides, imidazoles, imidazolinium halides, and mixtures thereof, in random or block configuration, cationic guar gum, cationic cellulose such as cationic hydroxyethyl cellulose, cationic starch, cationic polyacrylamides, and mixtures thereof.

The composition may further include dye transfer inhibiting agents, examples of which include manganese phthalocyanine, peroxidases, polyvinylpyrrolidone polymers, polyamine N-oxide polymers, copolymers of N-vinylpyrrolidone and N-vinylimidazole, polyvinyloxoazolidones and polyvinylimidazoles and/or mixtures thereof; chelating agents, examples of which include ethylene-diamine-tetraacetic acid (EDTA), diethylene triamine penta methylene phosphonic acid (DTPMP), hydroxy-ethane diphosphonic acid (HEDP), ethylenediamine N,N'-disuccinic acid (EDDS), methyl glycine diacetic acid (MGDA), diethylene triamine penta acetic acid (DTPA), propylene diamine tetracetic acid (PDT A), 2-hydroxypyridine-N-oxide (HPNO), or methyl glycine diacetic acid (MGDA), glutamic acid N,N-diacetic acid (N,N-dicarboxymethyl glutamic acid tetrasodium salt (GLDA), nitrilotriacetic acid (NTA), 4,5-dihydroxy-m-benzenedisulfonic acid, citric acid and any salts thereof, N-hydroxyethylethylenediaminetri-acetic acid (HEDTA), triethylenetetraminehexaacetic acid (TTHA), N-hydroxyethyliminodiacetic acid (HEIDA), dihydroxyethylglycine (DHEG), ethylenediaminetetrapropionic acid (EDTP), and derivatives thereof.

The composition preferably included enzymes (generally about 0.01 wt % active enzyme to 0.03 wt % active enzyme) selected from proteases, amylases, lipases, cellulases, choline oxidases, peroxidases/oxidases, pectate lyases, mannanases, cutinases, laccases, phospholipases, lysophospholipases, acyltransferases, perhydrolases, arylesterases, and any mixture thereof. The composition may include an enzyme stabilizer (examples of which include polyols such as propylene glycol or glycerol, sugar or sugar alcohol, lactic acid, reversible protease inhibitor, boric acid, or a boric acid derivative, e.g., an aromatic borate ester, or a phenyl boronic acid derivative such as 4-formylphenyl boronic acid).

The composition optionally include silicone or fatty-acid based suds suppressors; hueing dyes, calcium and magnesium cations, visual signaling ingredients, anti-foam (0.001 wt % to about 4.0 wt %), and/or structurant/thickener (0.01 wt % to 5 wt %, selected from the group consisting of diglycerides and triglycerides, ethylene glycol distearate, microcrystalline cellulose, cellulose based materials, microfiber cellulose, biopolymers, xanthan gum, gellan gum, and mixtures thereof).

The composition can be any liquid form, for example a liquid or gel form, or any combination thereof. The composition may be in any unit dose form, for example a pouch.

7.3. Heavy Duty Dry/Solid (HDD) Laundry Detergent Composition

Exemplary HDD laundry detergent compositions includes a detersive surfactant, including anionic detersive surfactants (e.g., linear or branched or random chain, substituted or unsubstituted alkyl sulphates, alkyl sulphonates, alkyl alkoxylated sulphate, alkyl phosphates, alkyl phosphonates, alkyl carboxylates and/or mixtures thereof), non-ionic detersive surfactant (e.g., linear or branched or random chain, substituted or unsubstituted $C_8$-$C_{18}$ alkyl ethoxylates, and/or $C_6$-$C_{12}$ alkyl phenol alkoxylates), cationic detersive surfactants (e.g., alkyl pyridinium compounds, alkyl quaternary ammonium compounds, alkyl quaternary phosphonium compounds, alkyl ternary sulphonium compounds, and mixtures thereof), zwitterionic and/or amphoteric detersive surfactants (e.g., alkanolamine sulpho-betaines), ampholytic surfactants, semi-polar non-ionic surfactants, and mixtures thereof; builders including phosphate free builders (for example zeolite builders examples which include zeolite A, zeolite X, zeolite P and zeolite MAP in the range of 0 wt % to less than 10 wt %), phosphate builders (for example sodium tri-polyphosphate in the range of 0 wt % to less than 10 wt %), citric acid, citrate salts and nitrilotriacetic acid, silicate salt (e.g., sodium or potassium silicate or sodium meta-silicate in the range of 0 wt % to less than 10 wt %, or layered silicate (SKS-6)); carbonate salt (e.g., sodium carbonate and/or sodium bicarbonate in the range of 0 wt % to less than 80 wt %); and bleaching agents including photobleaches (e.g., sulfonated zinc phthalocyanines, sulfonated aluminum phthalocyanines, xanthenes dyes, and mixtures thereof) hydrophobic or hydrophilic bleach activators (e.g., dodecanoyl oxybenzene sulfonate, decanoyl oxybenzene sulfonate, decanoyl oxybenzoic acid or salts thereof, 3,5,5-trimethyl hexanoyl oxybenzene sulfonate, tetraacetyl ethylene diamine-TAED, nonanoyloxybenzene sulfonate-NOBS, nitrile quats, and mixtures thereof), sources of hydrogen peroxide (e.g., inorganic perhydrate salts examples of which include mono or tetra hydrate sodium salt of perborate, percarbonate, persulfate, perphosphate, or persilicate), preformed hydrophilic and/or hydrophobic peracids (e.g., percarboxylic acids and salts, percarbonic acids and salts, perimidic acids and salts, peroxymonosulfuric acids and salts, and mixtures thereof), and/or bleach catalysts (e.g., imine bleach boosters (examples of which include iminium cations and polyions), iminium zwitterions, modified amines, modified amine oxides, N-sulphonyl imines, N-phosphonyl imines, N-acyl imines, thiadiazole dioxides, perfluoroamines, cyclic sugar ketones, and mixtures thereof, and metal-containing bleach catalysts (e.g., copper, iron, titanium, ruthenium, tungsten, molybdenum, or manganese cations along with an auxiliary metal cations such as zinc or aluminum and a sequestrate such as ethylenediaminetetraacetic acid, ethylenediaminetetra (methylenephosphonic acid), and water-soluble salts thereof).

The composition preferably includes enzymes, e.g., proteases, amylases, lipases, cellulases, choline oxidases, peroxidases/oxidases, pectate lyases, mannanases, cutinases, laccases, phospholipases, lysophospholipases, acyltransferase, perhydrolase, arylesterase, and any mixture thereof.

The composition may optionally include additional detergent ingredients including perfume microcapsules, starch encapsulated perfume accord, hueing agents, additional polymers, including fabric integrity and cationic polymers, dye-lock ingredients, fabric-softening agents, brighteners (for example C.I. Fluorescent brighteners), flocculating agents, chelating agents, alkoxylated polyamines, fabric deposition aids, and/or cyclodextrin.

7.4. Automatic Dishwashing (ADW) Detergent Composition

Exemplary ADW detergent composition includes non-ionic surfactants, including ethoxylated non-ionic surfactants, alcohol alkoxylated surfactants, epoxy-capped poly(oxyalkylated) alcohols, or amine oxide surfactants present in amounts from 0 to 10% by weight; builders in the range of 5-60% including phosphate builders (e.g., mono-phosphates, di-phosphates, tri-polyphosphates, other oligomeric-polyphosphates, sodium tripolyphosphate-STPP) and phosphate-free builders (e.g., amino acid-based compounds including methyl-glycine-diacetic acid (MGDA) and salts and derivatives thereof, glutamic-N,N-diacetic acid (GLDA) and salts and derivatives thereof, iminodisuccinic acid (IDS) and salts and derivatives thereof, carboxy methyl inulin and salts and derivatives thereof, nitrilotriacetic acid (NTA), diethylene triamine penta acetic acid (DTPA), B-alaninediacetic acid (B-ADA) and their salts, homopolymers and copolymers of poly-carboxylic acids and their partially or completely neutralized salts, monomeric polycarboxylic acids and hydroxycarboxylic acids and their salts in the range of 0.5% to 50% by weight; sulfonated/carboxylated polymers in the range of about 0.1% to about 50% by weight to provide dimensional stability; drying aids in the range of about 0.1% to about 10% by weight (e.g., polyesters, especially anionic polyesters, optionally together with further monomers with 3 to 6 functionalities—typically acid, alcohol or ester functionalities which are conducive to polycondensation, polycarbonate-, polyurethane- and/or polyurea-polyorganosiloxane compounds or precursor compounds, thereof, particularly of the reactive cyclic carbonate and urea type); silicates in the range from about 1% to about 20% by weight (including sodium or potassium silicates for example sodium disilicate, sodium meta-silicate and crystalline phyllosilicates); inorganic bleach (e.g., perhydrate salts such as perborate, percarbonate, perphosphate, persulfate and persilicate salts) and organic bleach (e.g., organic peroxyacids, including diacyl and tetraacylperoxides, especially diperoxydodecanedioc acid, diperoxytetradecanedioc acid, and diperoxyhexadecanedioc acid); bleach activators (i.e., organic peracid precursors in the range from about 0.1% to about 10% by weight); bleach catalysts (e.g., manganese triazacyclononane and related complexes, Co, Cu, Mn, and Fe bispyridylamine and related complexes, and pentamine acetate cobalt(III) and related complexes); metal care agents in the range from about 0.1% to 5% by weight (e.g., benzotriazoles, metal salts and complexes, and/or silicates); enzymes in the range from about 0.01 to 5.0 mg of active enzyme per gram of automatic dishwashing detergent composition (e.g., proteases, amylases, lipases, cellulases, choline oxidases, peroxidases/oxidases, pectate lyases, mannanases, cutinases, laccases, phospholipases, lysophospholipases, acyltransferase, perhydrolase, arylesterase, and mixtures thereof); and enzyme stabilizer components (e.g., oligosaccharides, polysaccharides, and inorganic divalent metal salts).

7.5. Additional Detergent Compositions

Additional exemplary detergent formulations to which the present amylase can be added are described, below, in the numbered paragraphs.

1) A detergent composition formulated as a granulate having a bulk density of at least 600 g/L comprising linear alkylbenzenesulfonate (calculated as acid) about 7% to about 12%; alcohol ethoxysulfate (e.g., $C_{12-18}$ alcohol, 1-2 ethylene oxide (EO)) or alkyl sulfate (e.g., $C_{16-18}$) about 1% to about 4%; alcohol ethoxylate (e.g., $C_{14-15}$ alcohol, 7 EO) about 5% to about 9%; sodium carbonate (e.g., $Na_2CO_3$) about 14% to about 20%; soluble silicate (e.g., $Na_2O$, $2SiO_2$) about 2 to about 6%; zeolite (e.g., $NaAlSiO_4$) about 15% to about 22%; sodium sulfate (e.g., $Na_2SO_4$) 0% to about 6%; sodium citrate/citric acid (e.g., $C_6H_5Na_3O_7/C_6H_8O_7$) about 0% to about 15%; sodium perborate (e.g., $NaBO_3H_2O$) about 11% to about 18%; TAED about 2% to about 6%; carboxymethylcellulose (CMC) and 0% to about 2%; polymers (e.g., maleic/acrylic acid, copolymer, PVP, PEG) 0-3%; enzymes (calculated as pure enzyme) 0.0001-0.1% protein; and minor ingredients (e.g., suds suppressors, perfumes, optical brightener, photobleach) 0-5%.

2) A detergent composition formulated as a granulate having a bulk density of at least 600 g/L comprising linear alkylbenzenesulfonate (calculated as acid) about 6% to about 11%; alcohol ethoxysulfate (e.g., $C_{12-18}$ alcohol, 1-2 EO) or alkyl sulfate (e.g., $C_{16-18}$) about 1% to about 3%; alcohol ethoxylate (e.g., $C_{14-15}$ alcohol, 7 EO) about 5% to about 9%; sodium carbonate (e.g., $Na_2CO_3$) about 15% to about 21%; soluble silicate (e.g., $Na_2O$, $2SiO_2$) about 1% to about 4%; zeolite (e.g., $NaAlSiO_4$) about 24% to about 34%; sodium sulfate (e.g., $Na_2SO_4$) about 4% to about 10%; sodium citrate/citric acid (e.g., $C_6H_5Na_3O_7/C_6H_8O_7$) 0% to about 15%; carboxymethylcellulose (CMC) 0% to about 2%; polymers (e.g., maleic/acrylic acid copolymer, PVP, PEG) 1-6%; enzymes (calculated as pure enzyme protein) 0.0001-0.1%; minor ingredients (e.g., suds suppressors, perfume) 0-5%.

3) A detergent composition formulated as a granulate having a bulk density of at least 600 g/L comprising linear alkylbenzenesulfonate (calculated as acid) about 5% to about 9%; alcohol ethoxylate (e.g., $C_{12-15}$ alcohol, 7 EO) about 7% to about 14%; Soap as fatty acid (e.g., $C_{16-22}$ fatty acid) about 1 to about 3%; sodium carbonate (as $Na_2CO_3$) about 10% to about 17%; soluble silicate (e.g., $Na_2O$, $2SiO_2$) about 3% to about 9%; zeolite (as $NaAlSiO_4$) about 23% to about 33%; sodium sulfate (e.g., $Na_2SO_4$) 0% to about 4%; sodium perborate (e.g., $NaBO_3H_2O$) about 8% to about 16%; TAED about 2% to about 8%; phosphonate (e.g., EDTMPA) 0% to about 1%; carboxymethylcellulose (CMC) 0% to about 2%; polymers (e.g., maleic/acrylic acid copolymer, PVP, PEG) 0-3%; enzymes (calculated as pure enzyme protein) 0.0001-0.1%; minor ingredients (e.g., suds suppressors, perfume, optical brightener) 0-5%.

4) A detergent composition formulated as a granulate having a bulk density of at least 600 g/L comprising linear alkylbenzenesulfonate (calculated as acid) about 8% to about 12%; alcohol ethoxylate (e.g., $C_{12-15}$ alcohol, 7 EO) about 10% to about 25%; sodium carbonate (as $Na_2CO_3$) about 14% to about 22%; soluble silicate (e.g., $Na_2O$, $2SiO_2$) about 1% to about 5%; zeolite (e.g., $NaAlSiO_4$) about 25% to about 35%; sodium sulfate (e.g., $Na_2SO_4$) 0% to about 10%; carboxymethylcellulose (CMC) 0% to about 2%; polymers (e.g., maleic/acrylic acid copolymer, PVP, PEG) 1-3%; enzymes (calculated as pure enzyme protein) 0.0001-0.1%; and minor ingredients (e.g., suds suppressors, perfume) 0-5%.

5) An aqueous liquid detergent composition comprising linear alkylbenzenesulfonate (calculated as acid) about 15% to about 21%; alcohol ethoxylate (e.g., $C_{12-15}$ alcohol, 7 EO or $C_{12-15}$ alcohol, 5 EO) about 12% to about 18%; soap as fatty acid (e.g., oleic acid) about 3% to about 13%; alkenylsuccinic acid ($C_{12-14}$) 0% to about 13%; aminoethanol about 8% to about 18%; citric acid about 2% to about 8%; phosphonate 0% to about 3%; polymers (e.g., PVP, PEG) 0% to about 3%; borate (e.g., $B_4O_7$) 0% to about 2%; ethanol 0% to about 3%; propylene glycol about 8% to about 14%; enzymes (calculated as pure enzyme protein) 0.0001-0.1%; and minor ingredients (e.g., dispersants, suds suppressors, perfume, optical brightener) 0-5%.

6) An aqueous structured liquid detergent composition comprising linear alkylbenzenesulfonate (calculated as acid) about 15% to about 21%; alcohol ethoxylate (e.g., $C_{12-15}$ alcohol, 7 EO, or $C_{12-15}$ alcohol, 5 EO) 3-9%; soap as fatty acid (e.g., oleic acid) about 3% to about 10%; zeolite (as $NaAlSiO_4$) about 14% to about 22%; potassium citrate about 9% to about 18%; borate (e.g., $B_4O_7$) 0% to about 2%; carboxymethylcellulose (CMC) 0% to about 2%; polymers (e.g., PEG, PVP) 0% to about 3%; anchoring polymers such as, e.g., lauryl methacrylate/acrylic acid copolymer; molar ratio 25:1, MW 3800) 0% to about 3%; glycerol 0% to about 5%; enzymes (calculated as pure enzyme protein) 0.0001-0.1%; and minor ingredients (e.g., dispersants, suds suppressors, perfume, optical brighteners) 0-5%.

7) A detergent composition formulated as a granulate having a bulk density of at least 600 g/L comprising fatty alcohol sulfate about 5% to about 10%; ethoxylated fatty acid monoethanolamide about 3% to about 9%; soap as fatty acid 0-3%; sodium carbonate (e.g., $Na_2CO_3$) about 5% to about 10%; Soluble silicate (e.g., $Na_2O$, $2SiO_2$) about 1% to about 4%; zeolite (e.g., $NaAlSiO_4$) about 20% to about 40%; Sodium sulfate (e.g., $Na_2SO_4$) about 2% to about 8%; sodium perborate (e.g., $NaBO_3H_2O$) about 12% to about 18%; TAED about 2% to about 7%; polymers (e.g., maleic/acrylic acid copolymer, PEG) about 1% to about 5%; enzymes (calculated as pure enzyme protein) 0.0001-0.1%; and minor ingredients (e.g., optical brightener, suds suppressors, perfume) 0-5%.

8) A detergent composition formulated as a granulate comprising linear alkylbenzenesulfonate (calculated as acid) about 8% to about 14%; ethoxylated fatty acid monoethanolamide about 5% to about 11%; soap as fatty acid 0% to about 3%; sodium carbonate (e.g., $Na_2CO_3$) about 4% to about 10%; soluble silicate ($Na_2O$, $2SiO_2$) about 1% to about 4%; zeolite (e.g., $NaAlSiO_4$) about 30% to about 50%; sodium sulfate (e.g., $Na_2SO_4$) about 3% to about 11%; sodium citrate (e.g., $C_6H_5Na_3O_7$) about 5% to about 12%; polymers (e.g., PVP, maleic/acrylic acid copolymer, PEG) about 1% to about 5%; enzymes (calculated as pure enzyme protein) 0.0001-0.1%; and minor ingredients (e.g., suds suppressors, perfume) 0-5%.

9) A detergent composition formulated as a granulate comprising linear alkylbenzenesulfonate (calculated as acid) about 6% to about 12%; nonionic surfactant about 1% to about 4%; soap as fatty acid about 2% to about 6%; sodium carbonate (e.g., $Na_2CO_3$) about 14% to about 22%; zeolite (e.g., $NaAlSiO_4$) about 18% to about 32%; sodium sulfate (e.g., $Na_2SO_4$) about 5% to about 20%; sodium citrate (e.g., $C_6H_5Na_3O_7$) about 3% to about 8%; sodium perborate (e.g., $NaBO_3H_2O$) about 4% to about 9%; bleach activator (e.g., NOBS or TAED) about 1% to about 5%; carboxymethylcellulose (CMC) 0% to about 2%; polymers (e.g., polycarboxylate or PEG) about 1% to about 5%; enzymes (calculated as pure enzyme protein) 0.0001-0.1%; and minor ingredients (e.g., optical brightener, perfume) 0-5%.

10) An aqueous liquid detergent composition comprising linear alkylbenzenesulfonate (calculated as acid) about 15% to about 23%; alcohol ethoxysulfate (e.g., $C_{12-15}$ alcohol, 2-3 EO) about 8% to about 15%; alcohol ethoxylate (e.g., $C_{12-15}$ alcohol, 7 EO, or $C_{12-15}$ alcohol, 5 EO) about 3% to about 9%; soap as fatty acid (e.g., lauric acid) 0% to about 3%; aminoethanol about 1% to about 5%; sodium citrate about 5% to about 10%; hydrotrope (e.g., sodium toluensulfonate) about 2% to about 6%; borate (e.g., $B_4O_7$) 0% to about 2%; carboxymethylcellulose 0% to about 1%; ethanol about 1% to about 3%; propylene glycol about 2% to about 5%; enzymes (calculated as pure enzyme protein) 0.0001-0.1%; and minor ingredients (e.g., polymers, dispersants, perfume, optical brighteners) 0-5%.

11) An aqueous liquid detergent composition comprising linear alkylbenzenesulfonate (calculated as acid) about 20% to about 32%; alcohol ethoxylate (e.g., $C_{12-15}$ alcohol, 7 EO, or $C_{12-15}$ alcohol, 5 EO) 6-12%; aminoethanol about 2% to about 6%; citric acid about 8% to about 14%; borate (e.g., $B_4O_7$) about 1% to about 3%; polymer (e.g., maleic/acrylic acid copolymer, anchoring polymer such as, e.g., lauryl methacrylate/acrylic acid copolymer) 0% to about 3%; glycerol about 3% to about 8%; enzymes (calculated as pure enzyme protein) 0.0001-0.1%; and minor ingredients (e.g., hydrotropes, dispersants, perfume, optical brighteners) 0-5%.

12) A detergent composition formulated as a granulate having a bulk density of at least 600 g/L comprising anionic surfactant (linear alkylbenzenesulfonate, alkyl sulfate, α-olefinsulfonate, α-sulfo fatty acid methyl esters, alkanesulfonates, soap) about 25% to about 40%; nonionic surfactant (e.g., alcohol ethoxylate) about 1% to about 10%; sodium carbonate (e.g., $Na_2CO_3$) about 8% to about 25%; soluble silicates (e.g., $Na_2O$, $2SiO_2$) about 5% to about 15%; sodium sulfate (e.g., $Na_2SO_4$) 0% to about 5%; zeolite ($NaAlSiO_4$) about 15% to about 28%; sodium perborate (e.g., $NaBO_3.4H_2O$) 0% to about 20%; bleach activator (TAED or NOBS) about 0% to about 5%; enzymes (calculated as pure enzyme protein) 0.0001-0.1%; minor ingredients (e.g., perfume, optical brighteners) 0-3%.

13) Detergent compositions as described in compositions 1)-12) supra, wherein all or part of the linear alkylbenzenesulfonate is replaced by ($C_{12}$-$C_{18}$) alkyl sulfate.

14) A detergent composition formulated as a granulate having a bulk density of at least 600 g/L comprising ($C_{12}$-$C_{18}$) alkyl sulfate about 9% to about 15%; alcohol ethoxylate about 3% to about 6%; polyhydroxy alkyl fatty acid amide about 1% to about 5%; zeolite (e.g., $NaAlSiO_4$) about 10% to about 20%; layered disilicate (e.g., SK56 from Hoechst) about 10% to about 20%; sodium carbonate (e.g., $Na_2CO_3$) about 3% to about 12%; soluble silicate (e.g., $Na_2O$, $2SiO_2$) 0% to about 6%; sodium citrate about 4% to about 8%; sodium percarbonate about 13% to about 22%; TAED about 3% to about 8%; polymers (e.g., polycarboxylates and PVP) 0% to about 5%; enzymes (calculated as pure enzyme protein) 0.0001-0.1%; and minor ingredients (e.g., optical brightener, photobleach, perfume, suds suppressors) 0-5%.

15) A detergent composition formulated as a granulate having a bulk density of at least 600 g/L comprising ($C_{12}$-$C_{18}$) alkyl sulfate about 4% to about 8%; alcohol ethoxylate about 11% to about 15%; soap about 1% to about 4%; zeolite MAP or zeolite A about 35% to about 45%; sodium carbonate (as $Na_2CO_3$) about 2% to about 8%; soluble silicate (e.g., $Na_2O$, $2SiO_2$) 0% to about 4%; sodium percarbonate about 13% to about 22%; TAED 1-8%; carboxymethylcellulose (CMC) 0% to about 3%; polymers (e.g., polycarboxylates and PVP) 0% to about 3%; enzymes (calculated as pure enzyme protein) 0.0001-0.1%; and minor ingredients (e.g., optical brightener, phosphonate, perfume) 0-3%.

16) Detergent formulations as described in 1)-15) supra, which contain a stabilized or encapsulated peracid, either as an additional component or as a substitute for already specified bleach systems.

17) Detergent compositions as described supra in 1), 3), 7), 9), and 12), wherein perborate is replaced by percarbonate.

18) Detergent compositions as described supra in 1), 3), 7), 9), 12), 14), and 15), which additionally contain a manganese catalyst. The manganese catalyst for example is one of the compounds described in "Efficient manganese catalysts for low-temperature bleaching," Nature 369: 637-639 (1994).

19) Detergent composition formulated as a non-aqueous detergent liquid comprising a liquid nonionic surfactant such as, e.g., linear alkoxylated primary alcohol, a builder system (e.g., phosphate), an enzyme(s), and alkali. The detergent may also comprise anionic surfactant and/or a bleach system.

As above, the present amylase polypeptide may be incorporated at a concentration conventionally employed in detergents. It is at present contemplated that, in the detergent composition, the enzyme may be added in an amount corresponding to 0.00001-1.0 mg (calculated as pure enzyme protein) of amylase polypeptide per liter of wash liquor.

The detergent composition may also contain other conventional detergent ingredients, e.g., deflocculant material, filler material, foam depressors, anti-corrosion agents, soil-suspending agents, sequestering agents, anti-soil redeposition agents, dehydrating agents, dyes, bactericides, fluorescers, thickeners, and perfumes.

The detergent composition may be formulated as a hand (manual) or machine (automatic) laundry detergent composition, including a laundry additive composition suitable for pre-treatment of stained fabrics and a rinse added fabric softener composition, or be formulated as a detergent composition for use in general household hard surface cleaning operations, or be formulated for manual or automatic dishwashing operations.

Any of the cleaning compositions described, herein, may include any number of additional enzymes. In general the enzyme(s) should be compatible with the selected detergent, (e.g., with respect to pH-optimum, compatibility with other enzymatic and non-enzymatic ingredients, and the like), and the enzyme(s) should be present in effective amounts. The following enzymes are provided as examples.

Proteases: Suitable proteases include those of animal, vegetable or microbial origin. Chemically modified or protein engineered mutants are included, as well as naturally processed proteins. The protease may be a serine protease or a metalloprotease, an alkaline microbial protease, a trypsin-like protease, or a chymotrypsin-like protease. Examples of alkaline proteases are subtilisins, especially those derived from *Bacillus*, e.g., subtilisin Novo, subtilisin Carlsberg, subtilisin 309, subtilisin 147, and subtilisin 168 (see, e.g., WO 89/06279). Examples of trypsin-like proteases are trypsin (e.g., of porcine or bovine origin), and *Fusarium* proteases (see, e.g., WO 89/06270 and WO 94/25583). Examples of useful proteases also include but are not limited to the variants described in WO 92/19729, WO 98/20115, WO 98/20116, and WO 98/34946. Commercially available protease enzymes include but are not limited to: ALCALASE®, SAVINASE®, PRIMASE™, DURALASE™, ESPERASE®, KANNASE™ and BLAZE™ (Novo Nordisk A/S and Novozymes A/S); MAXATASE®, MAXACAL™ MAXAPEM™, PROPERASE®, PURAFECT®, PURAFECT OXP™, FN2™, and FN3™ (Danisco US Inc.). Other exemplary proteases include NprE from *Bacillus amyloliquefaciens* and ASP from *Cellulomonas* sp. strain 69B4.

Lipases: Suitable lipases include those of bacterial or fungal origin. Chemically modified, proteolytically modified, or protein engineered mutants are included. Examples of useful lipases include but are not limited to lipases from *Humicola* (synonym *Thermomyces*), e.g., from *H. lanuginosa* (*T. lanuginosus*) (see e.g., EP 258068 and EP 305216), from *H. insolens* (see e.g., WO 96/13580); a *Pseudomonas* lipase (e.g., from *P. alcaligenes* or *P. pseudoalcaligenes*; see, e.g., EP 218 272), *P. cepacia* (see e.g., EP 331 376), *P. stutzeri* (see e.g., GB 1,372,034), *P. fluorescens, Pseudomonas* sp. strain SD 705 (see e.g., WO 95/06720 and WO 96/27002), *P. wisconsinensis* (see e.g., WO 96/12012); a *Bacillus* lipase (e.g., from *B. subtilis*; see e.g., Dartois et al. *Biochemica et Biophysica Acta*, 1131: 253-360 (1993)), *B. stearothermophilus* (see e.g., JP 64/744992), or *B. pumilus* (see e.g., WO 91/16422). Additional lipase variants contemplated for use in the formulations include those described for example in: WO 92/05249, WO 94/01541, WO 95/35381, WO 96/00292, WO 95/30744, WO 94/25578, WO 95/14783, WO 95/22615, WO 97/04079, WO 97/07202, EP 407225, and EP 260105. Some commercially available lipase enzymes include LIPOLASE® and LIPOLASE ULTRA™ (Novo Nordisk A/S and Novozymes A/S).

Polyesterases: Suitable polyesterases can be included in the composition, such as those described in, for example, WO 01/34899, WO 01/14629, and U.S. Pat. No. 6,933,140.

Amylases: The compositions can be combined with other amylases, such as non-production enhanced amylase. These can include commercially available amylases, such as but not limited to STAINZYME®, NATALASE®, DURAMYL®, TERMAMYL®, FUNGAMYL® and BAN™ (Novo Nordisk A/S and Novozymes A/S); RAPIDASE®, POWERASE®, and PURASTAR® (from Danisco US Inc.).

Cellulases: Cellulases can be added to the compositions. Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed for example in U.S. Pat. Nos. 4,435,307; 5,648,263; 5,691,178; 5,776,757; and WO 89/09259. Exemplary cellulases contemplated for use are those having color care benefit for the textile. Examples of such cellulases are cellulases described in for example EP 0495257, EP 0531372, WO 96/11262, WO 96/29397, and WO 98/08940. Other examples are cellulase variants, such as those described in WO 94/07998; WO 98/12307; WO 95/24471; PCT/DK98/00299; EP 531315; U.S. Pat. Nos. 5,457,046; 5,686,593; and 5,763,254. Commercially available cellulases include CELLUZYME® and CAREZYME® (Novo Nordisk A/S and Novozymes A/S); CLAZINASE® and PURADAX HA® (Danisco US Inc.); and KAC-500(B)™ (Kao Corporation).

Peroxidases/Oxidases: Suitable peroxidases/oxidases contemplated for use in the compositions include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257. Commercially available peroxidases include for example GUARDZYME™ (Novo Nordisk A/S and Novozymes A/S).

The detergent composition can also comprise 2,6-β-D-fructan hydrolase, which is effective for removal/cleaning of biofilm present on household and/or industrial textile/laundry.

The detergent enzyme(s) may be included in a detergent composition by adding separate additives containing one or more enzymes, or by adding a combined additive comprising all of these enzymes. A detergent additive, i.e. a separate additive or a combined additive, can be formulated e.g., as a granulate, a liquid, a slurry, and the like. Exemplary detergent additive formulations include but are not limited to granulates, in particular non-dusting granulates, liquids, in particular stabilized liquids or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (e.g., polyethyleneglycol, PEG) with mean molar weights of 1,000 to 20,000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in, for example, GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition may be in any convenient form, e.g., a bar, a tablet, a powder, a granule, a paste, or a liquid. A liquid detergent may be aqueous, typically containing up to about 70% water, and 0% to about 30% organic solvent. Compact detergent gels containing about 30% or less water are also contemplated. The detergent composition can optionally comprise one or more surfactants, which may be non-ionic, including semi-polar and/or anionic and/or cationic and/or zwitterionic. The surfactants can be present in a wide range, from about 0.1% to about 60% by weight.

When included therein the detergent will typically contain from about 1% to about 40% of an anionic surfactant, such as linear alkylbenzenesulfonate, α-olefinsulfonate, alkyl sulfate (fatty alcohol sulfate), alcohol ethoxysulfate, secondary alkanesulfonate, α-sulfo fatty acid methyl ester, alkyl- or alkenylsuccinic acid, or soap.

When included therein, the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl-N-alkyl derivatives of glucosamine ("glucamides").

The detergent may contain 0% to about 65% of a detergent builder or complexing agent such as zeolite, diphosphate, triphosphate, phosphonate, carbonate, citrate, nitrilotriacetic acid, ethylenediaminetetraacetic acid (EDTA), diethylenetriaminepentaacetic acid, alkyl- or alkenylsuccinic acid, soluble silicates or layered silicates (e.g., SKS-6 from Hoechst).

The detergent may comprise one or more polymers. Exemplary polymers include carboxymethylcellulose (CMC), poly(vinylpyrrolidone) (PVP), poly(ethylene glycol) (PEG), poly(vinyl alcohol) (PVA), poly(vinylpyridine-N-oxide), poly(vinylimidazole), polycarboxylates e.g., polyacrylates, maleic/acrylic acid copolymers), and lauryl methacrylate/acrylic acid copolymers.

The enzyme(s) of the detergent composition may be stabilized using conventional stabilizing agents, e.g., as polyol (e.g., propylene glycol or glycerol), a sugar or sugar alcohol, lactic acid, boric acid, or a boric acid derivative (e.g., an aromatic borate ester), or a phenyl boronic acid derivative (e.g., 4-formylphenyl boronic acid). The composition may be formulated as described in WO 92/19709 and WO 92/19708.

It is contemplated that in the detergent compositions, in particular the enzyme variants, may be added in an amount corresponding to about 0.01 to about 100 mg of enzyme protein per liter of wash liquor (e.g., about 0.05 to about 5.0 mg of enzyme protein per liter of wash liquor or 0.1 to about 1.0 mg of enzyme protein per liter of wash liquor).

Yet additional exemplary detergent formulations to which the present amylase can be added (or is in some cases identified as a component) are listed in the following Tables:

| HDL Detergent Composition | |
|---|---|
| Ingredient | wt % |
| Enzyme (s) (Protease + Lipase + Amylase) | 3 |
| Linear alkyl benzene sulphonic acid (HLAS) | 10 |
| C12-14 alkyl ethoxylated alcohol having an average degree of ethoxylation of 9 (AE9) | 2 |
| C12-14 alkyl ethoxylated sulphonic acid having an average degree of ethoxylation of 3 (HAES) | 23 |
| C16-17 alkyl mid chain branched alkyl sulphate | 4 |
| Amine oxide | 1 |
| C12-18 fatty acid | 2 |
| PE20 polymer | 3 |
| Polyethylene imine polymer | 3 |
| Chelant | 1.4 |
| FWA 15 Brightener | 0.4 |
| p-glycol (solvent) | 8 |
| DEG (solvent) | 0.5 |
| Ethanol | 3 |
| Monoethanolamine | 6 |
| Water | 26 |
| NaOH | 0.3 |
| Perfume | 1 |
| Silicone suds suppressor | 0.06 |
| Violet DD dye | 0.01 |
| Other dyes | 0.03 |
| Hydrogenated castor oil (structurant/thickener) | 0.1 |
| Mica | 0.2 |
| Calcium formate | 0.1 |
| Sodium formate | 0.2 |
| Miscellaneous | to 100 |

HDD Detergent Compositions

| Ingredient | Composition A | Composition B | Composition C | Composition D |
|---|---|---|---|---|
| Enzyme (Lipase + other enzymes) | 0.8 wt % | 0.8 wt % | 0.8 wt % | 0.8 wt % |
| Linear alkyl benzene sulphonate | 9 wt % | 9 wt % | 12 wt % | 8 wt % |
| Alkyl ethoxylated sulphate having an average degree of ethoxylation of from 0.5 to 3 | 3 wt % | 2 wt % | 1 wt % | 2 wt % |
| Cationic detersive surfactant | 0.5 wt % | 0.5 wt % | 0.5 wt % | 0.5 wt % |
| Sodium sulphate | 55 wt % | 55 wt % | 55 wt % | 55 wt % |
| Sodium carbonate | 8 wt % | 10 wt % | 5 wt % | 8 wt % |
| Glycerol carbonate | 9 wt % | 12 wt % | 8 wt % | 10 wt % |
| Oxaziridiniuym-based bleach catalyst | 0.005 wt % | 0.005 wt % | 0.005 wt % | 0.005 wt % |
| Sodium silicate | 3 wt % | 0 wt % | 3 wt % | 0 wt % |
| Carboxylate polymer | 2 wt % | 2 wt % | 2 wt % | 2 wt % |
| Brightener | 0.02 wt % | 0.02 wt % | 0.02 wt % | 0.02 wt % |
| Cellulosic polymer | 0.3 wt % | 0.3 wt % | 0.3 wt % | 0.3 wt % |
| Misc & Moisture | to 100 wt % | to 100 wt % | to 100 wt % | to 100 wt % |

HDD Detergent Compositions

| Ingredient | 1 (wt %) | 2 (wt %) | 3 (wt %) | 4 (wt %) | 5 (wt %) | 6 (wt %) |
|---|---|---|---|---|---|---|
| Sodium linear alkylbenzenesulfonate with average aliphatic chain length C11-12 | 10.3 | 10.7 | 14 | 17 | 12.2 | 8.3 |
| Sodium lauryl sulfate | 0 | 3.5 | 0 | 1.4 | 1.2 | 0 |
| Sodium C12-14 alcohol ethoxy-3-sulfate | 0 | 0 | 0.8 | 0 | 0 | 3 |
| C13-15 oxo alcohol ethoxylate with average 7 moles of ethoxylation (Lutensol ® A07) | 1.57 | 0 | 0 | 0 | 1.2 | 0 |
| C10-Guerbet (2-propylheptan-I-ol) alcohol ethoxylate with average 7 moles of ethoxylation (Lutensol ® XP70) | 0 | 1.5 | 0 | 0 | 1.2 | 0 |
| C16-18 alcohol ethoxylate with average 7 moles of ethoxylation | 0 | 0.5 | 0 | 0 | 0.3 | 0 |
| C12-18 alcohol ethoxylate with average 5 moles of ethoxylation | 0 | 0.3 | 0 | 0 | 0 | 0 |
| C12-14 alkyl hydroxyethyl dimethyl ammonium chloride (Praepagen ® HY) | 0 | 0 | 0.7 | 0.54 | 0.1 | 1 |
| Sodium tripolyphosphate | 0 | 0 | 0.6 | 0 | 1 | 0 |
| Zeolite A (builder) | 2.7 | 3.4 | 0 | 0 | 0.5 | 1.6 |
| Citric Acid | 1.8 | 2 | 0 | 1.4 | 0 | 2 |
| Sodium citrate | 0 | 1.9 | 0 | 0 | 0 | 0 |
| Sodium bicarbonate | 29 | 35 | 36.7 | 34 | 53 | 22 |
| Sodium sesquicarbonate dihydrate | 0 | 0 | 1.2 | 0 | 0 | 0 |
| Sodium carbonate | 1.2 | 0 | 1.9 | 0 | 0 | 0 |
| Sodium polyacrylate (MW 4000, Sokalan PA25 CL) | 0 | 0 | 1 | 0 | 0 | 0 |
| Sodium polyacrylate (MW 8000, Sokalan PA30 CL) | 1.45 | 1.6 | 0 | 0.97 | 1 | 0 |
| Sodium polyacrylate/maleate copolymer MW 70,000, | 0 | 0 | 0.3 | 0 | 0 | 3 |

HDD Detergent Compositions

| Ingredient | 1 (wt %) | 2 (wt %) | 3 (wt %) | 4 (wt %) | 5 (wt %) | 6 (wt %) |
|---|---|---|---|---|---|---|
| 70:30 ratio, Sokalan® CPS | | | | | | |
| Polyethylene glycol/vinyl acetate random graft copolymer | 0 | 0 | 0.8 | 1 | 1 | 0 |
| Carboxymethyl cellulose (Finnfix® GDA) | 1 | 0.9 | 0 | 0 | 0 | 0 |
| Carboxymethyl cellulose (Finnfix® V) | 0 | 0 | 0 | 0.3 | 1.1 | 0.92 |
| Hydrophobically modified carboxymethyl cellulose (Finnfix® SH-1) | 0 | 0 | 0.5 | 0 | 0 | 0 |
| C. I. Fluorescent Brightener 260 | 0.1 | 0.13 | 0.1 | 0.03 | 0.05 | 0.18 |
| C. I. Fluorescent Brightener 351 (Tinopal® CBS) | 0 | 0.06 | 0.08 | 0 | 0 | 0 |
| Diethylenetriamine pentaacetic acid | 0 | 0 | 0.2 | 0.1 | 0.2 | 0 |
| Tetrasodium S,S-ethylenediamine disuccinate | 0 | 0 | 0 | 0.3 | 0 | 0.3 |
| Diethylenetriamine penta (methylene phosphonic acid), heptasodium salt | 0 | 0.2 | 0 | 0 | 0 | 0 |
| 1-Hydroxyethane-1,1-diphosphonic acid | 0.1 | 0.2 | 0.3 | 0 | 0.2 | 0.4 |
| 2-Phosphonobutane 1,2,4-tricarboxylic acid (Bayhibit® AM) | 0 | 0 | 0 | 0.4 | 0 | 0 |
| MgS04 | 0 | 0 | 0 | 0.8 | 0 | 0.4 |
| Sodium percarbonate | 9 | 12 | 7 | 6 | 8 | 9 |
| Propylene glycol diacetate | 7 | 10 | 10.8 | 0 | 0 | 0 |
| Triethylene glycol diacetate | 0 | 0 | 0 | 5 | 7 | 3.9 |
| Oxaziridinium-based bleach booster | 0.03 | 0 | 0.03 | 0.02 | 0.05 | 0.02 |
| Protease 1 | 4.3 | 3.3 | 6.3 | 5.7 | 3.3 | 0 |
| Protease 2 | 0 | 0 | 0 | 0 | 0 | 2.2 |
| Amyalse | 2.2 | 1.51 | 1 | 2.2 | 1.9 | 3.3 |
| Lipase | 0 | 0 | 3.6 | 0 | 0 | 2.7 |
| Endoglucanase 1 | 0 | 0 | 5.3 | 3.3 | 0 | 0 |
| Endoglucanase 2 | 2.1 | 1.3 | 0 | 0 | 0 | 2.4 |
| Mannanase | 1.3 | 1.54 | 1.3 | 0 | 1.2 | 1.9 |
| Perhydrolase 1 | 2 | 0 | 1.8 | 0 | 2.1 | 1.9 |
| Perhydrolase 2 | 0 | 4.1 | 0 | 2.3 | 0 | 0 |
| Direct Violet 9 | 0 | 0 | 0.0003 | 0.0004 | 0 | 0 |
| Solvent Violet 13 | 0 | 0 | 0.002 | 0 | 0 | 0 |
| Texcare® SRA300F | 0.3 | 1.2 | 0 | 1 | 0.33 | 0.3 |
| Dye lock | 0.02 | 0.02 | 0 | 0 | 0 | 0 |
| (Tinolux® BMC) | 0 | 0 | 0 | 0 | 0 | 0.0015 |
| C.I. Food Red 14 | 0 | 0 | 0.001 | 0 | 0 | 0.001 |
| Suds suppressor granule | 0.2 | 0.2 | 0 | 0 | 0.3 | 0 |
| Moisture | 7 | 6.3 | 8.9 | 9.1 | 4.3 | 4.6 |
| Perfume | 0.2 | 0.3 | 0.4 | 0.3 | 0.2 | 0.3 |
| Sodium sulfate | Balance to 100% | Balance to 100% | Balance to 100% | Balance to 100% | Balance to 100% | Balance to 100% |

Automatic Dishwashing (ADW) Detergent Compositions

Solid ADW detergent composition

| Ingredient | 1 Level % wt | 2 Level % wt | 3 Level % wt | 4 Level % wt |
|---|---|---|---|---|
| STPP | 35 | 0 | 0 | 56 |
| Carbonate | 24 | 45 | 40 | 18.5 |
| Methylglycine diacetic acid (83% active) | 0 | 15 | 20 | 0 |
| Silicate | 7 | 7 | 7 | 1.5 |
| TEAD (Tetraacety lethylenediamine) | 0.5 | 0.5 | 0.5 | 3.8 |
| Zinc carbonate | 0.5 | 0.5 | 0.5 | 0 |
| SLF18 | 1.5 | 1.5 | 1.5 | 0 |
| Plurafac LF224 | | | | 0.6 |
| Penta Amine Acetato-cobalt(III) nitrate (1% active) | 0.5 | 0.5 | 0.5 | 0.6 |
| Percarbonate | 15 | 15 | 15 | 11 |
| Sulphonated polymer | 10 | 4 | 3 | 5.1 |
| Amylase (14.4 mg/g active) | 1.3 | 1.8 | 1.5 | 0.7 |
| Processing aids, perfume and sodium sulphate | To balance | To balance | To balance | To balance |

Liquid automatic dishwashing detergent composition

| Ingredient | 1 Level % wt | 2 Level % wt | 3 Level % wt | 4 Level % wt |
|---|---|---|---|---|
| Dipropylene glycol | 45 | 45 | 45 | 25 |
| SLF18 | 45 | 45 | 45 | 0 |
| Neodol1-9 | 3 | 3 | 3 | 2.6 |
| Lutensol T07 | | | | 30 |
| Plurafac LF224 | | | | 32.4 |
| Amine Oxide | | | | 3.6 |
| Glycerine | 2 | 2 | 2 | 4 |
| Processing aids and Dyes | To balance | To balance | To balance | To balance |

Second Liquid automatic dishwashing detergent composition (part of three compartment unit dose)

HDL Detergent Compositions

| Compound | I | II | III | IV | V |
|---|---|---|---|---|---|
| LAS | 24 | 32 | 6 | 3 | 6 |
| NaC$_{16}$-C$_{17}$HSAS | | | | 5 | |
| C$_{12}$-C$_{15}$ AE$_{1.8}$S | | | 8 | 7 | 5 |
| C$_8$-C$_{10}$ propyl dimethyl amine | 2 | 2 | 2 | 2 | 1 |
| C$_{12}$-C$_{14}$ alkyl dimethyl amine oxide | | | | | 2 |
| C$_{12}$-C$_{15}$ AS alkyl sulphate | | | 17 | | 8 |
| C12-C14 alkyl N-methyl glucamide (CFAA) surfactant | | 5 | 4 | 4 | 3 |
| C$_{12}$-C$_{14}$ Fatty alcohol ethoxylate | 12 | 6 | 1 | 1 | 1 |
| C$_{12}$-C$_{14}$ Fatty acid | 3 | | 4 | 2 | 3 |
| Citric acid (anhydrous) | 4.5 | 5 | 3 | 2 | 1 |
| DETPMP | | | 1 | 1 | 0.5 |
| Monoethanolamine | 5 | 5 | 5 | 5 | 2 |
| Sodium hydroxide | | | 2.5 | 1 | 1.5 |
| 1 N HCl aqueous solution | #1 | #1 | | | |
| Propanediol | 12.7 | 14.5 | 13.1 | 10 | 8 |
| Ethanol | 1.8 | 2.4 | 4.7 | 5.4 | 1 |
| DTPA | 0.5 | 0.4 | 0.3 | 0.4 | 0.5 |
| Pectin Lyase | | | | 0.005 | |
| Amylase | 0.001 | 0.002 | | | |
| Cellulase | | | 0.0002 | | 0.0001 |
| Lipase | 0.1 | | 0.1 | | 0.1 |
| Metalloprotease 1 (optional) | 0.05 | 0.3 | | 0.5 | 0.2 |
| Metalloprotease 2 | | | 0.08 | | |
| Protease A (optional) | | | | | 0.1 |
| Aldose Oxidase | | | 0.3 | | 0.003 |
| ZnCl2 | 0.1 | 0.05 | 0.05 | 0.05 | 0.02 |
| Ca formate | 0.05 | 0.07 | 0.05 | 0.06 | 0.07 |
| DETBCHD | | | 0.02 | 0.01 | |
| SRP1 (anionically end capped polyesters) | 0.5 | 0.5 | | 0.3 | 0.3 |
| Boric acid | | | | | 2.4 |
| Sodium xylene sulfonate | | | 3 | | |
| Sodium cumene sulfonate | | | | 0.3 | 0.5 |
| DC 3225C | 1 | 1 | 1 | 1 | 1 |
| 2-butyl-octanol | 0.03 | 0.04 | 0.04 | 0.03 | 0.03 |
| Brightener 1 | 0.12 | 0.1 | 0.18 | 0.08 | 0.1 |

Balance to 100% perfume/dye and/or water

1: Add 1 N HCl aq. soln to adjust the neat pH of the formula in the range from about 3 to about 5.
The pH of Examples above (I)-(II) is about 5 to about 7, and of (III)-(V) is about 7.5 to about 8.5.

| HDL Detergent Compositions | | | | | | |
|---|---|---|---|---|---|---|
| | Formulations | | | | | |
| Compound | I | II | III | IV | V | VI |
| LAS | 11.5 | 11.5 | 9 | — | 4 | — |
| $C_{12}$-$C_{15}AE_{2.85}S$ | — | — | 3 | 18 | — | 16 |
| $C_{14}$-$C_{15}E_{2.5}$ S | 11.5 | 11.5 | 3 | — | 16 | — |
| $C_{12}$-$C_{13}E_{9}$ | — | — | 3 | 2 | 2 | 1 |
| $C_{12}$-$C_{13}E_{7}$ | 3.2 | 3.2 | — | — | — | — |
| C12-C14 alkyl N-methyl glucamide (CFAA) surfactant | — | — | — | 5 | — | 3 |
| TPKFA (C12-C14 topped whole cut fatty acids) | 2 | 2 | — | 2 | 0.5 | 2 |
| Citric Acid (Anhydrous) | 3.2 | 3.2 | 0.5 | 1.2 | 2 | 1.2 |
| Ca formate | 0.1 | 0.1 | 0.06 | 0.1 | — | — |
| Na formate | 0.5 | 0.5 | 0.06 | 0.1 | 0.05 | 0.05 |
| ZnCl2 | 0.1 | 0.05 | 0.06 | 0.03 | 0.05 | 0.05 |
| Sodium Cumene Sulfonate | 4 | 4 | 1 | 3 | 1.2 | — |
| Borate | 0.6 | 0.6 | 1.5 | — | — | — |
| Sodium Hydroxide | 6 | 6 | 2 | 3.5 | 4 | 3 |
| Ethanol | 2 | 2 | 1 | 4 | 4 | 3 |
| 1,2 Propanediol | 3 | 3 | 2 | 8 | 8 | 5 |
| Monoethanolamine | 3 | 3 | 1.5 | 1 | 2.5 | 1 |
| TEPAE (tetraethylene pentaamine ethoxylate) | 2 | 2 | — | 1 | 1 | 1 |
| Metalloprotease 1 (optional) | 0.03 | 0.05 | — | 0.03 | — | 0.02 |
| Metalloprotease 2 | — | — | 0.01 | — | 0.08 | — |
| Protease A (optional) | — | — | 0.01 | — | — | — |
| Lipase | — | — | — | 0.002 | — | — |
| Amylase | — | — | — | — | 0.002 | — |
| Cellulase | — | — | — | — | — | 0.0001 |
| Pectin Lyase | 0.005 | 0.005 | — | — | — | — |
| Aldose Oxidase | 0.05 | — | — | 0.05 | — | 0.02 |
| Galactose oxidase | — | 0.04 | — | — | — | — |
| pentaamine acetate cobalt (III) salt PAAC | 0.03 | 0.03 | 0.02 | — | — | — |
| DETBCHD | — | — | — | 0.02 | 0.01 | — |
| SRP1 (anionically end capped polyesters) | 0.2 | 0.2 | — | 0.1 | — | — |
| DTPA | — | — | — | 0.3 | — | — |
| polyvinyl pyridine-N-Oxide (PVNO) | — | — | — | 0.3 | — | 0.2 |
| Brightener 1 | 0.2 | 0.2 | 0.07 | 0.1 | — | — |
| Silicone antifoam | 0.04 | 0.04 | 0.02 | 0.1 | 0.1 | 0.1 |
| Balance to 100% perfume/dye and/or water | | | | | | |

| Liquid Hand Dishwashing (Hand Dish Liquid) Detergent Compositions | | | | | | |
|---|---|---|---|---|---|---|
| | Formulations | | | | | |
| Compound | I | II | III | IV | V | VI |
| $C_{12}$-$C_{15}AE_{1.8}S$ | 30 | 28 | 25 | — | 15 | 10 |
| LAS | — | — | — | 5 | 15 | 12 |
| Paraffin Sulfonate | — | — | — | 20 | — | — |
| $C_{10}$-$C_{18}$ Alkyl Dimethyl Amine Oxide | 5 | 3 | 7 | — | — | — |
| Betaine | 3 | — | 1 | 3 | 1 | — |
| $C_{12}$ poly-hydroxy fatty acid amide | — | — | — | 3 | — | 1 |
| $C_{14}$ poly-OH fatty acid amide | — | 1.5 | — | — | — | — |
| $C_{11}E_{9}$ | 2 | — | 4 | — | — | 20 |
| DTPA | — | — | — | — | 0.2 | — |
| Tri-sodium Citrate dihydrate (builder) | 0.25 | — | — | 0.7 | — | — |
| Diamine (Dimethyl aminopropyl amine;1,6-hezane diamine; 1,3-propane diamine; 2-methyl-1,5-pentane diamine; 1,3-pentanediamine; 1-methyl-diaminopropane) | 1 | 5 | 7 | 1 | 5 | 7 |
| $MgCl_2$ | 0.25 | — | — | 1 | — | — |

Liquid Hand Dishwashing (Hand Dish Liquid) Detergent Compositions

| Compound | I | II | III | IV | V | VI |
|---|---|---|---|---|---|---|
| Metalloprotease 1 (optional) | 0.02 | 0.01 | — | 0.01 | — | 0.05 |
| Metalloprotease 2 | — | — | 0.03 | — | 0.02 | — |
| Protease A (optional) | — | 0.01 | — | — | — | — |
| Amylase | 0.001 | — | — | 0.002 | — | 0.001 |
| Aldose Oxidase | 0.03 | — | 0.02 | — | 0.05 | — |
| Sodim Cumene Sulfonate | — | — | — | 2 | 1.5 | 3 |
| pentaamine acetate cobalt (III) salt | 0.01 | 0.01 | 0.02 | — | — | — |
| DETBCHD | — | — | — | 0.01 | 0.02 | 0.01 |
| Balance to 100% perfume/dye and/or water | | | | | | |

The pH of Examples (I)-(VI) is about 8 to about 11.

Liquid Automatic Dish Washing Detergent Compositions

| Compound | I | II | III | IV | V |
|---|---|---|---|---|---|
| STPP (sodium tripoly phosphate) | 16.00 | 16.00 | 18.00 | 16.00 | 16.00 |
| Potassium Sulfate | | 10.00 | 8.00 | | 10.00 |
| 1,2 propanediol | 6.00 | 0.50 | 2.00 | 6.00 | 0.50 |
| Boric Acid | | | | 4.00 | 3.00 |
| CaCl2 dihydrate | 0.04 | 0.04 | 0.04 | 0.04 | 0.04 |
| Nonionic surfactant | 0.50 | 0.50 | 0.50 | 0.50 | 0.50 |
| Metalloprotease 1 (optional) | 0.10 | 0.03 | | 0.03 | |
| Metalloprotease 2 | | | 0.05 | | 0.06 |
| Protease B (optional) | | | | 0.01 | |
| Amylase | 0.02 | | 0.02 | 0.02 | |
| Aldose Oxidase | | 0.15 | 0.02 | | 0.01 |
| Galactose Oxidase | | | 0.01 | | 0.01 |
| pentaamine acetate obalt (III) salt PAAC (bleach catalyst) | 0.01 | | | 0.01 | |
| DETBCHD | | | 0.01 | | 0.01 |
| Balance to 100% perfume/dye and/or water | | | | | |

Granular and/or Tablet Detergent Compositions

| Compound | I | II | III | IV | V |
|---|---|---|---|---|---|
| $C_{14}$-$C_{15}$AS or TAS (sodium tallow alkyl sulfate) | 8 | 5 | 3 | 3 | 3 |
| LAS | 8 | | 8 | | 7 |
| $C_{12}$-$C_{15}$AE$_3$S | 0.5 | 2 | 1 | | |
| $C_{12}$-$C_{15}$E$_5$ or E$_3$ | 2 | | 5 | 2 | 2 |
| QAS (quarternary ammonium salt) | | | | 1 | 1 |
| Zeolite A | 20 | 18 | 11 | | 10 |
| SKS-6 (dry add) (layered silicate) | | | 9 | | |
| MA/AA (acrylate/maleate copolymer) | 2 | 2 | 2 | | |
| AA (polyacrylate polymer) | | | | | 4 |
| 3Na Citrate 2H$_2$0 | | 2 | | | |
| Citric Acid (Anhydrous) | 2 | | 1.5 | 2 | |
| DTPA | 0.2 | 0.2 | | | |
| EDDS | | | 0.5 | 0.1 | |
| HEDP | | | 0.2 | 0.1 | |
| PB1 (sodium perborate monohydrate) | 3 | 4.8 | | | 4 |
| Percarbonate | | | 3.8 | 5.2 | |
| NOBS | 1.9 | | | | |
| NACA OBS | | | 2 | | |
| TAED | 0.5 | 2 | 2 | 5 | 1 |
| BB1 (3-(3,4-Dihydroisoquinolinium)-propane sulfonate (DIPS)) | 0.06 | | 0.34 | | 0.14 |
| BB2 3-(3,4-Dihydroisoquinolinium)-decane-2-sulfate | | 0.14 | | 0.2 | |
| Anhydrous sodium carbonate | 15 | 18 | | 15 | 15 |
| Sulfate | 5 | 12 | 5 | 17 | 3 |
| Silicate | | 1 | | | 8 |
| Metalloprotease 1 (optional) | 0.03 | | 0.1 | 0.06 | |
| Metalloprotease 2 | | 0.05 | | | 0.1 |
| Protease B (optional) | | 0.01 | | | |
| Protease C (optional) | | | | 0.01 | |
| Lipase | | 0.008 | | | |
| Amylase | 0.001 | | | | 0.001 |
| Cellulase | | 0.0014 | | | |

Granular and/or Tablet Detergent Compositions

| Compound | Formulations | | | | |
|---|---|---|---|---|---|
| | I | II | III | IV | V |
| Pectin Lyase | 0.001 | 0.001 | 0.001 | 0.001 | 0.001 |
| Aldose Oxidase | 0.03 | — | 0.05 | — | — |
| pentaamine acetate cobalt (III) salt PAAC | — | 0.01 | — | — | 0.05 |
| Balance to 100% Moisture and/or Minors* | | | | | |

*Perfume, dye, brightener/SRP1/Na carboxymethylcellulose/photobleach/MgSO4/PVPVI/suds suppressor/high molecular PEG/clay.

High Density Automatic Dish Washing Detergent Compositions

| Compound | Formulations | | | | | |
|---|---|---|---|---|---|---|
| | I | II | III | IV | V | VI |
| STPP (sodium tripoly phosphate) | — | 45 | 45 | — | — | 40 |
| 3Na Citrate 2H$_2$O | 17 | — | — | 50 | 40.2 | — |
| Na Carbonate | 17.5 | 14 | 20 | — | 8 | 33.6 |
| Bicarbonate | — | — | — | 26 | — | — |
| Silicate | 15 | 15 | 8 | — | 25 | 3.6 |
| Metasilicate | 2.5 | 4.5 | 4.5 | — | — | — |
| PB1 (sodium perborate monohydrate) | — | — | 4.5 | — | — | — |
| PB4 (sodium perborate tetrahydrate) | — | — | — | 5 | — | — |
| Percarbonate | — | — | — | — | — | 4.8 |
| BB1 (3-(3,4-Dihydroisoquinolinium) propane sulfonate (DIPS)) | — | 0.1 | 0.1 | — | 0.5 | — |
| BB2 3-(3,4-Dihydroisoquinolinium)-decane-2-sulfate | 0.2 | 0.05 | — | 0.1 | — | 0.6 |
| Nonionic detergent | 2 | 1.5 | 1.5 | 3 | 1.9 | 5.9 |
| HEDP | 1 | — | — | — | — | — |
| DETPMP | 0.6 | — | — | — | — | — |
| pentaamine acetate cobalt (III) salt PAAC | 0.03 | 0.05 | 0.02 | — | — | — |
| Paraffin oil Winog 70 | 0.5 | 0.4 | 0.4 | 0.6 | — | — |
| Metalloprotease 1 (optional) | 0.072 | 0.053 | — | 0.026 | — | 0.01 |
| Metalloprotease 2 | — | — | 0.053 | — | 0.059 | — |
| Protease B (optional) | — | — | — | — | — | 0.01 |
| Amylase | 0.012 | — | 0.012 | — | 0.021 | 0.006 |
| Lipase | — | 0.001 | — | 0.005 | — | — |
| Pectin Lyase | 0.001 | 0.001 | 0.001 | — | — | — |
| Aldose Oxidase | 0.05 | 0.05 | 0.03 | 0.01 | 0.02 | 0.01 |
| BTA (benzotriazole) | 0.3 | 0.2 | 0.2 | 0.3 | 0.3 | 0.3 |
| Polycarboxylate | 6 | — | — | — | 4 | 0.9 |
| Perfume | 0.2 | 0.1 | 0.1 | 0.2 | 0.2 | 0.2 |
| Balance to 100% Moisture and/or Minors* | | | | | | |

*Brightener/dye/SRP1/Na carboxymethylcellulose/photobleach/MgSO4/PVPVI/suds suppressor/high molecular PEG/clay. The pH of Examples (I) through (VI) is from about 9.6 to about 11.3.

Tablet Detergent Compositions

| Compound | Formulations | | | | | | | |
|---|---|---|---|---|---|---|---|---|
| | I | II | III | IV | V | VI | VII | VIII |
| STPP (sodium tripoly phosphate) | — | 48.8 | 44.7 | 38.2 | — | 42.4 | 46.1 | 46 |
| 3Na Citrate 2H$_2$O | 20 | — | — | — | 35.9 | — | — | — |
| Na Carbonate | 20 | 5 | 14 | 15.4 | 8 | 23 | 20 | — |
| Silicate | 15 | 14.8 | 15 | 12.6 | 23.4 | 2.9 | 4.3 | 4.2 |
| Lipase | 0.001 | — | 0.01 | — | 0.02 | — | — | — |
| Protease B | 0.01 | — | — | — | — | — | — | — |
| Protease C | — | — | — | — | — | 0.01 | — | — |
| Metalloprotease 1 (optional) | 0.01 | 0.08 | — | 0.04 | — | 0.023 | — | 0.05 |

| Tablet Detergent Compositions ||||||||||
|---|---|---|---|---|---|---|---|---|
| | Formulations |||||||||
| Compound | I | II | III | IV | V | VI | VII | VIII |
| Metalloprotease 2 | — | — | 0.05 | — | 0.052 | — | 0.023 | — |
| Amylase | 0.012 | 0.012 | 0.012 | — | 0.015 | — | 0.017 | 0.002 |
| Pectin Lyase | 0.005 | — | — | 0.002 | — | — | — | — |
| Aldose Oxidase | — | 0.03 | — | 0.02 | 0.02 | — | 0.03 | — |
| PB1 (sodium perborate monohydrate) | — | — | 3.8 | — | 7.8 | — | — | 4.5 |
| Percarbonate | 6 | — | — | 6 | — | 5 | — | — |
| BB1 (3-(3,4-Dihydroisoquinolinium) propane sulfonate (DIPS)) | 0.2 | — | 0.5 | — | 0.3 | 0.2 | — | — |
| BB2 3-(3,4-Dihydroisoquinolinium)-decane-2-sulfate | — | 0.2 | — | 0.5 | — | — | 0.1 | 0.2 |
| Nonionic surfactant | 1.5 | 2 | 2 | 2.2 | 1 | 4.2 | 4 | 6.5 |
| pentaamine acetate cobalt (III) salt PAAC | 0.01 | 0.01 | 0.02 | — | — | — | — | — |
| DETBCHD | — | — | — | 0.02 | 0.02 | — | — | — |
| TAED | — | — | — | — | — | 2.1 | — | 1.6 |
| HEDP | 1 | — | — | 0.9 | — | 0.4 | 0.2 | — |
| DETPMP | 0.7 | — | — | — | — | — | — | — |
| Paraffin oil Winog 70 | 0.4 | 0.5 | 0.5 | 0.5 | — | — | 0.5 | — |
| BTA (benzotriazole) | 0.2 | 0.3 | 0.3 | 0.3 | 0.3 | 0.3 | 0.3 | — |
| Polycarboxylate | 4 | — | — | — | 4.9 | 0.6 | 0.8 | — |
| PEG 400-30,000 | — | — | — | — | — | 2 | — | 2 |
| Glycerol | — | — | — | — | — | 0.4 | — | 0.5 |
| Perfume | — | — | — | 0.05 | 0.2 | 0.2 | 0.2 | 0.2 |
| Balance to 100% Moisture and/or Minors* |||||||||

*Brightener/SRP1/Na carboxymethylcellulose/photobleach/MgSO4/PVPVI/suds suppressor/high molecular PEG/clay.

The pH of Examples (I) through (VII) is from about 10 to about 11.5; pH of (VIII) is from 8-10. The tablet weight of Examples (I) through (VIII) is from about 20 grams to about 30 grams.

| Liquid Hard Surface Detergent Compositions ||||||||
|---|---|---|---|---|---|---|---|
| | Formulations |||||||
| Compound | I | II | III | IV | V | VI | VII |
| $C_9$-$C_{11}E_5$ | 2.4 | 1.9 | 2.5 | 2.5 | 2.5 | 2.4 | 2.5 |
| $C_{12}$-$C_{14}E_5$ | 3.6 | 2.9 | 2.5 | 2.5 | 2.5 | 3.6 | 2.5 |
| $C_7$-$C_9E_6$ | — | — | — | — | — | — | — |
| $C_{12}$-$C_{14}E_{21}$ | 1 | 0.8 | 4 | 2 | 2 | 1 | 2 |
| LAS | — | — | — | 0.8 | 0.8 | — | 0.8 |
| Sodim Cumene Sulfonate | 1.5 | 2.6 | — | 1.5 | 1.5 | 1.5 | 1.5 |
| Isachem ® AS (branched alcohol alkyl sulfate) | 0.6 | 0.6 | — | — | — | 0.6 | — |
| $Na_2CO_3$ | 0.6 | 0.13 | 0.6 | 0.1 | 0.2 | 0.6 | 0.2 |
| 3Na Citrate 2$H_2O$ | 0.5 | 0.56 | 0.5 | 0.6 | 0.75 | 0.5 | 0.75 |
| NaOH | 0.3 | 0.33 | 0.3 | 0.3 | 0.5 | 0.3 | 0.5 |
| Fatty Acid | 0.6 | 0.13 | 0.6 | 0.1 | 0.4 | 0.6 | 0.4 |
| 2-butyl octanol | 0.3 | 0.3 | — | 0.3 | 0.3 | 0.3 | 0.3 |
| PEG DME-2000 ® | 0.4 | — | 0.3 | 0.35 | 0.5 | — | — |
| PVP (vinylpyrrolidone homopolymer) | 0.3 | 0.4 | 0.6 | 0.3 | 0.5 | — | — |
| MME PEG (2000) ® | — | — | — | — | — | 0.5 | 0.5 |
| Jeffamine ® ED-2001 (capped polyethylene glycol) | — | 0.4 | — | — | 0.5 | — | — |
| pentaamine acetate cobalt (III) salt PAAC | — | — | — | 0.03 | 0.03 | 0.03 | — |
| DETBCHD | 0.03 | 0.05 | 0.05 | — | — | — | — |
| Metalloprotease 1 (optional) | 0.07 | — | 0.08 | 0.03 | — | 0.01 | 0.04 |
| Metalloprotease 2 | — | 0.05 | — | — | 0.06 | — | — |
| Protease B (optional) | — | — | — | — | — | 0.01 | — |
| Amylase | 0.12 | 0.01 | 0.01 | — | 0.02 | — | 0.01 |
| Lipase | — | 0.001 | — | 0.005 | — | 0.005 | — |

-continued

Liquid Hard Surface Detergent Compositions

| Compound | I | II | III | IV | V | VI | VII |
|---|---|---|---|---|---|---|---|
| Pectin Lyase | 0.001 | — | 0.001 | — | — | — | 0.002 |
| ZnCl2 | 0.02 | 0.01 | 0.03 | 0.05 | 0.1 | 0.05 | 0.02 |
| Calcium Formate | 0.03 | 0.03 | 0.01 | — | — | — | — |
| PB1 (sodium perborate monohydrate) | — | 4.6 | — | 3.8 | — | — | — |
| Aldose Oxidase | 0.05 | — | 0.03 | — | 0.02 | 0.02 | 0.05 |
| Balance to 100% perfume/dye and/or water | | | | | | | |

The pH of Examples (I) through (VII) is from about 7.4 to about 9.5.

HDL Detergent Compositions

| Ingredient | Composition (wt % of composition) | | | |
|---|---|---|---|---|
| | 1 | 2 | 3 | 4 |
| $C_{12-15}$ Alkylethoxy(1.8)sulfate | 14.7 | 11.6 | | 16.31 |
| $C_{11.8}$ Alkylbenzene sulfonate | 4.3 | 11.6 | 8.3 | 7.73 |
| $C_{16-17}$ Branched alkyl sulfate | 1.7 | 1.29 | | 3.09 |
| $C_{12-14}$ Alkyl-9-ethoxylate | 0.9 | 1.07 | | 1.31 |
| $C_{12}$ dimethylamine oxide | 0.6 | 0.64 | | 1.03 |
| Citric acid | 3.5 | 0.65 | 3 | 0.66 |
| $C_{12-18}$ fatty acid | 1.5 | 2.32 | 3.6 | 1.52 |
| Sodium Borate (Borax) | 2.5 | 2.46 | 1.2 | 2.53 |
| Sodium $C_{12-14}$ alkyl ethoxy 3 sulfate | | | 2.9 | |
| $C_{14-15}$ alkyl-7-ethoxylate | | | 4.2 | |
| $C_{12-14}$ Alkyl-7-ethoxylate | | | 1.7 | |
| Ca formate | 0.09 | 0.09 | | 0.09 |
| A compound having the following general structure: bis(($C_2H_5O$)($C_2H_4O$)n)($CH_3$)—$N^+$—$C_xH_{2x}$—$N^+$—($CH_3$)—bis(($C_2H_5O$)($C_2H_4O$)n), wherein n = from 20 to 30, and x = from 3 to 8, or sulphated or sulphonated variants thereof | | | 1.2 | |
| Random graft co-polymer[1] | | 1.46 | 0.5 | |
| Ethoxylated Polyethylenimine[2] | 1.5 | 1.29 | | 1.44 |
| Diethylene triamine pentaacetic acid | 0.34 | 0.64 | | 0.34 |
| Diethylene triamine penta-(methylene phosphonic acid) | | | 0.3 | |
| Tinopal AMS-GX | | 0.06 | | |
| Tinopal CBS-X | 0.2 | 0.17 | | 0.29 |
| Amphiphilic alkoxylated grease cleaning polymer[3] | 1.28 | 1 | 0.4 | 1.93 |
| Ethanol | 2 | 1.58 | 1.6 | 5.4 |
| Propylene Glycol | 3.9 | 3.59 | 1.3 | 4.3 |
| Diethylene glycol | 1.05 | 1.54 | | 1.15 |
| Polyethylene glycol | 0.06 | 0.04 | | 0.1 |
| Monoethanolamine | 3.05 | 2.41 | 0.4 | 1.26 |
| NaOH | 2.44 | 1.8 | | 3.01 |
| Sodium Cumene Sulphonate | | | 1 | |
| Sodium Formate | | 0.11 | | 0.09 |
| Water, Aesthetics (Dyes, perfumes) and Minors (Enzymes, solvents, structurants) | balance | balance | balance | balance |

[1] Random graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units.
[2] Polyethylenimine (MW = 600) with 20 ethoxylate groups per —NH.
[3] Amphiphilic alkoxylated grease cleaning polymer is a polyethylenimine (MW = 600) with 24 ethoxylate groups per NH and 16 propoxylate groups per —NH.

Light-Duty Liquid Dishwashing Detergent Compositions

| Composition | 1 | 2 | 3 | 4 |
|---|---|---|---|---|
| Linear Alkylbenzene Sulfonate (1) | | | | |
| Alkyl Ethoxy Sulfate (2) | 18% | 17% | 17% | 18% |
| Paraffin Sulfonate (C15) | | | | |
| CAP = coco amido propyl Betaine | | | 9% | 5% |
| Nonionic (3) | | | 1% | |
| Amine Oxide (4) | 6% | 5.50% | | 4% |
| Alkylpolyglucoside | | | | 4% |
| Alcohol (5) | | | 5% | 7% |
| Pura = polypropyleneglycol | 1% | 0.80% | | |
| Citrate | | | 0.30% | 0.60% |
| Salt (6) | 1.20% | 1.00% | | 0.50% |
| SCS = sodium cumene sulfonate | | | 0.80% | |
| glycerol | 15% | 5% | 3% | |
| Na-lactate | | | | 5% |
| cationic polymer (7) | 0.10% | 0.10% | 0.30% | 0.20% |
| Present amylase | 0.0075 | 0.005 | 0.0025 | 0.03 |
| Glycol distearate from Euperlan® Cognis | 0.4 | 0 | 0.4 | 0 |
| Hydrogenated Castor Oil Thixcin® Elementis | 0 | 0.1 | 0 | 0.1 |
| Mica (BASF Mearlin superfine) | 0 | 0.05 | 0 | 0.05 |
| Minors* | Balance to 100% with water | | | |
| pH | 9 | 9 | 6 | 6 |

Optional Minors*: dyes, opacifier, perfumes, preservatives, hydrotropes, processing aids, and/or stabilizers.

(1) Linear Alkylbenzene Sulfonate: LAS: C11.4
(2) Alkyl Ethoxy Sulfate: AExS :
(3) Nonionic: AlkylEthoxylate
(4) Di-methyl coco alkyl amine oxide
(5) Alcohol: Ethanol
(6) Salt: NaCl
(7) cationically modified hydroxyethyl cellulose (Polyquaternium-10 UCARE LR-400 ex Amerchol).

Liquid laundry detergent compositions suitable for front-loading automatic washing machines

| Ingredient | Composition (wt % of composition) | | | | | | | |
|---|---|---|---|---|---|---|---|---|
| | 1 | 2 | 3 | 4 | 5 | 6 | 7 | 8 |
| Alkylbenzene sulfonic acid | 7 | 11 | 4.5 | 1.2 | 1.5 | 12.5 | 5.2 | 4 |
| Sodium $C_{12-14}$ alkyl ethoxy 3 sulfate | 2.3 | 3.5 | 4.5 | 4.5 | 7 | 18 | 1.8 | 2 |
| $C_{14-15}$ alkyl 8-ethoxylate | 5 | 8 | 2.5 | 2.6 | 4.5 | 4 | 3.7 | 2 |
| $C_{12}$ alkyl dimethyl amine oxide | — | — | 0.2 | — | — | — | — | — |
| $C_{12-14}$ alkyl hydroxyethyl dimethyl ammonium chloride | — | — | — | 0.5 | — | — | — | — |
| $C_{12-18}$ Fatty acid | 2.6 | 4 | 4 | 2.6 | 2.8 | 11 | 2.6 | 1.5 |
| Citric acid | 2.6 | 3 | 1.5 | 2 | 2.5 | 3.5 | 2.6 | 2 |
| Protease* | 0.05 | 0.03 | 0.04 | 0.03 | 0.04 | 0.03 | 0.03 | 0.02 |
| Amylase | 0.1 | 0.2 | 0.15 | — | 0.05 | 0.5 | 0.1 | 0.2 |
| Mannanase | 0.05 | 0.1 | 0.05 | — | — | 0.1 | 0.04 | — |
| Random graft co-polymer[1] | 1 | 0.2 | 1 | 0.4 | 0.5 | 2.7 | 0.3 | 1 |
| A compound having the following general structure: bis$((C_2H_5O)(C_2H_4O)n)(CH_3)$—$N^+$—$C_xH_{2x}$—$N^+$—$(CH_3)$-bis$((C_2H_5O)(C_2H_4O)n)$, wherein n = from 20 to 30, and x = from 3 to 8, or sulphated or sulphonated variants thereof | 0.4 | 2 | 0.4 | 0.6 | 1.5 | 1.8 | 0.7 | 0.3 |
| Ethoxylated Polyethylenimine[2] | — | — | — | — | — | 0.5 | — | — |
| Amphiphilic alkoxylated grease cleaning polymer[3] | 0.1 | 0.2 | 0.1 | 0.2 | 0.3 | 0.3 | 0.2 | 0.3 |
| Diethoxylated poly (1,2 propylene terephthalate) | — | — | — | — | — | — | 0.3 | — |
| Diethylenetriaminepenta(methylenephosphonic) acid | 0.2 | 0.3 | — | — | 0.2 | — | 0.2 | 0.3 |
| Hydroxyethane diphosphonic acid | — | — | 0.45 | — | — | 1.5 | — | 0.1 |
| FWA (fluorescent whitening agent) | 0.1 | 0.2 | 0.1 | — | — | 0.2 | 0.05 | 0.1 |
| Solvents (1,2 propanediol, ethanol), | 3 | 4 | 1.5 | 1.5 | 2 | 4.3 | 2 | 1.5 |
| Hydrogenated castor oil derivative | 0.4 | 0.4 | 0.3 | 0.1 | 0.3 | — | 0.4 | 0.5 |
| Boric acid | 1.5 | 2.5 | — | 1.5 | 1.5 | 0.5 | 1.5 | 1.5 |
| Na formate | — | — | — | 1 | — | — | — | — |
| Reversible protease inhibitor[4] | — | — | 0.002 | — | — | — | — | — |
| Perfume | 0.5 | 0.7 | 0.5 | 0.5 | 0.8 | 1.5 | 0.5 | 0.8 |
| Perfume MicroCapsules slurry (30% am) | 0.2 | 0.3 | 0.7 | 0.2 | 0.05 | 0.4 | 0.9 | 0.7 |
| Ethoxylated thiophene, Hueing Dye[5] | 0.005 | 0.007 | 0.01 | 0.008 | 0.008 | 0.007 | 0.007 | 0.008 |
| Buffers (sodium hydroxide, Monoethanolamine) | To pH 8.2 | | | | | | | |
| Water and minors (antifoam, aesthetics) | To 100% | | | | | | | |

[1]Random graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and nor more than 1 grafting point per 50 ethylene oxide units.
[2]Polyethylenimine (MW = 600) with 20 ethoxylate groups per —NH.
[3]Amphiphilic alkoxylated grease cleaning polymer is a polyethylenimine (MW = 600) with 24 ethoxylate groups per —NH and 16 propoxylate groups per —NH
[5]Ethoxylated thiophene Hueing Dye is as described in U.S. Pat. No. 7,208,459 B2.
*Remark: all enzyme levels expressed as % enzyme raw material, except for protease which is expressed as % of active protein added to the product.
[4]Reversible Protease inhibitor of structure shown below the Table.

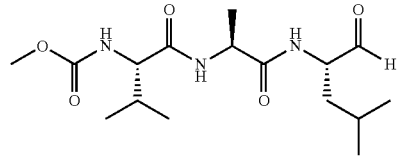 [SMILES: COC(=O)N[C@H](C(=O)N[C@@H](C)C(=O)N[C@H](C=O)CC(C)C)C(C)C]

Liquid laundry detergent compositions suitable for top-loading automatic washing machines

| Ingredient | Composition (wt % of composition) | | | | | | | |
|---|---|---|---|---|---|---|---|---|
| | 1 | 2 | 3 | 4 | 5 | 6 | 7 | 8 |
| $C_{12-15}$ Alkylethoxy(1.8)sulfate | 20.1 | 15.1 | 20 | 15.1 | 13.7 | 16.7 | 10 | 9.9 |
| $C_{11.8}$ Alkylbenzene sulfonate | 2.7 | 2 | 1 | 2 | 5.5 | 5.6 | 3 | 3.9 |
| $C_{16-17}$ Branched alkyl sulfate | 6.5 | 4.9 | | 4.9 | 3 | 9 | 2 | |
| $C_{12-14}$Alkyl-9-ethoxylate | 0.8 | 0.8 | 0.8 | 0.8 | 8 | 1.5 | 0.3 | 11.5 |
| $C_{12}$ dimethylamine oxide | | | 0.9 | | | | | |
| Citric acid | 3.8 | 3.8 | 3.8 | 3.8 | 3.5 | 3.5 | 2 | 2.1 |

| Liquid laundry detergent compositions suitable for top-loading automatic washing machines | | | | | | | | |
|---|---|---|---|---|---|---|---|---|
| | Composition (wt % of composition) | | | | | | | |
| Ingredient | 1 | 2 | 3 | 4 | 5 | 6 | 7 | 8 |
| $C_{12-18}$ fatty acid | 2 | 1.5 | 2 | 1.5 | 4.5 | 2.3 | | 0.9 |
| Protease* | 0.1 | 0.2 | 0.1 | 0.1 | 0.1 | 0.1 | 0.1 | 0.1 |
| Amylase 1 | 0.7 | 0.3 | 0.6 | 0.3 | 0.6 | 0.4 | | |
| Amylase 2 | | | | | | | | 1.1 |
| Mannanase | 0.1 | | | | | 0.1 | | |
| Pectate Lyase | 0.1 | | | | | 0.2 | | |
| Borax | 3 | 3 | | | 2 | 3 | 3 | 3.3 |
| Na & Ca formate | 0.2 | 0.2 | | 0.2 | 0.2 | | 0.7 | |
| A compound having the following general structure: bis(($C_2H_5O$)($C_2H_4O$)n)($CH_3$)—$N^+$—$C_xH_{2x}$—$N^+$—($CH_3$)—bis(($C_2H_5O$)($C_2H_4O$)n), wherein n = from 20 to 30, and x = from 3 to 8, or sulphated or sulphonated variants thereof | 1.6 | 1.6 | 3 | 1.6 | 2 | 1.6 | 1.3 | 1.2 |
| Random graft co-polymer[1] | 0.4 | 0.2 | 1 | 0.5 | 0.6 | 1 | 0.8 | 1 |
| Diethylene triamine pentaacetic acid | 0.4 | 0.4 | 0.4 | 0.4 | 0.2 | 0.3 | 0.8 | |
| Tinopal AMS-GX (brightener) | 0.2 | 0.2 | 0.2 | 0.2 | 0.2 | 0.3 | 0.1 | |
| Tinopal CBS-X (brightener) | | | | | | 0.1 | | 0.2 |
| Amphiphilic alkoxylated grease cleaning polymer [3] | 1 | 1.3 | 1.3 | 1.4 | 1 | 1.1 | 1 | 1 |
| Texcare 240N (Clariant) | | | | | 1 | | | |
| Ethanol | 2.6 | 2.6 | 2.6 | 2.6 | 1.8 | 3 | 1.3 | |
| Propylene Glycol | 4.6 | 4.6 | 4.6 | 4.6 | 3 | 4 | 2.5 | |
| Diethylene glycol | 3 | 3 | 3 | 3 | 3 | 2.7 | 3.6 | |
| Polyethylene glycol | 0.2 | 0.2 | 0.2 | 0.2 | 0.1 | 0.3 | 0.1 | 1.4 |
| Monoethanolamine | 2.7 | 2.7 | 2.7 | 2.7 | 4.7 | 3.3 | 1.7 | 0.4 |
| Triethanolamine | | | | | | | | 0.9 |
| NaOH | to pH 8.3 | to pH 8.3 | to pH 8.3 | to pH 8.3 | to pH 8.3 | to pH 8.3 | to pH 8.3 | to pH 8.5 |
| Suds suppressor | | | | | | | | |
| Dye | 0.01 | 0.01 | 0.01 | | 0.01 | 0.01 | 0.01 | 0 |
| Perfume | 0.5 | 0.5 | 0.5 | 0.5 | 0.7 | 0.7 | 0.8 | 0.6 |
| Perfume MicroCapsules slurry (30% am) | 0.2 | 0.5 | 0.2 | 0.3 | 0.1 | 0.3 | 0.9 | 1 |
| Ethoxylated thiophene Hueing Dye[5] | 0.003 | 0.002 | 0.002 | 0.005 | 0.002 | 0.004 | 0.004 | 0.003 |
| Water | balance | balance | balance | balance | balance | balance | balance | balance |

[1] Random graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units.
[3] Amphiphilic alkoxylated grease cleaning polymer is a polyethylenimine (MW = 600) with 24 ethoxylate groups per —NH and 16 propoxylate groups per —NH
[5] Ethoxylated thiophene Hueing Dye is as described in US 7,208,459 B2.
*Remark: all enzyme levels expressed as % enzyme raw material, except for protease which is expressed as % of active protein added to the product..

| Granular detergent compositions | | | | | | |
|---|---|---|---|---|---|---|
| Component | 1 | 2 | 3 | 4 | 5 | 6 |
| Linear alkylbenzenesulfonate with aliphatic carbon chain length $C_{11}$-$C_{12}$ | 15 | 12 | 20 | 10 | 12 | 13 |
| Other surfactants | 1.6 | 1.2 | 1.9 | 3.2 | 0.5 | 1.2 |
| Phosphate builder(s) | 2 | 3 | 4 | | | |
| Zeolite | | 1 | | 1 | 4 | 1 |
| Silicate | 4 | 5 | 2 | 3 | 3 | 5 |
| Sodium Carbonate | 2 | 5 | 5 | 4 | 0 | 3 |
| Polyacrylate (MW 4500) | 1 | 0.6 | 1 | 1 | 1.5 | 1 |
| Carboxymethyl cellulose (Finnfix BDA ex CPKelco) | 1 | — | 0.3 | — | 1.1 | — |
| Cellulase | 0.23 | 0.17 | 0.5 | 0.2 | 0.2 | 0.6 |
| Protease | 0.23 | 0.17 | 0.5 | 0.2 | 0.2 | 0.6 |
| Amylase | 0.23 | 0.17 | 0.5 | 0.2 | 0.2 | 0.6 |
| Fluorescent Brightener(s) | 0.16 | 0.06 | 0.16 | 0.18 | 0.16 | 0.16 |

| Granular detergent compositions | | | | | | |
|---|---|---|---|---|---|---|
| Component | 1 | 2 | 3 | 4 | 5 | 6 |
| Diethylenetriamine pentaacetic acid or Ethylene diamine tetraacetic acid | 0.6 | 0.6 | 0.25 | 0.6 | 0.6 | |
| $MgSO_4$ | 1 | 1 | 1 | 0.5 | 1 | 1 |
| Bleach(es) and Bleach activator(s) | 6.88 | | 6.12 | 2.09 | 1.17 | 4.66 |
| Ethoxylated thiophene Hueing Dye[5] | 0.002 | 0.001 | 0.003 | 0.003 | — | — |
| Direct Violet 9 ex Ciba Specialty Chemicals | | | | 0.0006 | 0.0004 | 0.0006 |
| Sulfate/Citric Acid/Sodium Bicarbonate/Moisture/perfume | Balance to 100% | | | | | |

[5]Ethoxylated thiophene Hueing Dye is as described in US 7,208,459 B2.

| Granular Laundry Detergent Compositions and Their Components | | | | | | |
|---|---|---|---|---|---|---|
| | Detergent Compositions | | | | | |
| Component | 1 | 2 | 3 | 4 | 5 | 6 |
| Linear alkylbenzenesulfonate with aliphatic carbon chain length $C_{11}$-$C_{12}$ | 15 | 12 | 20 | 10 | 12 | 13 |
| Other surfactants | 1.6 | 1.2 | 1.9 | 3.2 | 0.5 | 1.2 |
| Phosphate builder(s) | 2 | 3 | 4 | | | |
| Zeolite | | 1 | | 1 | 4 | 1 |
| Silicate | 4 | 5 | 2 | 3 | 3 | 5 |
| Sodium Carbonate | 2 | 5 | 5 | 4 | 0 | 3 |
| Polyacrylate (MW 4500) | 1 | 0.6 | 1 | 1 | 1.5 | 1 |
| Carboxymethyl cellulose | 1 | - | 0.3 | - | 1.1 | - |
| Cellulase (15.6 mg/g) | 0.23 | 0.17 | 0.5 | 0.2 | 0.2 | 0.6 |
| Protease | 0.23 | 0.17 | 0.05 | 0.2 | 0.03 | 0.1 |
| Amylase (14 mg/g) | 0.23 | 0.17 | 0.5 | 0.2 | 0.2 | 0.6 |
| Mannanase (4 mg/g) | 0.1 | | | 0.1 | | 0.1 |
| Lipase (18.6 mg/g) | 0.2 | | 0.1 | | 0.3 | |
| Fluorescent Brightener(s) | 0.16 | 0.06 | 0.16 | 0.18 | 0.16 | 0.16 |
| Diethylenetriamine pentaacetic acid or Ethylene diamine tetraacetic acid | 0.6 | | 0.6 | 0.25 | 0.6 | 0.6 |
| $MgSO_4$ | 1 | 1 | 1 | 0.5 | 1 | 1 |
| Bleach(es) and Bleach activator(s) | 6.88 | | 6.12 | 2.09 | 1.17 | 4.66 |
| Ethoxylated thiophene Hueing Dye[5] | 0.002 | 0.001 | 0.003 | 0.003 | — | — |
| Direct Violet 9 ex Ciba Specialty Chemicals | | | | 0.0006 | 0.0004 | 0.0006 |
| Sulfate/Citric Acid/Sodium Bicarbonate/Moisture/perfume | Balance to 100% | | | | | |

| | Detergent Composition | | | | |
|---|---|---|---|---|---|
| Component | 7 | 8 | 9 | 10 | 11 |
| Surfactants | 3.55 | 15.8 | | | |
| $C_{16-17}$ Branched alkyl sulfate | | | | | |
| $C_{12-14}$ alkyl sulphate | | | 1.5 | | |
| Sodium linear alkylbenzenesulfonate with aliphatic chain length $C_{11\text{-}C12}$ | 9.6 | | 10.6 | 7.5 | 9 |
| Sodium $C_{14/15}$ alcohol ethoxy-3-sulfate | 1.15 | | | 2.88 | |
| Sodium $C_{14/15}$ alkyl sulphate | 2.37 | | | | |
| $C_{14/15}$ alcohol ethoxylate with average 7 moles of ethoxylation | | | | 1.17 | 1 |
| mono-$C_{8-10}$ alkyl mono-hydroxyethyl di-methyl quaternary ammonium chloride | | | | | 0.45 |
| Di methyl hydroxyl ethyl lauryl ammonium chloride | | | 0.18 | | |
| Zeolite A | 13.9 | 4.7 | 0.01 | 2.9 | 1.8 |
| Sodium Silicate 1.6.ratio | 4 | 0.2 | | 4 | 4 |
| Sodium Silicate 2.35.ratio | | | 8 | | |
| Citric Acid | | | | 2.5 | 1.4 |
| Sodium tripolyphosphate | | | 5 | | |
| Sodium Carbonate | 24.1 | 30 | 16.9 | 24.4 | 21 |
| Nonanoyloxybenzenesuplhonate | 5.78 | 2.81 | 0.96 | | |
| Oxaziridinium-based bleach booster | | | | 0.03 | 0.017 |

-continued

| Granular Laundry Detergent Compositions and Their Components | | | | | |
|---|---|---|---|---|---|
| Tetrasodium S,S,-ethylenediaminedisuccinate | | | | 0.2 | |
| Diethylenetriamine penta (methylene phosphonic acid), heptasodium salt | 0.61 | | | | 0.33 |
| Hydroxyethane dimethylene phosphonic acid | | | | 0.29 | 0.45 |
| Ethylene diamine tetraacetate | | | 0.27 | | |
| MgSO4 | | | 0.47 | 0.5994 | 0.782 |
| Sodium Percarbonate | 7 | 4.4 | | 15.9 | 19.1 |
| Tetra Acetyl Ethylene Diamine | | | | 3.3 | 4.6 |
| Sodium Perborate Monohydrate | | | 1.2 | | |
| Carboxymethyl cellulose (e.g., Finnfix BDA ex CPKelco) | 0.1 | | 0.17 | 1.69 | 0.23 |
| Sodium Acrylic acid/maleic acid co-polymer (70/30) | 0.0236 | 3.8 | | 2 | 2.5 |
| Sodium polyacrylate (Sokalan PA30 CL) | 4 | | 0.84 | | |
| Terephthalate polymer | | | | 0.23 | |
| Polyethylene glycol/vinyl acetate random graft co polymer | | | 0.89 | 0.89 | 0.91 |
| Photobleach- zinc phthalocyanine tetrasulfonate | | | 0.005 | 0.001 | 0.002 |
| C.I. Fluorescent Brightener 260 | 0.11 | 0.15 | 0.04 | 0.23 | 0.15 |
| C.I. Fluorescent Brightener 351 (Tinopal ® CBS) | | | 0.1 | | |
| Suds suppressor granule | | 0.25 | | 0.07 | 0.04 |
| Hydrophobically modified carboxy methyl cellulose (Finnfix ® SH-1) | | | 0.019 | 0.028 | |
| Bentonite | | | 8.35 | | |
| Miscellaneous (Dyes, perfumes, process aids, moisture and sodium sulphate) | Balance | Balance | Balance | Balance | Balance |

[5] Ethoxylated thiophene Hueing Dye is as described in US 7,208,459 B2.

| Unit Dose Detergent Compositions | | | | | |
|---|---|---|---|---|---|
| Ingredients | 1 | 2 | 3 | 4 | 5 |
| Alkylbenzene sulfonic acid C 11-13, 23.5% 2-phenyl isomer | 14.5 | 14.5 | 14.5 | 14.5 | 14.5 |
| $C_{12-14}$ alkyl ethoxy 3 sulfate | 7.5 | 7.5 | 7.5 | 7.5 | 7.5 |
| $C_{12-14}$ alkyl 7-ethoxylate | 13 | 13 | 13 | 13 | 13 |
| Citric Acid | 0.6 | 0.6 | 0.6 | 0.6 | 0.6 |
| Fatty Acid | 14.8 | 14.8 | 14.8 | 14.8 | 14.8 |
| Enzymes (as % raw material not active) | 1.7 | 1.7 | 1.7 | 1.7 | 1.7 |
| Present amylase (as % active) | 0.05 | 0.1 | 0.02 | 0.03 | 0.03 |
| Ethoxylated Polyethylenimine[1] | 4 | 4 | 4 | 4 | 4 |
| Series 1 GG36 protease (as % active) | 0.02 | 0 | 0.01 | 0.02 | 0.03 |
| Hydroxyethane diphosphonic acid | 1.2 | 1.2 | 1.2 | 1.2 | 1.2 |
| Brightener | 0.3 | 0.3 | 0.3 | 0.3 | 0.3 |
| P-diol | 15.8 | 13.8 | 13.8 | 13.8 | 13.8 |
| Glycerol | 6.1 | 6.1 | 6.1 | 6.1 | 6.1 |
| MEA (monoethanolamide) brightener stabilizer | 8 | 8 | 8 | 8 | 8 |
| TIPA (triisopropanolamine) | | | 2 | | |
| TEA (triethanolamine) | | 2 | | | |
| Cumene sulphonate | | | | | 2 |
| cyclohexyl dimethanol | | | | 2 | |
| Water | 10 | 10 | 10 | 10 | 10 |
| Structurant | 0.14 | 0.14 | 0.14 | 0.14 | 0.14 |
| Perfume | 1.9 | 1.9 | 1.9 | 1.9 | 1.9 |
| Buffers (monoethanolamine) | To pH 8.0 | | | | |
| Solvents (1,2 propanediol, ethanol) | To 100% | | | | |

[1] Polyethylenimine (MW = 600) with 20 ethoxylate groups per —NH.

| Multiple Compartment Unit Dose Detergent Compositions | |
|---|---|
| Base Composition 1 | |
| Ingredients | % |
| Glycerol (min 99) | 5.3 |
| 1,2-propanediol | 10 |
| Citric Acid | 0.5 |
| Monoethanolamine | 10 |
| Caustic soda | — |
| Dequest 2010 | 1.1 |
| Potassium sulfite | 0.2 |
| Nonionic Marlipal C24EO7 | 20.1 |
| HLAS (surfactant) | 24.6 |
| Optical brightener FWA49 | 0.2 |
| C12-15 Fatty acid | 16.4 |
| Polymer Lutensit Z96 | 2.9 |
| Polyethyleneimine ethoxylate PEI600 E20 | 1.1 |
| MgCl2 | 0.2 |
| Solvents (1,2 propanediol, ethanol) | To 100% |

| Multi-compartment formulations | | | | | | |
|---|---|---|---|---|---|---|
| Composition | 1 | | | 2 | | |
| Compartment | A | B | C | A | B | C |
| Volume of each compartment | 40 ml | 5 ml | 5 ml | 40 ml | 5 ml | 5 ml |
| Active material in Wt.% | | | | | | |
| Perfume | 1.6 | 1.6 | 1.6 | 1.6 | 1.6 | 1.6 |
| Dyes | <0.01 | <0.01 | <0.01 | <0.01 | <0.01 | <0.01 |

| Multi-compartment formulations | | | | | | |
|---|---|---|---|---|---|---|
| Composition | 1 | | | 2 | | |
| Compartment | A | B | C | A | B | C |
| TiO2 | 0.1 | — | — | — | 0.1 | — |
| Sodium Sulfite | 0.4 | 0.4 | 0.4 | 0.3 | 0.3 | 0.3 |
| Acusol 305, Rohm&Haas | 1.2 | — | — | 2 | — | — |
| Hydrogenated castor oil | 0.14 | 0.14 | 0.14 | 0.14 | 0.14 | 0.14 |
| Base Composition 1 | Add to 100% | Add to 100% | Add to 100% | Add to 100% | Add to 100% | Add to 100% |

| Phosphate-Free Detergent: IEC-60436 WFK Type B (pH = 10.4 in 3 g/l) | |
|---|---|
| Component | Wt % |
| Sodium citrate dehydrate | 30 |
| Maleic acid/Acrylic acid copolymer sodium Salt SOKALAN® CP5 BASF | 12 |
| Sodium perborate monohydrate | 5 |
| TAED | 2 |
| Sodium disilicate: Protil A (Cognis) | 25 |
| Linear fatty alcohol ethoxylate | 2 |
| Sodium carbonate anhydrous | add to 100 |

| Phosphate-Containing Detergent: IEC-60436 WFK Type C (pH = 10.5 in 3 g/l) | |
|---|---|
| Component | Wt % |
| Sodium tripolyphosphate | 23 |
| Sodium citrate dehydrate | 22.3 |
| Maleic acid/Acrylic acid copolymer sodium salt | 4 |
| Sodium perborate monohydrate | 6 |
| TAED | 2 |
| Sodium disilicate: Protil A (Cognis) | 5 |
| Linear fatty alcohol ethoxylate | 2 |
| Sodium carbonate anhydrous | add to 100 |

Liquid laundry detergent compositions suitable for top-loading automatic washing machines (1 & 2) and front loading washing machines (3).

| Ingredient | Composition (wt % of composition) | | |
|---|---|---|---|
| | 1 | 2 | 3 |
| $C_{12-15}$ Alkylethoxy(1.8)sulfate | 14.7 | 11.6 | |
| $C_{11.8}$ Alkylbenzene sulfonate | 4.3 | 11.6 | 8.3 |
| $C_{16-17}$ Branched alkyl sulfate | 1.7 | 1.29 | |
| $C_{12-14}$ Alkyl-9-ethoxylate | 0.9 | 1.07 | |
| $C_{12}$ dimethylamine oxide | 0.6 | 0.64 | |
| Citric acid | 3.5 | 0.65 | 3 |
| $C_{12-18}$ fatty acid | 1.5 | 2.32 | 3.6 |
| Sodium Borate (Borax) | 2.5 | 2.46 | 1.2 |
| Sodium $C_{12-14}$ alkyl ethoxy 3 sulfate | | | 2.9 |
| $C_{14-15}$ alkyl 7-ethoxylate | | | 4.2 |
| $C_{12-14}$ Alkyl-7-ethoxylate | | | 1.7 |
| Ca formate | 0.09 | 0.09 | |
| A compound having the following general structure: bis(($C_2H_5O$)($C_2H_4O$)n)($CH_3$)—$N^+$—$C_xH_{2x}$—$N^+$—($CH_3$)—bis(($C_2H_5O$)($C_2H_4O$)n), wherein n = from 20 to 30, and x = from 3 to 8, or sulphated or sulphonated variants thereof | | | 1.2 |
| Random graft co-polymer[1] | | 1.46 | 0.5 |
| Ethoxylated Polyethylenimine[2] | 1.5 | 1.29 | |
| Diethylene triamine pentaacetic acid | 0.34 | 0.64 | |
| Diethylene triamine penta(methylene phosphonic acid) | | | 0.3 |
| Tinopal AMS-GX | | 0.06 | |
| Tinopal CBS-X | 0.2 | 0.17 | |
| Amphiphilic alkoxylated grease cleaning polymer[3] | 1.28 | 1 | 0.4 |
| Ethanol | 2 | 1.58 | 1.6 |
| Propylene Glycol | 3.9 | 3.59 | 1.3 |
| Diethylene glycol | 1.05 | 1.54 | |
| Polyethylene glycol | 0.06 | 0.04 | |
| Monoethanolamine | 3.05 | 2.41 | 0.4 |
| NaOH | 2.44 | 1.8 | |

Liquid laundry detergent compositions suitable for top-loading automatic washing machines (1 & 2) and front loading washing machines (3).

| Ingredient | Composition (wt % of composition) | | |
|---|---|---|---|
| | 1 | 2 | 3 |
| Sodium Cumene Sulphonate | | | 1 |
| Sodium Formate | | 0.11 | |
| Water, Aesthetics (Dyes, perfumes) and Minors (Enzymes, solvents, structurants) | balance | balance | balance |

[1] Random graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units.

[2] Polyethylenimine (MW = 600) with 20 ethoxylate groups per —NH.

[3] Amphiphilic alkoxylated grease cleaning polymer is a polyethylenimine (MW = 600) with 24 ethoxylate groups per —NH and 16 propoxylate groups per —NH Granular laundry detergent compositions suitable for top-loading automatic washing machines (1-3) and front loading washing machines (4-5).

| Ingredients | 1 | 2 | 3 | 4 | 5 |
|---|---|---|---|---|---|
| $C_{16-17}$ Branched alkyl sulfate | 3.55 | | | | |
| $C_{12-14}$ alkyl sulphate | | | 1.5 | | |
| Sodium linear alkylbenzenesulfonate with aliphatic chain length $C_{11}$-$C_{12}$ | 9.6 | 15.8 | 10.6 | 7.5 | 9 |
| Sodium $C_{14/15}$ alcohol ethoxy-3-sulfate | 1.15 | | | 2.88 | |
| Sodium $C_{14/15}$ alkyl sulphate | 2.37 | | | | |
| $C_{14/15}$ alcohol ethoxylate with average 7 moles of ethoxylation | | | | 1.17 | 1 |
| mono-$C_{8-10}$ alkyl mono-hydroxyethyl di-methyl quaternary ammonium chloride | | | | | 0.45 |
| Di-methyl hydroxyl ethyl lauryl ammonium chloride | | | 0.18 | | |
| Zeolite A | 13.9 | 4.7 | 0.01 | 2.9 | 1.8 |
| Sodium Silicate 1.6.ratio | 4 | 0.2 | | 4 | 4 |
| Sodium Silicate 2.35.ratio | | | 8 | | |
| Citric Acid | | | | 2.5 | 1.4 |
| Sodium tripolyphosphate | | | 5 | | |
| Sodium Carbonate | 24.1 | 30 | 16.9 | 24.4 | 21 |
| Nonanoyloxybenzenesuplhonate | 5.78 | 2.81 | 0.96 | | |
| Oxaziridinium-based bleach booster | | | | 0.03 | 0.017 |
| Tetrasodium S,S, ethylenediaminedisuccinate | | | | 0.2 | |
| Diethylenetriamine penta (methylene phosphonic acid), heptasodium salt | 0.61 | | | | 0.33 |
| Hydroxyethane dimethylene phosphonic acid | | | | 0.29 | 0.45 |
| Ethylene diamine tetraacetate | | | 0.27 | | |
| MgSO4 | | | 0.47 | 0.5994 | 0.782 |
| Sodium Percarbonate | 7 | 4.4 | | 15.9 | 19.1 |
| Tetra Acetyl Ethylene Diamine | | | | 3.3 | 4.6 |
| Sodium Perborate Monohydrate | | | 1.2 | | |
| Carboxymethyl cellulose (e g. Finnfix BDA ex CPKelco) | 0.1 | | 0.17 | 1.69 | 0.23 |
| Sodium Acrylic acid/maleic acid co-polymer (70/30) | 0.0236 | 3.8 | | 2 | 2.5 |
| Sodium polyacrylate (Sokalan PA30 CL) | 4 | | 0.84 | | |
| Terephthalate polymer | | | | 0.23 | |
| Polyethylene glycol/vinyl acetate random graft co-polymer | | | 0.89 | 0.89 | 0.91 |
| Photobleach-zinc phthalocyanine tetrasulfonate | | | 0.005 | 0.001 | 0.002 |
| C.I.Fluorescent Brightener 260 | 0.11 | 0.15 | 0.04 | 0.23 | 0.15 |
| C.I.Fluorescent Brightener 351 (Tinopal® CBS) | | | 0.1 | | |
| Suds suppressor granule | | 0.25 | | 0.07 | 0.04 |

-continued

| Granular laundry detergent compositions suitable for top-loading automatic washing machines (1-3) and front loading washing machines (4-5). | | | | | |
|---|---|---|---|---|---|
| Ingredients | 1 | 2 | 3 | 4 | 5 |
| Hyrdophobically modified carboxy methyl cellulose (Finnifix® SH-1) | | | 0.019 | 0.028 | |
| Bentonite | | | 8.35 | | |
| Miscellaneous (Dyes, perfumes, process aids, moisture and sodium sulphate) | Balance | Balance | Balance | Balance | Balance |

The present amylase is separately added to these formulations.

Granular Laundry Detergent Compositions and Their Components.
The present amylase is separately added to these formulations.

| Component Surfactants | Detergent Composition | | | | | | |
|---|---|---|---|---|---|---|---|
| | A | B | C | D | E | F | G |
| $C_{10}$ Nonionic | | | | 0.1843 | | 0.1142 | 0.2894 |
| $C_{16-17}$ Branched alkyl sulfate | 3.53 | 3.53 | 3.53 | | | | |
| $C_{12-14}$ alkyl sulphate | | | | | | | |
| Sodium linear alkylbenzenesulfonate with aliphatic chain length $C_{11}$-$C_{12}$ | 8.98 | 8.98 | 8.98 | 13.58 | 14.75 | 12.94 | 15.69 |
| Sodium $C_{14/15}$ alcohol ethoxy-3-sulfate | 1.28 | 1.28 | 1.28 | | | | |
| Sodium $C_{14/15}$ alkyl sulphate | 2.36 | 2.36 | 2.36 | | | | |
| $C_{12/14}$ alcohol ethoxylate with average 7 moles of ethoxylation | | | | | | 2.9 | |
| $C_{12/14}$ alcohol ethoxylate with average 3 moles of ethoxylation | | | | | | | |
| $C_{14/15}$ alcohol ethoxylate with average 7 moles of ethoxylation | | | | | | | |
| mono-$C_{8-10}$ alkyl mono-hydroxyethyl di-methyl quaternary ammonium chloride | | | | | | | |
| Di methyl hydroxyl ethyl lauryl ammonium chloride | | | | 0.1803 | | | 0.195 |
| Zeolite A | 15.31 | 15.31 | 15.31 | | 4.47 | 2.01 | 0.39 |
| Bentonite | | | | 8.35 | | | |
| Sodium Silicate 1.6.ratio | | | | | 0.16 | | |
| Sodium Silicate 2.0.ratio | 3.72 | 3.72 | 3.72 | 8.41 | | 10.1 | |
| Sodium Silicate 2.35.ratio | | | | | | 7.05 | |
| Citric Acid | | | | 0.0066 | | | |
| Sodium tripolyphosphate | | | | 5.06 | | | 5.73 |
| Sodium Carbonate | 26.1 | 26.18 | 26.1 | 15.9 | 29 | 12.65 | 15.93 |
| Nonanoyl oxybenzene suplhonate | 5.78 | 5.78 | 5.78 | 1.17 | 1.86 | | 1.73 |
| Oxaziridinium-based bleach booster | 0.037 | 0.037 | 0.037 | | | | |
| Tetrasodium S,S,-ethylene diaminedisuccinate | | | | | | | |
| Diethylenetriamine penta (methylene phosphonic acid), heptasodium salt | 0.62 | 0.62 | 0.62 | 0.327 | 0.3272 | | |
| Hydroxyethane dimethylene phosphonic acid | | | | | | | |
| Ethylene diamine tetraacetate | | | | 0.2701 | | | 0.28 |
| MgSO4 | 0.056 | 0.056 | 0.056 | 0.47 | | | 0.54 |
| Sodium Percarbonate | | 7.06 | 7.06 | | 3.64 | | |
| Tetra Acetyl Ethylene Diamine | | | | | | | |

-continued

Granular Laundry Detergent Compositions and Their Components.
The present amylase is separately added to these formulations.

| | | | | | | | |
|---|---|---|---|---|---|---|---|
| Sodium Perborate Monohydrate | | | | 1.47 | | | 5.55 |
| Carboxymethyl cellulose (e.g. Finnfix BDA ex CPKelco) | 0.38 | 0.38 | 0.38 | 0.173 | | 0.62 | 0.21 |
| Sodium Acrylic acid/maleic acid co-polymer (70/30) | 3.79 | 3.78 | 3.79 | | 3.64 | 0.4 | 2.61 |
| Sodium polyacrylate (Sokalan PA30 CL) | 3.78 | 3.78 | 3.78 | 0.842 | | | |
| Terephthalate polymer | | | | | | | |
| Polyethylene glycol/vinyl acetate random graft co polymer | | | | 0.89 | | 0.55 | 1.4 |
| Photobleach- zinc phthalocyanine tetrasulfonate | | | | | | | |
| C.I.Fluorescent Brightener 260 | 0.1125 | 0.1125 | 0.1125 | 0.043 | 0.15 | 0.1174 | 0.048 |
| C.I.Fluorescent Brightener 351 (Tinopal ® CBS) | | | | 0.0952 | | | 0.1049 |
| Suds suppressor granule | 0.015 | 0.015 | 0.015 | | 0.031 | | |
| Hyrdophobically modified carboxy methyl cellulose (Finnifix ® SH-1) | | | | | | | |
| Bentonite | | | | | | | |
| Miscellaneous (Dyes, perfumes, process aids, moisture and sodium sulphate) | Balance | Balance | Balance | Balance | Balance | Balance | Balance |

| | Detergent Composition | | | | | | |
|---|---|---|---|---|---|---|---|
| Component Surfactants | H | I | J | K | L | M | N |
| $C_{10}$ Nonionic | 0.1885 | 0.1846 | 0.1885 | 0.1979 | 0.1979 | 0.1979 | 0.1979 |
| $C_{16-17}$ Branched alkyl sulfate | | | | | | | |
| $C_{12-14}$ alkyl sulphate | | | | | | | |
| Sodium linear alkylbenzenesulfonate with aliphatic chain length $C_{11}$-$C_{12}$ | 9.01 | 8.42 | 9.51 | 8.92 | 8.92 | 11.5 | 11.5 |
| Sodium $C_{14/15}$ alcohol ethoxy-3-sulfate | | | | 1.62 | 1.62 | 1.125 | 1.125 |
| Sodium $C_{14/15}$ alkyl sulphate | | | | | | | |
| $C_{12/14}$ alcohol ethoxylate with average 7 moles of ethoxylation | | | | | | | |
| $C_{12/14}$ alcohol ethoxylate with average 3 moles of ethoxylation | | 2.44 | | | | | |
| $C_{14/15}$ alcohol ethoxylate with average 7 moles of ethoxylation | 0.97 | 1.17 | 0.97 | 1 | 1 | 1.5 | 1.5 |
| mono-$C_{8-10}$ alkyl mono-hydroxyethyl di-methyl quaternary ammonium chloride | 0.45 | | | | | | |
| Di methyl hydroxyl ethyl lauryl ammonium chloride | | | | | | | |
| Zeolite A | | | 0.45 | | | | |
| Bentonite | 1.83 | 2.58 | 0.59 | 1.63 | 1.63 | 2 | 2 |
| Sodium Silicate 1.6.ratio | | | | | | | |
| Sodium Silicate 2.0.ratio | 4.53 | 5.62 | 4.53 | 4.75 | 4.75 | 4.75 | 4.75 |
| Sodium Silicate 2.35.ratio | | | | | 0.06 | 0.06 | |
| Citric Acid | | | | | | | |
| Sodium tripolyphosphate | 1.4 | 1.84 | 1 | 1.1 | 1.1 | 1.1 | 1.1 |
| Sodium Carbonate | | | | | | | |

Granular Laundry Detergent Compositions and Their Components.
The present amylase is separately added to these formulations.

| | | | | | | | |
|---|---|---|---|---|---|---|---|
| Nonanoyl oxybenzene suplhonate | 21 | 27.31 | 20.2 | 23.3 | 23.3 | 23.3 | 23.3 |
| Oxaziridinium-based bleach booster | 0.0168 | 0.0333 | 0.024 | 0.021 | 0.021 | 0.015 | 0.015 |
| Tetrasodium S,S,-ethylene diaminedisuccinate | | | | 0.26 | 0.26 | 0.26 | 0.26 |
| Diethylenetriamine penta (methylene phosphonic acid), heptasodium salt | | | | | | | |
| Hydroxyethane dimethylene phosphonic acid | 0.45 | 0.2911 | 0.45 | 0.47 | 0.47 | 0.47 | 0.47 |
| Ethylene diamine tetraacetate | | 0.1957 | | | | | |
| $MgSO_4$ | | | | | | | |
| Sodium Percarbonate | 0.79 | 0.6494 | 0.793 | 0.83 | 0.83 | 0.82 | 0.82 |
| Tetra Acetyl Ethylene Diamine | 19.1 | 15.85 | 22.5 | 19.35 | 19.35 | 19.35 | 19.35 |
| Sodium Perborate Monohydrate | 4.554 | 3.71 | 5.24 | 4.51 | 4.51 | 4.51 | 4.51 |
| Carboxymethyl cellulose (e.g. Finnfix BDA ex CPKelco) | 0.23 | 1.07 | 0.2622 | 1.01 | 1.01 | 1.01 | 1.01 |
| Sodium Acrylic acid/maleic acid co-polymer (70/30) | 2.5 | 2 | 1.75 | 1.84 | 1.84 | 1.84 | 1.84 |
| Sodium polyacrylate (Sokalan PA30 CL) | 0.0055 | 0.011 | 0.008 | 0.007 | 0.007 | 0.005 | 0.005 |
| Terephthalate polymer | | 0.231 | | 0.179 | 0.179 | 0.179 | 0.179 |
| Polyethylene glycol/vinyl acetate random graft co polymer | 0.911 | 0.8924 | 0.911 | 0.96 | 0.96 | 0.96 | 0.96 |
| Photobleach- zinc phthalocyanine tetrasulfonate | | | | | | | |
| C.I.Fluorescent Brightener 260 | 0.1455 | 0.2252 | 0.1455 | 0.153 | 0.153 | 0.171 | 0.171 |
| C.I.Fluorescent Brightener 351 (Tinopal ® CBS) | | | | | | | |
| Suds suppressor granule | 0.04 | 0.065 8 | 0.04 | 0.042 | 0.042 | 0.042 | 0.042 |
| Hyrdophobically modified carboxy methyl cellulose (Finnifix ® SH-1) | | | | | | | |
| Bentonite | | | | | | | |
| Miscellaneous (Dyes, perfumes, process aids, moisture and sodium sulphate) | Balance | Balance | Balance | Balance | Balance | Balance | Balance |

Dishwashing Detergent Gel Compositions

| Ingredients | 1 (wt %) | 2 (wt %) | 3 (wt %) | 4 (wt %) | 5 (wt %) |
|---|---|---|---|---|---|
| Polytergent ® SLF-18 | 1 | 1.3 | 0.8 | 1 | 0.9 |
| Sodium Benzoate (33% active) | 0.61 | 0.61 | 0.61 | 0.6 | 0.6 |
| Xanthan gum | 1 | 0.8 | 1.2 | 1 | 1.1 |
| Sodium Sulphate | 10 | 10 | 10 | 8 | 10 |
| Perfume | 0.03 | 0.05 | 0.03 | 0.06 | 0.1 |
| Sodium Silicate | | | | | 2 |
| Citric Acid (50% active) | 12.5 | | 12 | | |
| GLDA | | 7 | | 8 | |
| Protease 1 (44 mg active/g | 0.7 | | 0.3 | | |
| 4-Formyl-Phenyl Boronic Acid | | | 0.05 | | |
| Protease 2 (10 mg/g) encapsulated | | 2 | | 0.6 | |
| Protease 3 (48 mg active/g) | | | | | 0.5 |
| Protease 4 (123 mg active/g) | | | | | |
| Ethanol | | | | 0.3 | |
| Potassium Hydroxide (45% active) | 14.6 | 14.6 | 14.6 | 14 | |
| Calcium Chloride (25% active) | 1.8 | 1.8 | 1.8 | 1.1 | 0.4 |
| Dye | 0.05 | 0.05 | 0.05 | 0.05 | 0.02 |
| Proxcel GXL™ (19% active) | 0.05 | 0.05 | 0.05 | 0.05 | 0.05 |
| Acusol™ 8209 | 0.34 | 0.34 | 0.3 | 0.35 | 0.3 |

Dishwashing Detergent Gel Compositions

| Ingredients | 1 (wt %) | 2 (wt %) | 3 (wt %) | 4 (wt %) | 5 (wt %) |
|---|---|---|---|---|---|
| Acusol™ 425N (50% active) | 3 | 3 | 3.5 | 2.5 | 2 |
| Amylases (25 mg/g active) | 0.2 | 0.5 | 0.4 | 0.3 | 0.1 |
| Water & other adjunct ingredients | Balance to 100% | Balance to 100% | Balance to 100% | Balance to 100% | Balance to 100% |

Powder Automatic Dishwashing Compositions

Composition 1

| Ingredients | Wt % |
|---|---|
| Nonionic surfactant | 0.4-2.5% |
| Sodium metasilicate | 0-20% |
| Sodium disilicate | 0-20% |
| Sodium triphosphate | 0-40% |
| Sodium carbonate | 0-20% |
| Sodium perborate | 2-9% |
| Tetraacetyl ethylene diamine (TAED) | 1-4% |
| Sodium sulfate | 5-33% |
| Enzymes | 0.0001-0.1% |

Composition 2

| Ingredients | Wt % |
|---|---|
| Nonionic surfactant (e.g. alcohol ethoxylate) | 1-2% |
| Sodium disilicate | 2-30% |
| Sodium carbonate | 10-50% |
| Sodium phosphonate | 0-5% |
| Trisodium citrate dehydrate | 9-30% |
| Nitrilotrisodium acetate (NTA) | 0-20% |
| Sodium perborate monohydrate | 5-10% |
| Tetraacetyl ethylene diamine (TAED) | 1-2% |
| Polyacrylate polymer (e.g. maleic acid/acrylic acid copolymer) | 6-25% |
| Enzymes | 0.0001-0.1% |
| Perfume | 0.1-0.5% |
| Water | 5-10 |

Composition 3

| Ingredients | Wt % |
|---|---|
| Nonionic surfactant | 0.5-2.0% |
| Sodium disilicate | 25-40% |
| Sodium citrate | 30-55% |
| Sodium carbonate | 0-29% |
| Sodium bicarbonate | 0-20% |
| Sodium perborate monohydrate | 0-15% |
| Tetraacetyl ethylene diamine (TAED) | 0-6% |
| Maleic acid/acrylic acid copolymer | 0-5% |
| Clay | 1-3% |
| Polyamino acids | 0-20% |
| Sodium polyacrylate | 0-8% |
| Enzymes | 0.0001-0.1% |

Composition 4

| Ingredients | Wt % |
|---|---|
| Nonionic surfactant | 1-2% |
| Zeolite MAP | 0-42% |
| Sodium disilicate | 0-34% |
| Sodium citrate | 0-12% |
| Sodium carbonate | 0-20% |
| Sodium perborate monohydrate | 7-15% |
| Tetraacetyl ethylene diamine (TAED) | 0-3% |
| Polymer | 0-4% |
| Maleic acid/acrylic acid copolymer | 0-5% |
| Organic phosphonate | 0-4% |
| Clay | 1-2% |
| Enzymes | 0.0001-0.1% |
| Sodium sulfate | Balance |

Composition 5

| Ingredients | Wt % |
|---|---|
| Nonionic surfactant | 1-7% |
| Sodium disilicate | 18-30% |
| Trisodium citrate | 10-24% |
| Sodium carbonate | 12-20% |
| Monopersulfate (2 KHSOsoKHS04 ° K2S04) | 15-21% |
| Bleach stabilizer | 0.1-2% |
| Maleic acid/acrylic acid copolymer | 0-6% |
| Diethylene triarnine pentaacetate, pentasodium salt | 0-2.5% |
| Enzymes | 0.0001-0.1% |
| Sodium sulfate, water | Balance |

Powder and Liquid Dishwashing Composition with Cleaning Surfactant System

| Ingredients | Wt % |
|---|---|
| Nonionic surfactant | 0-1.5% |
| Octadecyl dimethylamine N-oxide dihydrate | 0-5% |
| 80:20 wt C18/C16 blend of octadecyl dimethylamine N-oxide dihydrate and hexadecyldimethyl amine Noxide dehydrate | 0-4% |
| 70:30 wt C18/C16 blend ofoctadecyl bis (hydroxyethyl)amine N-oxide anhydrous and hexadecyl bis (hydroxyethyl)amine N-oxide anhydrous | 0-5% |
| C13-C1S alkyl ethoxysulfate with an average degree of ethoxylation of 3 | 0-10% |
| C12-C1S alkyl ethoxysulfate with an average degree of ethoxylation of 3 | 0-5% |
| C13-C1S ethoxylated alcohol with an average degree of ethoxylation of 12 | 0-5% |
| A blend of C 12-C IS ethoxylated alcohols with an average degree of ethoxylation of 9 | 0-6.5% |
| A blend of C 13-C IS ethoxylated alcohols with an average degree of ethoxylation of 30 | 0-4% |
| Sodium disilicate | 0-33% |
| Sodium tripolyphosphate | 0-46% |
| Sodium citrate | 0-28% |
| Citric acid | 0-29% |
| Sodium carbonate | 0-20% |
| Sodium perborate monohydrate | 0-11.5% |
| Tetraacetyl ethylene diamine (TAED) | 0-4% |
| Maleic acid/acrylic acid copolymer | 0-7.5% |
| Sodium sulfate | 0-12.5% |
| Enzymes | 0.0001-0.1% |

Non-Aqueous Liquid Automatic Dishwashing Composition

| Ingredients | Wt % |
|---|---|
| Liquid nonionic surfactant (e.g. alcohol ethoxylates) | 2.0-10.0% |
| Alkali metal silicate | 3.0-15.0% |
| Alkali metal phosphate | 0-40.0% |

Non-Aqueous Liquid Automatic Dishwashing Composition

| Ingredients | Wt % |
| --- | --- |
| Liquid carrier selected from higher glycols, polyglycols, polyoxides, glycol ethers | 25.0-45.0% |
| Stabilizer (e.g. a partial ester of phosphoric acid and a C16-C18 alkanol) | 0.5-7.0% |
| Foam suppressor (e.g. silicone) | 0-1.5% |
| Enzymes | 0.0001-0.1% |

Non-Aqueous Liquid Dishwashing Composition

| Ingredients | Wt% |
| --- | --- |
| Liquid nonionic surfactant (e.g. alcohol ethoxylates) | 2.0-10.0% |
| Sodium silicate | 3.0-15.0% |
| Alkali metal carbonate | 7.0-20.0% |
| Sodium citrate | 0.0-1.5% |
| Stabilizing system (e.g. mixtures of finely divided silicone and low molecular weight dialkyl polyglycol ethers) | 0.5-7.0% |
| Low molecule weight polyacrylate polymer | 5.0-15.0% |
| Clay gel thickener (e.g. bentonite) | 0.0-10.0% |
| Hydroxypropyl cellulose polymer | 0.0-0.6% |
| Enzymes | 0.0001-0.1% |
| Liquid carrier selected from higher lycols, polyglycols, polyoxides and glycol ethers | Balance |

Thixotropic Liquid Automatic Dishwashing Composition

| Ingredients | Wt % |
| --- | --- |
| C 12-C 14 fatty acid | 0-0.5% |
| Block co-polymer surfactant | 1.5-15.0% |
| Sodium citrate | 0-12% |
| Sodium tripolyphosphate | 0-15% |
| Sodium carbonate | 0-8% |
| Aluminium tristearate | 0-0.1% |
| Sodium cumene sulfonate | 0-1.7% |
| Polyacrylate thickener | 1.32-2.5% |
| Sodium polyacrylate | 2.4-6.0% |
| Boric acid | 0-4.0% |
| Sodium formate | 0-0.45% |
| Calcium formate | 0-0.2% |
| Sodium n-decydiphenyl oxide disulfonate | 0-4.0% |
| Monoethanol amine (MEA) | 0-1.86% |
| Sodium hydroxide (50%) | 1.9-9.3% |
| 1,2-Propanediol | 0-9.4% |
| Enzymes | 0.0001-0.1% |
| Suds suppressor, dye, perfumes, water | Balance |

Liquid Automatic Dishwashing Composition

| Ingredients | Wt % |
| --- | --- |
| Alcohol ethoxylate | 0-20% |
| Fatty acid ester sulfonate | 0-30% |
| Sodium dodecyl sulfate | 0-20% |
| Alkyl polyglycoside | 0-21% |
| Oleic acid | 0-10% |
| Sodium disilicate monohydrate | 0-33% |
| Sodium citrate dihydrate | 0-33% |
| Sodium stearate | 0-2.5% |
| Sodium perborate monohydrate | 0-13% |
| Tetraacetyl ethylene diamine (TAED) | 0-8% |
| Maleic acid/acrylic acid copolymer | 4-8% |
| Enzymes | 0.0001-0.1% |

Liquid Automatic Dishwashing Composition Containing Protected Bleach Particles

| Ingredients | Wt % |
| --- | --- |
| Sodium silicate | 5-10% |
| Tetrapotassium pyrophosphate | 0-25% |
| Sodium triphosphate | 0-2% |
| Potassium carbonate | 4-8% |
| Protected bleach particles, e.g. chlorine | 5-10% |
| Polymeric thickener | 0.7-1.5% |
| Potassium hydroxide | 0-2% |
| Enzymes | 0.0001-0.1% |
| Water | Balance |

| | Composition of Model Detergent A: | | Composition of Model Detergent B: | |
| --- | --- | --- | --- | --- |
| Compound | Amount g/100 g | % active ingredient | Amount g/100 g | % active ingredient |
| Surfactants | | | | |
| Na-LAS (92%) (Nacconol90G) (anionic) (linear alkylbenzene sulfonate) | 10.87 | 10 | 10.87 | 10 |
| STEOL CS-370E (70%) (anionic), CH3(CH2)m—(OCH2CH2)3—OS03—, where m~11-13 | 7.14 | 5 | 7.14 | 5 |
| Bio-soft N25-7 (99.5%) (non-ionic),: CH3(CH2)m—(OCH2CH2h—OH, where and m~1-14 | 5 | 5 | 5 | 5 |
| Oleic acid (fatty acid) | 2 | 2 | 2 | 2 |

| Compound | Composition of Model Detergent A: Amount g/100 g | Composition of Model Detergent A: % active ingredient | Composition of Model Detergent B: Amount g/100 g | Composition of Model Detergent B: % active ingredient |
|---|---|---|---|---|
| Solvents | | | | |
| H20 | 62 | 65 | 62 | 65 |
| Ethanol | 0.5 | 0.5 | 0.5 | 0.5 |
| STS (sodium p-toluene sulfonate (40%)) | 3.75 | 1.5 | 3.75 | 1.5 |
| Mono propylene glycol | 2 | 2 | 2 | 2 |
| Builder | | | | |
| Tri-sodium-citrate | 4 | 4 | 0 | 0 |
| Diethylene triamine penta acetic acid (DTPA) | 0 | 0 | 1.5 | 1.5 |
| Triethanolamine (TEA) | 0.5 | 0.5 | 0.5 | 0.5 |
| Stabilizer | | | | |
| Boric Acid | 1.5 | 1.5 | 1.5 | 1.5 |
| Minors | | | | |
| 10N NaOH (for adjustment to pH 8.5) | 0.8 | 0.8 | 0.8 | 0.8 |

All purpose Alkaline detergent Compositions (all-purpose. glass. kitchen)
Hard surface cleaning detergent composition

| Composition [% by wt.] | E1 | E2 | E3 | E4 |
|---|---|---|---|---|
| Citric acid | 0.5 | 0.5 | 0.5 | 0.5 |
| Fatty acid | 0.5 | 0.5 | 0.5 | 1.0 |
| Ethanol | 5 | 3 | 5 | 3 |
| Perfume | 0.2 | 0.2 | 0.2 | 0.2 |
| Water | To 100 | To 100 | To 100 | To 100 |

Acidic Detergent Compositions (bath, toilet)

| Composition [% by wt.] | E5 | E6 | E7 | E8 |
|---|---|---|---|---|
| Fatty alcohol ether sulfate C12-2EO sodium salt | 2 | 3 | 5 | 2 |
| Ethanol | 3 | 3 | 3 | 3 |
| Citric acid | 3 | 10 | 3 | 10 |
| Thickener xanthan Kelzan ASX-T | | 0.05 | | 0.05 |
| Perfume | 0.1 | 0.1 | 0.1 | 0.1 |
| Water | To 100 | To 100 | To 100 | To 100 |

Liquid Detergent and Cleaning Agent Compositions

| Ingredients | E1 | E2 | E3 | C1 | C2 | C3 | C4 | C5 |
|---|---|---|---|---|---|---|---|---|
| Gellan gum | 0.2 | 0.2 | 0.15 | 0.15 | | | | |
| Xanthan gum | | | 0.15 | | 0.15 | 0.5 | 0.2 | |
| Polyacrylate (Carbopol Aqua 30) | 0.4 | 0.4 | | | | | 0.6 | 0.6 |
| $C_{12-14}$-fatty alcohol with 7 EO | 22 | 10 | 10 | 10 | 10 | 10 | 10 | 10 |
| $C_{9-13}$-alkylbenzenesulfonate, Na salt | | 10 | 10 | 10 | 10 | 10 | 10 | 10 |
| $C_{12-14}$-alkylpolyglycoside | 1 | | | | | | | |
| Citric acid | 1.6 | 3 | 3 | 3 | 3 | 3 | 3 | 3 |
| Dequest ® 2010 Hydroxyethylidene-1,1-diphosphonic acid, tetrasodium salt (from Solutia) | 0.5 | 1 | 1 | 1 | 1 | 1 | 1 | 1 |
| Sodium lauryl ether sulfate with 2 EO | 10 | 5 | 5 | 5 | 5 | 5 | 5 | 5 |
| Monoethanolarnine | 3 | 3 | 3 | 3 | 3 | 3 | 3 | 3 |
| $C_{12-18}$-fatty acid | 7.5 | 7.5 | 7.5 | 7.5 | 7.5 | 7.5 | 7.5 | 7.5 |
| Propylene glycol | | 6.5 | 6.5 | 6.5 | 6.5 | 6.5 | 6.5 | 6.5 |
| Sodium cumene sulfonate | | 2 | 2 | 2 | 2 | 2 | 2 | 2 |
| Enzymes, dyes, stabilizers | + | + | + | + | + | + | + | + |
| Microcapsules with about 2000 μm diameter | 0.5 | 0.5 | 0.5 | 0.5 | 0.5 | 0.5 | 0.5 | 0.5 |
| Water | To 100 | To 100 | To 100 | To 100 | To 100 | To 100 | To 100 | To 100 |
| Flow limit (Pas) | 0.58 | 1.16 | 1.16 | no | no | no | yes | no |

All purpose Alkaline detergent Compositions (all-purpose. glass. kitchen)
Hard surface cleaning detergent composition

| Composition [% by wt.] | E1 | E2 | E3 | E4 |
|---|---|---|---|---|
| Fatty alcohol ethoxylate C12-7EO | 1 | 3 | 5 | 0.5 |
| Alkylbenzenesulfonic acid Na salt | 3 | 1 | 2 | 4 |
| Octyl sulfate | 3 | 2 | 2 | 2 |
| Sodium carbonate | 1.5 | 0.5 | 1.0 | 1.5 |

Cleaning Paste Composition

| Composition [% by wt.] | E9 |
|---|---|
| C 12 Fatty alcohol sulfate | 20 |
| C16-18 Fatty alcohol ethoxylate 25 EO | 20 |
| C 12-18 Fatty acid monoethanolamide | 10 |
| Sodium sulfate | 40 |
| Sodium carbonate | 5 |

| Cleaning Paste Composition | |
|---|---|
| Composition [% by wt.] | E9 |
| Cellulose | 4.899 |
| Dye | 0.001 |
| Perfume | 0.1 |

| Self Foaming Cleaning Powder Composition | |
|---|---|
| Composition [% by wt.] | E10 |
| C 12 Fatty alcohol sulfate | 2 |
| Sodium sulfate | 37.899 |
| Sodium carbonate | 25 |
| Citric Acid | 35 |
| Dye | 0.001 |
| Perfume | 0.1 |

| Compositions of a Clear Aqueous Detergent and Cleaning Agent having a flow limit | | | | | | |
|---|---|---|---|---|---|---|
| Ingredients | V1 | E1 | E2 | E3 | E4 | E5 |
| 1,2 Propane diol | 8 | 0 | 2 | 6 | 4 | 2 |
| Dipropylene glycol | 0 | 8 | 6 | 2 | 4 | 2 |
| Polyacrylate (Carbopol Aqua 30) | 3 | 3 | 3 | 3 | 3 | — |
| Polyacrylate (Polygel W301) | — | — | — | — | — | 1.8 |
| $C_{12-14}$-fatty alcohol with 7 EO | 10 | 10 | 10 | 10 | 10 | 10 |
| $C_{9-13}$-alkylbenzenesulfonate, Na salt | 10 | 10 | 10 | 10 | 10 | — |
| Citric Acid | 3 | 3 | 3 | 3 | 3 | 2 |
| Dequest ® 2010 Hydroxyethylidene-1,1-diphosphonic acid, tetrasodium salt (ex Solutia) | 1 | 1 | 1 | 1 | 1 | — |
| Dequest ® 2066 Diethylene triamine penta (methylenephosphonic acid) hepta Na salt (ex Solutia) | — | — | — | — | — | 0.7 |
| Sodium lauryl ether sulfate with 2 EO | 10 | 10 | 10 | 10 | 10 | 5 |
| Monoethanolamine | 3 | 3 | 3 | 3 | 3 | 2 |
| $C_{12-18}$-fatty acid Na salt | 5.5 | 5.5 | 5.5 | 5.5 | 5.5 | 5.5 |
| Enzymes, dyes, stabilizers Microcapsules with about 2000 μm diameter | 0.5 | 0.5 | 0.5 | 0.5 | 0.5 | 0.5 |
| Water | To 100 | To 100 | To 100 | To 100 | To 100 | To 100 |
| Flow limit (Pas) | 0.4 | 0.6 | 0.6 | 0.8 | 1.0 | 0.6 |
| Appearance | Cloudy | Clear | Clear | Clear | Clear | Clear |

| Liquid Laundry Detergent | |
|---|---|
| Ingredients | Wt % |
| ABS (alkyl benzenesulphonate) | 10 |
| FAEOS | 5 |
| $C_{12/14}$ 7EO | 10 |
| $C_{12/18}$ Fatty Acid | 5 |
| Glycerol | 5 |
| Sodium citrate | 3 |
| Protease/Amylase/Cellulase | 1 |
| Tinopal ® DMS-X (optical brightener manufactured by Ciba) | 0.2 |
| Water | To 100 |

| Granular Laundry Detergent | |
|---|---|
| Ingredients | Wt % |
| ABS (alkyl benzenesulphonate) | 11 |
| $C_{13/15}$ 7E0 | 3 |
| Sodium carbonate | 20 |
| Sodium hydrogencarbonate | 5 |
| Sodium sulphate | 25 |
| Sodium silicate | 5 |
| Sodium percarbonate | 13 |
| TAED | 5 |
| Sodium polyacrylate | 4.5 |
| Enzymes (protease, amylase, and cellulose) | 3.5 |
| Water | To 100 |

| Aqueous Liquid Washing Product Formulations (without-FWM1 and with-FWM2 0.5% hyperbranched polyesteramide) | | |
|---|---|---|
| Formulation | FWM1 | FWM2 |
| $C_{12-14}$-fatty alcohol with 2 EO | 5 | 5 |
| LAS | 10 | 10 |
| $Cu_{12-18}$-fatty alcohol with 7 EO | 10 | 10 |
| $C_{12-18}$ soap | 8 | 8 |
| Citrate | 4 | 4 |
| 1,2-propanediol | 5 | 5 |
| Hybrane ® SIP 2100 (manufactured by DSM) | | 0.5 |

| Liquid Laundry Detergent Compositions | | | |
|---|---|---|---|
| | Wt % | | |
| Detergent Composition | E1 | E2 | E3 |
| $C_{12-14}$ fatty alcohol with 7 EO | 5 | 4 | 10 |
| $C_{9-13}$ alkylbenzene sulfonate, Na salt | 10 | 10 | 10 |
| Sodium lauryl ether sulfate with 2 EO | — | — | 8 |
| Active substance (specific polycarbonate-, polyurethane-, and/or polyureapolyorganosiloxane compounds or precursor compounds thereof of the reactive cyclic carbonate and urea type | 1 | 1 | 1 |
| Polyacrylate thickener | — | — | 1 |
| Sodium percarbonate | 15 | 18 | — |
| TAED | 3 | 3 | — |
| $C_{12-18}$ fatty acid, Na salt | 1 | 1.5 | 7.5 |
| PVA/Maleic acid copolymer | 4.5 | 2 | — |
| Citric acid, Na salt | 2.5 | — | 2 |
| Phosphonic acid, Na salt | 0.5 | 0.5 | 1 |
| Sodium carbonate | 10 | 20 | — |
| Propane diol | — | — | 6.5 |
| Zeolite A | 25 | 25 | — |
| Boric Acid Sodium salt | — | — | 1.2 |
| Silicone defoamer | 2.5 | 1.3 | 0.1 |
| Enzymes (protease, amylase, cellulase) | + | + | + |
| Colorant | + | + | + |
| Perfume | 0.5 | 0.2 | 0.8 |
| Water | — | — | To 100 |
| Sodium sulfate | — | To 100 | — |
| Sodium bicarbonate | To 100 | — | — |

| Example formulations of preferred phosphate-free automatic dishwashing agents | | | | |
|---|---|---|---|---|
| Ingredient | Formulation 1 (wt %) | Formulation 2 (wt %) | Formulation 3 (wt %) | Formulation 4 (wt %) |
| Citrate | 5 to 60 | 10 to 55 | 15 to 50 | 15 to 50 |
| Sodium percarbonate | 1 to 20 | 2 to 15 | 4 to 10 | 4 to 10 |
| Bleach catalyst | 0.01 to 3 | 0.02 to 2 | 0.02 to 2 | 0.02 to 1 |
| Copolymer[1] | 0.1 to 30 | 0.5 to 25 | 1.0 to 20 | 1.0 to 20 |
| Nonionic surfactant[2] | 1 to 10 | 2 to 8 | 2 to 8 | 3 to 6 |
| Misc | To 100 | To 100 | To 100 | To100 |
| Ingredient | Formulation 5 (wt %) | Formulation 6 (wt %) | Formulation 7 (wt %) | Formulation 8 (wt %) |
| Citrate | 5 to 60 | 10 to 55 | 15 to 50 | 15 to 50 |
| Sodium percarbonate | 1 to 20 | 2 to 15 | 4 to 10 | 4 to 10 |
| Phosphonate | 2 to 8 | 2 to 8 | 2 to 8 | 2 to 8 |
| Copolymer[1] | 0.1 to 30 | 0.5 to 25 | 1.0 to 20 | 1.0 to 20 |
| Nonionic surfactant[2] | 1 to 10 | 2 to 8 | 2 to 8 | 3 to 6 |
| Misc | To 100 | To 100 | To 100 | To 100 |
| Ingredient | Formulation 9 (wt %) | Formulation 10 (wt %) | Formulation 11 (wt %) | Formulation 12 (wt %) |
| Citrate | 5 to 60 | 10 to 55 | 15 to 50 | 15 to 50 |
| Sodium percarbonate | 1 to 20 | 2 to 15 | 4 to 10 | 4 to 10 |
| Enzyme | 0.1 to 6 | 0.2 to 5 | 0.4 to 5 | 0.4 to 5 |
| Copolymer[1] | 0.1 to 30 | 0.5 to 25 | 1.0 to 20 | 1.0 to 20 |
| Nonionic surfactant[2] | 1 to 10 | 2 to 8 | 2 to 8 | 3 to 6 |
| Misc | To 100 | To 100 | To 100 | To 100 |
| Ingredient | Formulation 13 (wt %) | Formulation 14 (wt %) | Formulation 15 (wt %) | Formulation 16 (wt %) |
| Citrate | 5 to 60 | 10 to 55 | 15 to 50 | 15 to 50 |
| Carbonate/hydrogen carbonate | 2 to 40 | 2 to 40 | 2 to 40 | 2 to 40 |
| Silicate | 0 to 15 | 0 to 15 | 0 to 15 | 0.1 to 10 |
| Phosphonate | 0 to 14 | 0 to 14 | 0 to 14 | 2 to 8 |
| Sodium percarbonate | 1 to 20 | 2 to 15 | 4 to 10 | 4 to 10 |
| Bleach catalyst | 0.01 to 3 | 0.02 to 2 | 0.02 to 2 | 0.02 to 1 |
| Copolymer[1] | 0.1 to 30 | 0.5 to 25 | 1.0 to 20 | 1.0 to 20 |
| Nonionic surfactant[2] | 1 to 10 | 2 to 8 | 2 to 8 | 3 to 6 |

| Example formulations of preferred phosphate-free automatic dishwashing agents | | | | |
|---|---|---|---|---|
| Enzyme | 0.1 to 6 | 0.2 to 5 | 0.4 to 5 | 0.4 to 5 |
| Misc | To 100 | To 100 | To 100 | To 100 |

[1] Copolymer comprising i) monomers from the group of mono- or polyunsaturated carboxylic acids ii) monomers of the general formula $R^1(R^2)C=C(R^3)-X-R^4$, in which $R^1$ to $R^3$ mutually independently denote —H, —$CH_3$ or —$C_2H_5$, X denotes an optionally present spacer group which is selected from —$CH_2$—, —C(O)O— and —C(O)—NH—, and $R^4$ denotes a straight chain or branched saturated alkyl residue with 2 to 22 carbon atoms or denotes an unsaturated, preferably aromatic residue with 6 to 22 carbon atoms iii) optionally further monomers

[2] Nonionic surfactant of the general formula $R^1$—CH(OH)CH$_2$O—(AO)w—(A'0)$_x$—(A"0)$_y$—(A"0)$_z$—R$_2$, in which $R^1$ denotes a straight-chain or branched, saturated or mono- or polyunsaturated C6-24 alkyl or alkenyl residue; $R^2$ denotes a linear or branched hydrocarbon residue with 2 to 26 carbon atoms; A, A', A" and A"' mutually independently denote a residue from the group comprising —$CH_2CH_2$—, —$CH_2CH_2$—$CH_2$—, —$CH_2CH_2$—CH(CH$_3$), CH$_2$—CH$_2$—$CH_2CH_2$, —$CH_2$—CH—(CH$_3$)—$CH_2$—, —$CH_2$—CH(CH$_2$—CH$_3$), w, x, y and z denote values between 0.5 and 120, wherein x, y and/or z may also be 0.

| Composition of phosphate-free automatic dishwashing detergents | | |
|---|---|---|
| Raw material | V1 | E1 |
| Citrate | 23 | 23 |
| MGDA | 8 | 8 |
| Copolymer[1] | 12 | 12 |
| HEDP | 2 | 2 |
| Soda | 28 | 28 |
| Sodium percarbonate | 10 | 10 |
| TAED | 2.4 | 2.4 |
| Protease | 2 | 2 |
| Amylase | 1.8 | 1.8 |
| Non-ionic surfactant[2] | 5 | |
| Non-ionic surfactant[3] | | 5 |
| Misc | To 100 | To 100 |

| Textile Washing Agent | |
|---|---|
| Ingredient | wt % pure substance |
| Xanthan | 0.3-0.5 |
| Anti foaming agent | 0.2-0.4 |
| Glycerol | 6-7 |
| Ethanol | 0.3-0.5 |
| FAEOS | 4-7 |
| Non ionic surfactant (FAEO, APG among others) | 24-28 |
| Boric acid | 1 |
| Sodium citrate dihydrate | 1-2 |
| Soda | 2-4 |
| Coconut fatty acids | 14-16 |
| HEDP | 0.5 |
| PVP | 0-0.4 |
| Optical brightener | 0-0.05 |
| Dye | 0-0.001 |
| Perfume | 0-2 |
| Water demineralized | remainder |

| Example detergent compositions for application to a substrate | | | | | |
|---|---|---|---|---|---|
| | Weight Percent (actives %) | | | | |
| Ingredients | D1 | D2 | D3 | D4 | D5 |
| Sodium dodecyl benzene sulfonate | 26.09 | 17.30 | 15.60 | 17.70 | 16.70 |
| Sodium alkyl $C_{14-15}$/7EO ether sulfate | 13.80 | — | — | — | — |
| Linear alcohol ethoxylate $C_{14-15}$/7EO | 13.44 | 5.4 | 14.6 | 5.5 | 5.2 |
| Polyethylene glycol PEG 75 | 2 | 1.4 | 1.3 | 1.4 | 1.4 |
| Polyoxyethylene (100) stearyl ether | 21.99 | 15.6 | 14.1 | 15.9 | 15.1 |
| Sodium silicate SiO$_2$/Na$_2$O ratio 1.6-1.8 | 3.72 | 16.6 | 15 | 17 | 16 |
| Sodium Silicate (Britesil® C24) | 7 | — | — | — | — |
| Sodium Carbonate | — | 6.5 | 5.9 | 6.7 | 6.3 |
| Sodium tetraborate decahydrate | — | 11.9 | 10.8 | 12.2 | 11.5 |
| Sodium polyacrylate ~4500 MW | — | 1.8 | 1.7 | — | 5.2 |
| EDTA-tetrasodium salt | — | 0.1 | 0.1 | 0.1 | 0.1 |
| Optical brightener (Tinopal® CBS-X) | 0.15 | 0.1 | 0.09 | 0.1 | 0.1 |
| Dyes and fragrances | 0.9 | 0.9 | 0.81 | 1.01 | 0.91 |
| Water | 10.92 | 22.10 | 19.90 | 22.4 | 21.5 |

| Example fabric conditioning compositions for application to a substrate | | | | | |
|---|---|---|---|---|---|
| | Weight Percent (actives %) | | | | |
| Ingredients | FS1 | FS2 | FS3 | FS4 | FS5 |
| Di-(hydrogenated tallow) dimethyl ammonium methyl sulfate | 33.6 | 33.2 | 44.4 | 22.2 | 33.2 |
| Unsaturated trialkylglycerides | 16.8 | 16.6 | 22.2 | 11.1 | 16.6 |
| Hydrogenated tallow fatty acid | 16.8 | 16.6 | 22.2 | 11.1 | 16.6 |
| $C_{12-18}$ coco fatty acid | 11.2 | 11.1 | — | 11.1 | — |

Example fabric conditioning compositions for application to a substrate

| Ingredients | Weight Percent (actives %) | | | | |
| --- | --- | --- | --- | --- | --- |
| | FS1 | FS2 | FS3 | FS4 | FS5 |
| $C_{12-18}$ fatty alcohol ethoxylate (7EO) | 11.2 | 11.1 | — | — | 16.6 |
| Fragrance oil | 10.4 | 11.4 | 11.2 | 11.2 | 17 |

Exemplary Automatic Dishwashing Agents

| Ingredient | Wt % | | | |
| --- | --- | --- | --- | --- |
| | Formula 1 | Formula 2 | Formula 3 | Formula 4 |
| Citrate | 12-50 | 15-40 | 12-50 | 15-40 |
| Dicarboxylic acid | 1-18 | 1-18 | 2-16 | 4-12 |
| Phosphate | — | — | — | — |
| Bleaching Agent | — | — | — | — |
| Misc | To 100 | To 100 | To 100 | To 100 |

Additional Exemplary Automatic Dishwashing Agents

| Ingredient | Wt % | | | |
| --- | --- | --- | --- | --- |
| | Formula 1 | Formula 2 | Formula 3 | Formula 4 |
| Citrate | 12-50 | 15-40 | 12-50 | 15-40 |
| Dicarboxylic acid | 1-18 | 1-18 | 2-16 | 4-16 |
| Carbonate | 5-50 | 10-40 | 5-50 | 10-40 |
| Phosphate | — | — | — | — |
| Bleaching Agent | — | — | — | — |
| Misc | To 100 | To 100 | To 100 | To 100 |

Additional Exemplary Automatic Dishwashing Agents

| Ingredient | Wt % | | | |
| --- | --- | --- | --- | --- |
| | Formula 1 | Formula 2 | Formula 3 | Formula 4 |
| Citrate | 12-50 | 15-40 | 12-50 | 15-40 |
| Dicarboxylic acid | 1-18 | 1-18 | 2-16 | 4-12 |
| Carbonate | 5-50 | 10-30 | 5-50 | 10-30 |
| Phosphonate | 1-8 | 1-8 | 1.2-6 | 1.2-6 |
| Phosphate | — | — | — | — |
| Bleaching Agent | — | — | — | — |
| Misc | To 100 | To 100 | To 100 | To 100 |

Preferred Automatic Dishwashing Agents

| Ingredient | Wt % | | | |
| --- | --- | --- | --- | --- |
| | Formula 1 | Formula 2 | Formula 3 | Formula 4 |
| Citrate | 12-50 | 15-40 | 12-50 | 15-40 |
| Dicarboxylic acid | 1-18 | 1-18 | 2-16 | 4-12 |
| Carbonate | 0-50 | 0-30 | 0-30 | 0-30 |
| Phosphonate | 0-8 | 0-8 | 0-8 | 0-8 |
| Phosphate | — | — | — | — |
| Bleaching Agent | — | — | — | — |
| Misc | To 100 | To 100 | To 100 | To 100 |

Additional Preferred Automatic Dishwashing Agents

| Ingredient | Wt % | | | |
| --- | --- | --- | --- | --- |
| | Formula 1 | Formula 2 | Formula 3 | Formula 4 |
| Citrate | 12-50 | 15-40 | 12-50 | 15-40 |
| Maleic acid | 1-18 | 1-18 | 2-16 | 4-12 |
| Carbonate | 5-50 | 10-30 | 5-50 | 10-30 |
| Phosphonate | 1-8 | 1-8 | 1.2-6 | 1.2-6 |
| Phosphate | — | — | — | — |
| Bleaching Agent | — | — | — | — |
| Misc | To 100 | To 100 | To 100 | To 100 |

Preferred Automatic Dishwashing Agents

| Ingredient | Wt % | | | |
| --- | --- | --- | --- | --- |
| | Formula 1 | Formula 2 | Formula 3 | Formula 4 |
| Citrate | 12-50 | 15-40 | 12-50 | 15-40 |
| Dicarboxylic acid | 1-18 | 1-18 | 2-16 | 4-12 |
| Carbonate | 0-50 | 0-30 | 0-30 | 0-30 |
| Phosphonate | 0-8 | 0-8 | 0-8 | 0-8 |
| Non-ionic surfactant | 0.1-15 | 0.1-15 | 0.5-8 | 0.5-8 |
| Phosphate | — | — | — | — |
| Bleaching Agent | — | — | — | — |
| Misc | To 100 | To 100 | To 100 | To 100 |

Additional Preferred Automatic Dishwashing Agents

| Ingredient | Wt % | | | |
| --- | --- | --- | --- | --- |
| | Formula 1 | Formula 2 | Formula 3 | Formula 4 |
| Citrate | 12-50 | 15-40 | 12-50 | 15-40 |
| Maleic acid | 1-18 | 1-18 | 2-16 | 4-12 |
| Carbonate | 5-50 | 10-30 | 5-50 | 10-30 |
| Phosphonate | 1-8 | 1-8 | 1.2-6 | 1.2-6 |
| Non-ionic surfactant | 0.1-15 | 0.1-15 | 0.5-8 | 0.5-8 |
| Phosphate | — | — | — | — |
| Bleaching Agent | — | — | — | — |
| Misc | To 100 | To 100 | To 100 | To 100 |

Preferred Automatic Dishwashing Agents

| Ingredient | Wt % | | | |
| --- | --- | --- | --- | --- |
| | Formula 1 | Formula 2 | Formula 3 | Formula 4 |
| Citrate | 12-50 | 15-40 | 12-50 | 15-40 |
| Dicarboxylic acid | 1-18 | 1-18 | 2-16 | 4-12 |
| Carbonate | 0-50 | 0-30 | 0-30 | 0-30 |
| Phosphonate | 0-8 | 0-8 | 0-8 | 0-8 |
| Sulfo copolymer | 0-20 | 0-20 | 0-20 | 0-20 |
| Non-ionic surfactant | 0-15 | 0-15 | 0-8 | 0-8 |
| Enzyme preparations | 0.1-12 | 0.1-12 | 0.5-8 | 0.5-8 |
| Phosphate | — | — | — | — |
| Bleaching Agent | — | — | — | — |
| Misc | To 100 | To 100 | To 100 | To 100 |

| Additional Preferred Automatic Dishwashing Agents | | | | |
|---|---|---|---|---|
| | Wt % | | | |
| Ingredient | Formula 1 | Formula 2 | Formula 3 | Formula 4 |
| Citrate | 12-50 | 15-40 | 12-50 | 15-40 |
| Maleic acid | 1-18 | 1-18 | 2-16 | 4-12 |
| Carbonate | 5-50 | 10-30 | 5-50 | 10-30 |
| Phosphonate | 1-8 | 1-8 | 1.2-6 | 1.2-6 |
| Sulfo copolymer | 0-20 | 0-20 | 0-20 | 0-20 |
| Non-ionic surfactant | 0.1-15 | 0.1-15 | 0.5-8 | 0.5-8 |
| Enzyme preparations | 0.1-12 | 0.1-12 | 0.5-8 | 0.5-8 |
| Phosphate | — | — | — | — |
| Bleaching Agent | — | — | — | — |
| Misc | To 100 | To 100 | To 100 | To 100 |

| Additional Preferred Automatic Dishwashing Agents | | | | |
|---|---|---|---|---|
| | Wt % | | | |
| Ingredient | Formula 1 | Formula 2 | Formula 3 | Formula 4 |
| Citrate | 12-50 | 15-40 | 12-50 | 15-40 |
| Dicarboxylic acid | 1-18 | 1-18 | 2-16 | 4-12 |
| Carbonate | 5-50 | 10-30 | 5-50 | 10-30 |
| Phosphonate | 1-8 | 1-8 | 1.2-6 | 1.2-6 |
| Sulfo copolymer | 0-20 | 0-20 | 0-20 | 0-20 |
| Non-ionic surfactant | 0.1-15 | 0.1-15 | 0.5-8 | 0.5-8 |
| Enzyme preparations | 0.1-12 | 0.1-12 | 0.5-8 | 0.5-8 |
| Organic Solvent | 0.1-15 | 0.5-8 | 0.1-15 | 0.5-8 |
| Phosphate | — | — | — | — |
| Bleaching Agent | — | — | — | — |
| Misc | To 100 | To 100 | To 100 | To 100 |

| Preferred Automatic Dishwashing Agents | | | | |
|---|---|---|---|---|
| | Wt % | | | |
| Ingredient | Formula 1 | Formula 2 | Formula 3 | Formula 4 |
| Citrate | 12-50 | 15-40 | 12-50 | 15-40 |
| Dicarboxylic acid | 1-18 | 1-18 | 2-16 | 4-12 |
| Carbonate | 0-50 | 0-30 | 0-30 | 0-30 |
| Phosphonate | 0-8 | 0-8 | 0-8 | 0-8 |
| Sulfo copolymer | 0-20 | 0-20 | 0-20 | 0-20 |
| Non-ionic surfactant | 0-15 | 0-15 | 0-8 | 0-8 |
| Enzyme preparations | 0-12 | 0-12 | 0-8 | 0-8 |
| Organic Solvent | 0.1-15 | 0.5-8 | 0.1-15 | 0.5-8 |
| Phosphate | — | — | — | — |
| Bleaching Agent | — | — | — | — |
| Misc | To 100 | To 100 | To 100 | To 100 |

| Automatic Dishwashing Agents | | |
|---|---|---|
| | Wt % | |
| Ingredient | C 1 | E 1 |
| Sodium citrate | 9 | 9 |
| Potassium hydroxide | 7 | 7 |
| Sodium carbonate | 14 | 14 |
| Maleic acid | — | 1 |
| Sulfo polymer | 4.2 | 4.2 |
| HEDP | 1.5 | 1.5 |
| Non-ionic surfactant | 2 | 2 |
| Protease preparation | 2 | 2 |
| Amylase preparation | 0.8 | 0.8 |
| Alkanolamine | 1.5 | 1.5 |
| Thickener | 2 | 2 |
| Water, misc | To 100 | To 100 |

| Manual Dishwashing Agents | | | | | | | |
|---|---|---|---|---|---|---|---|
| | Wt % | | | | | | |
| Ingredient | Invention 1 | Invention 2 | Invention 3 | Invention 4 | Invention 5 | Invention 6 | Invention 7 |
| Fatty alcohol ether sulfate | 10 | 13.33 | 12 | 12 | 13.3 | 13.3 | 13.3 |
| Cocamidopropylbetaine | 2.5 | 3.33 | 3.1 | 3.1 | 3 | 3 | 3 |
| Sce. Alkanesulfonate | 2.5 | 3.33 | 2.9 | 2.9 | 3.7 | 3.7 | 3.7 |
| Fatty alcohol ethoxylate | 9 | 6 | — | — | — | — | — |
| Sodium chloride | 24 | 24 | 22 | 24 | 20 | 24 | 20 |
| Ethanol | — | — | 2 | 2 | 2.5 | 2.5 | 4 |
| Perfume | 0.2 | 0.3 | 0.3 | 0.3 | 0.3 | 0.3 | 0.3 |
| Colorant | 0.2 | 0.2 | 0.2 | 0.2 | 0.2 | 0.2 | 0.2 |
| Water | 51.60 | 49.51 | 57.5 | 55.5 | 57 | 53 | 55.5 |

| Antibacterially active detergent/cleaning agent | | | | | | |
|---|---|---|---|---|---|---|
| Ingredient | V1 | E1 | E2 | E3 | E4 | E5 |
| $C_{12-18}$ fatty alcohol with 7EO | 12 | 12 | 12 | 5 | 5 | — |
| N-cocoalkyl N, N dimethylamineoxide | 1.95 | 1.95 | 1.95 | 2 | 2 | — |

| Antibacterially active detergent/cleaning agent | | | | | | |
|---|---|---|---|---|---|---|
| Ingredient | V1 | E1 | E2 | E3 | E4 | E5 |
| Esterquat (N-methyl-N-(2 hydroxyethyl)-N-N-(ditallowacyloxyethyl) ammonium methosulfate | — | — | — | — | — | 15 |
| AgNO$_3$.H$_2$O | 0.0043 | 0.0043 | 0.0043 | 0.004 | 0.004 | 0.004 |
| C14 fatty acid | 5 | 5 | — | — | — | — |
| Farnesol | 0.02 | 0.02 | 0.02 | 0.02 | 0.02 | 0.02 |
| Coco Fatty acid | 2.5 | 2.5 | 2.5 | 12 | — | — |
| Citric Acid | — | — | — | 1.0 | 0.1 | — |
| H$_2$O$_2$ | — | 0.5 | 0.035 | 2 | 5 | 0.5 |
| NaOH | 0.35 | 0.35 | 0.35 | 1.9 | — | — |
| NH$_4$OH | 0.04 | 0.04 | 0.04 | 0.06 | — | — |
| 2-Propanol | — | — | — | — | — | 1.67 |
| MgCl$_2$ × 6H$_2$O | — | — | — | — | — | 0.01 |
| Perfume A | 1.00 | 1.00 | 1.00 | 1.00 | 1.00 | 0.75 |
| Water | To 100 | To 100 | To 100 | To 100 | To 100 | To 100 |
| pH | 8.5 | 8.5 | 8.5 | 8.5 | 5.5 | 2.6 |

| Detergent containing anti-grey agent | |
|---|---|
| Ingredients | M1 (wt %) |
| C$_{9-13}$ alkylbenzenesulfonate sodium salt | 10 |
| Sodium lauryl ether sulfate with 2EO | 5 |
| C$_{12-18}$ fatty alcohol with 7EO | 10 |
| C$_{12-14}$ alkyl polyglycoside | 2 |
| C$_{12-18}$ fatty acid sodium salt | 8 |
| Glycerol | 5 |
| Trisodium citrate | 1 |
| Polyacrylate | 2 |
| Active ingredient (anti-grey agent-a polycarbonate-, polyurethane-, and/or polyurea-polyorganosiloxane compound or a precursor compound use in the production thereof) | 1 |
| Enzyme, dye, optical brightener | + |
| Water | To 100 |

| Example detergent compositions for application to a substrate | | | | | |
|---|---|---|---|---|---|
| | Weight Percent (actives %) | | | | |
| Ingredients | D1 | D2 | D3 | D4 | D5 |
| Sodium dodecyl benzene sulfonate | 26.09 | 17.30 | 15.60 | 17.70 | 27.00 |
| Sodium alkyl C$_{14-15}$/7EO ether sulfate | 13.80 | | | | 14.00 |
| Linear alcohol ethoxylate C$_{14-15}$/7EO | 13.44 | 5.40 | 14.60 | 5.50 | 14.00 |
| Linear alcohol ethoxylate C$_{12-20}$/7EO | | | | | 23.00 |
| Polyethylene Glycol PEG-75 | 2.00 | 1.40 | 1.30 | 1.40 | 2.00 |
| Polyoxyethylene (100) stearyl ether | 21.99 | 15.60 | 14.10 | 15.90 | |
| Sodium Silicate SiO$_2$/Na$_2$O ratio 1.6-1.8 | 3.72 | 16.60 | 15.00 | 17.00 | |
| Sodium Silicate (Britesil ® C24) | 7.00 | | | | 11.00 |
| Sodium Carbonate | | 6.50 | 5.90 | 6.70 | |
| Sodium tetraborate decahydrate | | 11.90 | 10.80 | 12.20 | |
| Sodium polyacrylate –4,500 MW | | 1.80 | 1.70 | | |
| EDTA—tetrasodium salt | | 0.10 | 0.10 | 0.10 | |
| Optical brightener (Tinopal ® CBS-X) | 0.15 | 0.10 | 0.09 | 0.10 | 0.20 |
| Dyes and fragrances | 0.90 | 0.90 | 0.81 | 1.01 | 0.35 |
| Water | 10.92 | 22.10 | 19.90 | 22.40 | 9.55 |

Example enzyme containing compositions for application to a substrate

| Ingredients | Weight Percent (actives %) | | | | |
|---|---|---|---|---|---|
| | E1 | E2 | E3 | E4 | E5 |
| Polyethylene Glycol PEG-75 | 98.60 | 99.10 | | | |
| Fatty acid based matrix 1 | | | 98.9 | | 99.10 |
| Fatty acid based matrix 2 | | | | 98.80 | |
| Protease | 0.10 | 0.10 | 0.12 | 0.10 | 0.10 |
| Mannanase | 0.02 | | | 0.02 | 0.02 |
| Amylase | 0.12 | 0.25 | 0.1 | 0.12 | 0.25 |
| Cellulase | 0.08 | | 0.1 | 0.08 | |
| Lipase | 0.08 | | | 0.08 | |
| Pectate Lyase | | | | 0.05 | |
| Enzyme Stabilizers | 1.00 | 0.55 | 0.75 | 0.75 | 0.55 |

Fatty acid based matrix 1 is comprised of 20 wt. % of the sodium salt of coconut fatty acid, 50 wt. % of non polymeric polyols (sorbitol, glycerin, propylene glycol, sucrose and glucose), 15 wt. % of anionic and nonionic surfactants, and 15 wt. % of water.

Fatty acid based matrix 2 is comprised of 20 wt. % of the sodium salt of stearic acid, 3 wt. % of the sodium salt of lauric acid, 3 wt. % of the sodium salt of myristic acid, 50 wt. % of non polymeric polyols (sorbitol, glycerin, and propylene glycol), 2 wt. % of lauric acid, 2 wt. % of stearic acid, 10 wt. % of anionic surfactant, and 10 wt. % of water.

Detergent Composition

| Ingredients | (% by weight) |
|---|---|
| Soap (saturated $C_{12-24}$ fatty acid soaps and oleic acid soap) | 5.42 |
| Sodium $C_{12-14}$ alkyl benzenesulfonate | 22.67 |
| Sodium $C_{14-16}$ fatty alcohol sulfate | 4.59 |
| $C_{12-18}$ fatty alcohol. 5EO | 0.81 |
| Sodium carbonate | 4.55 |
| Zeolite A | 29.86 |
| Sodium silicate | 8.00 |
| Acrylic acid/maleic acid copolymer | 16.16 |
| Opt. brightener | 0.45 |
| Phosphonate | 2.30 |
| NaOH, 50% | 0.63 |
| Water | 3.88 |
| Other salts | 0.68 |
| Detergent composition | 59.5% |
| Coated bleaching agent (Na percarbonate) | 23.3% |
| Coated bleach activator (TAED) | 7% |
| Citric acid monohydrate | 10.2% |

Particulate detergent composition

| Ingredient | % wt |
|---|---|
| sodium dodecylbenzenesulphonate | 8.5 |
| c12-C15 primary alcohol, condensed with 7 moles of ethylene oxide | 4 |
| sodium-hardened rapeseed oil soap | 1.5 |
| sodium triphosphate | 33 |
| sodium carbonate | 5 |
| sodium silicate | 6 |
| sodium sulphate | 20 |
| water | 9 |
| fluorescers, soil-suspending agents, dyes, perfumes | minor amounts |
| sodium perborate | 12 |
| tetraacetyl ethylene diamine (TAED) (granules) | 2 |
| proteolytic enzyme (Savinase ex. Novo) | 0.4 |

Detergent composition A

9% anionic detergent
1% nonionic detergent
21.5% sodium tripolyphosphate
7% sodium perborate
0.6% Savinase (a proteolytic enzyme)
balance sodium sulphate + minor ingredients Detergent composition B 9% anionic detergent
4% nonionic detergent
28% zeolite
4.5% nitrilotriacetate
5.5% sodium perborate
3.5% tetraacetylethylenediamine
0.5% Savinase
balance sodium sulphate + minor ingredients Detergent composition C 5% anionic detergent
4% nonionic detergent
1% soap
30% zeolite
3.% copolymer of acrylic acid with mateic anhydride
7.5% sodium perborate
3% tetraacetylethylenediamine
balance sodium sulphate + minor ingredients Detergent composition D 8% anionic synthetic detergent
4% nonionic synthetic detergent
4% soap
35.% sodium carbonate
20% powdered calcite
6% sodium perborate
2% tetraacetylethylenediamine
0.5% Savinase
balance sodium sulphate + minor ingredients Laundry detergent composition

| Ingredients | Parts by weight |
|---|---|
| Sodium dodecyl benzene sulphonate | 8.5 |
| C12-C15 primary alcohol, condensed with 7 moles of ethylene oxide | 4 |
| Sodium-hardened rapeseed oil soap | 1.5 |
| Sodium triphosphate | 33 |
| Sodium carbonate | 5 |
| Sodium silicate | 6 |
| Sodium sulphate | 20 |
| Water | 9 |
| Fluorescers, soil-suspending agents, dyes, perfumes | minor amount |
| Sodium perborate | 12 |
| Tetraacetyl ethylene diamine (TAED) (granules) | 2 |
| Proteolytic enzyme (Savinase ex NOVO) | 0.4 |

Laundry detergent compositions

| | A | B | C | D |
|---|---|---|---|---|
| sodium dodecylbenzene sulphonate | 9 | 9 | 9 | 9 |
| C13-C15 linear primary alcohol, condensed with 7 moles of ethylene oxide (e.g. Synperonic A7) | 1 | 4 | 4 | 1 |
| C13-C15 linear primary alcohol, condensed with 3 | 3 | 0 | 0 | 3 |

Laundry detergent compositions

| | A | B | C | D |
|---|---|---|---|---|
| moles of ethylene oxide (e.g. Synperonic A3) | | | | |
| sodium tripolyphosphate | 23 | 23 | 0 | 0 |
| zeolite type 4A | 0 | 0 | 24 | 24 |
| copolymer of acrylic acid with maleic anhydride | | | 4 | 4 |
| sodium polyacrylate | 2 | 2 | 0 | 0 |
| alkaline silicate | 5 | 5 | | |
| fluorescer | 0.25 | 0.25 | 0.16 | 0.16 |
| EDTA | 0.15 | 0.15 | 0.18 | 0.18 |
| SCMC | 0.5 | 0.5 | 0.55 | 0.55 |
| salt | 2 | 2 | | |
| sodium sulphate | 26.8 | 26.8 | 22.31 | 22.31 |
| sodium carbonate | 0 | 0 | 10.3 | 10.3 |
| moisture | 10 | 10 | 11 | 11 |
| TAED | 3 | 3 | 3.3 | 3.3 |
| sodium perborate monohydrate | 10 | 10 | 8 | 8 |
| calcium Dequest® 2047 | 0.7 | 0.7 | 0.3 | 0.3 |
| foam depressor | 3 | 3 | 2.5 | 2.5 |
| perfume | 0.2 | 0.2 | 0 | 0 |
| alkaline protease (Savinase (A) 6T) | 0.4 | 0.4 | 0.4 | 0.4 |

Detergent composition

| Ingredients Material | Ex. 1 Level (parts as is) | Ex. 2 Level (parts as is) | Ex.3 Level (parts as is) | Ex.4 Level (parts as is) |
|---|---|---|---|---|
| Glycerol | 3.17 | 3.17 | 3.17 | 3.17 |
| MPG | 5.7 | 5.7 | 5.7 | 5.7 |
| NaOH | 2.13 | 2.13 | 2.13 | 2.13 |
| TEA | 2.05 | 2.05 | 2.05 | 2.05 |
| Neodol 25-7 | 12.74 | 12.74 | 12.74 | 12.74 |
| F-Dye | 0.18 | 0.18 | 0.18 | 0.18 |
| Citric Acid | 1.71 | 1.71 | 1.71 | 1.71 |
| LAS (as LAS Acid) | 8.49 | 8.49 | 8.49 | 8.49 |
| Fatty acid | 3.03 | 3.03 | 3.03 | 3.03 |
| Empigen BB | 1.5 | 1.5 | 1.5 | 1.5 |
| SLES | 4.24 | 4.24 | 4.24 | 4.24 |
| Dequest 2066 | 0.875 | 0.875 | 0.875 | 0.875 |
| Patent Blue | 0.00036 | 0.00036 | 0.00036 | 0.00036 |
| Acid Yellow | 0.00005 | 0.00005 | 0.00005 | 0.00005 |
| Opacifier | 0.0512 | 0.0512 | 0.0512 | 0.0512 |
| Perfume | 0.734 | 0.734 | 0.734 | 0.734 |
| Borax | 10 | 10 | 10 | 10 |
| Savinase | 2.362 | 2.362 | 2.362 | 2.362 |
| Stainzyme | 0.945 | 0.945 | 0.945 | 0.945 |
| Soap | 3.03 | 3.03 | 3.03 | 3.03 |
| EPEI 20E0 (ex Nippon Shokubai) polyethyleneimine having a weight average molecular weight of about 600, and wherein the polyethyleneimine has been modified by alkoxylation with an average 20 ethylene oxide moieties | 5.5 | 5.5 | 5.5 | 9 |
| Lipex ® (ex Novozymes) | 3 | 3 | 3 | 3 |
| Texcare SRN170 (ex Clariant) soil release polymer | 0 | 7.5 | 0 | 0 |
| Sokolan CP5 (ex BASF) Soil-release polymer | 0 | 0 | 20 | 0 |

7.6. Methods of Assessing Amylase Activity in Detergent Compositions

Numerous α-amylase cleaning assays are known in the art, including swatch and micro-swatch assays. The appended Examples describe only a few such assays.

In order to further illustrate the compositions and methods, and advantages thereof, the following specific examples are given with the understanding that they are illustrative rather than limiting.

8. Brewing Compositions

The present variant amylase may be a component of a brewing composition used in a process of brewing, i.e., making a fermented malt beverage. Non-fermentable carbohydrates form the majority of the dissolved solids in the final beer. This residue remains because of the inability of malt amylases to hydrolyze the alpha-1,6-linkages of the starch. The non-fermentable carbohydrates contribute about 50 calories per 12 ounces of beer. an amylase, in combination with a glucoamylase and optionally a pullulanase and/or isoamylase, assist in converting the starch into dextrins and fermentable sugars, lowering the residual non-fermentable carbohydrates in the final beer.

The principal raw materials used in making these beverages are water, hops and malt. In addition, adjuncts such as common corn grits, refined corn grits, brewer's milled yeast, rice, sorghum, refined corn starch, barley, barley starch, dehusked barley, wheat, wheat starch, torrified cereal, cereal flakes, rye, oats, potato, tapioca, and syrups, such as corn syrup, sugar cane syrup, inverted sugar syrup, barley and/or wheat syrups, and the like may be used as a source of starch.

For a number of reasons, the malt, which is produced principally from selected varieties of barley, has the greatest effect on the overall character and quality of the beer. First, the malt is the primary flavoring agent in beer. Second, the malt provides the major portion of the fermentable sugar. Third, the malt provides the proteins, which will contribute to the body and foam character of the beer. Fourth, the malt provides the necessary enzymatic activity during mashing. Hops also contribute significantly to beer quality, including flavoring. In particular, hops (or hops constituents) add desirable bittering substances to the beer. In addition, the hops act as protein precipitants, establish preservative agents and aid in foam formation and stabilization.

Grains, such as barley, oats, wheat, as well as plant components, such as corn, hops, and rice, also are used for brewing, both in industry and for home brewing. The components used in brewing may be unmalted or may be malted, i.e., partially germinated, resulting in an increase in the levels of enzymes, including α-amylase. For successful brewing, adequate levels of α-amylase enzyme activity are necessary to ensure the appropriate levels of sugars for fermentation. an amylase, by itself or in combination with another α-amylase(s), accordingly may be added to the components used for brewing.

As used herein, the term "stock" means grains and plant components that are crushed or broken. For example, barley used in beer production is a grain that has been coarsely ground or crushed to yield a consistency appropriate for producing a mash for fermentation. As used herein, the term "stock" includes any of the aforementioned types of plants and grains in crushed or coarsely ground forms. The methods described herein may be used to determine α-amylase activity levels in both flours and stock.

Processes for making beer are well known in the art. See, e.g., Wolfgang Kunze (2004) "Technology Brewing and Malting," Research and Teaching Institute of Brewing, Berlin (VLB), 3rd edition. Briefly, the process involves: (a) preparing a mash, (b) filtering the mash to prepare a wort, and (c) fermenting the wort to obtain a fermented beverage, such as beer. Typically, milled or crushed malt is mixed with water and held for a period of time under controlled temperatures to permit the enzymes present in the malt to convert the starch present in the malt into fermentable sugars. The mash is then transferred to a mash filter where the liquid is separated from the grain residue. This sweet liquid is called "wort," and the left over grain residue is called "spent grain." The mash is typically subjected to an extraction, which involves adding water to the mash in order to recover the residual soluble extract from the spent grain. The wort is then boiled vigorously to sterilizes the wort and help develop the color, flavor and odor. Hops are added at some point during the boiling. The wort is cooled and transferred to a fermentor.

The wort is then contacted in a fermentor with yeast. The fermentor may be chilled to stop fermentation. The yeast flocculates and is removed. Finally, the beer is cooled and stored for a period of time, during which the beer clarifies and its flavor develops, and any material that might impair the appearance, flavor and shelf life of the beer settles out. The beer usually contains from about 2% to about 10% v/v alcohol, although beer with a higher alcohol content, e.g., 18% v/v, may be obtained. Prior to packaging, the beer is carbonated and, optionally, filtered and pasteurized.

The brewing composition comprising an amylase, in combination with a glucoamylase and optionally a pullulanase and/or isoamylase, may be added to the mash of step (a) above, i.e., during the preparation of the mash. Alternatively, or in addition, the brewing composition may be added to the mash of step (b) above, i.e., during the filtration of the mash. Alternatively, or in addition, the brewing composition may be added to the wort of step (c) above, i.e., during the fermenting of the wort.

A fermented beverage, such as a beer, can be produced by one of the methods above. The fermented beverage can be a beer, such as full malted beer, beer brewed under the "Reinheitsgebot," ale, IPA, lager, bitter, Happoshu (second beer), third beer, dry beer, near beer, light beer, low alcohol beer, low calorie beer, porter, bock beer, stout, malt liquor, non-alcoholic beer, non-alcoholic malt liquor and the like, but also alternative cereal and malt beverages such as fruit flavored malt beverages, e.g., citrus flavored, such as lemon-, orange-, lime-, or berry-flavored malt beverages, liquor flavored malt beverages, e.g., vodka-, rum-, or tequila-flavored malt liquor, or coffee flavored malt beverages, such as caffeine-flavored malt liquor, and the like.

9. Reduction of Iodine-Positive Starch

Variant amylases may reduce the iodine-positive starch (IPS), when used in a method of liquefaction and/or saccharification. One source of IPS is from amylose that escapes hydrolysis and/or from retrograded starch polymer. Starch retrogradation occurs spontaneously in a starch paste, or gel on ageing, because of the tendency of starch molecules to bind to one another followed by an increase in crystallinity. Solutions of low concentration become increasingly cloudy due to the progressive association of starch molecules into larger articles. Spontaneous precipitation takes place and the precipitated starch appears to be reverting to its original condition of cold-water insolubility. Pastes of higher concentration on cooling set to a gel, which on ageing becomes steadily firmer due to the increasing association of the starch molecules. This arises because of the strong tendency for hydrogen bond formation between hydroxy groups on adjacent starch molecules. See J. A. Radley, ed., STARCH AND ITS DERIVATIVES 194-201 (Chapman and Hall, London (1968)).

The presence of IPS in saccharide liquor negatively affects final product quality and represents a major issue with downstream processing. IPS plugs or slows filtration system, and fouls the carbon columns used for purification. When IPS reaches sufficiently high levels, it may leak through the carbon columns and decrease production efficiency. Additionally, it may results in hazy final product upon storage, which is unacceptable for final product quality. The amount of IPS can be reduced by isolating the saccharification tank and blending the contents back. IPS nevertheless will accumulate in carbon columns and filter systems, among other things. The use of variant amylases is expected to improve overall process performance by reducing the amount of IPS.

All references cited herein are herein incorporated by reference in their entirety for all purposes. In order to further illustrate the compositions and methods, and advantages thereof, the following specific examples are given with the understanding that they are illustrative rather than limiting.

EXAMPLES

Example 1: Assays

In the following examples, various assays were used as set forth below for ease in reading. Any deviations from the protocols provided below are indicated in the relevant sections. In these experiments, a spectrophotometer was used to measure the absorbance of the products formed after the completion of the reactions.

A. Performance Index

The performance index (PI) compares the performance or stability of the variant (measured value) and the standard enzyme (theoretical value) at the same protein concentration. In addition, the theoretical values can be calculated, using the parameters of the Langmuir equation of the standard enzyme. A performance index (PI) that is greater than 1 (PI>1) indicates improved performance by a variant as compared to the standard (e.g., wild-type *Bacillus* sp. 707 α-amylase, also called Amy707 or Amy #707), while a PI of 1 (PI=1) identifies a variant that performs the same as the standard, and a PI that is less than 1 (PI<1) identifies a variant that performs worse than the standard.

B. Protein Content Assay

This assay is performed using filtered culture supernatant from cultures grown in microtiter plates (MTPs) over 3 days at 37° C. with shaking at 300 rpm and 80% humidity. A fresh 96-well V-bottom MTP containing 50 µl supernatant per well is used for the High Performance Liquid Chromatography (HPLC) protein determination method.

For the 24-site SEL libraries described in Example 3, supernatants were diluted three-fold into 10 mM potassium phosphate buffer pH 7.25 containing 5% acetonitrile and 10% sodium chloride and 10 µl of each diluted sample was analyzed. An Agilent 1100 (Hewlet Packard) HPLC equipped with a Swift™ RP-all PN 68-1030-041 column (Teledyne Isco, Inc.) was used. For the full SEL libraries described in Example 4, supernatants were diluted nine-fold into 25 mM MOPS, 0.1 mM $CaCl_2$, pH 7.15, 10% TFA, and 204, of each diluted sample was analyzed. An Agilent 1200 (Hewlet Packard) HPLC equipped with a Poroshell 300SB-C8 (Agilent Technologies) column was used.

In both cases, the solvent system consists of 0.1% trifluoroacetic acid in aqueous phase and 0.07% trifluoroacetic acid in acetonitrile. Absorbance is read at 222 nm and protein concentration of samples is determined based on a calibration curve (18 ppm-400 ppm) using purified wild-type Amy707 protein.

C. Ceralpha α-Amylase Activity Assay

The Ceralpha α-amylase assay is performed using the Ceralpha HR Kit (Megazyme, Wicklow, Ireland). The assay involves incubating culture supernatant with a substrate mixture under defined conditions, and the reaction is terminated (and color developed) by the addition of Trizma base solution. The substrate is a mixture of the defined oligosaccharide "nonreducing-end blocked p-nitrophenyl maltoheptaoside" (BPNPG7) and excess levels of glucoamylase and β-glucosidase (which have no action on the native substrate due to the presence of the "blocking group"). On hydrolysis of the oligosaccharide by endoacting α-amylase, the excess quantities of α-glucosidase and glucoamylase present in the mixture give instantaneous and quantitative hydrolysis of the p-nitrophenyl maltosaccharide fragment to glucose and free p-nitrophenol. The absorbance at 405 nm is measured, and this relates directly to the level of α-amylase in the sample analysed.

The equipment used for this set of assays includes a Biomek FX Robot (Beckman Coulter); a SpectraMAX MTP Reader (type 340-Molecular Devices) and iEMS incubator/shaker (Thermo Scientific). In this assay system, the reagent and solutions used are:

1) p-nitrophenyl maltoheptaoside (BPNPG7) substrate (Megazyme Ceralpha HR kit);
2) 50 mM MOPS, 50 mM NaCl, 0.1 mM $CaCl_2$), 0.005% TWEEN® 80 buffer, pH 7.15 (for the 24-site SEL libraries described in Example 3) or 50 mM MOPS, 0.005% TWEEN® 80 buffer, pH 7 (for the full SEL libraries described in Example 4); and
3) 200 mM Boric acid/NaOH buffer, pH 10.2 (STOP buffer).

A vial containing 54.5 mg BPNPG7 substrate is dissolved in 10 ml of milliQ water. The amylase samples (fermentation supernatant) are diluted in MOPS buffer. The assay is performed by adding 25 µl of diluted amylase solution into the wells of a MTP followed by the addition of 25 µl 5.45 mg/ml BPNPG7 substrate solution. The solutions are mixed and the MTP is sealed with a plate seal and placed in an incubator/shaker (iEMS-Thermo Scientific) for 30 minutes at 25° C. and 900 rpm. The reaction is terminated by adding 50 µl STOP buffer and the absorbance is read at wavelength 405 nm in an MTP-Reader. A non-enzyme control is used to correct for background absorbance values.

D. CS-28 Rice Starch Microswatch Assay

The principle of this α-amylase assay is the liberation of an orange-dye due to the hydrolysis of rice starch incorporated in the microswatch. The absorbance at 488 nm is measured and this relates to the level of amylase activity in the sample analysed, at the desired conditions (pH, temperature, and buffer).

The equipment used for this set of assays includes a Biomek FX Robot (Beckman Coulter), a SpectraMAX MTP Reader (type 340-Molecular Devices) and iEMS incubator/shaker (Thermo Scientific). In this assay system the reagent and solutions used are:

1) CS-28 Microswatches (rice starch, colored);
2) 25 mM HEPES, 2 mM $CaCl_2$), 0.005% TWEEN 80 buffer, pH 8.0 (for the 24-site SEL libraries described in Example 3) or 10 mM HEPES, 2 mM $CaCl_2$), 0.005% TWEEN 80 buffer, pH 8.0, conductivity 1 mS/cm (for the full SEL libraries described in Example 4);
3) 25 mM CAPS, 2 mM $CaCl_2$), 0.005% TWEEN 80 buffer, pH 10.0; and
4) 10 mM NaCl, 0.1 mM $CaCl_2$), 0.005% TWEEN 80 (Dilution buffer).

CS-28 Microswatches of 5.5 mm circular diameter were delivered by the Center for Testmaterials (CFT, Vlaardingen, The Netherlands). Two microswatches are placed in each well of a 96-well MTP. The amylase samples (fermentation supernatant) are tested at appropriate concentrations in several conditions, pre-diluted in 10 mM NaCl, 0.1 mM $CaCl_2$), 0.005% TWEEN® 80 solution:

1) pH 8 (25 mM HEPES buffer) and 16° C.; final amylase conc. in assay <0.3 µg/ml;
2) pH 8 (25 mM HEPES buffer) and 32° C.; final amylase conc. in assay <0.05 µg/ml;
3) pH 8 (25 mM HEPES buffer) and 50° C.; final amylase conc. in assay <0.005 µg/ml;
4) pH 10 (25 mM CAPS buffer) and 16° C.; final amylase conc. in assay <0.75 µg/ml; and
5) pH 10 (25 mM CAPS buffer) and 50° C.; final amylase conc. in assay <0.0075 µg/ml.

The incubator/shaker is set at the desired temperature, 16° C. (cold storage chamber or refrigerator), 32° C. or 50° C. The culture supernatant samples are diluted in dilution buffer to 20× the desired final concentration. 190 µl of either HEPES or CAPS buffer is added to each well of a microswatch-MTP and subsequently 10 µl of enzyme solution is added to each well resulting in a total volume of 200 µl/well. The MTP is sealed with a plate seal and placed in the iEMS incubator/shaker and incubated for 60 minutes at 1150 rpm at the desired temperature (16°, 32° or 50° C.). Following incubation under the appropriate conditions, 100 µl of solution from each well is transferred to a new MTP, and the absorbance at 488 nm is measured using a MTP-spectrophotometer. Controls containing two microswatches and buffer but no enzyme are included for background subtraction.

To calculate wash performance, the obtained absorbance value is corrected for the blank value (obtained after incubation of microswatches in the absence of enzyme), and the resulting absorbance is a measure of hydrolytic activity. A performance index (PI) is calculated for each sample. For the PI calculation for the wash performance indices, a curve-fit is made based on the wild-type Amy707 enzyme (SEQ ID NO: 3), using the Langmuir equation. Using the protein concentration of the variants, the expected performance based on the curvefit is calculated. The observed performance is divided by the calculated performance and this is then divided by the performance of the wild-type Amy707 enzyme (SEQ ID NO: 3).

E. Thermostability Assay—Determination of Initial and Residual Activities

The thermostability of the amylase variant in relation to a reference amylase (wild-type Amy707, SEQ ID NO: 3) is determined by incubating the amylase samples under defined conditions in MOPS buffer, pH 7.15. The temperature of the incubation is selected such that approximately 70% of the initial reference amylase activity is lost. The initial and residual amylase activities are determined using the Ceralpha α-amylase method described in section C above.

The equipment used for this set of assays includes a Biomek FX Robot (Beckman Coulter); a SpectraMAX MTP Reader (type 340-Molecular Devices) and iEMS incubator/shaker (Thermo Scientific). In this assay system, the reagent solutions used are:

1) p-nitrophenyl maltoheptaoside (BPNPG7) substrate (Megazyme Ceralpha HR kit);
2) 10 mM NaCl, 0.1 mM $CaCl_2$), 0.005% TWEEN® 80 buffer (Dilution buffer);
3) 50 mM MOPS, 50 mM NaCl, 0.1 mM $CaCl_2$), 0.005% TWEEN®80 buffer, pH 7.15;
4) 200 mM Boric acid/NaOH buffer, pH 10.2 (STOP buffer); and
5) Amylase culture supernatants, containing 50-150 µg/ml protein.

A "master dilution" plate is prepared by diluting the culture supernatant 20× in dilution buffer, followed by a 42× dilution step in MOPS buffer. From the master dilution 25 µl is used to determine the initial amylase activity and 100 µl is used for heat incubation. The 100 µl sample is put in each well of a 96 well PCR plate (VWR 211-0297) that is sealed with an aluminum seal and incubated at 69° C. for 30 minutes in a Tetrad PCR block (Biorad). To determine the initial ($t_{00}$) and residual ($t_{30}$) activity, a 25 µl sample is transferred into a MTP, containing 25 µl of BPNPG7 solution per well and incubated at 25° C. for 30 minutes. The Ceralpha α-amylase assay is performed as described above in Section C.

For each variant, the ratio of the residual and initial amylase activities is used to calculate thermostability as follows: Thermostability=$[t_{-30}$ value]/$[t_{-00}$ value], so the thermostability activity ratio is calculated based on enzyme activity after the heat incubation, divided by enzyme activity before the heat incubation. The performance index for thermostability is determined by dividing the activity ratio of the variant enzyme, with that of the similarly treated wild-type Amy707 enzyme (SEQ ID NO: 3). Thermostability assays were only performed for the 24-site SEL libraries described in Example 3.

F. Detergent Stability Assay

The stability of the reference amylase and variants thereof is measured after incubation under defined conditions in the presence of 10% commercially purchased Persil Color detergent, Henkel (purchased in 2008). The detergent is heat inactivated before use, and the initial and residual amylase activities are determined using the Ceralpha α-amylase assay as described in section C above.

The equipment used for this set of assays includes a Biomek FX Robot (Beckman Coulter); a SpectraMAX MTP Reader (type 340-Molecular Devices) and iEMS incubator/shaker (Thermo Scientific). In this assay system, the reagent solutions used are:

1) p-nitrophenyl maltoheptaoside (BPNPG7) substrate (Megazyme Ceralpha HR kit):
2) liquid detergent (HDL commercial product, enzyme-inactivated, 2 hrs at 60° C.);
3) 10.5% detergent in 25 mM HEPES buffer, pH 8.0;
4) 50 mM MOPS, 50 mM NaCl, 0.1 mM $CaCl_2$, 0.005% TWEEN®80 buffer, pH 7.15 (for the 24-site SEL libraries described in Example 3) or 50 mM MOPS, 0.1 mM $CaCl_2$, 0.005% TWEEN®80 buffer, pH 7 (for the full SEL libraries described in Example 4);
5) 200 mM Boric acid/NaOH buffer, pH 10.2 (STOP buffer); and
6) Amylase culture supernatants containing 50-150 µg/ml protein.

To a 96 well PCR plate, 95 µl of a 10.5% detergent solution is added, and mixed with 5 µl of culture supernatant. A 3 µl aliquot is removed for determination of the initial amylase activity. The PCR plate is incubated in on a Tetrad PCR block at 41° for 30 minutes. After incubation the residual amylase activity is measured using 3 µl of the detergent-enzyme mixture. To determine the initial ($t_0$) and residual ($t_{30}$) amylase activity, 3 µl 'detergent-enzyme' mix is diluted in 122 µl MOPS buffer and subsequently 25 µl is used to determine the amylase activity using the Ceralpha α-amylase assay described above in section C.

For each variant, the ratio of the residual and initial amylase activities is used to calculate the detergent stability as follows: Detergent stability=$[t_{-30}$ value]/$[t_{-00}$ value], so the detergent stability activity ratio is calculated based on enzyme activity after the heat incubation, divided by enzyme activity before the heat incubation.

For each sample (variants) the performance index (PI) is calculated. The performance index for detergent stability is determined by comparing the detergent stability of the variant enzyme, with that of the similarly treated wild-type Amy707 enzyme (SEQ ID NO: 3).

Example 2: Generation of *B. subtilis* Strains Expressing Amy707 and Variants Thereof In this example, the construction of *Bacillus subtilis* strains expressing wild-type Amy707 α-amylase and variants, thereof, are described. Amy707 is the G6-amylase (1,4-α-D-glucan maltohexaohydrolase) of alkalophilic *Bacillus* sp. #707 for which the nucleotide sequence was described by Tsukamoto et al. (1988) *Biochem. Biophys. Res. Commun.* 151: 25-31.

A synthetic DNA fragment (SEQ ID NO: 1, herein referred to as "Amy707 DNA") encoding Amy707 (SEQ ID NO: 3) α-amylase was produced by GENEART AG (Regensburg, Germany) and served as template DNA for the construction of *Bacillus subtilis* strains expressing Amy707 α-amylase and variants, thereof.

SEQ ID NO:1 includes a codon-modified nucleotide sequence encoding the mature form of Amy707 α-amylase adjacent to a sequence encoding the LAT signal peptide (underlined):

ATGAAACAACAAAAACGGCTTTACGCCCGATTGCTGACGCTGTTATTTG

CGCTCATCTTCTTGCTGCCTCATTCTGCAGCTTCAGCACATCATAATGG

CACAAACGGCACGATGATGCAGTATTTTGAATGGTATCTGCCGAACGAT

GGAAACCATTGGAACCGCCTGAATAGCGATGCGAGCAACCTGAAAAGCA

AAGGCATCACAGCAGTTTGGATTCCGCCGGCATGGAAAGGAGCAAGCCA

AAACGACGTCGGCTATGGAGCGTATGATCTGTATGACCTGGGCGAATTT

AACCAAAAAGGCACGGTCCGCACGAAATATGGCACGCGCAGCCAACTTC

AAGCAGCAGTCACGAGCCTTAAAAACAACGGCATCCAGGTCTATGGAGA

TGTCGTCATGAACCATAAAGGCGGAGCAGATGCGACAGAAATGGTCAGA

GCGGTCGAAGTCAACCCGAACAACCGCAATCAAGAAGTCACGGGCGAAT

ATACAATCGAAGCGTGGACGCGCTTTGATTTTCCGGGCAGAGGCAATAC

ACATAGCAGCTTTAAATGGCGCTGGTATCATTTTGATGGCGTCGATTGG

GATCAAAGCCGCAGACTGAACAACCGCATCTATAAATTTCGCGGCCATG

GCAAAGCATGGGATTGGGAAGTCGATACGGAAAACGGCAACTATGACTA

TCTGATGTATGCGGACATCGATATGGATCATCCGGAAGTCGTCAACGAA

CTGAGAAATTGGGGCGTCTGGTATACAAATACGCTGGGCCTGGATGGCT

TTAGAATCGACGCGGTCAAACATATCAAATATAGCTTTACGCGCGACTG

GATCAATCATGTCAGAAGCGCGACGGGCAAAAATATGTTTGCGGTCGCG

GAATTTTGGAAAAATGATCTGGGCGCGATCGAAAACTATCTGCAAAAAA

CGAACTGGAACCATAGCGTCTTTGATGTCCCGCTGCATTATAACCTGTA

TAACGCGAGCAAAAGCGGCGGCAATTATGATATGCGCAACATCTTTAAC

GGCACGGTCGTTCAAAGACATCCGAGCCATGCGGTCACGTTTGTCGATA

ACCATGATAGCCAACCGGAAGAAGCGCTGGAAAGCTTTGTCGAAGAATG

GTTTAAACCGCTGGCGTATGCACTGACACTGACGAGAGAACAAGGATAT

CCGAGCGTCTTTTATGGCGACTATTATGGCATCCCGACACATGGAGTTC

CGGCGATGAGAAGCAAAATCGACCCGATCCTGGAAGCGAGACAGAAATA

TGCGTATGGCAAACAGAACGACTATCTGGACCATCATAACATCATCGGC

TGGACGAGAGAAGGAAATACGGCGCATCCGAATTCAGGACTGGCGACGA

TTATGTCAGATGGAGCGGGCGGAAGCAAATGGATGTTTGTCGGCAGAAA

CAAAGCAGGACAAGTCTGGAGCGATATCACGGGCAATAGAACGGGAACG

GTCACGATCAATGCAGATGGCTGGGGCAACTTTAGCGTTAATGGCGGAA

GCGTCAGCATCTGGGTCAACAAA

The precursor form of the Amy707 polypeptide produced from the pHPLT-Amy707 vector is shown, below, as SEQ ID NO: 2. The LAT signal peptide is underlined:

<u>MKQQKRLYARLLTLLFALIFLLPHSAASA</u>HHNGTNGTMMQYFEWYLPND

GNHWNRLNSDASNLKSKGITAVWIPPAWKGASQNDVGYGAYDLYDLGEF

NQKGTVRTKYGTRSQLQAAVTSLKNNGIQVYGDVVMNHKGGADATEMVR

AVEVNPNNRNQEVTGEYTIEAWTRFDFPGRGNTHSSFKWRWYHFDGVDW

DQSRRLNNRIYKFRGHGKAWDWEVDTENGNYDYLMYADIDMDHPEVVNE

LRNWGVWYTNTLGLDGFRIDAVKHIKYSFTRDWINHVRSATGKNMFAVA

EFWKNDLGAIENYLQKTNWNHSVFDVPLHYNLYNASKSGGNYDMRNIFN

GTVVQRHPSHAVTFVDNHDSQPEEALESFVEEWFKPLAYALTLTREQGY

PSVFYGDYYGIPTHGVPAMIRSKIDPILEARQKYAYGKQNDYLDHHNII

GWTREGNTAHPNSGLATEVISDGAGGSKWMFVGRNKAGQVWSDITGNRT

GTVTINADGWGNFSVNGGSVSIWVNK

The mature form of the Amy707 polypeptide produced from the pHPLT-Amy707 vector is shown, below, as SEQ ID NO: 3.

HEINGTNGTMMQYFEWYLPNDGNHWNRLNSDASNLKSKGITAVWIPPAW

KGASQNDVGYGAYDLYDLGEFNQKGTVRTKYGTRSQLQAAVTSLKNNGI

QVYGDVVMNHKGGADATEMVRAVEVNPNNRNQEVTGEYTIEAWTRFDFP

GRGNTHSSFKWRWYHFDGVDWDQSRRLNNRIYKFRGHGKAWDWEVDTEN

GNYDYLMYADIDMDHPEVVNELRNWGVWYTNTLGLDGFRIDAVKHIKYS

FTRDWINHVRSATGKNMFAVAEFWKNDLGAIENYLQKTNWNHSVFDVPL

HYNLYNASKSGGNYDWIRNIFNGTVVQRHPSHAVTFVDNHDSQPEEALE

SFVEEWFKPLAYALTLTREQGYPSVFYGDYYGIPTHGVPAMRSKIDPIL

EARQKYYGKQNDYLDHHNIIGWTREGNTAHPNSGLATIMSDGAGGSKWM

FVGRNKAGQVWSDITGNRTGTVTINADGWGNFSVNGGSVSIWVNK

To express Amy707, the Amy707 DNA fragment was cloned into the pHPLT vector (Solingen et al. (2001) Extremophiles 5:333-341) by GENEART and fused in-frame to the AmyL (LAT) signal peptide using the unique PstI and HpaI restriction sites, resulting in plasmid pHPLT-Amy707. The pHPLT expression vector contains the *B. licheniformis* LAT promoter (Plat) and additional elements from pUB110 (McKenzie et al. (1986) Plasmid, 15: 93-103) including a replicase gene (reppUB), a neomycin/kanamycin resistance gene (neo) and a bleomycin resistance marker (bleo). A map of the pHPLT vector containing the Amy707 gene (pHPLT-Amy707) is shown in FIG. 2.

A suitable *B. subtilis* strain was transformed with pHPLT-Amy707 plasmid DNA using a method known in the art (WO 02/14490). The *B. subtilis* transformants were selected on agar plates containing heart infusion agar (Difco, Catalog No. 244400) and 10 mg/L neomycin sulfate (Sigma, Catalog No. N-1876; contains 732 μg neomycin per mg). Selective growth of *B. subtilis* transformants harboring the pHPLT-Amy707 plasmid was performed in shake flasks containing MBD medium (a MOPS based defined medium), 5 mM CaCl$_2$) and 10 mg/L neomycin. Growth resulted in the production of secreted Amy707 amylase with starch hydrolyzing activity.

Example 3: Generation and Evaluation of a 24-Site Amy707 Site Evaluation Libraries A. Generation of the Library Site evaluation libraries (SELs) were created by GENEART using a proprietary process (WO 2004/059556A3), and using methods and devices for optimizing a nucleotide sequence for the purpose of expression of a protein by PCR, and the manufacture of DNA molecules utilized technology owned by or licensed to GENEART (European Patent Nos. 0 200 362 and 0 201 184; and U.S. Pat. Nos. 4,683,195, 4,683,202 and 6,472,184). The construction of Amy707 SELs described in this example was performed by GENEART using their technology platform for gene optimization, gene synthesis and library generation under proprietary GENEART know how and/or intellectual property. The sequential permutation approach of GENEART, to produce SELs, is described in general on the company's web site.

The pHPLT-Amy707 plasmid DNA served as template to produce SELs at pre-selected sites in the mature region (SEQ ID NO: 3) shown on Table 3.1. GENEART was commissioned to create the SELs at those positions using their standard protocols. The corresponding codons for each site were each substituted with codons for at least 16 (out of a possible 19) different amino acids. The codon-mutagenized pHPLT-Amy707 mixes were used to transform competent *B. subtilis* cells as known in the art (WO 2002/014490) to generate the Amy707 SELs. Transformation mixes were plated on HI-agar plates (Heart Infusion agar) containing 10 mg/L neomycin sulfate. For each library, single bacterial colonies were picked and grown in TSB (tryptone and soy-based broth) liquid medium with 10 mg/ml neomycin selection for subsequent DNA isolation and gene sequence analysis. Sequence analysis data revealed a maximum of 19 Amy707 mature variants per library. To generate Amy707 and variant enzyme samples for biochemical characterization, selective growth of the variants was performed in 96 well MTPs at 37° C. for 68 hours in MBD medium. A total of 402 out of the 456 possible variants were obtained for the 24 positions mutagenized.

TABLE 3.1

Amy707 Site Evaluation Library Positions.

| H001 | S083 | N125 | N128 | V131 | Y160 | K179 |
| H183 | G184 | A186 | E190 | S244 | Q280 | N306 |
| R320 | H321 | P380 | H408 | A434 | I454 | N475 |
| G476 | G477 | N484 | | | | |

B. Identification of Combinable and Productive Mutations

Performance index (PI) values were determined for all the Amy707 amylase variants tested using the assays described in Example 1: α-amylase activity, CS-28 microswatch assay (at both pH8 and pH10), detergent stability, thermostability assays, and protein determination.

Productive positions are described as those positions within a molecule that are most useful for making combinatorial variants exhibiting an improved characteristic, where the position itself allows for at least one combinable mutation. Combinable mutations are mutations at any amino acid position that can be used to make combinatorial variants. Combinable mutations improve at least one desired property of the molecule, while not significantly decreasing either expression, activity, or stability. Combinable mutations can be grouped as follows:

Group A: A mutation that produces a variant wherein the minimum performance indices (PI) relative to a defined parental protein for: (i) protein expression, (ii) activity, (iii) CS-28 microswatch activity at pH 8 (16° C., 32° C., or 50° C.) or pH10 (16° C. or 50° C.), and (iv) detergent stability or thermostability are greater than or equal to 0.9, and in addition have a PI for any one of these tests that is greater than or equal to 1.0.

Group B: A mutation that produces a variant wherein the minimum performance indices (PI) relative to a defined parental protein for: (i) protein expression, (ii) activity, (iii) CS-28 microswatch activity at pH 8 (16° C., 32° C., or 50° C.) or pH10 (16° C. or 50° C.), and (iv) detergent stability or thermostability are greater than or equal to 0.8, and in in addition have a PI for any one of these tests that is greater than or equal to 1.2.

Group C: A mutation that produces a variant wherein the minimum performance indices (PI) relative to a defined parental protein for: (i) protein expression, (ii) activity, (iii) CS-28 microswatch activity at pH 8 (16° C., 32° C., or 50° C.) or pH10 (16° C. or 50° C.), and (iv) detergent stability or thermostability are greater than or equal to 0.5, and in in addition have a PI for any one of these tests that is greater than or equal to 1.5.

The properties of combinable mutations are summarized in the following Table.

TABLE 3.2

Properties for each group of combinable mutations

| | Performance Index (PI) | | | | |
|---|---|---|---|---|---|
| Group | Expression | Cleaning (pH 6 or 8) | Synthetic substrate activity | Stability (detergent or thermal) | Minimum PI in one or more tests |
| A | ≥0.9 | ≥0.9 | ≥0.9 | ≥0.9 | X ≥ 1.0 |
| B | ≥0.8 | ≥0.8 | ≥0.8 | ≥0.8 | X ≥ 1.2 |
| C | ≥0.5 | ≥0.5 | ≥0.5 | ≥0.5 | X ≥ 1.5 |

Preferred combinable mutations are at "productive positions," as described, below. In the case of the present α-amylases, "activity" refers to α-amylase activity, which can be measured as described, herein.

Productive positions are amino acid positions that are tolerant to substitution with different amino acid residues, wherein the resulting variants meet a set of performance criteria for combinability, as set forth above. Productive positions can be assigned a Productivity Score as follows: Positions where less than 15% of the substitutions at a given position fall within groups A, B, or C are given a Productivity Score of "1". Positions where less than 40%, but greater than, or equal to 15% of the substitutions at a given position fall within groups A, B, or C are given a Productivity Score of "2". Positions where less than 75%, but greater than, or equal to 40% of the substitutions at a given position fall within groups A, B, or C are given a Productivity Score of "3". Positions where 75% or more of the substitutions at a given position fall within groups A, B, or C are given a Productivity Score of "4". Preferred productive positions are combinable mutations.

Suitability score refers to the ability of one or more combinable mutations to be used to make combinatorial variants, based on the performance criteria for combinability, (i.e., A, B, and C, as set forth, above) in which each of the mutations fall. A higher suitability score indicates a mutation or mutations that are more suitable for use in making combinatorial variants. Suitability scores are described in the following Table.

TABLE 3.3

Definitions of suitability scores

| Substitutions Occur in Group(s) | Suitability Score |
|---|---|
| A, B and C | +++++ |
| A and B | ++++ |
| A or (B and C) | +++ |
| B | ++ |
| C | + |

Table 3.4 shows the Productivity Score (4, 3, or 2) calculated for each position in the Amy707 protein. No positions were calculated to have a productivity score of 1. For each Amy707 position, variants are listed according to the suitability score they received (+, ++, +++, ++++, or +++++). Position numbering is based on the mature Amy707 protein listed in SEQ ID NO: 3.

TABLE 3.4

Productivity Score for each position in the Amy707 protein.

| POS | Productivity score | VARIANTS SUITABILITY SCORE | | | | |
|---|---|---|---|---|---|---|
| | | (+) | (++) | (+++)* | (++++) | (+++++) |
| 1 | 3 | | | HILTFWQ | ACK | RM |
| 83 | 3 | | A | SCTNG | IRK | |
| 125 | 4 | | RTY | NLMVGH | ISFW | C |
| 128 | 2 | EY | D | NL | | C |
| 131 | 2 | RKS | | VCT | | |
| 160 | 4 | L | | YIG | ARKSHQ | CDEN |
| 179 | 3 | LEVNW | | KICM | Q | G |
| 183 | 4 | | T | HGLF | RCSDEMVNWYQ | AP |
| 184 | 3 | I | ALQ | G | CN | DE |
| 186 | 2 | | R | ADSG | EMN | |
| 244 | 2 | | | STN | KDEHQ | |
| 280 | 2 | | CT | QDE | IKN | |
| 306 | 3 | | | NIKDTEVG | AR | |
| 320 | 3 | | HQ | RDEN | AST | K |
| 321 | 2 | MV | | HFY | | |
| 380 | 3 | | | PDTEGHQ | C | KS |
| 408 | 3 | | | HIMNPQ | RSTEG | K |
| 434 | 4 | L | | AIRDEMGPHQ | CKSTVN | |
| 454 | 2 | | M | ICSV | | |
| 475 | 2 | | | NRCSD | | |
| 476 | 2 | | | GRNHQ | CDE | |
| 477 | 2 | T | A | GKDNQ | | R |
| 484 | 3 | W | DG | NTQ | ARS | |

*The first listed amino acid residue is the wild-type residue.

Example 4: Generation and Evaluation of a Full Amy707 Site Evaluation Libraries

A. Generation of the Libraries

Site evaluation libraries (SELs) were created by GENEART using a proprietary process (WO 2004/059556A3), and using methods and devices for optimizing a nucleotide sequence for the purpose of expression of a protein by PCR, and the manufacture of DNA molecules utilized technology owned by or licensed to GENEART (European Patent Nos. 0 200 362 and 0 201 184; and U.S. Pat. Nos. 4,683,195, 4,683,202 and 6,472,184). The construction of Amy707 SELs described in this example was performed by GENEART using their technology platform for gene optimization, gene synthesis and library generation under proprietary GENEART know how and/or intellectual property. The sequential permutation approach of GENEART, to produce SELs, is described in general on the company's web site.

The pHPLT-Amy707 plasmid DNA served as template to produce SELs at all sites in the mature region (SEQ ID NO: 3). GENEART was commissioned to create the SELs at these positions using their standard protocols. The corresponding codons for each site were each substituted with codons for at least 16 (out of a possible 19) different amino acids. The codon-mutagenized pHPLT-Amy707 mixes were used to transform competent B. subtilis cells as known in the art (WO 2002/014490) to generate the Amy707 SELs. Transformation mixes were plated on HI-agar plates (Heart Infusion agar) containing 10 mg/L neomycin sulfate. For each library, single bacterial colonies were picked and grown in TSB (tryptone and soy-based broth) liquid medium with 10 mg/ml neomycin selection for subsequent DNA isolation and gene sequence analysis. Sequence analysis data revealed a maximum of 19 Amy707 mature variants per library. To generate Amy707 and variant enzyme samples for biochemical characterization, selective growth of the variants was performed in 96 well MTPs at 37° C. for 68 hours in MBD medium.

B. Identification of Combinable and Productive Mutations

Performance index (PI) values were determined for all the Amy707 amylase variants tested using the assays described in Example 1: α-amylase activity, CS-28 microswatch assay (at both pH8 and pH10), detergent stability, thermostability assays, and protein determination.

Productive positions are described as those positions within a molecule that are most useful for making combinatorial variants exhibiting an improved characteristic, where the position itself allows for at least one combinable mutation. Combinable mutations are mutations at any amino acid position that can be used to make combinatorial variants. Combinable mutations improve at least one desired property of the molecule, while not significantly decreasing either expression, activity, or stability. Combinable mutations can be grouped as follows:

Group A: A mutation that produces a variant wherein the minimum performance indices (PI) relative to a defined parental protein for: (i) protein expression, (ii) activity, (iii) CS-28 microswatch activity at pH 8 (16° C., 32° C., or 50° C.) or pH10 (16° C. or 50° C.), and (iv) detergent stability are greater than or equal to 0.9, and in addition have a PI for any one of these tests that is greater than or equal to 1.0.

Group B: A mutation that produces a variant wherein the minimum performance indices (PI) relative to a defined parental protein for: (i) protein expression, (ii) activity, (iii) CS-28 microswatch activity at pH 8 (16° C., 32° C., or 50° C.) or pH10 (16° C. or 50° C.), and (iv) detergent stability are greater than or equal to 0.8, and in in addition have a PI for any one of these tests that is greater than or equal to 1.2.

Group C: A mutation that produces a variant wherein the minimum performance indices (PI) relative to a defined parental protein for: (i) protein expression, (ii) activity, (iii) CS-28 microswatch activity at pH 8 (16° C., 32° C., or 50° C.) or pH10 (16° C. or 50° C.), and (iv) detergent stability are greater than or equal to 0.5, and in in addition have a PI for any one of these tests that is greater than or equal to 1.5.

The properties of combinable mutations are summarized in the following Table.

TABLE 4.1

Properties for each group of combinable mutations

| | | Performance Index (PI) | | | |
|---|---|---|---|---|---|
| Group | Expression | Cleaning (pH 8 or 10) | Synthetic substrate activity | Detergent Stability | Minimum PI in one or more tests |
| A | ≥0.9 | ≥0.9 | ≥0.9 | ≥0.9 | X ≥ 1.0 |
| B | ≥0.8 | ≥0.8 | ≥0.8 | ≥0.8 | X ≥ 1.2 |
| C | ≥0.5 | ≥0.5 | ≥0.5 | ≥0.5 | X ≥ 1.5 |

Preferred combinable mutations are at "productive positions," as described, below. In the case of the present α-amylases, "activity" refers to α-amylase activity, which can be measured as described, herein.

Productive positions are amino acid positions that are tolerant to substitution with different amino acid residues, wherein the resulting variants meet a set of performance criteria for combinability, as set forth above. Productive positions can be assigned a Productivity Score as follows: Positions where less than 15% of the substitutions at a given position fall within groups A, B, or C are given a Productivity Score of "1". Positions where less than 30%, but greater than, or equal to 15% of the substitutions at a given position fall within groups A, B, or C are given a Productivity Score of "2". Positions where less than 50%, but greater than, or equal to 30% of the substitutions at a given position fall within groups A, B, or C are given a Productivity Score of "3". Positions where 50% or more of the substitutions at a given position fall within groups A, B, or C are given a Productivity Score of "4". Preferred productive positions are combinable mutations.

Suitability score refers to the ability of one or more combinable mutations to be used to make combinatorial variants, based on the performance criteria for combinability, (i.e., A, B, and C, as set forth, above) in which each of the mutations fall. A higher suitability score indicates a mutation or mutations that are more suitable for use in making combinatorial variants. Suitability scores are described in the following Table.

TABLE 4.2

Definitions of suitability scores

| Substitutions Occur in Group(s) | Suitability Score |
|---|---|
| A, B and C | +++++ |
| A and B | ++++ |
| A or (B and C) | +++ |
| B | ++ |
| C | + |

Table 4.3 shows the Productivity Score (Prod. Score, 4, 3, 2, or 1) calculated for each position in the Amy707 protein. For each Amy707 position, variants are listed according to the suitability score they received (+, ++, +++, ++++, or +++++). Position numbering is based on the mature Amy707 protein listed in SEQ ID NO: 3.

TABLE 4.3

Productivity Score for each position in the Amy707 protein

| POS | Prod. Score | (+) | (++) | (+++) * | (++++) | (+++++) |
|---|---|---|---|---|---|---|
| 1 | 4 | E | C | HFKNQRT | AILMW | |
| 2 | 4 | | A | HCDEFGIKNPQSW | LM | |
| 3 | 4 | | | NCDFKLQSTV | AEM | |
| 4 | 4 | | DKM | GFHPSTW | EIL | |
| 5 | 4 | | CN | THIQSVW | DGM | A |
| 6 | 3 | EGQT | | NS | | A |
| 7 | 4 | A | DILTY | GMS | HPQRV | |
| 10 | 1 | IL | | M | | |
| 12 | 1 | | | Y | A | |
| 16 | 3 | HT | | YAENW | D | |
| 17 | 3 | D | V | LS | AGT | |
| 18 | 1 | AE | | P | | |
| 19 | 1 | L | | N | | D |
| 20 | 3 | | EHI | DS | GNY | AC |
| 22 | 4 | GMV | I | NELQSTW | | R |
| 23 | 2 | | | HQ | FMT | |
| 25 | 4 | | M | NSTV | ACGKY | |
| 26 | 2 | | | RKQT | | |
| 27 | 2 | | A | LIV | | |
| 28 | 4 | | | NADQWY | CEGHKR | |
| 29 | 4 | | | SCDEFHKMRTVWY | AN | |
| 30 | 2 | | | DEMNQR | | |
| 31 | 1 | | | AS | | |
| 32 | 4 | | CDEG | SN | MWY | ILQR |
| 33 | 4 | | | NHIKQTVWY | CDMR | |
| 34 | 1 | | | LFM | | |
| 35 | 4 | | CEFIL | KMNQ | AGH | |
| 36 | 2 | | | SDGKQT | | |
| 40 | 1 | K | | T | N | |
| 41 | 3 | IKM | DQ | A | S | C |
| 47 | 2 | | GMP | AS | | |
| 50 | 2 | | | GC | | S |

TABLE 4.3-continued

Productivity Score for each position in the Amy707 protein

| POS | Prod. Score | VARIANTS SUITABILITY SCORE |||||
|---|---|---|---|---|---|---|
| | | (+) | (++) | (+++)* | (++++) | (+++++) |
| 52 | 2 | | L | ST | KM | R |
| 53 | 1 | | | Q | A | |
| 54 | 4 | | M | NADEFGQSVW | C | |
| 56 | 2 | | NS | V | E | |
| 61 | 1 | | | Y | F | |
| 63 | 2 | | NQ | LM | | |
| 64 | 1 | | | YH | | |
| 66 | 1 | | V | L | M | |
| 68 | 2 | | D | EA | Q | |
| 70 | 4 | | R | NEGHKV | CDFIMS | L |
| 72 | 1 | | | K | | R |
| 73 | 4 | D | EW | GQRT | KMSY | |
| 74 | 2 | | G | T | | S |
| 75 | 1 | | M | VI | | |
| 77 | 2 | A | S | TI | NV | |
| 81 | 3 | | | TACDFIKNPS | | |
| 82 | 3 | | Q | RACFSVY | IKM | |
| 83 | 2 | | M | SKNQRT | | |
| 84 | 3 | | CFL | QEN | DK | M |
| 86 | 4 | | H | QEIRTVWY | K | |
| 87 | 3 | | | ADKT | M | |
| 88 | 1 | | | A | M | |
| 89 | 2 | | | VAC | I | |
| 90 | 2 | | | TGMQRS | | |
| 91 | 3 | | M | SHKQRTV | AEN | |
| 93 | 1 | | H | KR | | |
| 94 | 4 | | | NFH | ACDGKLM | QR |
| 95 | 4 | G | D | NCFHIQRSTY | A | |
| 96 | 2 | DEN | | G | | |
| 97 | 1 | V | | I | | |
| 98 | 3 | | | QCDEGHKR | A | |
| 99 | 2 | | A | VC | I | |
| 100 | 2 | | | Y | CFI | |
| 101 | 1 | A | | G | | |
| 103 | 2 | F | I | VL | CT | A |

TABLE 4.3-continued

Productivity Score for each position in the Amy707 protein

| POS | Prod. Score | VARIANTS SUITABILITY SCORE ||||| 
| | | (+) | (++) | (+++)* | (++++) | (+++++) |
| --- | --- | --- | --- | --- | --- | --- |
| 110 | 2 | | PS | GA | | |
| 111 | 1 | S | | A | | |
| 112 | 1 | C | | D | E | |
| 113 | 4 | | IVY | A | CEFGHKMR | |
| 115 | 1 | | | E | Q | |
| 116 | 4 | | PV | MDIQ | ACEFGLNRW | T |
| 117 | 3 | L | | VEPS | R | T |
| 118 | 3 | | DLV | RW | EQT | G |
| 119 | 1 | | | AC | S | |
| 122 | 1 | | | VC | | |
| 123 | 2 | ACL | | N | | |
| 124 | 1 | NT | | P | | |
| 125 | 4 | | Y | NGHISTW | CFLMR | |
| 126 | 1 | | | N | D | |
| 128 | 2 | | E | N | LY | C |
| 129 | 1 | | V | Q | | |
| 132 | 1 | | | TS | | |
| 133 | 3 | | | GAHQST | DP | |
| 134 | 2 | | V | ES | DT | P |
| 135 | 2 | | Q | YFL | CM | |
| 136 | 4 | | FY | TCKLQR | DGMNP | |
| 138 | 2 | DLMN | | E | | |
| 139 | 2 | | CG | A | | |
| 140 | 1 | | | WF | Y | |
| 142 | 3 | | T | RS | CEFGHKY | |
| 144 | 3 | | | DEISY | KM | |
| 145 | 1 | | | FMY | | |
| 146 | 4 | ACDEFGHMRSWY | | P | | |
| 147 | 2 | | | GDIL | A | |
| 149 | 4 | | PW | GCDEFHKRV | AL | |
| 150 | 2 | L | HM | NPS | R | |
| 151 | 4 | | D | TEGHILMQV | | |
| 153 | 1 | | N | S | | |
| 154 | 2 | | LRY | S | | |
| 155 | 1 | | W | F | | |

TABLE 4.3-continued

Productivity Score for each position in the Amy707 protein

| POS | Prod. Score | VARIANTS SUITABILITY SCORE | | | | |
|---|---|---|---|---|---|---|
| | | (+) | (++) | (+++)* | (++++) | (+++++) |
| 156 | 2 | | AD | KS | | |
| 158 | 2 | | AL | RKQ | CN | |
| 160 | 4 | GILMP | F | YAC | HQS | DEKNR |
| 162 | 1 | M | | F | | |
| 165 | 1 | | | V | CT | |
| 167 | 1 | M | F | W | | |
| 168 | 1 | C | | D | | |
| 169 | 4 | FGIKWY | S | QCMN | | ADEHV |
| 170 | 2 | | | SC | AEK | |
| 171 | 2 | | | RT | MS | |
| 172 | 4 | | Y | RCEGHQ | AMS | |
| 173 | 4 | | DKN | L | ACFHWY | |
| 174 | 4 | | | NDGHILPSTV | | |
| 175 | 3 | | M | NRS | ADEL | |
| 176 | 1 | | KT | R | | |
| 178 | 1 | W | | Y | | |
| 179 | 2 | CL | | KM | Q | |
| 181 | 4 | ALNT | | REF | CIMQV | SY |
| 182 | 1 | C | | GD | | |
| 183 | 4 | | N | HCQVWY | DEFLMP | A |
| 184 | 2 | AEL | D | G | N | C |
| 186 | 2 | | | AG | EN | D |
| 195 | 2 | FY | | NW | L | |
| 196 | 1 | | | G | C | |
| 203 | 1 | | | Y | | N |
| 206 | 2 | NS | H | IM | C | T |
| 210 | 3 | ACEMNQRS | | H | | D |
| 211 | 4 | | L | P | CDMNQS | AFKV |
| 215 | 3 | FL | | NKM | DQ | |
| 216 | 3 | GLN | | EY | ACST | HQ |
| 217 | 1 | | M | L | | |
| 218 | 3 | ACEFHM | K | R | | |
| 219 | 3 | ACM | | NRT | D | |
| 221 | 1 | | IV | G | | |

TABLE 4.3-continued

Productivity Score for each position in the Amy707 protein

| | | VARIANTS SUITABILITY SCORE | | | | |
|---|---|---|---|---|---|---|
| POS | Prod. Score | (+) | (++) | (+++)* | (++++) | (+++++) |
| 222 | 4 | | EM | VDFGNY | AHILRST | |
| 225 | 2 | A | | TR | K | |
| 226 | 2 | Y | | NDE | AK | |
| 227 | 2 | | | TE | AK | |
| 228 | 1 | | | L | IM | |
| 229 | 2 | FV | C | G | | |
| 230 | 1 | | M | L | | |
| 231 | 2 | | | DE | GT | |
| 233 | 3 | L | CHMY | FAW | | |
| 235 | 2 | | | ILMV | | |
| 238 | 1 | I | | V | | |
| 243 | 1 | | | YF | | |
| 244 | 2 | | | S | N | DEHQ |
| 245 | 1 | E | M | F | | |
| 247 | 2 | | L | RT | AE | |
| 249 | 2 | M | FL | W | | |
| 250 | 2 | | | ILMV | | |
| 251 | 4 | | AH | NPTVY | CGW | KLQRS |
| 252 | 2 | | | HDEKN | | |
| 253 | 1 | | M | V | | |
| 257 | 2 | | | TMS | A | |
| 258 | 3 | IMV | PS | GDN | K | R |
| 259 | 3 | | DERT | KCP | AGHQ | |
| 260 | 2 | | | N | DP | KR |
| 261 | 3 | | G | MCI | AEQT | |
| 262 | 4 | ACDEG LQS | HKRY | FM | | |
| 263 | 1 | | | AS | | |
| 265 | 1 | | | AS | G | |
| 273 | 4 | | CK | GV | DEHLMPQS TY | |
| 276 | 1 | C | | ET | | |
| 280 | 2 | | MV | QDHK | N | |
| 283 | 1 | | | NG | D | |
| 285 | 2 | | | NEKST | M | |
| 286 | 3 | F | N | HLV | ACEM | T |
| 287 | 2 | ADNY | | S | | |
| 288 | 2 | L | C | V | IT | |

TABLE 4.3-continued

Productivity Score for each position in the Amy707 protein

| POS | Prod. Score | (+) | (++) | (+++)* | (++++) | (+++++) |
|---|---|---|---|---|---|---|
| 292 | 1 | LM | | P | | |
| 296 | 1 | | | NQ | | |
| 297 | 1 | | | L | | M |
| 298 | 2 | | | YFRW | | |
| 299 | 3 | | MY | NGHRST | | |
| 301 | 1 | | | SAG | | |
| 302 | 2 | | T | KCM | EQS | R |
| 303 | 4 | | | SEQR | ACDGLM | |
| 304 | 2 | | C | GKRSV | | |
| 306 | 2 | | | NG | AD | |
| 307 | 1 | | | YAF | | |
| 310 | 1 | | | RQS | | |
| 311 | 4 | | | NFT | DEGHKLMQRY | |
| 312 | 2 | | L | IV | M | |
| 313 | 1 | | MY | F | | |
| 314 | 4 | | M | NADEGHIKLSTVY | Q | |
| 317 | 1 | | L | V | | |
| 318 | 2 | | MS | VCI | LT | |
| 319 | 3 | Y | | QADEGHNR | | |
| 320 | 4 | | DY | RHNST | AEKMQ | |
| 321 | 1 | | | HWY | | |
| 322 | 1 | D | | P | | |
| 323 | 4 | A | P | SFHIL | CGRVY | DEMT |
| 324 | 2 | ACM | K | H | Y | |
| 326 | 3 | H | C | VNT | AM | |
| 327 | 1 | | | T | L | |
| 328 | 1 | | | FV | | |
| 329 | 1 | | | V | I | |
| 334 | 1 | T | | S | | |
| 337 | 3 | Y | A | ECDST | NQ | |
| 339 | 2 | GT | | A | S | |
| 341 | 2 | FGK | | EH | ADY | |
| 343 | 1 | | | FTY | | |
| 344 | 1 | | | VI | C | |
| 345 | 4 | | | EAGHKLMNQSTY | | |

TABLE 4.3-continued

Productivity Score for each position in the Amy707 protein

| POS | Prod. Score | (+) | (++) | (+++)* | (++++) | (+++++) |
|---|---|---|---|---|---|---|
| 346 | 4 | | | E | ACHKRTVY | DGMNQS |
| 347 | 1 | A | D | W | | |
| 350 | 1 | | | PE | | |
| 351 | 2 | | AC | LM | Q | |
| 352 | 1 | | | AS | | |
| 354 | 1 | | | AS | | |
| 355 | 2 | | | LIKMV | | |
| 356 | 2 | Q | CV | T | IL | |
| 357 | 2 | H | A | L | M | |
| 358 | 2 | AI | G | T | C | |
| 359 | 2 | I | W | RV | | |
| 360 | 4 | | | EACFHLNPQRTVY | K | |
| 361 | 4 | V | HT | QDSW | C | AEG |
| 363 | 3 | IW | V | YE | ADKNQ | M |
| 364 | 2 | CG | | P | | A |
| 365 | 2 | GV | | S | AN | |
| 366 | 2 | C | | V | IL | |
| 367 | 1 | | | FY | | |
| 368 | 2 | | GL | Y | MQ | |
| 369 | 1 | S | A | G | | |
| 372 | 3 | | R | YHIKM | QTV | |
| 374 | 2 | C | | IQ | NS | |
| 375 | 4 | | Q | PDGHIRTVY | AEKM | |
| 377 | 2 | | A | HKM | GT | |
| 378 | 2 | | L | GEHMN | | |
| 379 | 3 | | AL | VIQS | MNRY | |
| 380 | 2 | | | PDEGHKQS | | |
| 381 | 2 | | | AGNQRST | | |
| 382 | 1 | | K | M | | |
| 386 | 1 | | LV | I | | |
| 387 | 2 | EN | | DG | | |
| 388 | 4 | | FINS | PACFGKLQRTVY | D | |
| 389 | 3 | | F | IV | EGLMQS | |
| 390 | 1 | M | | LV | | |
| 391 | 4 | | S | ECHIW | AGKLNR | |

TABLE 4.3-continued

Productivity Score for each position in the Amy707 protein

| POS | Prod. Score | (+) | (++) | (+++)* | (++++) | (+++++) |
|---|---|---|---|---|---|---|
| 392 | 2 | | | ACG | | S |
| 394 | 3 | | EH | QCDGLRV | Y | |
| 395 | 4 | | V | KDEMST | AGQR | |
| 396 | 2 | | | YN | K | M |
| 397 | 1 | | | AG | | |
| 400 | 4 | | AI | KF | GHLMQTVW | |
| 401 | 1 | | | QH | M | |
| 402 | 3 | | V | NCIKLSY | | |
| 403 | 1 | | ET | D | | |
| 405 | 2 | A | | LCMNTV | | |
| 406 | 2 | ACL | Q | D | N | |
| 408 | 4 | | | HEGNQRST | KMP | |
| 410 | 1 | | N | I | | |
| 411 | 1 | | | I | V | |
| 412 | 1 | | | GAS | | |
| 413 | 2 | | | WFHIY | L | |
| 414 | 2 | | | TACV | S | |
| 415 | 2 | W | CY | R | | |
| 416 | 4 | | | EFHQRTVWY | ADGKLN | |
| 417 | 1 | A | | G | | |
| 418 | 4 | | I | NADKMQSTV | L | |
| 419 | 4 | | | TDEHKLNPQRW | MSY | |
| 420 | 4 | DFGHILMQRSTVW | | A | | |
| 421 | 4 | | V | HCI | DEKLMRWY | AN |
| 422 | 4 | A | | PGVY | CEFLMT | |
| 423 | 4 | | | NCDEFHILRST | | |
| 424 | 4 | N | EV | SCDG | AIQTW | |
| 425 | 1 | | | GA | | |
| 426 | 2 | | | L | ANS | |
| 427 | 1 | | | ACT | | |
| 428 | 1 | | | TNS | | |
| 429 | 1 | | | IM | | |
| 430 | 2 | | | MGIL | V | |

TABLE 4.3-continued

Productivity Score for each position in the Amy707 protein

| POS | Prod. Score | (+) | (++) | (+++)* | (++++) | (+++++) |
|---|---|---|---|---|---|---|
| 431 | 1 | AC | | S | | |
| 433 | 3 | M | C | GDEKNR | A | |
| 434 | 4 | | | ACDEFHIKNPQRSTV | M | |
| 435 | 4 | | ET | GKMQR | ACNP | |
| 436 | 2 | ACQ | D | GS | | |
| 437 | 3 | | C | SKNT | AD | |
| 438 | 2 | | CE | KS | H | |
| 439 | 2 | L | | WH | MQ | |
| 441 | 2 | | | FH | NY | |
| 442 | 1 | A | | VC | | |
| 444 | 2 | | AQ | RK | | |
| 445 | 3 | | C | NGKRT | AEQ | |
| 446 | 3 | T | Y | KCFS | AHMQ | |
| 448 | 1 | F | N | G | | |
| 450 | 3 | | AL | VEIQRST | | |
| 451 | 1 | | | WF | | |
| 452 | 4 | | H | SCEFQTW | AKNY | |
| 454 | 3 | F | CMS | IAV | L | |
| 457 | 2 | T | | NGHQR | | |
| 458 | 4 | L | D | RHSTVY | CEKMN | |
| 459 | 4 | ADEGH | CP | TL | NS | |
| 460 | 3 | KN | | GQ | EHS | |
| 461 | 4 | | F | TDV | ACEGKLNPQRY | |
| 463 | 2 | | L | TEKPQR | | |
| 465 | 2 | | Q | N | DG | |
| 466 | 4 | | | ADEGKNPQRS | | |
| 467 | 1 | | | D | E | |
| 469 | 1 | | Y | W | | |
| 471 | 3 | | | NHQRY | CDE | |
| 473 | 1 | | | SP | | |
| 474 | 1 | | | V | S | |
| 475 | 1 | | | NDE | | |
| 476 | 2 | | FIN | GDR | E | |
| 477 | 3 | PT | DK | GAR | NQ | |
| 478 | 1 | | A | SG | | |

TABLE 4.3-continued

Productivity Score for each position in the Amy707 protein

| | Prod. | | | VARIANTS SUITABILITY SCORE | | |
|---|---|---|---|---|---|---|
| POS | Score | (+) | (++) | (+++)* | (++++) | (+++++) |
| 479 | 1 | | | VT | | |
| 481 | 2 | | | I | LTV | |
| 482 | 1 | | | WY | | |
| 483 | 3 | | | VHMR | CGST | |
| 484 | 3 | | | NAEGHQRS | | |
| 485 | 3 | | MP | KHQST | | |

*The first listed amino acid residue is the wild-type residue.

The productive positions in Amy 707 that fall within the previously described Productivity Scores of "4" and the substitutions within those positions that are combinable are listed below. Position numbering is based on the mature Amy707 protein listed in SEQ ID NO: 3.
1(H,A,C,E,F,I,K,L,M,N,Q,R,T,W); 2(H,A,C,D,E,F,G,I,K,L,M,N,P,Q,S,W); 3(N,A,C,D,E,F,K,L,M,Q,S,T,V); 4(G,D,E,F,H,I,K,L,M,P,S,T,W); 5(T,A,C,D,G,H,I,M,N,Q,S,V,W); 7(G,A,D,H,I,L,M,P,Q,R,S,T,V,Y); 22(N,E,G,I,L,M,Q,R,S,T,V,W); 25(N,A,C,G,K,M,S,T,V,Y); 28(N,A,C,D,E,G,H,K,Q,R,W,Y); 29(S,A,C,D,E,F,H,K,M,N,R,T,V,W,Y); 32(S,C,D,E,G,I,L,M,N,Q,R,W,Y); 33(N,C,D,H,I,K,M,Q,R,T,V,W,Y); 35(K,A,C,E,F,G,H,I,L,M,N,Q); 54(N,A,C,D,E,F,G,M,Q,S,V,W); 70(N,C,D,E,F,G,H,I,K,L,M,R,S,V); 73(G,D,E,K,M,Q,R,S,T,W,Y); 86(Q,E,H,I,K,R,T,V,W,Y); 94(N,A,C,D,F,G,H,K,L,M,Q,R); 95(N,A,C,D,F,G,H,I,Q,R,S,T,Y); 113(A,C,E,F,G,H,I,K,M,R,V,Y); 116(M,A,C,D,E,F,G,I,L,N,P,Q,R,T,V,W); 125(N,C,F,G,H,I,L,M,R,S,T,W,Y); 136(T,C,D,F,G,K,L,M,N,P,Q,R,Y); 146(P,A,C,D,E,F,G,H,M,R,S,W,Y); 149(G,A,C,D,E,F,H,K,L,P,R,V,W); 151(T,D,E,G,H,I,L,M,Q,V); 160(Y,A,C,D,E,F,G,H,I,K,L,M,N,P,Q,R,S); 169(Q,A,C,D,E,F,G,H,I,K,M,N,S,V,W,Y); 172(R,A,C,E,G,H,M,Q,S,Y); 173(L,A,C,D,F,H,K,N,W,Y); 174(N,D,G,H,I,L,P,S,T,V); 181(R,A,C,E,F,I,L,M,N,Q,S,T,V,Y); 183(H,A,C,D,E,F,L,M,N,P,Q,V,W,Y); 211(P,A,C,D,F,K,L,M,N,Q,S,V); 222(V,A,D,E,F,G,H,I,L,M,N,R,S,T,Y); 251(N,A,C,G,H,K,L,P,Q,R,S,T,V,W,Y); 262(F,A,C,D,E,G,H,K,L,M,Q,R,S,Y); 273(G,C,D,E,H,K,L,M,P,Q,S,T,V,Y); 303(S,A,C,D,E,G,L,M,Q,R); 311(N,D,E,F,G,H,K,L,M,Q,R,T,Y); 314(N,A,D,E,G,H,I,K,L,M,Q,S,T,V,Y); 320(R,A,D,E,H,K,M,N,Q,S,T,Y); 323(S,A,C,D,E,F,G,H,I,L,M,P,R,T,V,Y); 345(E,A,G,H,K,L,M,N,Q,S,T,Y); 346(E,A,C,D,G,H,K,M,N,Q,R,S,T,V,Y); 360(E,A,C,F,H,K,L,N,P,Q,R,T,V,Y); 361(Q,A,C,D,E,G,H,S,T,V,W); 375(P,A,D,E,G,H,I,K,M,Q,R,T,V,Y); 388(P,A,C,D,F,G,H,K,L,N,Q,R,S,T,V,Y); 391(E,A,C,G,H,I,K,L,N,R,S,W); 395(K,A,D,E,G,M,Q,R,S,T,V); 400(K,A,F,G,H,I,L,M,Q,T,V,W); 408(H,E,G,K,M,N,P,Q,R,S,T); 416(E,A,D,F,G,H,K,L,N,Q,R,T,V,W,Y); 418(N,A,D,I,K,L,M,Q,S,T,V); 419(T,D,E,H,K,L,M,N,P,Q,R,S,W,Y); 420(A,D,F,G,H,I,L,M,Q,R,S,T,V,W); 421(H,A,C,D,E,I,K,L,M,N,R,V,W,Y); 422(P,A,C,E,F,G,L,M,T,V,Y); 423(N,C,D,E,F,H,I,L,R,S,T); 424(S,A,C,D,E,G,I,N,Q,T,V,W); 434(A,C,D,E,F,H,I,K,M,N,P,Q,R,S,T,V); 435(G,A,C,A,E,K,M,N,P,Q,R,T); 452(S,A,C,E,F,H,K,N,Q,T,W,Y); 458(R,C,D,E,H,K,L,M,N,S,T,V,Y); 459(T,A,C,D,E,G,H,L,N,P,S); 461(T,A,C,D,E,F,G,K,L,N,P,Q,R,V,Y); and 466(A,D,E,G,K,N,P,Q,R,S).

The productive positions in Amy 707 that fall within the previously described Productivity Scores of "3 and 4" and the substitutions within those positions that are combinable are listed below. Position numbering is based on the mature Amy707 protein listed in SEQ ID NO: 3.
1(H,A,C,E,F,I,K,L,M,N,Q,R,T,W); 2(H,A,C,D,E,F,G,I,K,L,M,N,P,Q,S,W); 3(N,A,C,D,E,F,K,L,M,Q,S,T,V); 4(G,D,E,F,H,I,K,L,M,P,S,T,W); 5(T,A,C,D,G,H,I,M,N,Q,S,V,W); 6(N,A,E,G,Q,S,T); 7(G,A,D,H,I,L,M,P,Q,R,S,T,V,Y); 16(Y,A,D,E,H,N,T,W); 17(L,A,D,G,S,T,V); 20(D,A,C,E,G,H,I,N,S,Y); 22(N,E,G,I,L,M,Q,R,S,T,V,W); 25(N,A,C,G,K,M,S,T,V,Y); 28(N,A,C,D,E,G,H,K,Q,R,W,Y); 29(S,A,C,D,E,F,H,K,M,N,R,T,V,W,Y); 32(S,C,D,E,G,I,L,M,N,Q,R,W,Y); 33(N,C,D,H,I,K,M,Q,R,T,V,W,Y); 35(K,A,C,E,F,G,H,I,L,M,N,Q); 41(A,C,D,I,K,M,Q,S); 54(N,A,C,D,E,F,G,M,Q,S,V,W); 70(N,C,D,E,F,G,H,I,K,L,M,R,S,V); 73(G,D,E,K,M,Q,R,S,T,W,Y); 81(T,A,C,D,F,I,K,N,P,S); 82(R,A,C,F,I,K,M,Q,S,V,Y); 84(Q,C,D,E,F,K,L,M,N); 86(Q,E,H,I,K,R,T,V,W,Y); 87(A,D,K,M,T); 91(S,A,E,H,K,M,N,Q,R,T,V); 94(N,A,C,D,F,G,H,K,L,M,Q,R); 95(N,A,C,D,F,G,H,I,Q,R,S,T,Y); 98(Q,A,C,D,E,G,H,K,R); 113(A,C,E,F,G,H,I,K,M,R,V,Y); 116(M,A,C,D,E,F,G,I,L,N,P,Q,R,T,V,W); 117(V,E,L,P,R,S,T); 118(R,D,E,G,L,Q,T,V,W); 125(N,C,F,G,H,I,L,M,R,S,T,W,Y); 133(G,A,D,H,P,Q,S,T); 136(T,C,D,F,G,K,L,M,N,P,Q,R,Y); 142(R,C,E,F,G,H,K,S,T,Y); 144(D,E,I,K,M,S,Y); 146(P,A,C,D,E,F,G,H,M,R,S,W,Y); 149(G,A,C,D,E,F,H,K,L,P,R,V,W); 151(T,D,E,G,H,I,L,M,Q,V); 160(Y,A,C,D,E,F,G,H,I,K,L,M,N,P,Q,R,S); 169(Q,A,C,D,E,F,G,H,I,K,M,N,S,V,W,Y); 172(R,A,C,E,G,H,M,Q,S,Y); 173(L,A,C,D,F,H,K,N,W,Y); 174(N,D,G,H,I,L,P,S,T,V); 175(N,A,D,E,L,M,R,S); 181(R,A,C,E,F,I,L,M,N,Q,S,T,V,Y); 183(H,A,C,D,E,F,L,M,N,P,Q,V,W,Y); 210(H,A,C,D,E,M,N,Q,R,S); 211(P,A,C,D,F,K,L,M,N,Q,S,V); 215(N,D,F,K,L,M,Q); 216(E,A,C,G,H,L,N,Q,S,T,Y); 218(R,A,C,E,F,H,K,M); 219(N,A,C,D,M,R,T); 222(V,A,D,E,F,G,H,I,L,M,N,R,S,T,Y); 233(F,A,C,H,L,M,W,Y); 251(N,A,C,G,H,K,L,P,Q,R,S,T,V,W,Y); 258(G,D,I,K,M,N,P,R,S,V); 259(K,A,C,D,E,G,H,P,Q,R,T); 261(M,A,C,E,G,I,Q,T); 262(F,A,C,D,E,G,H,K,L,M,Q,R,S,Y); 273(G,C,D,E,H,K,L,M,P,Q,S,T,V,Y); 286(H,A,C,E,F,L,M,N,T,V); 299(N,G,H,M,R,S,T,Y); 303(S,A,C,D,E,G,L,M,Q,R); 311(N,D,E,F,G,H,K,L,M,Q,R,T,Y); 314(N,A,D,E,G,H,I,K,L,M,Q,S,T,V,Y); 319(Q,A,D,E,G,H,N,R,Y); 320(R,A,D,E,H,K,M,N,Q,S,T,Y); 323(S,A,C,D,E,F,G,H,I,L,M,P,R,T,V,Y); 326(V,A,C,H,M,N,T); 337(E,A,C,D,N,Q,S,T,Y); 345(E,A,G,H,K,L,M,N,Q,S,T,Y); 346(E,A,C,D,G,H,K,M,N,Q,R,S,T,V,Y); 360(E,A,C,F,H,K,L,N,P,Q,R,T,V,Y); 361

(Q,A,C,D,E,G,H,S,T,V,W); 363(Y,A,D,E,I,K,M,N,Q,V,W); 372(Y,H,I,K,M,Q,R,T,V); 375(P,A,D,E,G,H,I,K,M,Q,R,T,V,Y); 379(V,A,I,L,M,N,Q,R,S,Y); 388(P,A,C,D,F,G,H,K,L,N,Q,R,S,T,V,Y); 389(I,E,F,G,L,M,Q,S,V); 391(E,A,C,G,H,I,K,L,N,R,S,W); 394(Q,C,D,E,G,H,L,R,V,Y); 395(K,A,D,E,G,M,Q,R,S,T,V); 400(K,A,F,G,H,I,L,M,Q,T,V,W); 402(N,C,I,K,L,S,V,Y); 408(H,E,G,K,M,N,P,Q,R,S,T); 416(E,A,D,F,G,H,K,L,N,Q,R,T,V,W,Y); 418(N,A,D,I,K,L,M,Q,S,T,V); 419(T,D,E,H,K,L,M,N,P,Q,R,S,W,Y); 420(A,D,F,G,H,I,L,M,Q,R,S,T,V,W); 421(H,A,C,D,E,I,K,L,M,N,R,V,W,Y); 422(P,A,C,E,F,G,L,M,T,V,Y); 423(N,C,D,E,F,H,I,L,R,S,T); 424(S,A,C,D,E,G,I,N,Q,T,V,W); 433(G,A,C,D,E,K,M,N,R); 434(A,C,D,E,F,H,I,K,M,N,P,Q,R,S,T,V); 435(G,A,C,E,K,M,N,P,Q,R,T); 437(S,A,C,D,K,N,T); 445(N,A,C,E,G,K,Q,R,T); 446(K,A,C,F,H,M,Q,S,T,Y); 450(V,A,E,I,L,Q,R,S,T); 452(S,A,C,E,F,H,K,N,Q,T,W,Y); 454(I,A,C,F,L,M,S,V); 458(R,C,D,E,H,K,L,M,N,S,T,V,Y); 459(T,A,C,D,E,G,H,L,N,P,S); 460(G,E,H,K,N,Q,S); 461(T,A,C,D,E,F,G,K,L,N,P,Q,R,V,Y); 466(A,D,E,G,K,N,P,Q,R,S); 471(N,C,D,E,H,Q,R,Y); 477(G,A,D,K,N,P,Q,R,T); 483(V,C,G,H,M,R,S,T); 484(N,A,E,G,H,Q,R,S); and 485(K,H,M,P,Q,S,T).

The productive positions in Amy 707 that fall within the previously described Productivity Scores of "2, 3 and 4" and the substitutions within those positions that are combinable are listed below. Position numbering is based on the mature Amy707 protein listed in SEQ ID NO: 3.

1(H,A,C,E,F,I,K,L,M,N,Q,R,T,W); 2(H,A,C,D,E,F,G,I,K,L,M,N,P,Q,S,W); 3(N,A,C,D,E,F,K,L,M,Q,S,T,V); 4(G,D,E,F,H,I,K,L,M,P,S,T,W); 5(T,A,C,D,G,H,I,M,N,Q,S,V,W); 6(N,A,E,G,Q,S,T); 7(G,A,D,H,I,L,M,P,Q,R,S,T,V,Y); 16(Y,A,D,E,H,N,T,W); 17(L,A,D,G,S,T,V); 20(D,A,C,E,G,H,I,N,S,Y); 22(N,E,G,I,L,M,Q,R,S,T,V,W); 23(H,F,M,Q,T); 25(N,A,C,G,K,M,S,T,V,Y); 26(R,K,Q,T); 27(L,A,I,V); 28(N,A,C,D,E,G,H,K,Q,R,W,Y); 29(S,A,C,D,E,F,H,K,M,N,R,T,V,W,Y); 30(D,E,M,N,Q,R); 32(S,C,D,E,G,I,L,M,N,Q,R,W,Y); 33(N,C,D,H,I,K,M,Q,R,T,V,W,Y); 35(K,A,C,E,F,G,H,I,L,M,N,Q); 36(S,D,G,K,Q,T); 41(A,C,D,I,K,M,Q,S); 47(A,G,M,P,S); 50(G,C,S); 52(S,K,L,M,R,T); 54(N,A,C,D,E,F,G,M,Q,S,V,W); 56(V,E,N,S); 63(L,M,N,Q); 68(E,A,D,Q); 70(N,C,D,E,F,G,H,I,K,L,M,R,S,V); 73(G,D,E,K,M,Q,R,S,T,W,Y); 74(T,G,S); 77(T,A,I,N,S,V); 81(T,A,C,D,F,I,K,N,P,S); 82(R,A,C,F,I,K,M,Q,S,V,Y); 83(S,K,M,N,Q,R,T); 84(Q,C,D,E,F,K,L,M,N); 86(Q,E,H,I,K,R,T,V,W,Y); 87(A,D,K,M,T); 89(V,A,C,I); 90(T,G,M,Q,R,S); 91(S,A,E,H,K,M,N,Q,R,T,V); 94(N,A,C,D,F,G,H,K,L,M,Q,R); 95(N,A,C,D,F,G,H,I,Q,R,S,T,Y); 96(G,D,E,N); 98(Q,A,C,D,E,G,H,K,R); 99(V,A,C,I); 100(Y,C,F,I); 103(V,A,C,F,I,L,T); 110(G,A,P,S); 113(A,C,E,F,G,H,I,K,M,R,V,Y); 116(M,A,C,D,E,F,G,I,L,N,P,Q,R,T,V,W); 117(V,E,L,P,R,S,T); 118(R,D,E,G,L,Q,T,V,W); 123(N,A,C,L); 125(N,C,F,G,H,I,L,M,R,S,T,W,Y); 128(N,C,E,L,Y); 133(G,A,D,H,P,Q,S,T); 134(E,D,P,S,T,V); 135(Y,C,F,L,M,Q); 136(T,C,D,F,G,K,L,M,N,P,Q,R,Y); 138(E,D,L,M,N); 139(A,C,G); 142(R,C,E,F,G,H,K,S,T,Y); 144(D,E,I,K,M,S,Y); 146(P,A,C,D,E,F,G,H,M,R,S,W,Y); 147(G,A,D,I,L); 149(G,A,C,D,E,F,H,K,L,P,R,V,W); 150(N,H,L,M,P,R,S); 151(T,D,E,G,H,I,L,M,Q,V); 154(S,L,R,Y); 156(K,A,D,S); 158(R,A,C,K,L,N,Q); 160(Y,A,C,D,E,F,G,H,I,K,L,M,N,P,Q,R,S); 169(Q,A,C,D,E,F,G,H,I,K,M,N,S,V,W,Y); 170(S,A,C,E,K); 171(R,M,S,T); 172(R,A,C,E,G,H,M,Q,S,Y); 173(L,A,C,D,F,H,K,N,W,Y); 174(N,D,G,H,I,L,P,S,T,V); 175(N,A,D,E,L,M,R,S); 179(K,C,L,M,Q); 181(R,A,C,E,F,I,L,M,N,Q,S,T,V,Y); 183(H,A,C,D,E,F,L,M,N,P,Q,V,W,Y); 184(G,A,C,D,E,L,N); 186(A,D,E,G,N); 195(N,F,L,W,Y); 206(I,C,H,M,N,S,T); 210(H,A,C,D,E,M,N,Q,R,S); 211(P,A,C,D,F,K,L,M,N,Q,S,V); 215(N,D,F,K,L,M,Q); 216(E,A,C,G,H,L,N,Q,S,T,Y); 218(R,A,C,E,F,H,K,M); 219(N,A,C,D,M,R,T); 222(V,A,D,E,F,G,H,I,L,M,N,R,S,T,Y); 225(T,A,K,R); 226(N,A,D,E,K,Y); 227(T,A,E,K); 229(G,C,F,V); 231(D,E,G,T); 233(F,A,C,H,L,M,W,Y); 235(I,L,M,V); 244(S,D,E,H,N,Q); 247(R,A,E,L,T); 249(W,F,L,M); 250(I,L,M,V); 251(N,A,C,G,H,K,L,P,Q,R,S,T,V,W,Y); 252(H,D,E,K,N); 257(T,A,M,S); 258(G,D,I,K,M,N,P,R,S,V); 259(K,A,C,D,E,G,H,P,Q,R,T); 260(N,D,K,P,R); 261(M,A,C,E,G,I,Q,T); 262(F,A,C,D,E,G,H,K,L,M,Q,R,S,Y); 273(G,C,D,E,H,K,L,M,P,Q,S,T,V,Y); 280(Q,D,H,K,M,N,V); 285(N,E,K,M,S,T); 286(H,A,C,E,F,L,M,N,T,V); 287(S,A,D,N,Y); 288(V,C,I,L,T); 298(Y,F,R,W); 299(N,G,H,M,R,S,T,Y); 302(K,C,E,M,Q,R,S,T); 303(S,A,C,D,E,G,L,M,Q,R); 304(G,C,K,R,S,V); 306(N,A,D,G); 311(N,D,E,F,G,H,K,L,M,Q,R,T,Y); 312(I,L,M,V); 314(N,A,D,E,G,H,I,K,L,M,Q,S,T,V,Y); 318(V,C,I,L,M,S,T); 319(Q,A,D,E,G,H,N,R,Y); 320(R,A,D,E,H,K,M,N,Q,S,T,Y); 323(S,A,C,D,E,F,G,H,I,L,M,P,R,T,V,Y); 324(H,A,C,K,M,Y); 326(V,A,C,H,M,N,T); 337(E,A,C,D,N,Q,S,T,Y); 339(A,G,S,T); 341(E,A,D,F,G,H,K,Y); 345(E,A,G,H,K,L,M,N,Q,S,T,Y); 346(E,A,C,D,G,H,K,M,N,Q,R,S,T,V,Y); 351(L,A,C,M,Q); 355(L,I,K,M,V); 356(T,C,I,L,Q,V); 357(L,A,H,M); 358(T,A,C,G,I, 359(R,I,V,W); 360(E,A,C,F,H,K,L,N,P,Q,R,T,V,Y); 361(Q,A,C,D,E,G,H,S,T,V,W); 363(Y,A,D,E,I,K,M,N,Q,V,W); 364(P,A,C,G); 365(S,A,G,N,V); 366(V,C,I,L); 368(Y,G,L,M,Q); 372(Y,H,I,K,M,Q,R,T,V); 374(I,C,N,Q,S); 375(P,A,D,E,G,H,I,K,M,Q,R,T,V,Y); 377(H,A,G,K,M,T); 378(G,E,H,L,M,N); 379(V,A,I,L,M,N,Q,R,S,Y); 380(P,D,E,G,H,K,Q,S); 381(A,G,N,Q,R,S,T); 387(D,E,G,N); 388(P,A,C,D,F,G,H,K,L,N,Q,R,S,T,V,Y); 389(I,E,F,G,L,M,Q,S,V); 391(E,A,C,G,H,I,K,L,N,R,S,W); 392(A,C,G,S); 394(Q,C,D,E,G,H,L,R,V,Y); 395(K,A,D,E,G,M,Q,R,S,T,V); 396(Y,K,M,N); 400(K,A,F,G,H,I,L,M,Q,T,V,W); 402(N,C,I,K,L,S,V,Y); 405(L,A,C,M,N,T,V); 406(D,A,C,L,N,Q); 408(H,E,G,K,M,N,P,Q,R,S,T); 413(W,F,H,I,L,Y); 414(T,A,C,S,V); 415(R,C,W,Y); 416(E,A,D,F,G,H,K,L,N,Q,R,T,V,W,Y); 418(N,A,D,I,K,L,M,Q,S,T,V); 419(T,D,E,H,K,L,M,N,P,Q,R,S,W,Y); 420(A,D,F,G,H,I,L,M,Q,R,S,T,V,W); 421(H,A,C,D,E,I,K,L,M,N,R,V,W,Y); 422(P,A,C,E,F,G,L,M,T,V,Y); 423(N,C,D,E,F,H,I,L,R,S,T); 424(S,A,C,D,E,G,I,N,Q,T,V,W); 426(L,A,N,S); 430(M,G,I,L,V); 433(G,A,C,D,E,K,M,N,R); 434(A,C,D,E,F,H,I,K,M,N,P,Q,R,S,T,V); 435(G,A,C,E,K,M,N,P,Q,R,T); 436(G,A,C,D,Q,S); 437(S,A,C,D,K,N,T); 438(K,C,E,H,S); 439(W,H,L,M,Q); 441(F,H,N,Y); 444(R,A,K,Q); 445(N,A,C,E,G,K,Q,R,T); 446(K,A,C,F,H,M,Q,S,T,Y); 450(V,A,E,I,L,Q,R,S,T); 452(S,A,C,E,F,H,K,N,Q,T,W,Y); 454(I,A,C,F,L,M,S,V); 457(N,G,H,Q,R,T); 458(R,C,D,E,H,K,L,M,N,S,T,V,Y); 459(T,A,C,D,E,G,H,L,N,P,S); 460(G,E,H,K,N,Q,S); 461(T,A,C,D,E,F,G,K,L,N,P,Q,R,V,Y); 463(T,E,K,L,P,Q,R); 465(N,D,G,Q); 466(A,D,E,G,K,N,P,Q,R,S); 471(N,C,D,E,H,Q,R,Y); 476(G,D,E,H,N,R); 477(G,A,D,K,N,P,Q,R,T); 481(I,L,T,V); 483(V,C,G,H,M,R,S,T); 484(N,A,E,G,H,Q,R,S); and 485(K,H,M,P,Q,S,T).

The productive positions in Amy 707 that fall within the previously described Productivity Scores of "1, 2, 3 and 4" and the substitutions within those positions that are combinable are listed below. Position numbering is based on the mature Amy707 protein listed in SEQ ID NO: 3.

1(H,A,C,E,F,I,K,L,M,N,Q,R,T,W); 2(H,A,C,D,E,F,G,I,K,L,M,N,P,Q,S,W); 3(N,A,C,D,E,F,K,L,M,Q,S,T,V); 4(G,D,E,F,H,I,K,L,M,P,S,T,W); 5(T,A,C,D,G,H,I,M,N,Q,S,V,W); 6(N,A,E,G,Q,S,T); 7(G,A,D,H,I,L,M,P,Q,R,S,T,V,Y); 10(M,I,L); 12(Y,A); 16(Y,A,D,E,H,N,T,W); 17(L,A,D,G,S,T,V); 18(P,A,E); 19(N,D,L); 20(D,A,C,E,G,H,I,N,S,Y); 22(N,E,G,I,L,M,Q,R,S,T,V,W); 23(H,F,M,Q,T); 25(N,A,C,G,K,M,S,T,V,Y); 26(R,K,Q,T); 27(L,A,I,V); 28(N,A,C,D,E,G,H,K,Q,R,W,Y); 29(S,A,C,D,E,F,H,K,M,N,R,T,V,W,Y); 30(D,E,M,N,Q,R); 31(A,S); 32(S,C,D,E,G,I,L,M,N,Q,R,W,Y); 33(N,C,D,H,I,K,M,Q,R,T,V,W,Y); 34(L,F,M); 35(K,A,

C,E,F,G,H,I,L,M,N,Q); 36(S,D,G,K,Q,T); 40(T,K,N); 41(A,C,D,I,K,M,Q,S); 47(A,G,M,P,S); 50(G,C,S); 52(S,K,L,M,R,T); 53(Q,A); 54(N,A,C,D,E,F,G,M,Q,S,V,W); 56(V,E,N,S); 61(Y,F); 63(L,M,N,Q); 64(Y,H); 66(L,M,V); 68(E,A,D,Q); 70(N,C,D,E,F,G,H,I,K,L,M,R,S,V); 72(K,R); 73(G,D,E,K,M,Q,R,S,T,W,Y); 74(T,G,S); 75(V,I,M); 77(T,A,I,N,S,V); 81(T,A,C,D,F,I,K,N,P,S); 82(R,A,C,F,I,K,M,Q,S,V,Y); 83(S,K,M,N,Q,R,T); 84(Q,C,D,E,F,K,L,M,N); 86(Q,E,H,I,K,R,T,V,W,Y); 87(A,D,K,M,T); 88(A,M); 89(V,A,C,I); 90(T,G,M,Q,R,S); 91(S,A,E,H,K,M,N,Q,R,T,V); 93(K,H,R); 94(N,A,C,D,F,G,H,K,L,M,Q,R); 95(N,A,C,D,F,G,H,I,Q,R,S,T,Y); 96(G,D,E,N); 97(I,V); 98(Q,A,C,D,E,G,H,K,R); 99(V,A,C,I); 100(Y,C,F,I); 101(G,A); 103(V,A,C,F,I,L,T); 110(G,A,P,S); 111(A,S); 112(D,C,E); 113(A,C,E,F,G,H,I,K,M,R,V,Y); 115(E,Q); 116(M,A,C,D,E,F,G,I,L,N,P,Q,R,T,V,W); 117(V,E,L,P,R,S,T); 118(R,D,E,G,L,Q,T,V,W); 119(A,C,S); 122(V,C); 123(N,A,C,L); 124(P,N,T); 125(N,C,F,G,H,I,L,M,R,S,T,W,Y); 126(N,D); 128(N,C,E,L,Y); 129(Q,V); 132(T,S); 133(G,A,D,H,P,Q,S,T); 134(E,D,P,S,T,V); 135(Y,C,F,L,M,Q); 136(T,C,D,F,G,K,L,M,N,P,Q,R,Y); 138(E,D,L,M,N); 139(A,C,G); 140(W,F,Y); 142(R,C,E,F,G,H,K,S,T,Y); 144(D,E,I,K,M,S,Y); 145(F,M,Y); 146(P,A,C,D,E,F,G,H,M,R,S,W,Y); 147(G,A,D,I,L); 149(G,A,C,D,E,F,H,K,L,P,R,V,W); 150(N,H,L,M,P,R,S); 151(T,D,E,G,H,I,L,M,Q,V); 153(S,N); 154(S,L,R,Y); 155(F,W); 156(K,A,D,S); 158(R,A,C,K,L,N,Q); 160(Y,A,C,D,E,F,G,H,I,K,L,M,N,P,Q,R,S); 162(F,M); 165(V,C,T); 167(W,F,M); 168(D,C); 169(Q,A,C,D,E,F,G,H,I,K,M,N,S,V,W,Y); 170(S,A,C,E,K); 171(R,M,S,T); 172(R,A,C,E,G,H,M,Q,S,Y); 173(L,A,C,D,F,H,K,N,W,Y); 174(N,D,G,H,I,L,P,S,T,V); 175(N,A,D,E,L,M,R,S); 176(R,K,T); 178(Y,W); 179(K,C,L,M,Q); 181(R,A,C,E,F,I,L,M,N,Q,S,T,V,Y); 182(G,C,D); 183(H,A,C,D,E,F,L,M,N,P,Q,V,W,Y); 184(G,A,C,D,E,L,N); 186(A,D,E,G,N); 195(N,F,L,W,Y); 196(G,C); 203(Y,N); 206(I,C,H,M,N,S,T); 210(H,A,C,D,E,M,N,Q,R,S); 211(P,A,C,D,F,K,L,M,N,Q,S,V); 215(N,D,F,K,L,M,Q); 216(E,A,C,G,H,L,N,Q,S,T,Y); 217(L,M); 218(R,A,C,E,F,H,K,M); 219(N,A,C,D,M,R,T); 221(G,I,V); 222(V,A,D,E,F,G,H,I,L,M,N,R,S,T,Y); 225(T,A,K,R); 226(N,A,D,E,K,Y); 227(T,A,E,K); 228(L,I,M); 229(G,C,F,V); 230(L,M); 231(D,E,G,T); 233(F,A,C,H,L,M,W,Y); 235(I,L,M,V); 238(V,I); 243(Y,F); 244(S,D,E,H,N,Q); 245(F,E,M); 247(R,A,E,L,T); 249(W,F,L,M); 250(I,L,M,V); 251(N,A,C,G,H,K,L,P,Q,R,S,T,V,W,Y); 252(H,D,E,K,N); 253(V,M); 257(T,A,M,S); 258(G,D,I,K,M,N,P,R,S,V); 259(K,A,C,D,E,G,H,P,Q,R,T); 260(N,D,K,P,R); 261(M,A,C,E,G,I,Q,T); 262(F,A,C,D,E,G,H,K,L,M,Q,R,S,Y); 263(A,S); 265(A,G,S); 273(G,C,D,E,H,K,L,M,P,Q,S,T,V,Y); 276(E,C,T); 280(Q,D,H,K,M,N,V); 283(N,D,G); 285(N,E,K,M,S,T); 286(H,A,C,E,F,L,M,N,T,V); 287(S,A,D,N,Y); 288(V,C,I,L,T); 292(P,L,M); 296(N,Q); 297(L,M); 298(Y,F,R,W); 299(N,G,H,M,R,S,T,Y); 301(S,A,G); 302(K,C,E,M,Q,R,S,T); 303(S,A,C,D,E,G,L,M,Q,R); 304(G,C,K,R,S,V); 306(N,A,D,G); 307(Y,A,F); 310(R,Q,S); 311(N,D,E,F,G,H,K,L,M,Q,R,T,Y); 312(I,L,M,V); 313(F,M,Y); 314(N,A,D,E,G,H,I,K,L,M,Q,S,T,V,Y); 317(V,L); 318(V,C,I,L,M,S,T); 319(Q,A,D,E,G,H,N,R,Y); 320(R,A,D,E,H,K,M,N,Q,S,T,Y); 321(H,W,Y); 322(P,D); 323(S,A,C,D,E,F,G,H,I,L,M,P,R,T,V,Y); 324(H,A,C,K,M,Y); 326(V,A,C,H,M,N,T); 327(T,L); 328(F,V); 329(V,I); 334(S,T); 337(E,A,C,D,N,Q,S,T,Y); 339(A,G,S,T); 341(E,A,D,F,G,H,K,Y); 343(F,T,Y); 344(V,C,I); 345(E,A,G,H,K,L,M,N,Q,S,T,Y); 346(E,A,C,D,G,H,K,M,N,Q,R,S,T,V,Y); 347(W,A,D); 350(P,E); 351(L,A,C,M,Q); 352(A,S); 354(A,S); 355(L,I,K,M,V); 356(T,C,I,L,Q,V); 357(L,A,H,M); 358(T,A,C,G,I); 359(R,I,V,W); 360(E,A,C,F,H,K,L,N,P,Q,R,T,V,Y); 361(Q,A,C,D,E,G,H,S,T,V,W); 363(Y,A,D,E,I,K,M,N,Q,V,W); 364(P,A,C,G); 365(S,A,G,N,V); 366(V,C,I,L); 367(F,Y); 368(Y,G,L,M,Q); 369(G,A,S); 372(Y,H,I,K,M,Q,R,T,V); 374(I,C,N,Q,S); 375(P,A,D,E,G,H,I,K,M,Q,R,T,V,Y); 377(H,A,G,K,M,T); 378(G,E,H,L,M,N); 379(V,A,I,L,M,N,Q,R,S,Y); 380(P,D,E,G,H,K,Q,S); 381(A,G,N,Q,R,S,T); 382(M,K); 386(I,L,V); 387(D,E,G,N); 388(P,A,C,D,F,G,H,K,L,N,Q,R,S,T,V,Y); 389(I,E,F,G,L,M,Q,S,V); 390(L,M,V); 391(E,A,C,G,H,I,K,L,N,R,S,W); 392(A,C,G,S); 394(Q,C,D,E,G,H,L,R,V,Y); 395(K,A,D,E,G,M,Q,R,S,T,V); 396(Y,K,M,N); 397(A,G); 400(K,A,F,G,H,I,L,M,Q,T,V,W); 401(Q,H,M); 402(N,C,I,K,L,S,V,Y); 403(D,E,T); 405(L,A,C,M,N,T,V); 406(D,A,C,L,N,Q); 408(H,E,G,K,M,N,P,Q,R,S,T); 410(I,N); 411(I,V); 412(G,A,S); 413(W,F,H,I,L,Y); 414(T,A,C,S,V); 415(R,C,W,Y); 416(E,A,D,F,G,H,K,L,N,Q,R,T,V,W,Y); 417(G,A); 418(N,A,D,I,K,L,M,Q,S,T,V); 419(T,D,E,H,K,L,M,N,P,Q,R,S,W,Y); 420(A,D,F,G,H,I,L,M,Q,R,S,T,V,W); 421(H,A,C,D,E,I,K,L,M,N,R,V,W,Y); 422(P,A,C,E,F,G,L,M,T,V,Y); 423(N,C,D,E,F,H,I,L,R,S,T); 424(S,A,C,D,E,G,I,N,Q,T,V,W); 425(G,A); 426(L,A,N,S); 427(A,C,T); 428(T,N,S); 429(I,M); 430(M,G,I,L,V); 431(S,A,C); 433(G,A,C,D,E,K,M,N,R); 434(A,C,D,E,F,H,I,K,M,N,P,Q,R,S,T,V); 435(G,A,C,E,K,M,N,P,Q,R,T); 436(G,A,C,D,Q,S); 437(S,A,C,D,K,N,T); 438(K,C,E,H,S); 439(W,H,L,M,Q); 441(F,H,N,Y); 442(V,A,C); 444(R,A,K,Q); 445(N,A,C,E,G,K,Q,R,T); 446(K,A,C,F,H,M,Q,S,T,Y); 448(G,F,N); 450(V,A,E,I,L,Q,R,S,T); 451(W,F); 452(S,A,C,E,F,H,K,N,Q,T,W,Y); 454(I,A,C,F,L,M,S,V); 457(N,G,H,Q,R,T); 458(R,C,D,E,H,K,L,M,N,S,T,V,Y); 459(T,A,C,D,E,G,H,L,N,P,S); 460(G,E,H,K,N,Q,S); 461(T,A,C,D,E,F,G,K,L,N,P,Q,R,V,Y); 463(T,E,K,L,P,Q,R); 465(N,D,G,Q); 466(A,D,E,G,K,N,P,Q,R,S); 467(D,E); 469(W,Y); 471(N,C,D,E,H,Q,R,Y); 473(S,P); 474(V,S); 475(N,D,E); 476(G,D,E,H,N,R); 477(G,A,D,K,N,P,Q,R,T); 478(S,A,G); 479(V,T); 481(I,L,T,V); 482(W,Y); 483(V,C,G,H,M,R,S,T); 484(N,A,E,G,H,Q,R,S); and 485(K,H,M,P,Q,S,T).

What is claimed is:

1. A variant α-amylase polypeptide derived from a parental α-amylase polypeptide, comprising at least two combinable mutations at productive amino acid positions; wherein the mutations are at position H1 and E391, wherein the variant has at least 90% amino acid sequence identity with SEQ ID NO: 3.

2. The variant amylase of claim 1, wherein the mutations are H1A and E391A.

3. The variant amylase of claim 1, further comprising a plurality of combinable mutations.

4. The variant amylase of claim 1, further comprising a deletion corresponding to one or more residue selected from the group consisting of Arg-181, Gly-182, His-183, and Gly-184, using SEQ ID NO: 3 for numbering.

5. The variant amylase of claim 1, further comprising deletions corresponding to residues Arg-181 and Gly-182, using SEQ ID NO: 3 for numbering.

6. A composition comprising the variant amylase of claim 1.

7. The composition of claim 6, wherein the composition is effective for removing starchy stains from laundry, dishes, or textiles.

8. The composition of claim 6, further comprising a surfactant.

* * * * *